(12) United States Patent
Gurskis et al.

(10) Patent No.: US 12,023,274 B2
(45) Date of Patent: Jul. 2, 2024

(54) APPARATUS AND METHOD FOR LOCALIZED HYPOTHERMIA OF THE PANCREAS

(71) Applicant: Arctx Medical, Inc., Raleigh, NC (US)

(72) Inventors: Donnell W. Gurskis, Belmont, CA (US); Robert B. Peliks, San Francisco, CA (US); Robert Rosenthal, Raleigh, NC (US); Steven R. Bacich, Half Moon Bay, CA (US)

(73) Assignee: Arctx Medical, Inc., Raleigh, NC (US)

( * ) Notice: Subject to any disclaimer, the term of this patent is extended or adjusted under 35 U.S.C. 154(b) by 0 days.

(21) Appl. No.: 18/310,508

(22) Filed: May 1, 2023

(65) Prior Publication Data

US 2023/0346594 A1 Nov. 2, 2023

Related U.S. Application Data

(60) Provisional application No. 63/492,189, filed on Mar. 24, 2023, provisional application No. 63/381,520, (Continued)

(51) Int. Cl.
*A61F 7/00* (2006.01)
*A61B 18/02* (2006.01)
(Continued)

(52) U.S. Cl.
CPC .............. *A61F 7/123* (2013.01); *A61B 18/02* (2013.01); *A61B 18/04* (2013.01); *A61F 7/0085* (2013.01);
(Continued)

(58) Field of Classification Search
CPC .............. A61F 7/123; A61F 2007/0018; A61F 2007/0056; A61F 2007/0096; A61F 2007/126
See application file for complete search history.

(56) References Cited

U.S. PATENT DOCUMENTS 3,254,652 A 6/1966 Smith et al.
3,425,419 A 2/1969 Dato
(Continued)

FOREIGN PATENT DOCUMENTS

EP 0278937 10/1993
EP 1089780 10/2012
(Continued)

OTHER PUBLICATIONS

"Blazer Open Irrigated Temperature Ablation Catheter" webpage https://www.bostonscientific.com/en-US/products/catheters--ablation/blazer-oi.html, 3 pages, retrieved on Apr. 26, 2023.
(Continued)

*Primary Examiner* — Tigist S Demie
(74) *Attorney, Agent, or Firm* — Levine Bagade Han LLP

(57) ABSTRACT

Thermal therapy systems, devices, and methods of using the same disclosed. A localized hypothermia of the pancreas with a delivery and placement procedure in the stomach of a patient comprising a cooling balloon system is disclosed that can be used for the treatment of pancreatitis in a patient. The cooling balloon system can have mechanisms for affecting the pancreas without impacting or inducing hypothermia in the patient in a systemic fashion. The localized hypothermia system can have a simplified delivery system and can be intended to reduce patient discomfort while reducing the metabolic activity of the inflamed pancreas of the patient.

17 Claims, 84 Drawing Sheets

Related U.S. Application Data filed on Oct. 28, 2022, provisional application No. 63/363,926, filed on Apr. 29, 2022.

(51) Int. Cl.
*A61B 18/04* (2006.01)
*A61F 7/12* (2006.01)
*A61B 18/00* (2006.01)

(52) U.S. Cl.
CPC ...... *A61F 7/12* (2013.01); *A61B 2018/00005* (2013.01); *A61B 2018/00011* (2013.01); *A61B 2018/00482* (2013.01); *A61B 2018/00494* (2013.01); *A61B 2018/0212* (2013.01); *A61B 2018/046* (2013.01); *A61F 2007/0001* (2013.01); *A61F 2007/0018* (2013.01); *A61F 2007/0022* (2013.01); *A61F 2007/0054* (2013.01); *A61F 2007/0056* (2013.01); *A61F 2007/0096* (2013.01); *A61F 2007/126* (2013.01)

(56) References Cited

U.S. PATENT DOCUMENTS

| | | |
|---|---|---|
| 3,460,538 A | 8/1969 | Armstrong |
| 3,768,484 A | 10/1973 | Gawura |
| 4,133,315 A | 1/1979 | Berman et al. |
| 4,543,089 A | 9/1985 | Moss |
| 4,718,429 A | 1/1988 | Smidt |
| 5,007,437 A | 4/1991 | Sterzer |
| 5,103,804 A | 4/1992 | Abele et al. |
| 5,151,100 A | 9/1992 | Abele et al. |
| 5,382,231 A | 1/1995 | Shlain |
| 6,019,783 A | 2/2000 | Philips et al. |
| 6,042,559 A | 3/2000 | Dobak |
| 6,051,019 A | 4/2000 | Dobak, III |
| 6,427,089 B1 * | 7/2002 | Knowlton ............ A61B 18/18 607/101 |
| 6,558,412 B2 | 5/2003 | Dobak, III et al. |
| 6,589,271 B1 | 7/2003 | Tzeng et al. |
| 6,607,517 B1 | 8/2003 | Dae et al. |
| 6,726,708 B2 | 4/2004 | Lasheras |
| 6,749,625 B2 | 6/2004 | Pompa et al. |
| 6,796,995 B2 | 9/2004 | Pham et al. |
| 6,818,011 B2 | 11/2004 | Dobak, III et al. |
| 7,063,718 B2 | 6/2006 | Dobak, III et al. |
| 7,077,825 B1 | 7/2006 | Stull |
| 7,201,738 B1 | 4/2007 | Bengmark |
| RE40,559 E | 8/2008 | Lev |
| 7,422,601 B2 | 9/2008 | Becker et al. |
| 7,491,223 B2 | 2/2009 | Lasheras |
| 7,566,341 B2 | 7/2009 | Keller et al. |
| 7,567,843 B2 | 7/2009 | Eggers et al. |
| 7,758,623 B2 | 7/2010 | Dzeng et al. |
| 7,896,009 B2 | 3/2011 | Stull |
| 8,128,595 B2 | 3/2012 | Walker et al. |
| 8,163,000 B2 | 4/2012 | Doback, III et al. |
| 8,231,664 B2 | 7/2012 | Kulstad et al. |
| 8,361,132 B2 | 1/2013 | Arad |
| 8,444,684 B2 | 5/2013 | Kulstad et al. |
| 8,523,929 B2 | 9/2013 | Kulstad et al. |
| 8,529,612 B2 | 9/2013 | Singh |
| 8,608,696 B1 | 12/2013 | Dimeo et al. |
| 8,628,554 B2 | 1/2014 | Sharma |
| 8,696,725 B2 | 4/2014 | Kulstad et al. |
| 8,968,378 B2 | 3/2015 | Ginsburg et al. |
| 9,005,151 B2 | 4/2015 | Lee |
| 9,138,344 B2 | 9/2015 | Stull |
| 9,192,510 B2 | 11/2015 | Singh |
| 9,237,964 B2 | 1/2016 | Keller et al. |
| 9,301,871 B2 | 4/2016 | Kulstad et al. |
| 9,326,890 B2 | 5/2016 | Kulstad et al. |
| 9,427,353 B2 | 8/2016 | Hammack et al. |
| 9,492,633 B2 | 11/2016 | Dabrowiak |
| 9,622,909 B2 | 4/2017 | Kulstad et al. |
| 9,717,626 B2 | 8/2017 | Singh |
| 10,010,439 B2 | 7/2018 | Sharma et al. |
| 10,085,880 B2 | 10/2018 | Machold et al. |
| 10,159,489 B2 | 12/2018 | Bhagchandani et al. |
| 10,195,075 B2 | 2/2019 | Scott et al. |
| 10,335,566 B2 | 7/2019 | Kulstad |
| 10,363,162 B2 | 7/2019 | Kulstad et al. |
| 10,398,590 B2 | 9/2019 | Kulstad et al. |
| 10,413,444 B2 | 9/2019 | Kulstad et al. |
| 10,420,675 B2 | 9/2019 | Stull |
| 10,537,387 B2 | 1/2020 | Oren et al. |
| 10,561,527 B2 | 2/2020 | Rozenberg et al. |
| 10,716,703 B2 | 7/2020 | Kulstad et al. |
| 10,736,773 B2 | 8/2020 | Kulstad et al. |
| 10,842,668 B2 | 11/2020 | Singh |
| 2001/0007951 A1 | 7/2001 | Dobak, III |
| 2002/0077625 A1 | 6/2002 | Lev |
| 2003/0220674 A1 | 11/2003 | Anderson et al. |
| 2004/0210214 A1 | 10/2004 | Knowlton |
| 2004/0210281 A1 | 10/2004 | Dzeng et al. |
| 2004/0215180 A1 | 10/2004 | Starkebaum et al. |
| 2005/0096638 A1 | 5/2005 | Starkbauem et al. |
| 2005/0203501 A1 | 9/2005 | Aldrich et al. |
| 2005/0240250 A1 | 10/2005 | Dobak, III et al. |
| 2007/0198071 A1 | 8/2007 | Ting et al. |
| 2007/0225781 A1 | 9/2007 | Saadat et al. |
| 2007/0265608 A1 | 11/2007 | Hernandez |
| 2008/0077211 A1 | 3/2008 | Levinson et al. |
| 2008/0287839 A1 | 11/2008 | Rosen et al. |
| 2009/0018623 A1 | 1/2009 | Levinson et al. |
| 2009/0018626 A1 | 1/2009 | Levinson et al. |
| 2009/0048514 A1 | 2/2009 | Azhari et al. |
| 2009/0076573 A1 | 3/2009 | Burnett et al. |
| 2009/0105696 A1 | 4/2009 | Lee et al. |
| 2009/0118722 A1 | 5/2009 | Ebbers et al. |
| 2009/0149929 A1 | 6/2009 | Levinson et al. |
| 2009/0312597 A1 | 12/2009 | Bar et al. |
| 2009/0312676 A1 | 12/2009 | Rousso et al. |
| 2010/0030190 A1 * | 2/2010 | Singh .................. A61F 7/123 607/105 |
| 2010/0121159 A1 * | 5/2010 | Burnett ................ A61B 5/01 600/549 |
| 2010/0152824 A1 | 6/2010 | Allison |
| 2010/0168739 A1 | 7/2010 | Wu et al. |
| 2010/0198319 A1 | 8/2010 | Arad |
| 2010/0217361 A1 | 8/2010 | Kulstad et al. |
| 2010/0280582 A1 | 11/2010 | Baker et al. |
| 2011/0238051 A1 | 9/2011 | Levinson et al. |
| 2011/0239682 A1 | 10/2011 | Raines et al. |
| 2012/0221083 A1 | 8/2012 | Cruzada |
| 2012/0239123 A1 | 9/2012 | Weber et al. |
| 2012/0290051 A1 | 11/2012 | Boyden et al. |
| 2013/0013037 A1 | 1/2013 | Adams |
| 2013/0131764 A1 | 5/2013 | Grove |
| 2013/0172966 A1 | 7/2013 | Arad et al. |
| 2013/0204331 A1 | 8/2013 | Harikrishna et al. |
| 2013/0289438 A1 | 10/2013 | Lyon |
| 2013/0338741 A1 | 12/2013 | Singh |
| 2014/0018788 A1 | 1/2014 | Engelman et al. |
| 2014/0051905 A1 | 2/2014 | Sako et al. |
| 2014/0277308 A1 | 9/2014 | Cronise et al. |
| 2017/0304113 A1 | 10/2017 | Singh |
| 2020/0107881 A1 | 4/2020 | Oren et al. |
| 2021/0069013 A1 | 3/2021 | Singh |
| 2021/0251804 A1 | 8/2021 | Burnett et al. |
| 2022/0409257 A1 * | 12/2022 | Catanzaro ............ A61B 18/04 |
| 2023/0037101 A1 | 2/2023 | Kashintsev et al. |
| 2023/0346448 A1 | 11/2023 | Gurskis et al. |
| 2023/0346591 A1 | 11/2023 | Gurskis et al. |
| 2023/0346592 A1 | 11/2023 | Gurskis et al. |
| 2023/0346593 A1 | 11/2023 | Gurskis et al. |

FOREIGN PATENT DOCUMENTS

| | | |
|---|---|---|
| EP | 2162186 | 9/2014 |
| EP | 3578228 | 12/2019 |
| EP | 4034218 | 8/2022 |
| KR | 101811136 | 12/2017 |

(56) References Cited

FOREIGN PATENT DOCUMENTS

| SU | 1378835 A1 * | 3/1985 | ............... A61F 7/12 |
|---|---|---|---|
| SU | 1378835 A1 * | 12/1985 | ............... A61F 7/12 |
| SU | 1378835 | 3/1988 | |
| WO | WO 2002/039915 | 5/2002 | |
| WO | WO 2008/049082 | 4/2008 | |
| WO | WO 2021/137739 | 7/2021 | |
| WO | WO 2023/075634 | 5/2023 | |
| WO | WO 2023/212415 | 11/2023 | |

OTHER PUBLICATIONS

"Freezor Cardiac Cryoablation Catheters—Cardiac Ablation Products for Atrial Fibrillation" webpage https://www.medtronic.com/US-en/healthcare-professionals/products/cardiac-rhythm/ablation-atrial-fibrillation/freezor-cardiac-cryoablation-catheters.html, 35 pages, retrieved on May 13, 2023.
"Indications, Safety, and warnings Ablation Products for Atrial Fibrillation." webpage https://www.medtronic.com/US-en/healthcare-professionals/products/cardiac-rhythm/ablation-atrial-fibrillation/indications-safety-warnings.html, 21 pages, retrieved on May 10, 2023.
"Our Solutions" Avanos Medical webpage https://avanos.com/our-solutions/, 6 pages, retrieved on May 1, 2023.
"The Freezor Family of Cardiac Cryoablation Catheters." webpage https://www.medtronic.com/content/dam/medtronic-com/products/cardiac-rhythm/ablation-arrhythmias/cas-freezor-family-sell-sheet.pdf, 2 pages, retrieved on May 17, 2023.
"Zoll Defibrillators Meet Stringent FDA Premarket Approval Regulations" webpage https://www.zoll.com/products/temperature-management/catheter, 6 pages, retrieved on Apr. 26, 2023.
Bai et al., "Meta-analysis: allopurinol in the prevention of postendoscopic retrograde cholangiopancreatography pancreatitis," Alimentary Pharmacology & Therapeutics, 2008, 28:557-564.
Buchan, "Gastric freezing in the rat," Gut. 1965;6(5):494-499.
Buchler et al., "Gabexate mesilate in human acute pancreatitis," Gastroenterology. 1993, 104:1165-1170.
Cho et al., "Endoscopic cryotherapy for the management of gastric antral vascular ectasia," Gastrointest. Endosc., 2008;68(5):895-902.
Everhart and Ruhl, "Burden of digestive diseases in the United States part I: overall and unner gastrointestinal diseases," Gastroenterology, 2009, 136:376-386.
Fischer et al., "Phosphatidylinositol 3-kinase facilitates bile acid-induced Ca2+ responses in pancreatic acinar cells," Am J. Physiol Gastrointest Liver Physiol., 2007, 292:G875-886.
Furuhashi, "Identification and characterization of a cathepsin B-like protease in Physarum sclerotium," The International Journal of Biochemistry & Cell Biology, 2002, 34(10):1308-1316.
Gaggiotti et al., "Adjustable Totally Implantable Intragastric Prosthesis (ATIIP)—Endogast® for Treatment of Morbid Obesity: One year follow-up of a Multicenter Prospective Clinical Survey," Obes. Surg., 2007;17(7):949-956.
Genco et al., "BioEnterics ' Intragstric Balloon (BIB®): a short-term, double-blind, randomised, controlled, crossover study on weight reduction in rnorbidly obese patients," int. J. Obes. (Lond.), 2006;30:129-133.
Gukovskaya et al., "Cell death in pancreatitis: effects of alcohol," Journal of Gastroenterology and Henatology, 2006, 21:SI0-SI3.
Gukovskaya et al., "Ethanol metabolism and transcription factor activation in pancreatic acinar cells in rats," Gastroenterology, 2002, 122:106-118.
Hagiwara et al., "Changes in cell culture temperature alter release of inflammatory mediators in murine macrophagic RAW264.7 cells," Inflamm Res., 2007, 56:297-303.
Johnson et al., "Double blind, randomised, placebo controlled study of a platelet activating factor antagonist, lexipafant, in the treatment and prevention of organ failure in predicted severe acute pancreatitis," Gut, 2001, 48:62-69.

Lu et al., "Alcohols enhance caerulein-induced zymogen activation in pancreatic acinar cells," Am. J. Physiol. Gastrointest. Liver Physiol., 2002, 282:G501-G507.
Lunding et al., "Pressure-induced gastric accommodation studied with a new distension paradigm. Abnormally low accommodation rate in patients with functional dyspepsia," Scand. J. Gastroenterol., 2006;41:544-552.
Matsuoka et al., "Effects of Moderate Hypothermia on Proinflaimnatory Cytokine Production in a Rat Model of Caerulein-Induced Pancreatitis," Pancreas, 2003;26(1):e12-e17.
McFarland et al., "The clinical place of gastric hypothermia," Ann. R. Coll. Surg. Engl., 1968; delivered at the Royal College of Surgeons of England on Apr. 27, 1967;42(3):182-205.
Melnyk et al., "Gastric Freezing in Dogs," Ann. Surg., 1965;162:135-144.
Mundt et al., "Fundal dysaccornmodation in functional dyspepsia: head-to-head comparison between the barostat and three-dimensional ultrasonograpbic technique," Gut, 2006;55:1725-1730.
Mutinga et al., "Does mortality occur early or late in acute pancreatitis?" Int J Pancreatol., 2000, 28(2):91-95.
Nabseth et al., "Studies on the effect of intragastric cooling on acute experimental pancreatitis," Surgery, 1960;47(4):542-547.
Patitutko et al., "Ways of improving results of gastro pancreatoduodenal resection in tumors of the bilio-pancreatoduodenai area," Khirurgila (Mosk), 1995;(3):26-29 (abstract only).
Preub et al., "Pancreatic changes in cases of death due to hypothermia," Forensic Science Inlernational, 2007;166:194-198.
Rakonczay et al., "The Effects of Hypo- and Hypothermic PreTeatment on Sodium Taurocholate-Induced Acute Pancreatitis in Rats," Pancreas, 2002;24(1):83 89.
Ranson and Berman, "Long peritoneal lavage decreases pancreatic sepsis in acute pancreatitis," Ann Sur2:., 1990, 211(6):708-716.
Renner et al., "Death due to acute pancreatitis. A retrospective analysis of 405 autopsy cases," Di2:estive Diseases and Sciences, 1985, 30(10):1005-1018.
Roddenberry et al., "Hypothermia in the Treatment of Acute Pancreatitis,".J. Am. Med. Assoc., 1967;201(11):825-827.
Sahani et al., "Autoimmune Pancreatitis: Disease Evolution, Staging, Response Assessment, and CT Features That Predict Response to Corticosteroid Therapy," Radiolo2:v, 2009, 250(1):118-129.
Schroder et al., "Pancreatic resection versus peritoneal lavage in acute necrotizing pancreatitis. A prospective randomized trial," Ann Sur2:., 1991, 214(6):663-666.
Singh and Mcniven, "Src-mediated cortactin phosphorylation regulates actin localization and iniurious blebbing in acinar cells," Molecular Biolo2:v of the Cell 2008, 19:2339-2347.
Singh et al., "Nelfinavir/Ritonavir Reduces Acinar Injury But Not Inflammation During Mouse Caerulein Pancreatitis," Am J Physiol Gastrointest Liver Physiol., 2009, 296:GI040-GI046.
Singh et al., "Phosphatidylinositol 3-kinase-dependent activation oftrypsinogen modulates the severity of acute pancreatitis," The Journal of Clinical Investigation, 2001, 108(9):1387-1395.
Singh et al., "Protease-activated receptor-2 protects against pancreatitis by stimulating exocrine secretion," Gut, 2007, 56:958-964.
Singh et al., "Serine protease inhibitor causes F-actin redistribution and inhibition of calcium- mediated secretion in pancreatic acini," Gastroenterology, 2001, 120:1818-1827.
Sipos et al., "Temperature-dependent activation of trypsin by calcium," Biochem. Biophys. Res. Commun., 1968;31(4):522-527.
Stiff et al., "Hypothermia and acute pancreatitis: myth or reality?" JRoyal Soc. Med., 2003;96(5):228-229.
Symbas et al., "Influence on Hypothermia on Pancreatic Function," Ann. Surg., 1961;154(4):509-515.
Tenner, "Initial Management of Acute Pancreatitis: Critical Issues During the First 72 hours," Am. J. Gastro., 2004;99:2489-2494.
Thrower et al., "Molecular basis for pancreatitis," Current Opinion in Gastroenterology. 2008, 24:580-585.
Van Acker et al., "Cathepsin B inhibition prevents trypsinogen activation and reduces pancreatitis severity," American J Physiol. Gastrointest Liver Physiol, 2002, 283:G794-G800.
Wels et al., "Hypothermia in acute hemorrhagic pancreatitis," Arch. Surg., 1962;85:817-821.

(56) References Cited

OTHER PUBLICATIONS

White et al., "Problems and Complications of Gastiic Freezing," Annals of Surgery, 1964; 159(5):765-768.
Yokoyama et al., "Intense PET signal in the degenerative necrosis superimposed on chronic pancreatitis," Pancreas, 2005, 31:192-194.

* cited by examiner

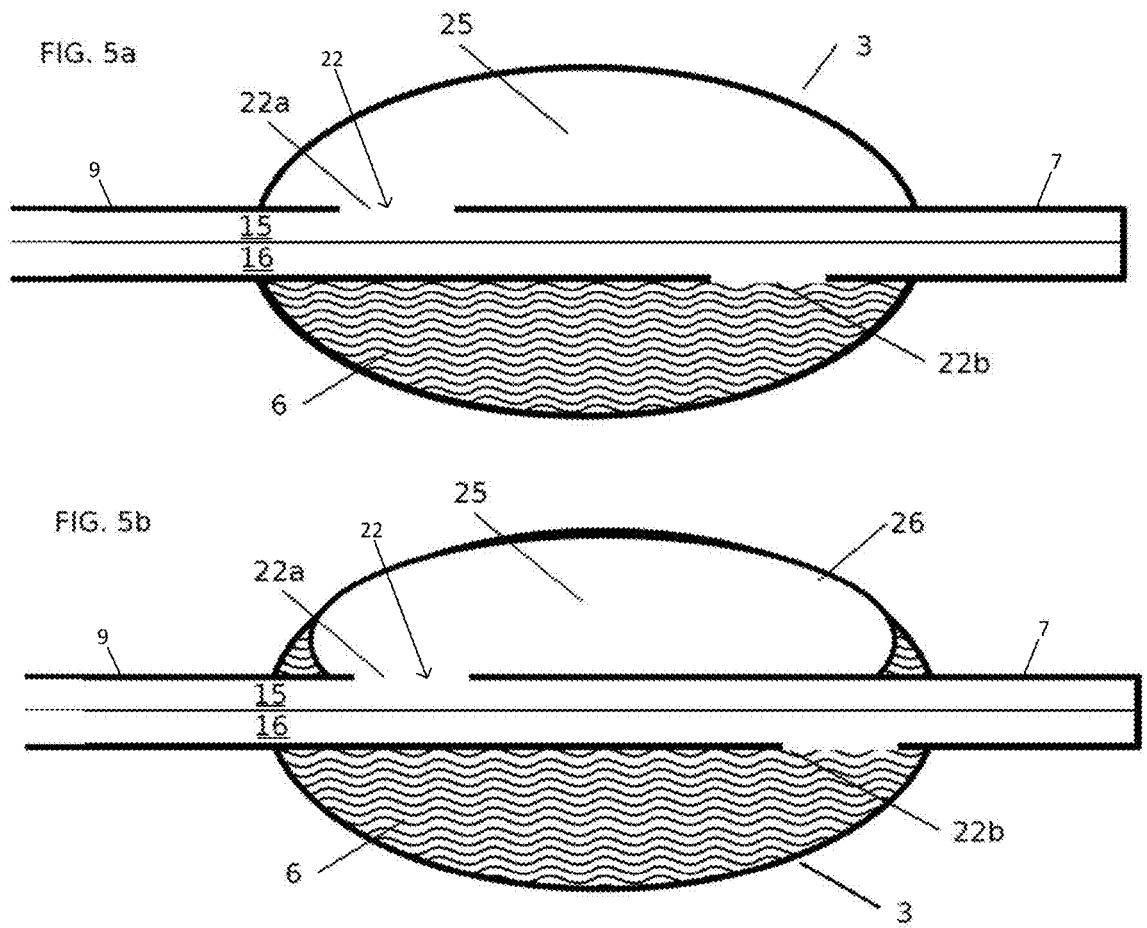
FIG. 5a
FIG. 5b
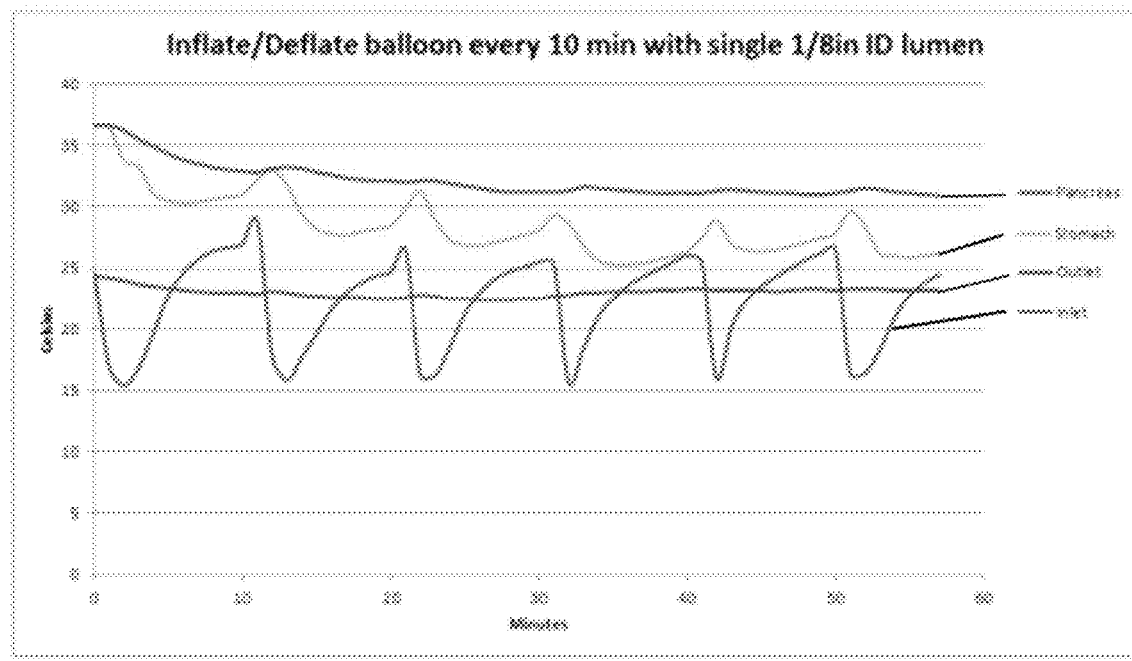
FIG. 6

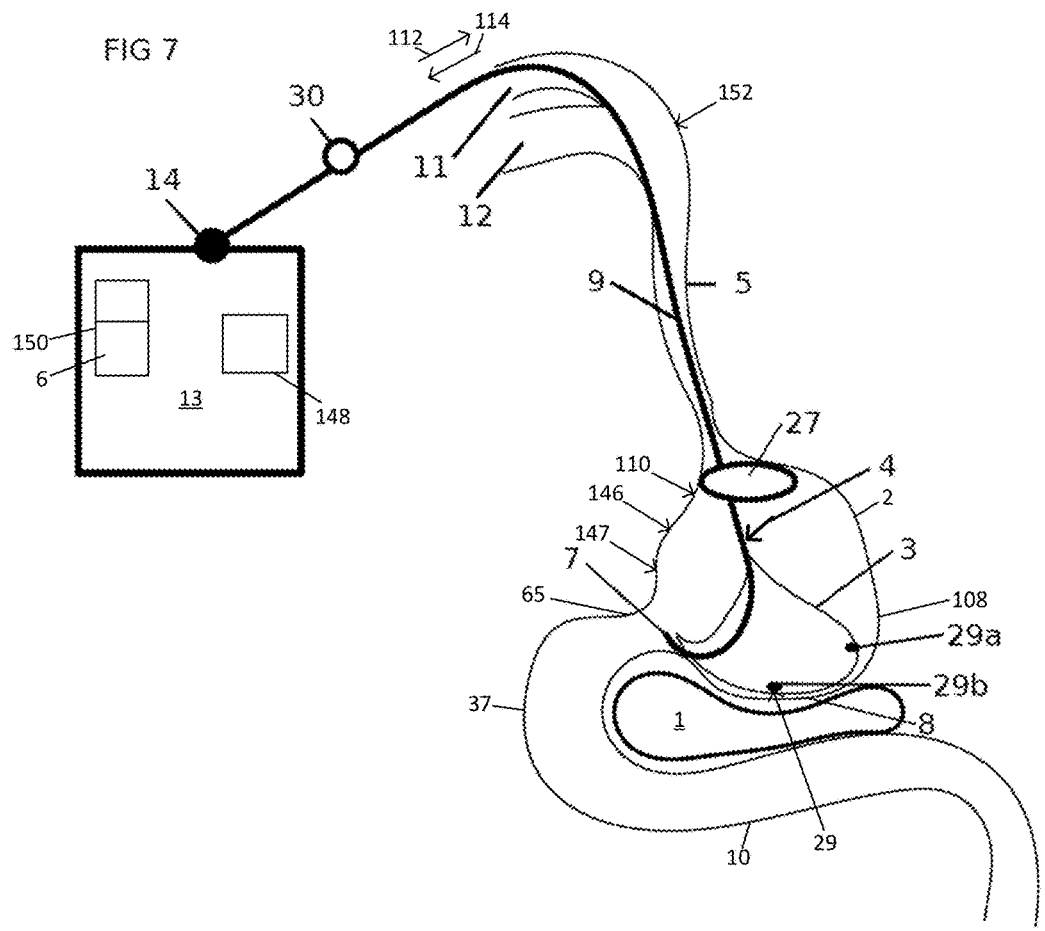
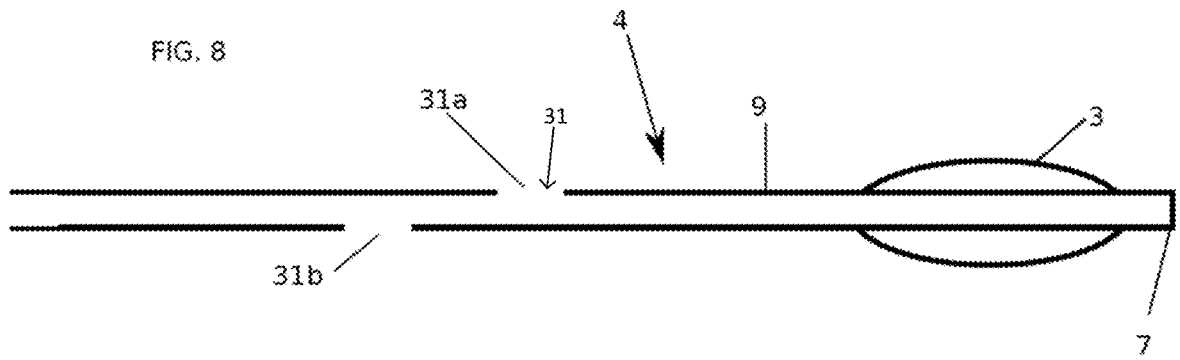
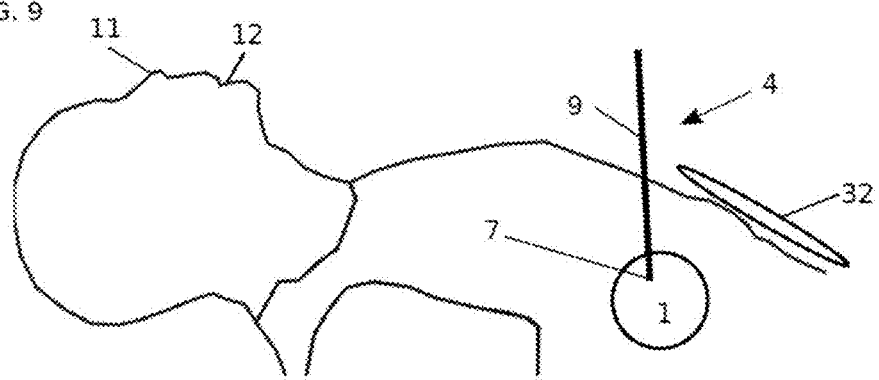

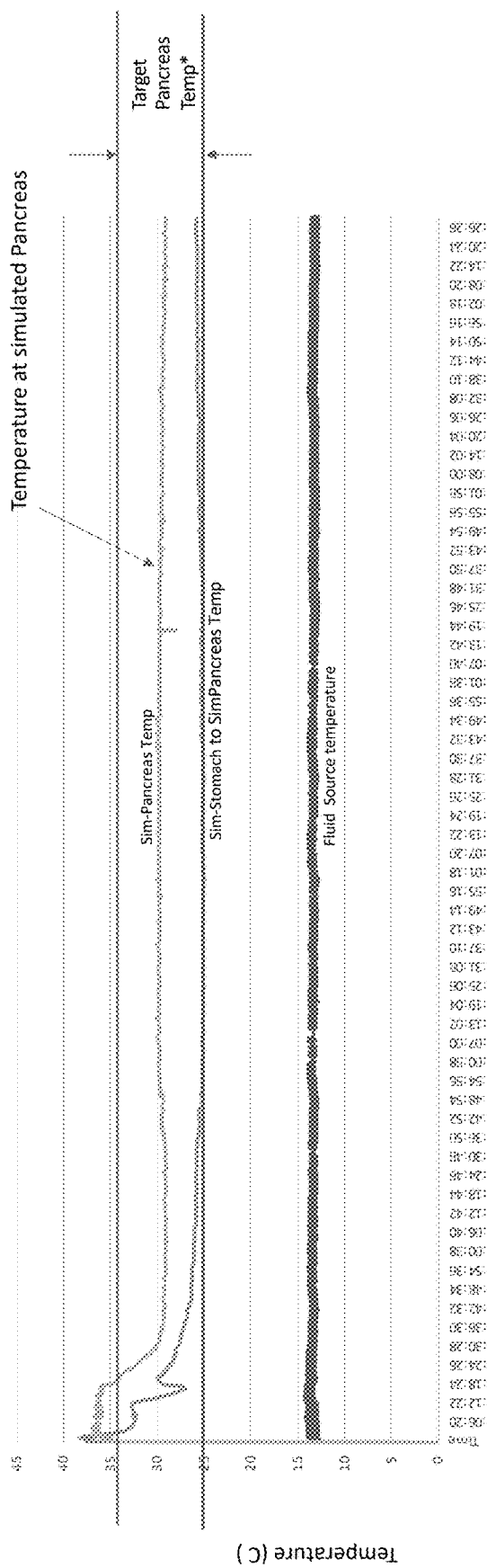

FIG 12

- Research has shown that a pancreas temperature of 25-34 C reduces metabolic and enzymatic function*

* Multimodal Transgastric Local Pancreatic Hypothermia Reduces Severity of Acute Pancreatitis in Rats and Increases Survival
Cristiane de Oliveira,1 Biswajit Khatua,1 Arup Bag,1 Bara El-Kurdi,1 Krutika Patel,1 Vivek Mishra,2 Sarah Navina,3 and Vijay P. Singh1 1Department of Medicine, Mayo Clinic, Scottsdale, Arizona; 2Department of Medicine, University of Pittsburgh, Pittsburgh, Pennsylvania; and 3Department of Pathology, University of Pittsburgh

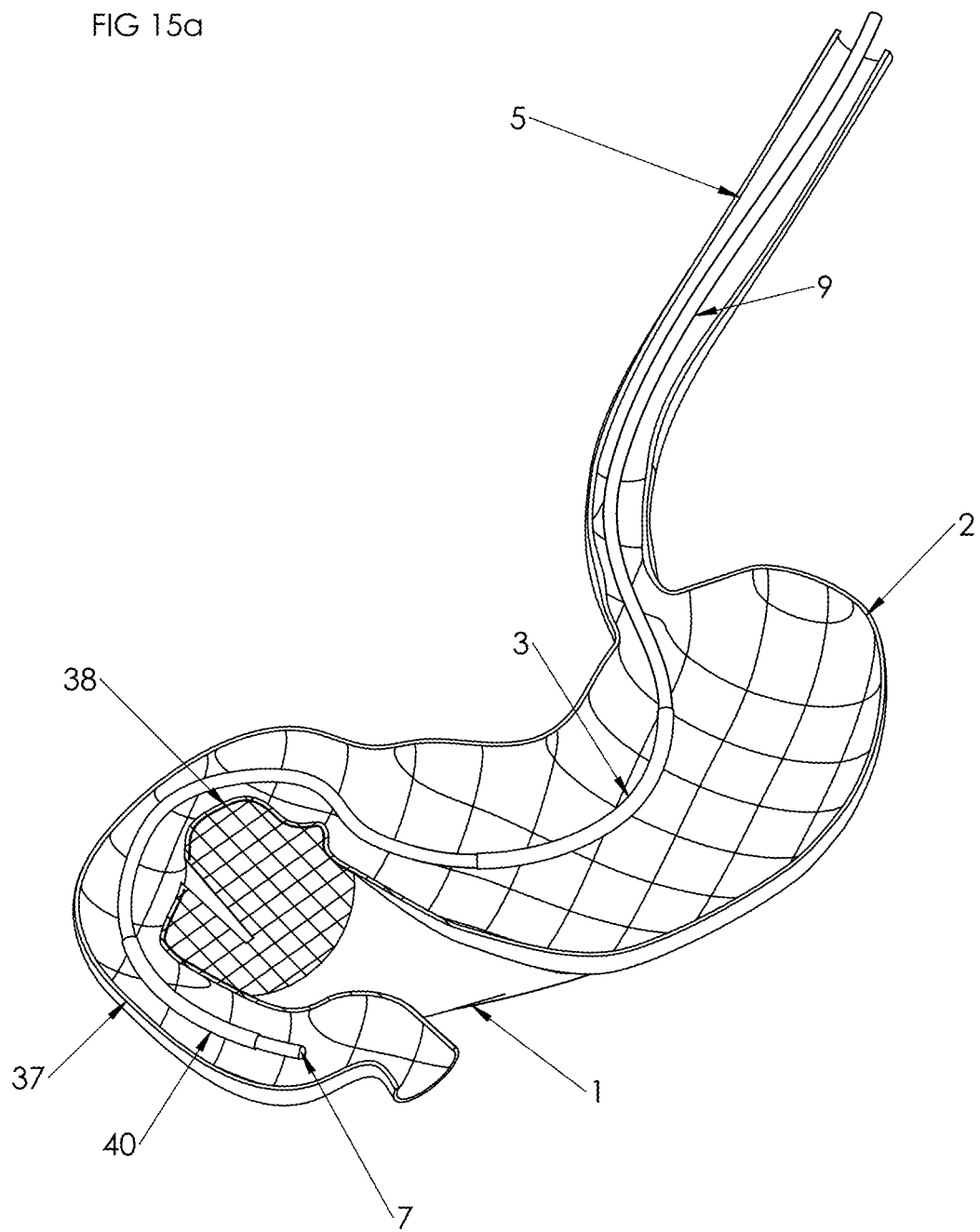

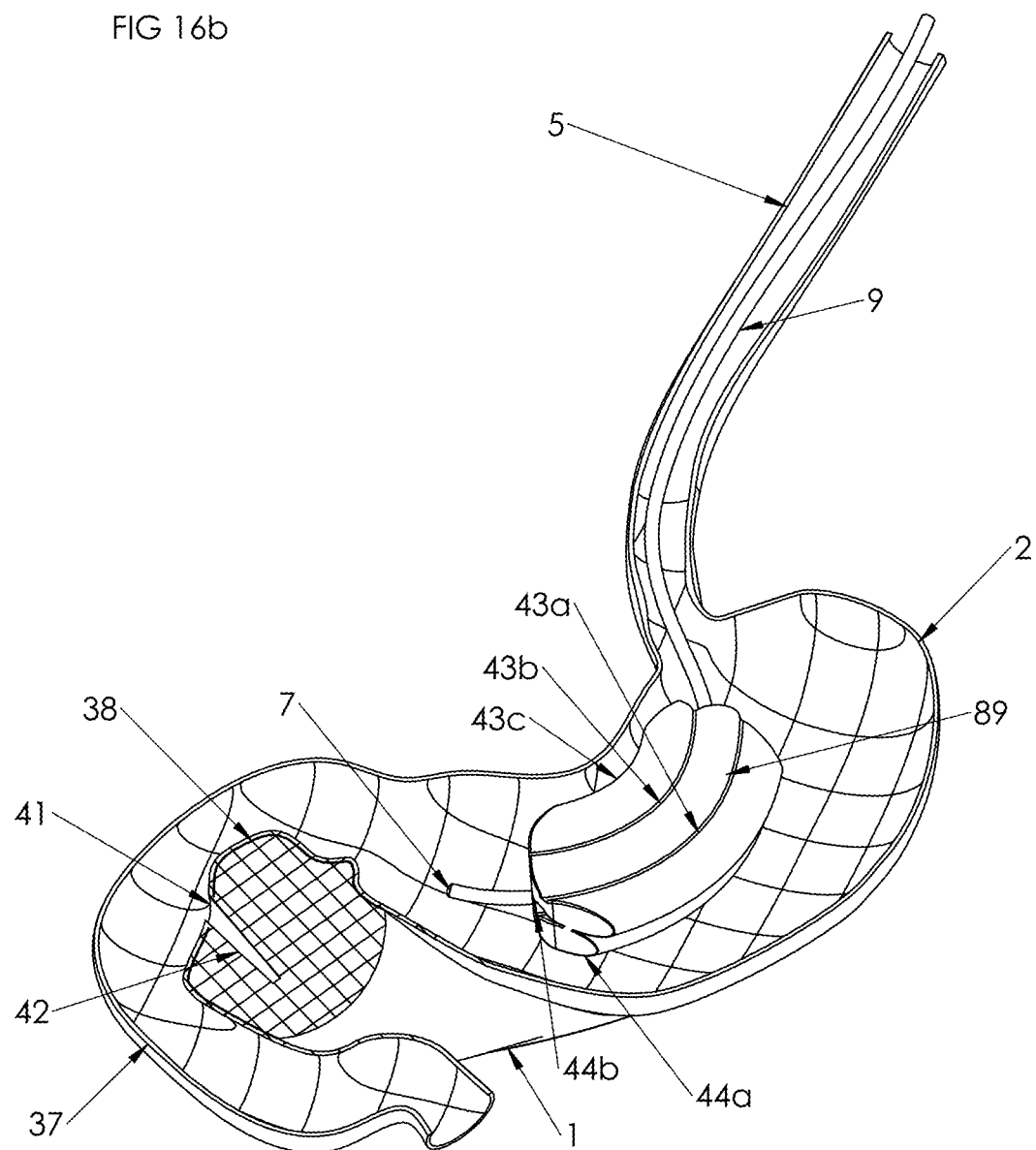

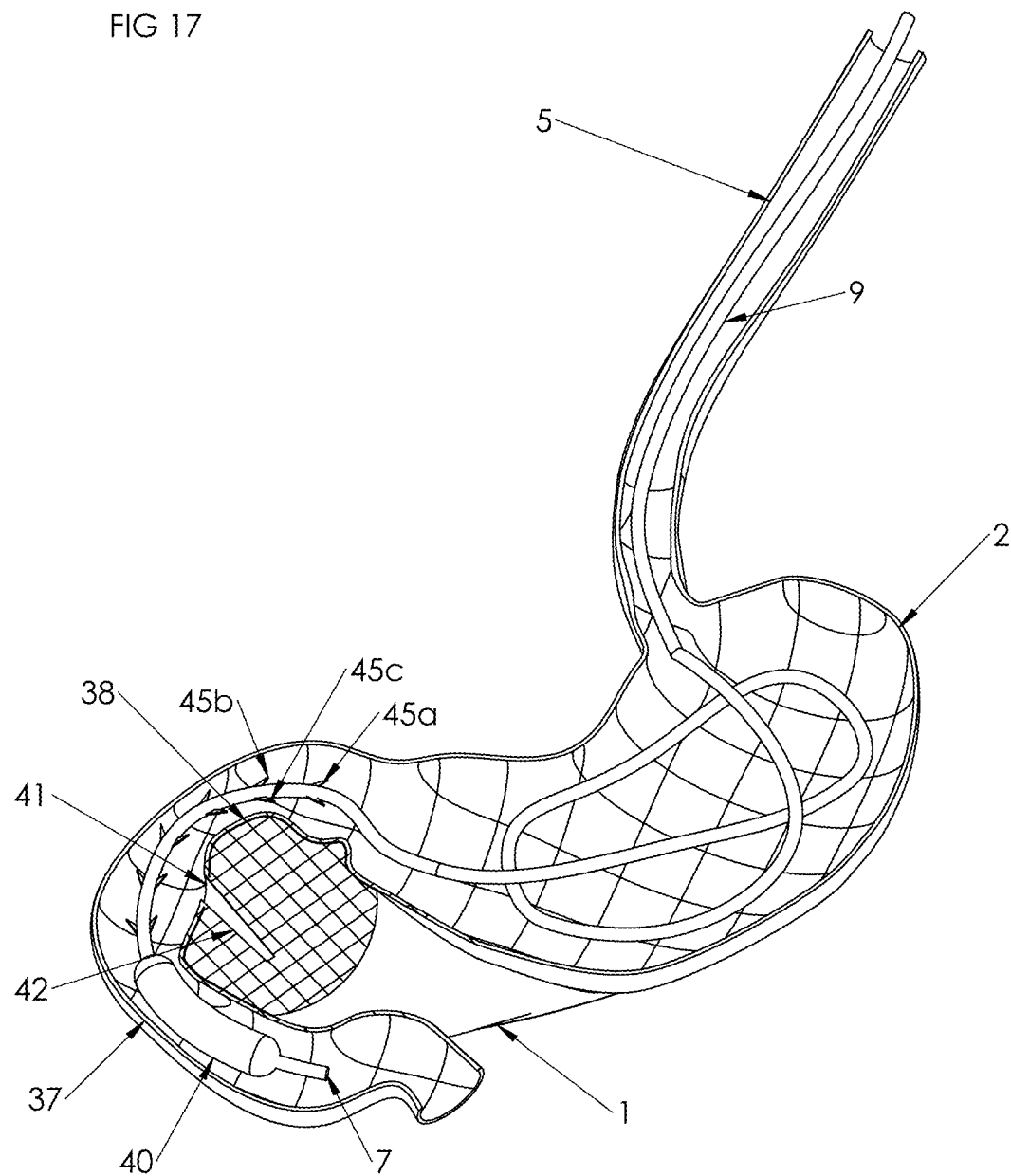

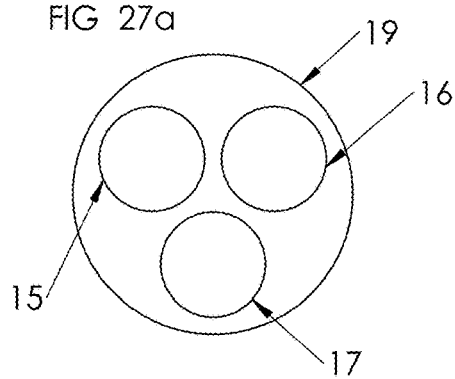
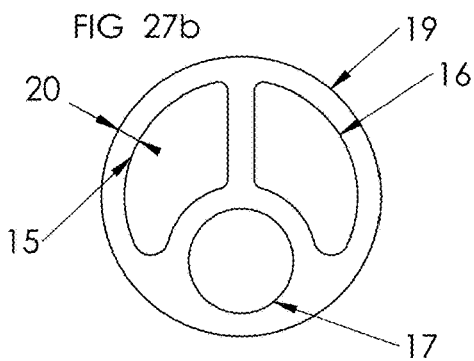
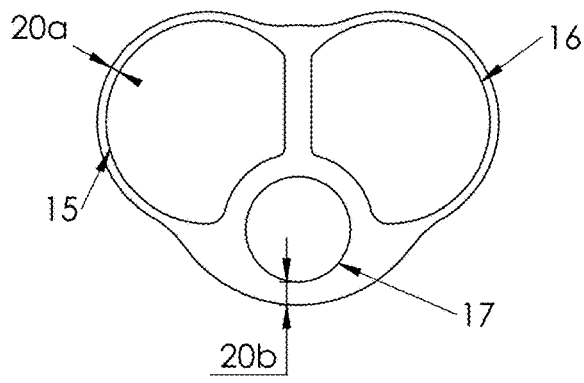
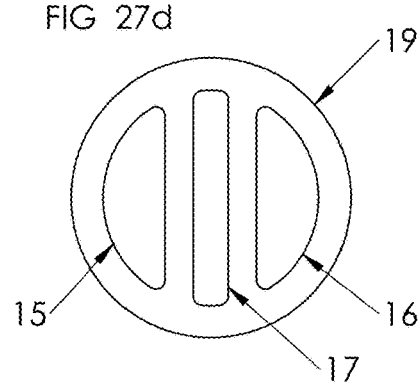
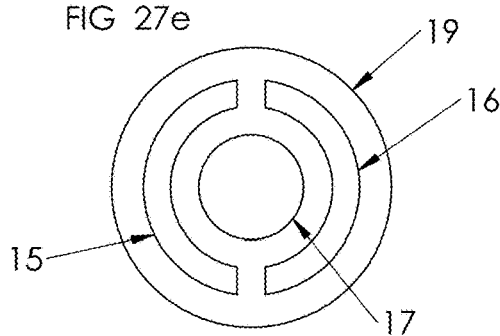
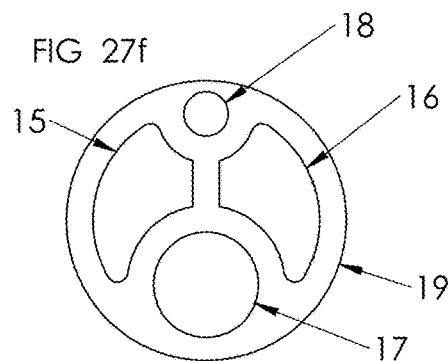

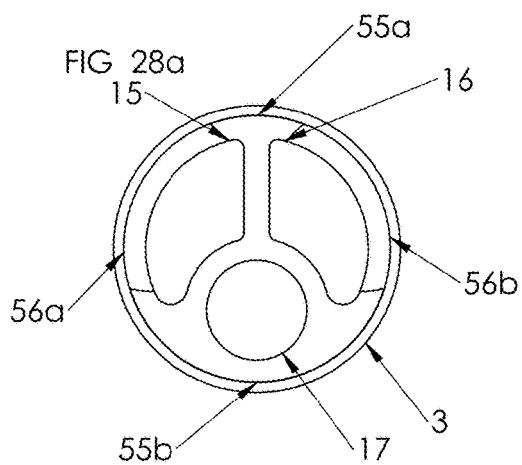
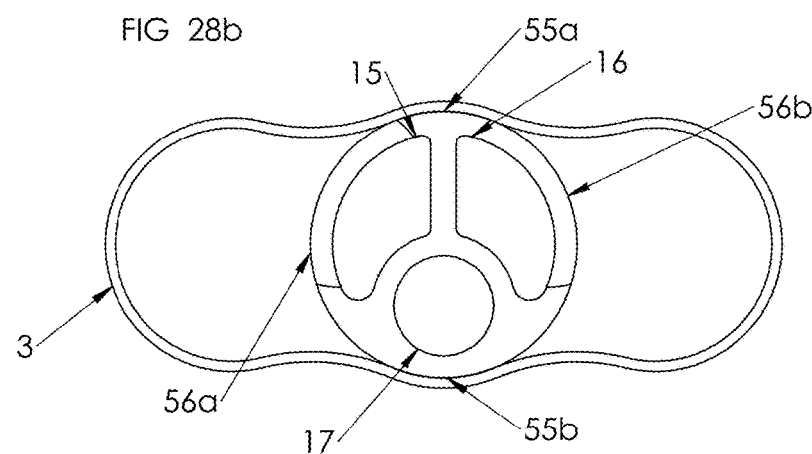
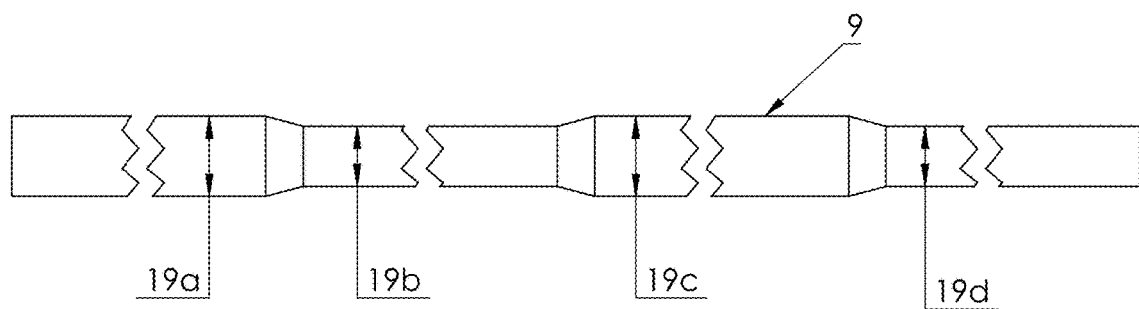

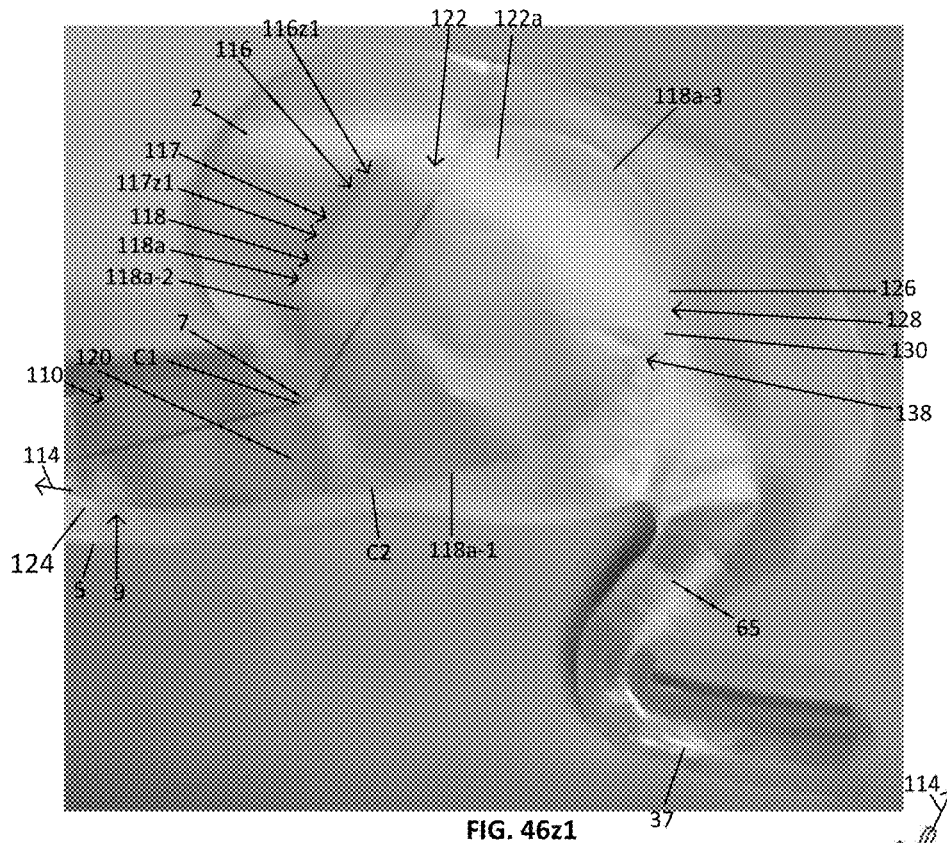
FIG. 46z1
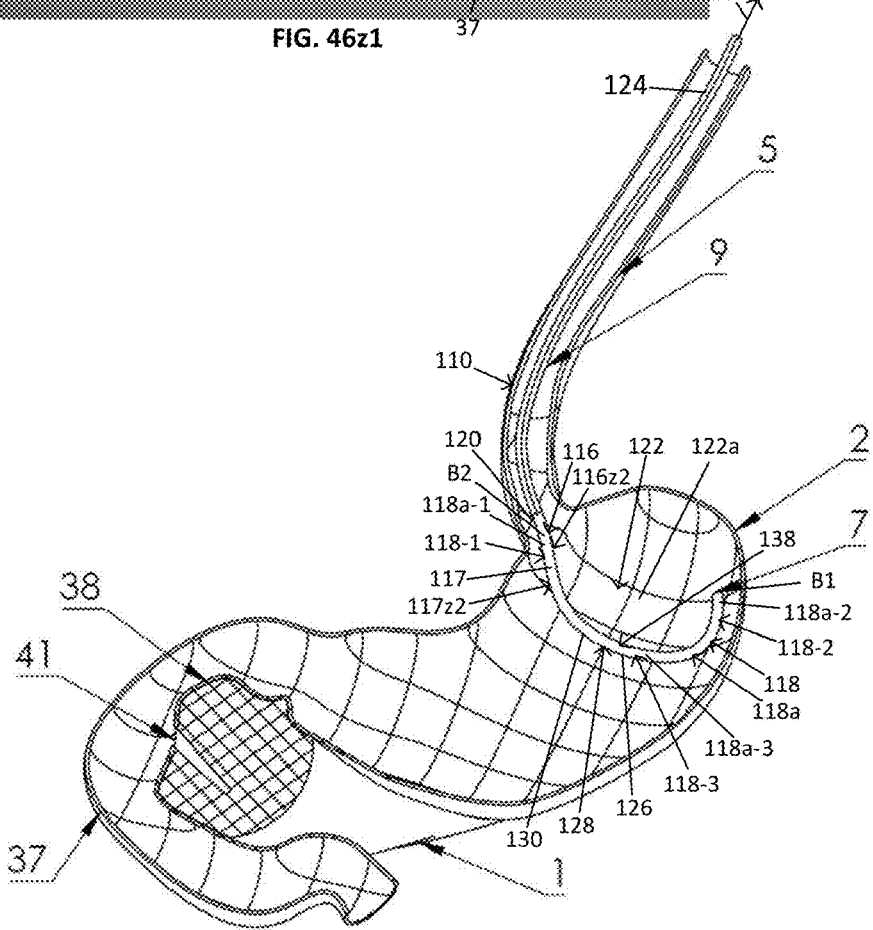
FIG. 46z2

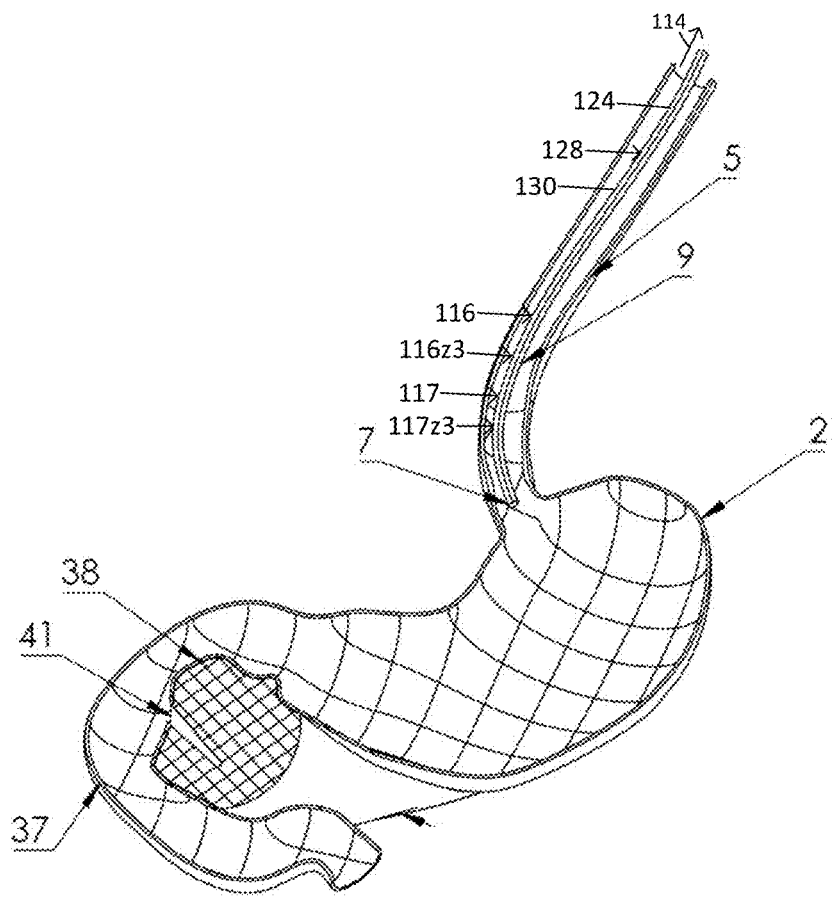
FIG. 46z3
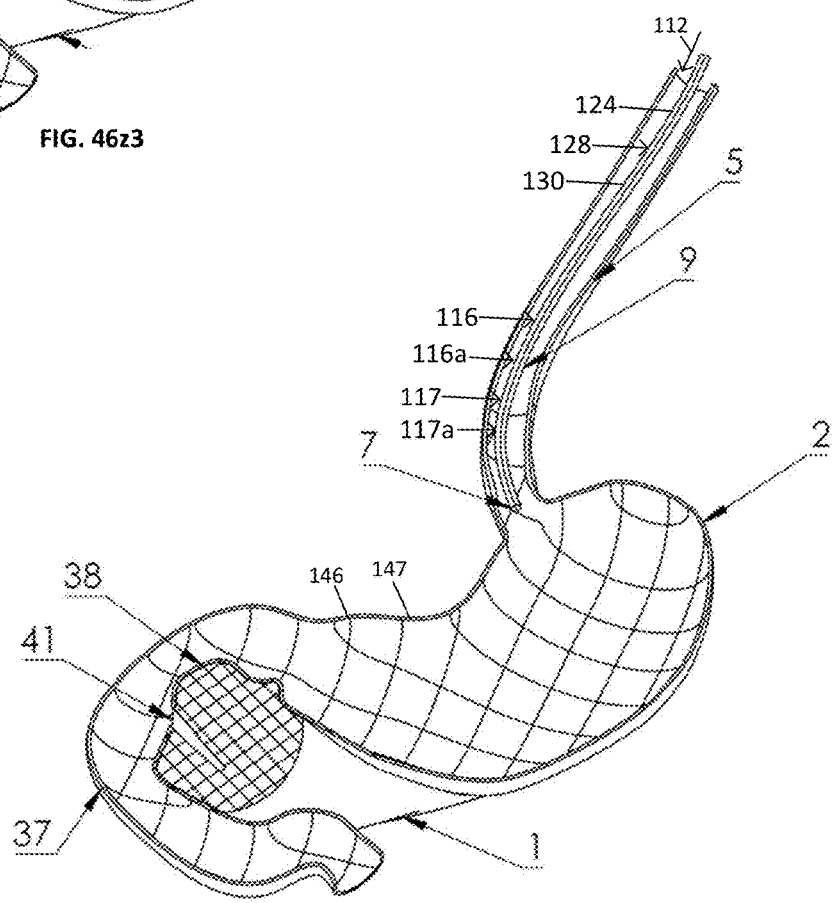
FIG. 47a

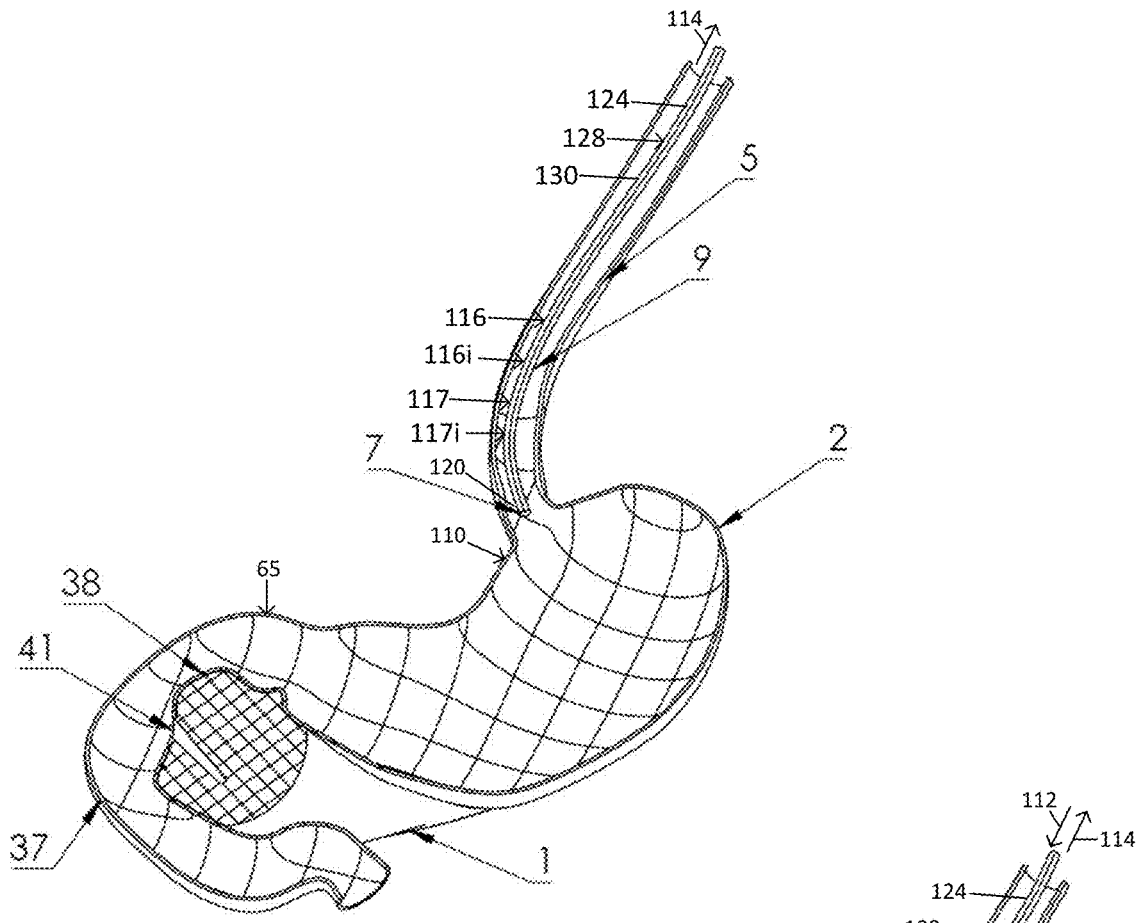
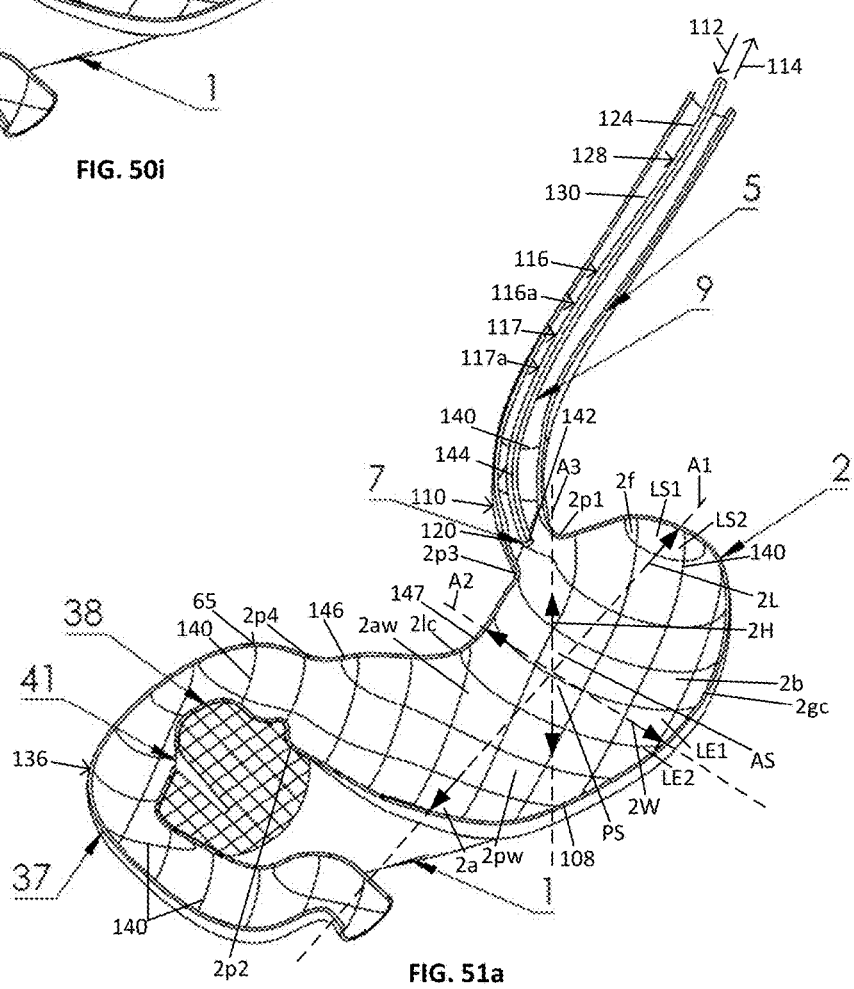
FIG. 50i
FIG. 51a

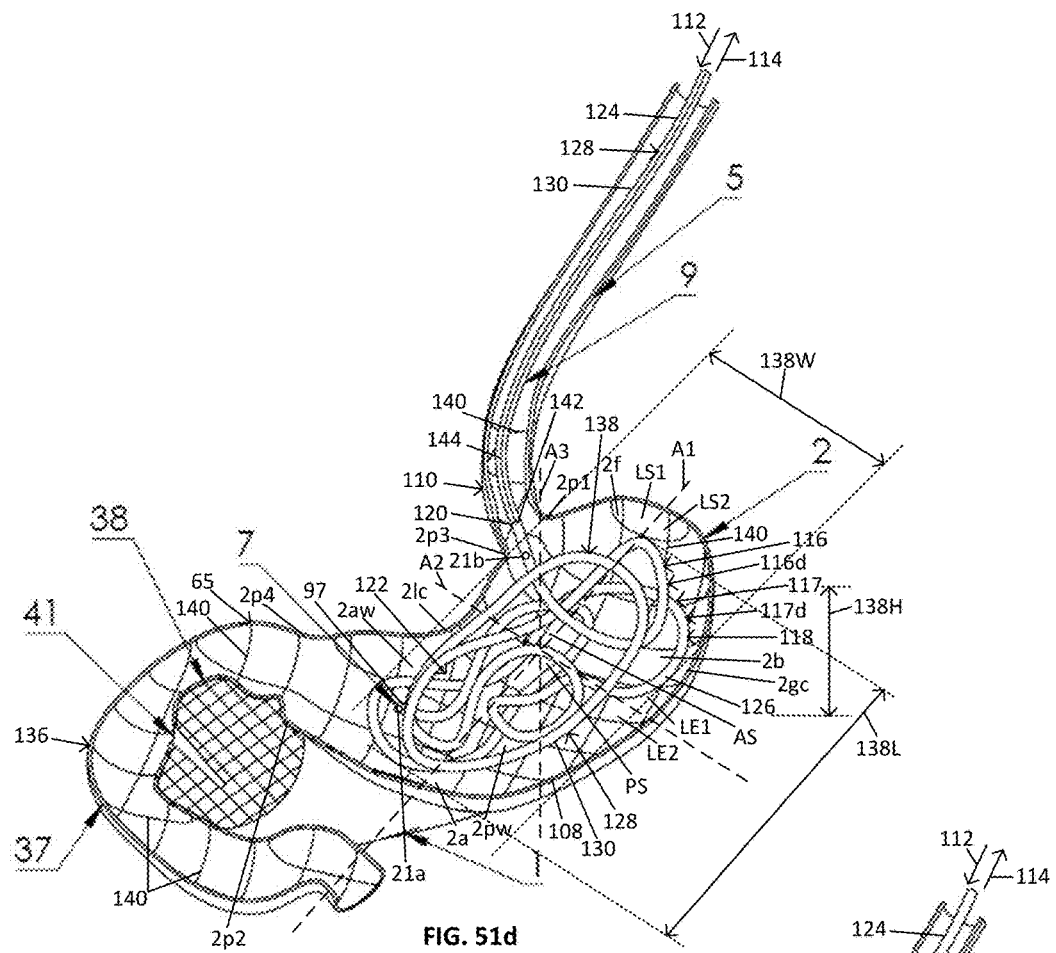
FIG. 51d
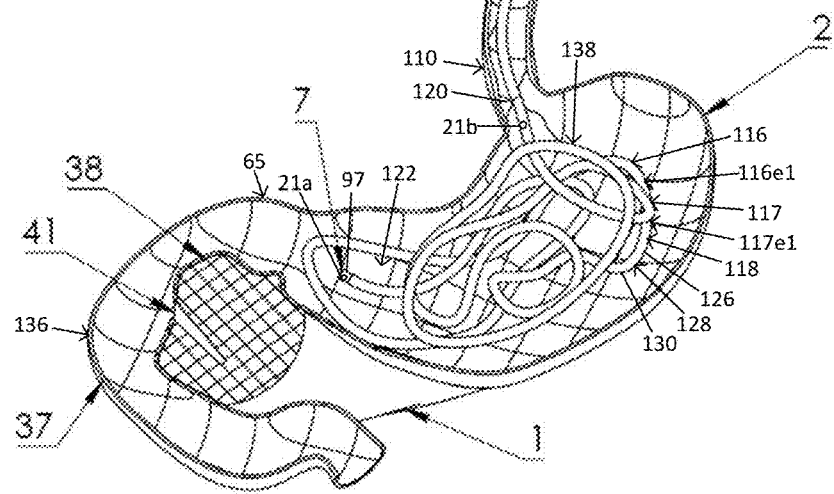
FIG. 51e1

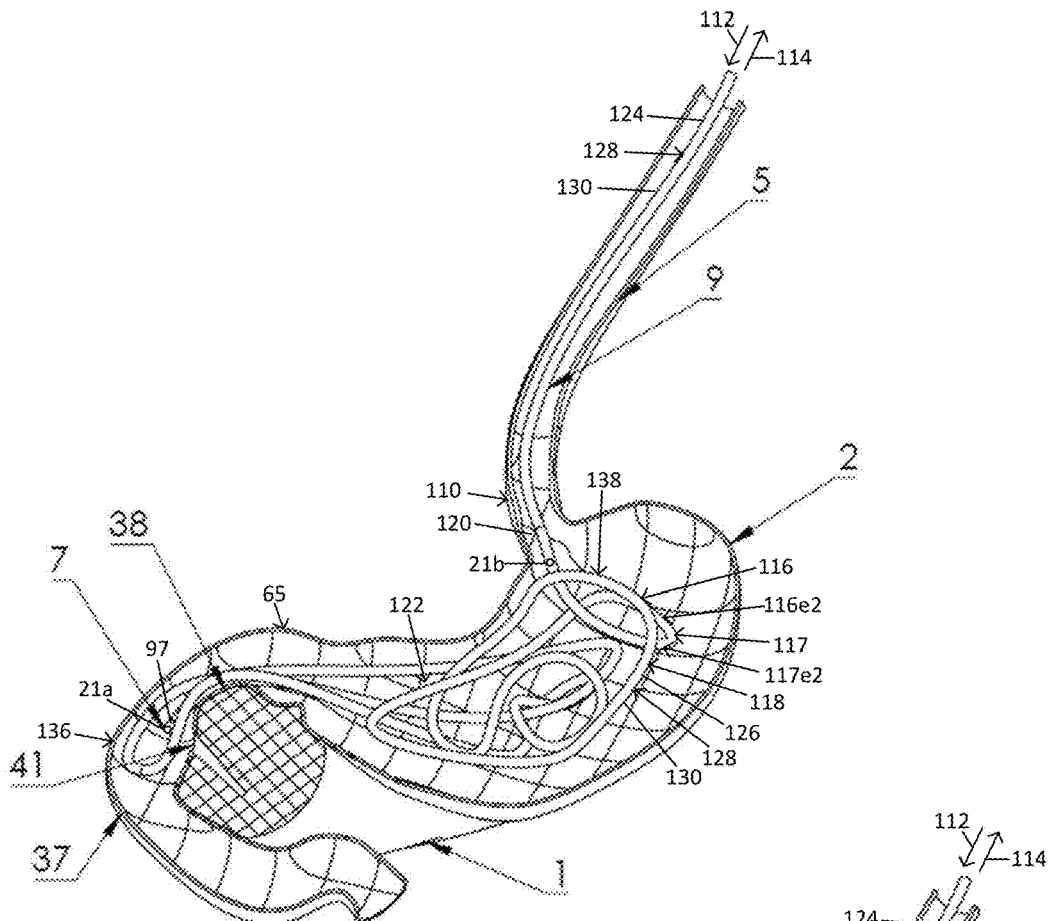
FIG. 51e2
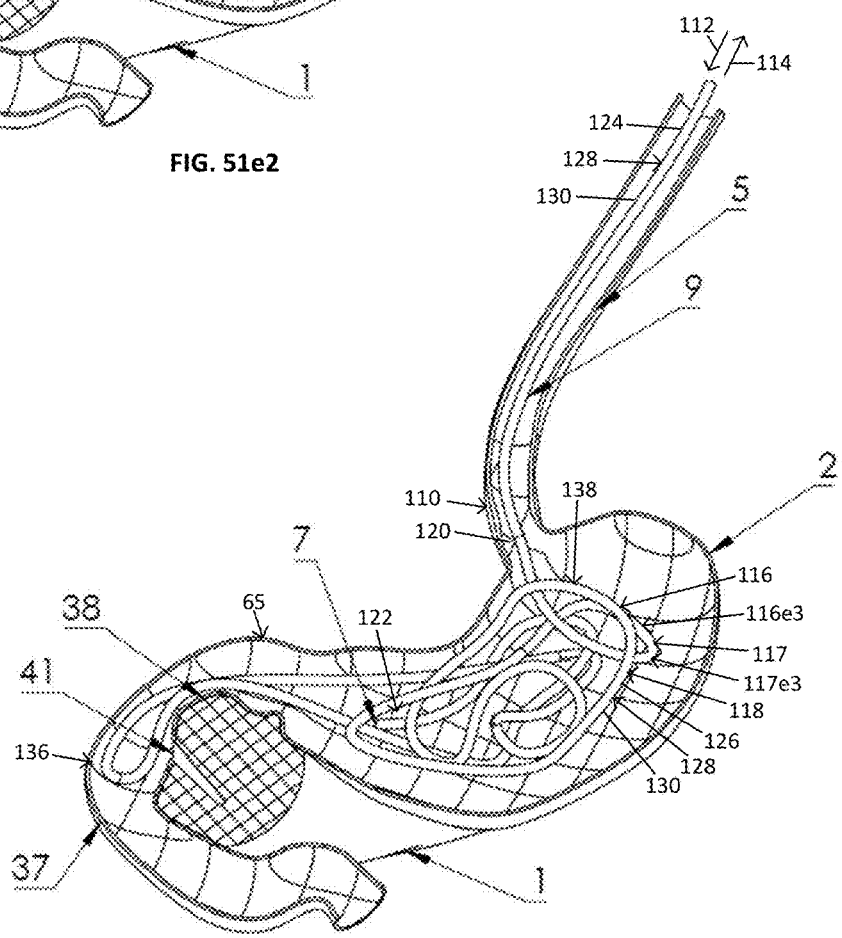
FIG. 51e3

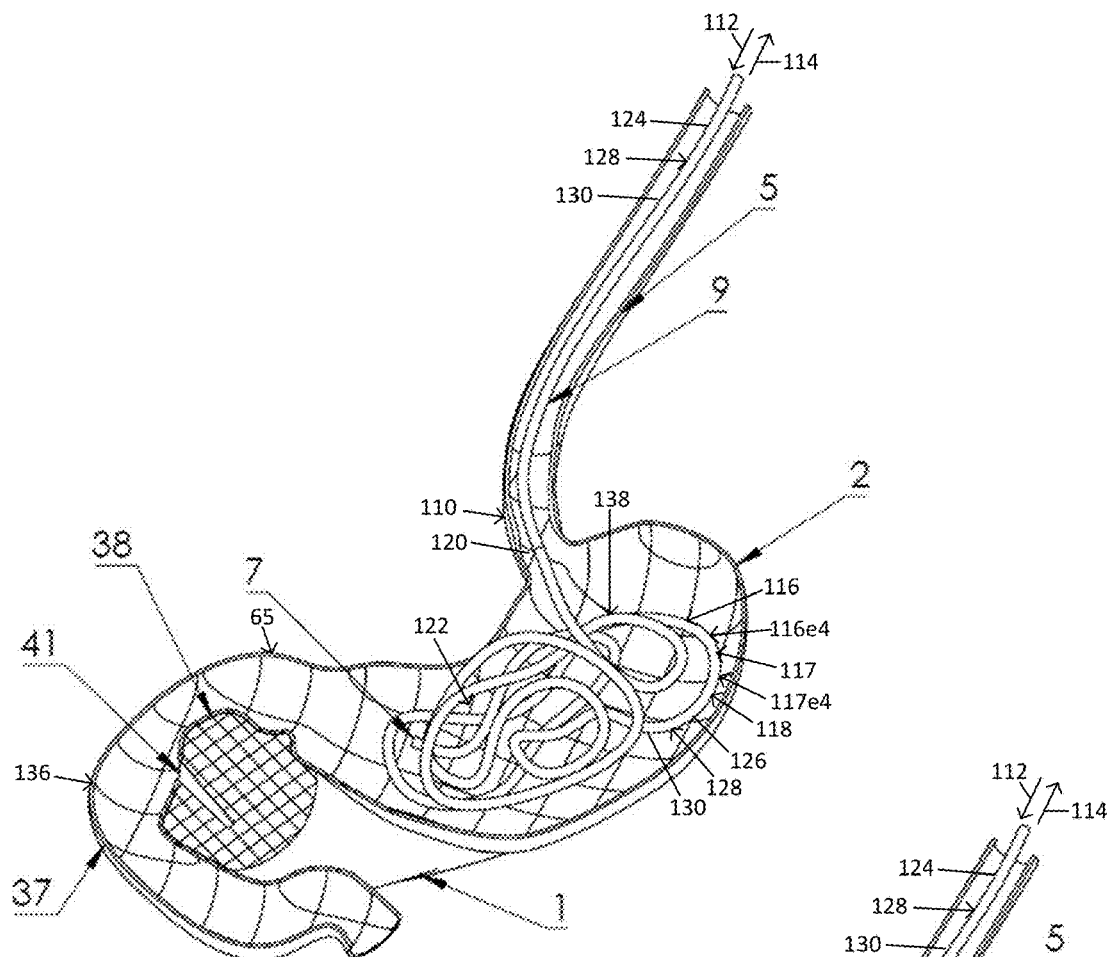
FIG. 51e4
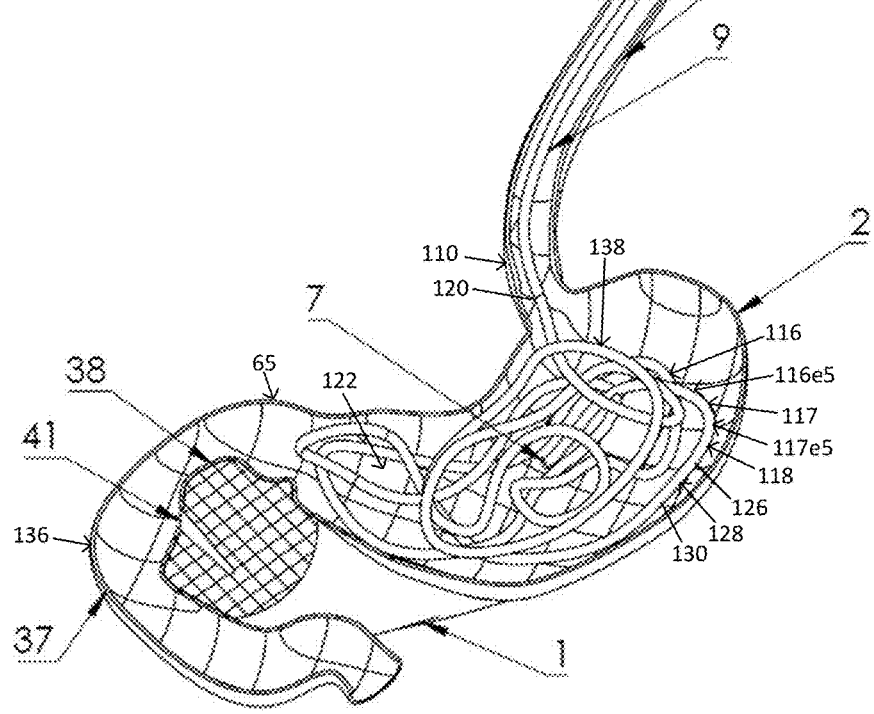
FIG. 51e5

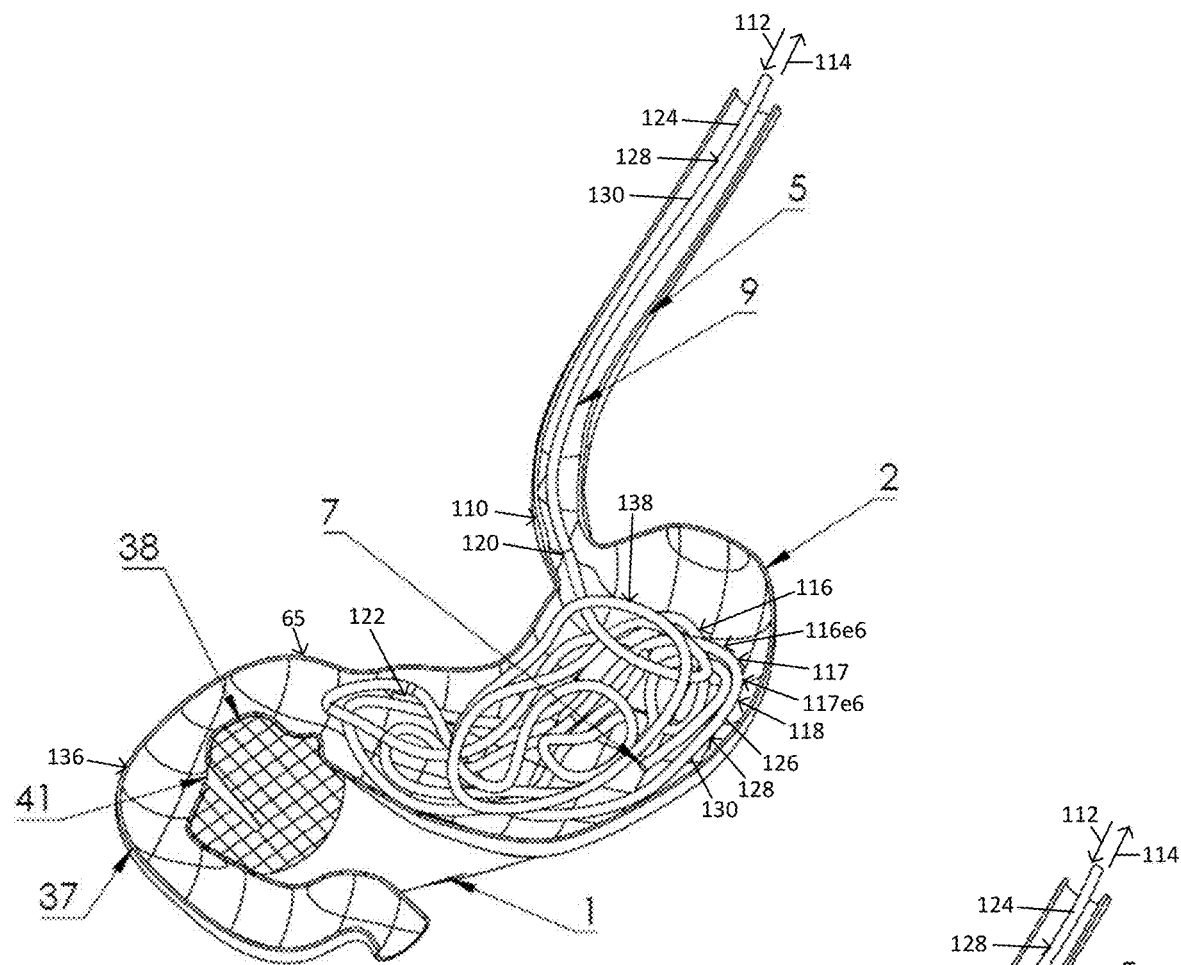
FIG. 51e6
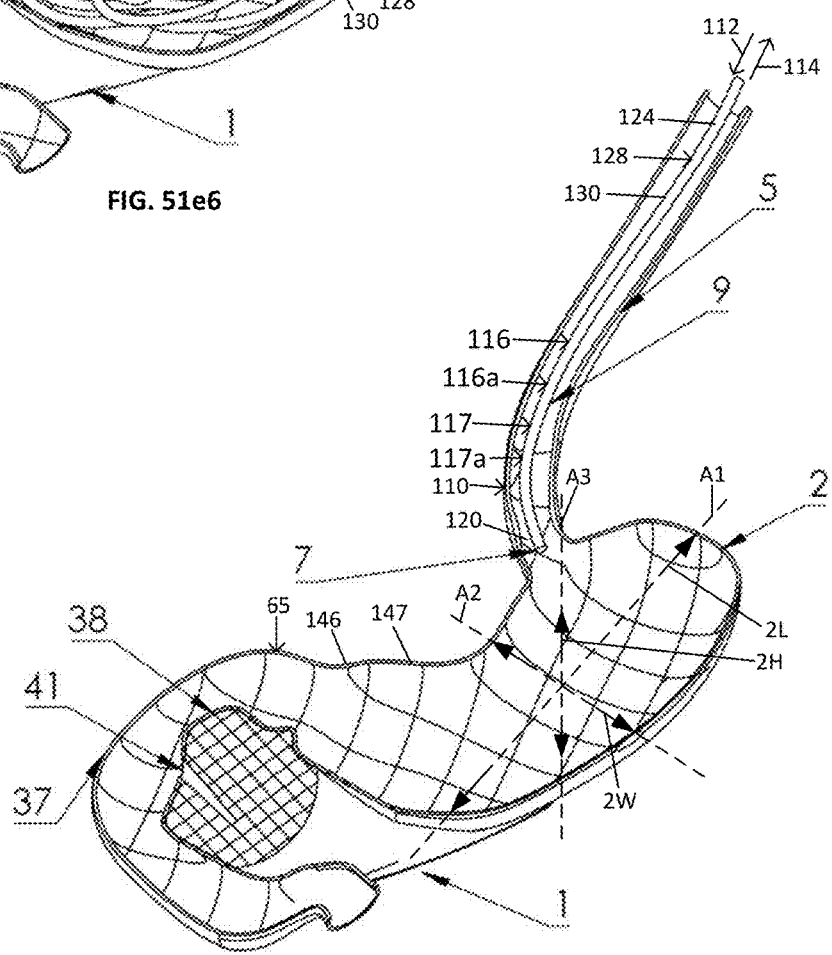
FIG. 52a

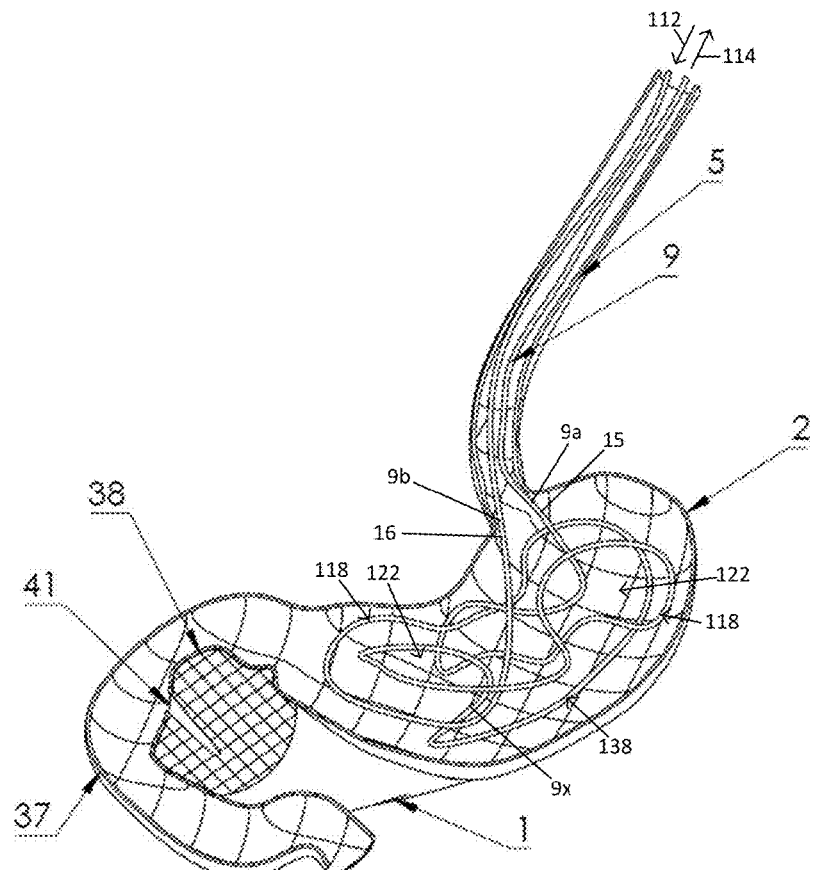
FIG. 53b
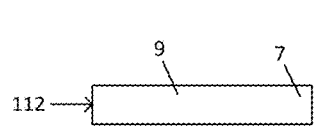 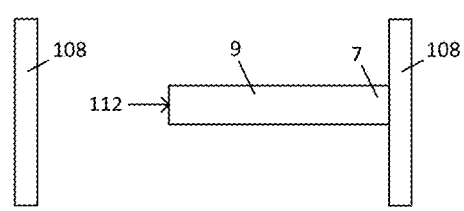
FIG. 54a  FIG. 54b
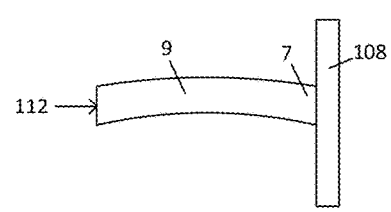
FIG. 54c
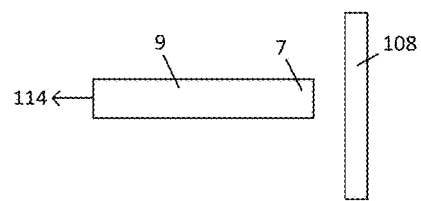
FIG. 54d

APPARATUS AND METHOD FOR LOCALIZED HYPOTHERMIA OF THE PANCREAS

CROSS-REFERENCE TO RELATED APPLICATIONS

This application claims the benefit of priority to U.S. Provisional Application No. 63/363,926 filed Apr. 29, 2022, U.S. Provisional Application No. 63/381,520 filed Oct. 28, 2022, and U.S. Provisional Application No. 63/492,189 filed Mar. 24, 2023, each of which is incorporated herein by reference in its entirety for all purposes.

BACKGROUND

Systems that can provide localized hypothermia treatment for inflammation of the pancreas and/or pancreatitis and use of the systems for treatments for obesity, pancreatic cancer, hypothermia to other bodily structures and organs, and general regulation of body temperature are disclosed. The methods and apparatus disclosed can be used for both hypothermia and hyperthermia, or the combination of both thermal applications during a medical procedure.

Pancreatitis can be classified as acute and/or chronic. Pancreatitis has many etiologies including, but not limited to the following: alcohol induced, gallbladder and/or gallstone related, and/or other causes/idiopathic. In each case, the pancreas can experience inflammation that can impact endocrine and exocrine functions of the patient. Severe pancreatitis occurs in one and four patients with an associated mortality rate of 5%.

Systems that can provide relief of inflammation of the pancreas with a reduction of metabolic activity can benefit patients, physicians, and/or healthcare systems that require ICU hospitalization for patients suffering from pancreatitis.

Localized hypothermia that can be provided with internal and external heat exchangers and warming and/or cooling devices to raise and/or lower body temperature are disclosed.

Systems for localized hypothermia are particularly useful for treating specific bodily injury or inflammation. A common form of localized hypothermia is demonstrated in the placement of ice packs on a sprained ankle or circulating cooling pads following orthopedic procedures.

SUMMARY

Heat therapy systems, devices, and methods are disclosed.

A method of changing a temperature of a stomach via a catheter is disclosed. The catheter can have an inflow channel, an outflow channel, a first temperature sensor, a second temperature sensor, and a proboscis. The proboscis can have the first temperature sensor. When the catheter is in a straight configuration, the proboscis and the first temperature sensor can be distal the inflow channel, the outflow channel, and the second temperature sensor. The method can include positioning the catheter in the stomach. Positioning the catheter in the stomach can include positioning the first temperature sensor and the proboscis closer to the pylorus than the second temperature sensor. The method can include transferring heat to and/or from the stomach via the catheter positioned in the stomach.

A method of changing a temperature of a stomach via a catheter is disclosed. The catheter can have an inflow channel, an outflow channel, a first temperature sensor, a second temperature sensor, and a proboscis. The proboscis can have the first temperature sensor. When the catheter is in a straight configuration, the proboscis and the first temperature sensor can be distal the inflow channel, the outflow channel, and the second temperature sensor. The method can include positioning the catheter in the stomach. Positioning the catheter in the stomach can include positioning the first temperature sensor and the proboscis farther from the pylorus than the second temperature sensor. The method can include transferring heat to and/or from the stomach via the catheter positioned in the stomach.

A method of changing a temperature of a stomach via a catheter is disclosed. The catheter can have an inflow channel, an outflow channel, a first temperature sensor, a second temperature sensor, and a proboscis. The proboscis can have the first temperature sensor. The method can include positioning the catheter in the stomach in a first operational configuration. When the catheter is in the first operational configuration, the first temperature sensor and the second temperature sensor can be in the stomach. The catheter can move from the first operational configuration to a second operational configuration. When the catheter is in the second operational configuration, the first temperature sensor can be in the pylorus or the duodenum and the second temperature sensor can be in the stomach.

Systems for inducing localized hypothermia are described herein. The pancreas can be warmed and/or cooled directly and/or indirectly. For example, the pancreas can be cooled directly by inserting a needle into the pancreas. The needle and/or catheter can be inserted transabdominally and/or laparoscopically. The needle can remove heat directly from the pancreas. The pancreas can be cooled indirectly by cooling organs, fluids (liquid or gas) and/or tissue adjacent to the pancreas. For example, the stomach wall, dermis and/or duodenum adjacent to the pancreas can be cooled, thereby cooling the pancreas.

The heat exchange process can occur external to the patient and/or inside of the patient. The method of heat exchange can include thermoelectric cooling, vapor-compression refrigeration, phase change, Carnot cycle refrigeration, reverse rankine refrigeration, evaporative cooling, thermotunnel cooling, magnetic refrigeration, cyclic refrigeration, non-cyclic refrigeration, sortpion cycle, elastocaloric refrigeration, fridget gate, vortex tube, pulse tube refrigeration and/or thermoacoustics.

A catheter can be introduced orally and/or nasally. The catheter can extend into the stomach, duodenum, intestine, jejunum, and/or the Ampulla of Vater. The catheter can transport a cold fluid to cool the stomach, duodenum, intestine, jejunum, and/or the Ampulla of Vater; thereby, the pancreas can be cooled indirectly. The catheter can have one and/or multiple lumens. The catheter can circulate the fluid. For example, the catheter can have an inflow and/or an outflow lumen; the inflow lumen can transport colder fluid than the outflow lumen. The catheter can have one lumen for transporting the cooling fluid in and/or out of the patient; for example, cold fluid can be introduced, remain in the patient for a period of time and then removed once it has heated up.

The heat transfer fluid can be in direct contact with the patient's organs, tissue and/or fluids; the heat transfer fluid can have indirect contact with the patient's organs, tissue and/or fluids; for example, the heat transfer fluid can be in the catheter, a balloon and/or multiple balloons.

The catheter and/or balloons can be positioned using magnets. Various imaging modalities can be used to visualize the position of the catheter and/or the balloons, including but not limited to: x-ray, CT, MRI and ultrasound. The catheter can include multiple lumens. The catheter can include one or multiple lumens for aspiration, to deliver additional tools, to deliver additional sensors, to deliver medication and/or to deliver nutrients.

An external cooling pad or pads can be placed on the exterior surface of the patient's stomach in close proximity to the patient's pancreas to provide a cooling energy that can work in conjunction with the interior cooling system for hypothermia. These pads can be connected to the same cooling box that drives the interior catheter system and/or an independent component from the cooling box.

The external cooling pad can have a magnetic source that can promote apposition of the catheter and/or balloon to the portion of the stomach immediately adjacent to the pancreas. The external cooling pad can have a magnetic source that facilitates articulation of the distal end of the catheter system for placement of additional balloons within the duodenum of the patient.

The external cooling pad can provide electromagnetic energy to drive or rotate rods within the balloon system to promote circulation of the cooling media within the balloon. The electromagnetic energy can be used to open or close valves for circulation of cooling media between different sections or chambers of the balloon or multiple balloons, or within the catheter system. The electromagnetic energy can be used to open or close valves for the administration of nutrition to the patient. The electromagnetic energy can be used to expand structures or stents within the catheter system to open lumens or deflect and articulate the catheter.

A mechanical structure can be deployed to aid in positioning the catheter and/or the balloon. Components within the catheter can assist the physician or operator in providing greater apposition of the balloon against the inner wall of the stomach to more efficiently transfer cooling energy to the pancreas. Mechanisms for improving deployment and positioning of the catheter system and balloon include torquing or articulating elements within the catheter that allows for manipulation of the distal end of the catheter system by the operator.

The catheter system can have inflatable or deployable protrusions that can force the hypothermia balloon portion of the system against the inner wall of the stomach closest to the pancreas. These protrusions can be inflatable balloon extensions to push the balloon towards the pancreas. Other protrusions can be deployed mechanically by pull wires or coils that can protrude upon rotation by the operator.

The catheter system and balloon can be designed to reduce the amount of distension or mass in the stomach while providing a greater amount of surface area contact with the inner wall of the stomach.

Multiple sensors can be used to monitor the patient and/or the cooling system. Contact and/or non-contact temperature probes can be used to monitor various tissue, organ and/or fluids of the patient. Contact and/or non-contact temperature probes can be used to monitor the temperature of the heat transfer fluid in one and/or multiple positions. A PH sensor can be used to monitor the acidity of the stomach fluid. Sensors can be used to monitor the position of the patient, catheter and/or the balloon(s). Internal pressure sensors within the catheter system can provide a signal to the operator and physician that the patient is experiencing reflux, cramping, or an integrity failure within the catheter system.

The distal end of the catheter system can have an endoscope to provide visualization of the stomach wall. The distal end of the catheter and balloon can have an endoscope to provide visualization of the stomach wall. Visualization source can assist the operator in placing additional balloons within the duodenum.

The catheter can be insulated. An insulated catheter can be more efficient at transporting cold fluid into the patient. An insulated catheter can reduce any unintended cooling to other organs, including, but not limited to the esophagus. The catheter can include material that has a low thermal conductivity. The catheter can be configured such that the cold fluid can be located in the center of the catheter. Air can be circulated outside of the central lumen of the catheter to keep an insulating layer of air between the cooling media and areas of the body to be left untreated.

The outer surface of the catheter can be insulated and covered with a distensible membrane that can be filled with air or warming media. The distensible membrane can inflate to a diameter that is greater than the catheter at the time of insertion. This dimension can be 1 mm, 5 mm, or 10 mm in diameter. The insertion diameter of the catheter system can be reduced to improve patient comfort. Once placed in the body, the insulating membrane can be inflated in a section of the catheter that can be insulated. For example, the insulation membrane can be inflated with air or warming media in the esophagus or nasal pharyngeal region.

The air or warming media for insulation can be dynamic in that once cooled media is introduced into the balloon, non-balloon portions of the system can be isolated with air or warmer media that circulates for active insulation to provide a greater temperature for intended treatment areas of the body.

Insulation can be provided by isolating the cooling media in the hypothermia balloon from the remaining portions of the catheter system. The isolation process can occur with a valved catheter. Air can be introduced within the system once cooling media is infused.

The catheter can have communication ports that can provide the operator a mechanism to administer analgesics to soothe or numb the bodily orifice, esophagus, and stomach. The analgesics can be administered to reduce tissue irritation over the duration of the treatment.

The external surface of the catheter system can be hydrophilically coated to reduce friction for the insertion of the instrument and effects of friction over time while the catheter system is positioned in the body.

Communication ports to the external surface of the balloon can improve the contact of the balloon to the inner wall of the stomach. The communication ports can deliver finite amounts of cooled media directly to the stomach wall.

The catheter system can be designed to enter the duodenum through the pylorus to provide further cooling within the large intestine and in closer anatomical proximity to the pancreatic head.

The distal end of the catheter system can have a spiral configuration to facilitate entry into the duodenum.

The distal end of the catheter system can have a spiral configuration and can be designed to rotate about the central axis of the catheter independently from the proximal portion of the catheter system. This configuration can stabilize the catheter system in the patient's nasopharyngeal section whereas the distal end independently rotates to facilitate entry into the duodenum.

The catheter system can have expandable lumens to reduce the profile of the system for entry.

The catheter system can have expandable lumens in the distal portion of the catheter to facilitate thermal transfer in the desired section for cooling in the patient's anatomy.

For the localized hypothermia procedure itself, the following steps outline the method for performing the treatment on a patient and variations. Once diagnosed with pancreatitis, the patient can be placed into position for the procedure with the catheter supplies and cooling box prepared for use.

System Preparation: The hypothermia catheter system package can be prepared for use as per the instructions for use which can include pre-filling the internal lumen of the system, flushing media through any through-lumens, testing the integrity of the balloon, and coating the outside of the catheter system with analgesic prior to insertion in the patient. The cooling box can be prepared with media such as saline and placed into a cooling cycle or mode. The catheter system can be coupled to the cooling box with system checks by sensors for integrity, flow rate, and other sensors.

Method of Localized Hypothermia of the Pancreas

Connection to the Cooling Box: The connection to the cooling box can be programmed with an identifier or EEPROM to ensure single patient use. The cooling box can have on-screen displays illustrating the system prep procedure, condition of sensors and other real time temperature, fluid pressure, media flow rate, and other values. The cooling box can have software/firmware for the production of various cooling regimes or programs with general or specific hypothermia parameters. The cooling box can be mounted on a bed-side IV pole, stand, or standalone on the floor or table. The cooling box can be a wearable box that can be miniaturized, battery-powered, and fitted to be worn on the patient to allow for portability. The patient can be transported easily from bedside, or mobile on their own while treatment is occurring. The cooling box can be configured to communicate via Bluetooth or Wi-Fi to be controlled remotely by medical professionals.

Insertion of Catheter System into Patient: The catheter system can be placed via nasal, oral, or transgastric routes. The catheter system can be delivered in a low profile state in which the balloon can be sheathed, housed, and/or contained within the distal portions of the catheter system.

Placement of the Catheter in the Stomach: The catheter system can have the flexibility to be delivered to the stomach. Within the catheter, pull wires can articulate the distal end of the catheter for deflection. Inside the lumen of the catheter, braid material or mandrels can provide stiffness for torque to rotate a curved section of the catheter selectively. The mandrel within the catheter can be removed by the operator once placed in the stomach to provide further flexibility or provide a lumen for fluid, media, aspiration, or the injection of nutrients to the patient. The distal end of the catheter can have an echogenic tip or sonographic sensor that facilitates the identification of the distal tip of the catheter with external ultrasound or audio equipment.

Deployment of the Balloon in the Stomach: The balloon on the distal end of the catheter can be unrolled or unsheathed by separating, pulling, or rotating a portion of the catheter to unveil the balloon. The deployment of the balloon can be facilitated by internal stents within the balloon to facilitate a predetermined shape for the balloon.

Filling the Balloon with Media: The catheter system can be coupled to the cooling box to fill the balloon with cooling media. As a precursor step, the balloon can be filled with air to allow the balloon to fully deploy prior to filling with media, or to check and verify the position of the balloon. The cooling box can deliver filtered air, $CO_2$, or other gas, followed by cooling media. The delivery of cooling media can be followed by air to provide an insulation means to the esophagus and upper nasal and oral passageway.

Apposition of the Balloon to the Stomach Wall: The balloon can be situated in the lower stomach through the effects of gravity. Further apposition near the area of the pancreas can be achieved by torquing and articulating the distal end of the catheter system in the stomach. Actuating a pull wire or multiple pull wires within the catheter system can articulate the distal end of the catheter system within a curved shape that forces the balloon to be situated nearer the inner stomach wall. The catheter system can have protrusions that can provide an opposing force to position the balloon against the inner stomach wall nearer to the pancreas. These protrusions can be deployed similar to a stent, basket, or deflecting ribs. The protrusions can be inflatable nubs, cones, or balloons that can push the distal end of the catheter nearer to the inner wall of the stomach. The distal end of the catheter system can have a ferromagnetic material that can engage external magnetic forces to allow the balloon nearer to the pancreas.

Distension of the Balloon: Air, liquid, gas, and media, and combination of these can be used to fill the balloon on the distal end of the catheter. Distension of the balloon can be monitored and measured by pressure and the total volume of air, liquid, gas or media delivered. Distension media can be supplied into the balloon by openings or ports within the catheter that can fluidically communicate with an inner lumen or multiple lumens.

Distension Methods that Reduce Pressure in the Stomach: Cooling media can be supplied and monitored to the balloon in a manner to reduce overall pressure in the stomach to minimize patient discomfort. Pressure sensors in the cooling balloon can record responsive contractions within the stomach acting on the balloon and catheter system. In response to increases in pressure due to forces acting on the catheter system from the stomach, distension media and pressure and or volume of distension media within the balloon can be reduced, or increased, in response to the monitored and recorded forces in the stomach.

Monitoring of Hypothermia Treatment: As the hypothermia treatment is being performed, thermocouples on the catheter system can provide feedback of temperatures in the distension media, in the catheter, at the external surface of the balloon, and multiple external surfaces of the balloon that are in contact with the stomach wall nearer to the pancreas and areas away from the pancreas area. Hypothermia treatment can be monitored by time and checked by the body temperature of the patient. Ongoing real-time body temperature of the patient can be coupled to the cooling box by a wearable thermometer thereby providing a feedback to excessive hypothermia, or adding additional cooling media as appropriate.

Concurrent Procedures Including Endoscopy, Diagnostic Fluid or Content Sampling, Ultrasound and Fluoroscopy, and Drug Delivery during Hypothermia Treatment: The catheter system can allow for an endoscope to be inserted for internal visualization, or can be constructed with an integrated endoscope. The catheter system can have ports that allow for the sampling of fluid or materials in the stomach for diagnostic purposes. The catheter system can be configured with echogenic or radiopaque materials or members that facilitate ultrasound or fluoroscopic detection. Doppler ultrasound can be used to record the flow of distension media in the catheter system and the vasculature of the stomach and area near the pancreas. The catheter system can be configured with ports that allow for the delivery of drugs to the patient. Ports can be located in specific locations in the catheter system to apply medications or analgesics to the nasal, oral, and esophageal passageways, and the stomach.

Ports can be located on the external portions of the balloon to deliver medications and analgesics directly to the inner stomach wall nearer to the pancreas.

Patient Nutrition During Treatment: The catheter system can have a lumen to supply nutrition, such as nutritional media, to the patient. The nutrient delivery can be supplied with external pressure or mechanical force supplied by the medical professional or the cooling box directly. The catheter system can have an expandable lumen that responds and expands to the mechanical force of the supplied nutrition that then allows the nutrition to reach the gastrointestinal tract of the patient. The expandable lumen allows for a minimal insertion and wearing profile to the catheter system that can be expanded upon use in conjunction with patient nutrition.

Confirmation of Hypothermia Treatment: Overall enzymatic activity of the pancreas can be monitored during treatment to demonstrate and monitor procedural effectiveness. Metabolic activity of the pancreas can be monitored via a PET scan. Temperature measurements of the stomach wall and other locations in and external to the catheter system in the patient can provide a determination of the amount of hypothermia treatment.

Continuation or Protocols of Treatment: The duration of hypothermia treatment can be cycled in an on-off fashion, or remain continuous during a procedure. Hypothermia treatment can begin at one cooling temperature, and then profile lower in a stepwise fashion. The stepwise fashion can proceed at one lower temperature setting followed by another after a certain duration of time, or can return to baseline and then back to a lower temperature setting. Protocols of treatment can be pre-programmed within the cooling box, or respond to feedback from temperature sensors in the catheter system or patient body temperature measurements.

Completion of Treatment: Hypothermia treatment can be stopped by completion of known cooling protocol or a patient body temperature measurement reaching a certain predetermined stopping point. The treatment can be stopped by the patient achieving certain level of improvement in symptoms, enzymatic measurements, or metabolic activity.

Removal of the Device from the Patient: Once the treatment is completed, all balloons and external protrusions can have distension media and gas removed, and articulations or stiffeners of the distal end of the catheter can be minimized, to reduce stiffness of the system for removal from the patient.

Local pancreatic hypothermia, without systemic hypothermia, has been shown to reduce severity of acute pancreatitis, induced by different methods in rats.

BRIEF DESCRIPTION OF THE DRAWINGS

The drawings shown and described are exemplary variations and non-limiting. Like reference numerals indicate identical or functionally equivalent features throughout.

FIGS. 5a and 5b illustrate a cross-section of the distal end of additional embodiments of the cooling device with the balloon partially inflated.

FIG. 6 illustrates data from a simulated localized cooling system.

FIG. 7 illustrates a schematic of another embodiment of a thermal therapy system deployed in a patient's digestive system.

FIG. 8 illustrates a cross-section of the distal end of additional embodiments of the cooling device with the balloon partially inflated.

FIG. 9 illustrates a schematic of another embodiment of a thermal therapy system deployed transabdominally.

FIG. 12 illustrates that target temperatures of the pancreas can be achieved within a simulated pancreas (using bovine tissue) using a chilled fluid circulating in a cooling balloon placed inside of the simulated stomach (using bovine stomach tissue) in a body temperature (37C) water bath.

FIG. 14a illustrates a catheter located in the stomach with an elastic balloon in a deflated configuration. FIG. 14b illustrates the catheter located in the stomach with the elastic balloon in an inflated configuration.

FIGS. 15a-15c illustrate the stomach and pancreas in an isometric view with the anterior half removed. FIG. 15a illustrates a catheter located in the stomach and the duodenum with an inelastic gastric balloon in a deflated configuration and a duodenal balloon in a deflated configuration. FIG. 15b illustrates the catheter located in the stomach and the duodenum with the elastic balloon in an inflated configuration and the duodenal balloon in the deflated configuration. FIG. 15c illustrates the catheter located in the stomach and the duodenum with the elastic balloon in an inflated configuration and the duodenal balloon in an inflated configuration.

FIGS. 16a-16c illustrate the stomach and pancreas in an isometric view with the anterior half removed. FIG. 16a illustrates a catheter located in the stomach with 3 inflatable balloons. FIG. 16b illustrates a catheter located in the stomach with 6 inflatable balloons. FIG. 16c illustrates a catheter located in the stomach with multiple inflatable balloons on the anterior and posterior side.

FIG. 17 illustrates the stomach and pancreas in an isometric view with the anterior half removed. FIG. 17 illustrates a catheter extending through the stomach to the duodenum in an unconstrained configuration. The catheter includes catheter barbs and a duodenal device.

FIG. 18 illustrates a catheter residing in the stomach in a spiral configuration.

FIG. 19 illustrates a catheter extending through the stomach through a percutaneous port and/or a port on the stomach wall.

FIG. 20 illustrates a catheter with coils in the stomach and the duodenum.

FIG. 21 illustrates a catheter extending from an introducer.

FIG. 22 illustrates a catheter in the stomach with multiple inflatable balloons.

FIG. 23 illustrates a catheter in the stomach with multiple inflatable lumens and/or balloons.

FIG. 24 illustrates a catheter in the stomach with an intestinal plug in the duodenum.

FIG. 25 illustrates a catheter extending through the stomach, through a pylorus plug and into a pancreatic duct.

FIG. 26 illustrates a cooling device placed on the surface of the pancreas.

FIGS. 27a-27f illustrate various cross-sections of the catheter.

FIGS. 28a-28b illustrate cross-sections of the catheter and balloon in an inflated and a deflated configuration.

FIG. 29 illustrates a side-view of the catheter with multiple break lines.

FIG. 34 illustrates a catheter with the distal end formed into a tapered coil.

FIGS. 35a-35d illustrate a catheter with an inverting membrane connecting an inner and external catheter. FIG. 35a illustrates the catheter proximal to the pylorus; FIG. 35b illustrates a detailed view of the tip of the catheter illustrated in FIG. 35a. FIG. 35c illustrates the catheter entering the pylorus; FIG. 35d illustrates a detailed view of the tip of the catheter illustrated in FIG. 35c.

FIG. 36 illustrates a coiled catheter positioned in the esophagus.

FIG. 39a illustrates a side-view of the proboscis tip and FIG. 39b illustrates a cross-sectional side-view of the proboscis tip.

FIGS. 46a, 46b, 46z2, and 46z3 illustrate the stomach, duodenum, and pancreas in an isometric view with the anterior half removed. FIGS. 46b-46z1 illustrate the stomach in an anterior view with the anterior half of the stomach shown transparent. FIGS. 46a-46o illustrate the catheter being introduced to the stomach and FIGS. 46o-46z3 illustrate the catheter being removed from the stomach.

FIGS. 47a-47i illustrate the stomach, duodenum, and pancreas in an isometric view with the anterior half removed. FIGS. 47a-47e illustrate the catheter being introduced to the stomach and FIGS. 47e-47i illustrate the catheter being removed from the stomach.

FIGS. 48a-48e illustrate the catheter being introduced to the stomach and FIGS. 48e-48i illustrate the catheter being removed from the stomach.

FIGS. 49a-49i illustrate the catheter in the body.

FIGS. 50a-50i illustrate the stomach, duodenum, and pancreas in an isometric view with the anterior half removed. FIGS. 50a-50i illustrate the catheter in the body.

FIGS. 51a-51e6 illustrate the stomach, duodenum, and pancreas in an isometric view with the anterior half removed. FIGS. 51a-51e6 illustrate the catheter in the body.

FIGS. 52a-52d illustrate the stomach, duodenum, and pancreas in an isometric view with the anterior half removed. FIGS. 52a-52d illustrate the catheter in the body.

FIGS. 53a-53b illustrate the stomach, duodenum, and pancreas in an isometric view with the anterior half removed. FIGS. 53a-53b illustrate the catheter in the body.

FIGS. 54a-54d illustrate a variation of a catheter bending and unbending.

DETAILED DESCRIPTION

Figure 1:
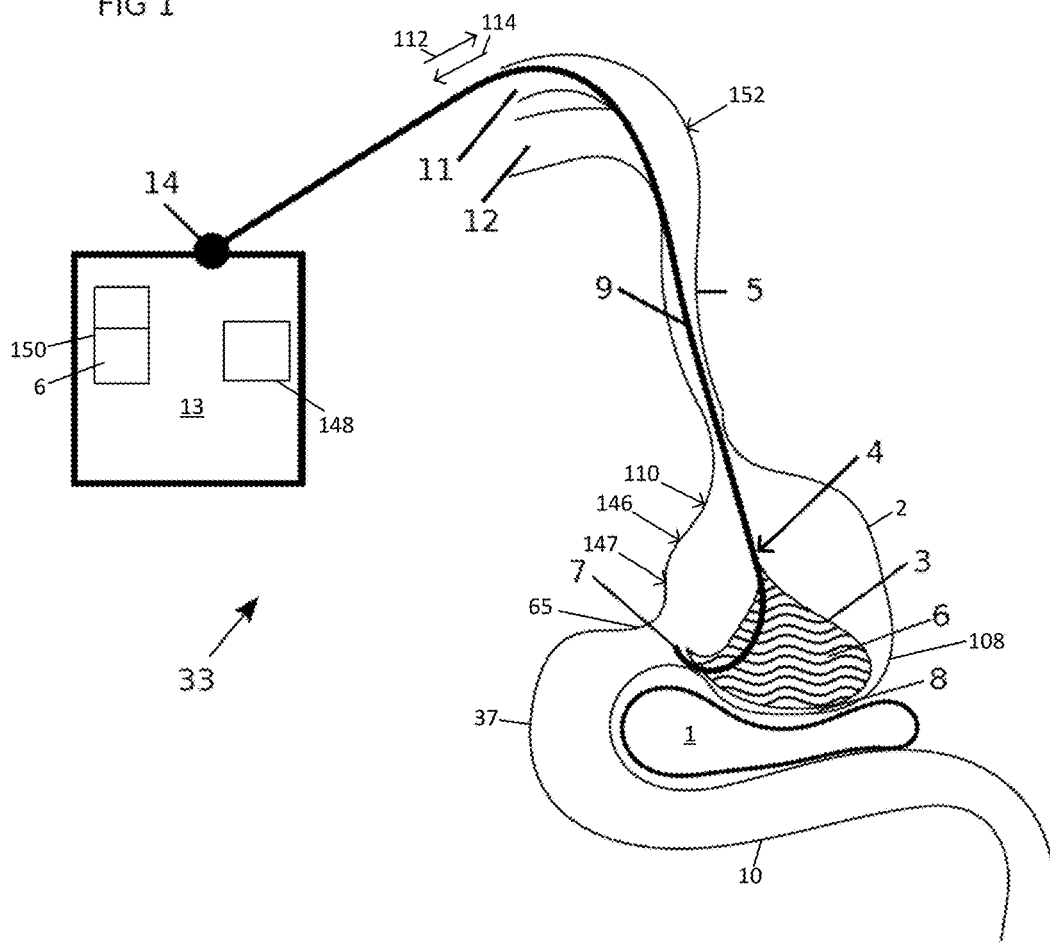
FIG. 1 illustrates a schematic of a thermal therapy system deployed in a patient's digestive system.

FIG. 1 illustrates a variation of a thermal therapy system 33. The thermal therapy system 33 can be, for example, a localized thermal therapy system. The thermal therapy system 33 can be, for example, a heat transfer therapy system. For example, the thermal therapy system 33 can be a warming therapy system and/or a cooling therapy system. For example, the thermal therapy system 33 can deliver thermal therapy (e.g., warming therapy and/or cooling therapy) to a heat transfer target 146. The thermal therapy system 33 can, for example, transfer heat to and/or from the heat transfer target 146. Transferring heat to the heat transfer target 146 can include, for example, increasing a temperature of the heat transfer target 146 and/or warming the heat transfer target 146. Transferring heat from the heat transfer target 146 can include, for example, decreasing a temperature of the heat transfer target 146 and/or cooling the heat transfer target 146. The heat transfer target 146 can include, for example, one or multiple organs. The one or multiple organs can include one or more organs of the gastrointestinal tract 110, one or multiple organs adjacent the gastrointestinal tract 110, or any combination thereof. For example, the heat transfer target 146 can include the esophagus 5, the stomach 2, the pancreas 1, the pylorus 65, the duodenum 37, the jejunum 10, any portion along the gastrointestinal tract 110 caudal the jejunum 10, or any combination thereof.

FIG. 1 illustrates that the thermal therapy system 33 can include a heat transferer 4 and/or a heat exchange system 13. FIG. 1 illustrates that the heat transferer 4 can be connected (e.g., removably connected) to the heat exchange system 13. The heat exchange system 13 can be, for example, an external heat exchange system. The heat transferer 4 can transfer heat to and/or from the heat transfer target 146. The heat transferer 4 can, for example, increase and/or decrease a temperature of the heat transfer target 146. The heat transferer 4 can, for example, warm and/or cool the heat transfer target 146.

FIG. 1 illustrates that the heat transferer 4 can have and/or can be, for example, a catheter 9, a balloon 3, or any combination thereof. For example, the heat transferer 4 include the catheter 9 but not the balloon 3. As another example, the transferer 4 can include the balloon 3 but not the catheter 9. As yet another example, the heat transferer 4 can include the catheter 9 and the balloon 3. As still yet another example, the heat transferer 4 can be the catheter 9. As still yet another example, the heat transferer 4 can be the balloon 3. As still yet another example, the heat transferer 4 can be the catheter 9 and the balloon 3. FIG. 1 illustrates that the catheter 9 and/or the balloon 3 can transfer heat to and/or from the heat transfer target 146. FIG. 1 illustrates that the catheter 9 and/or the balloon 3 can increase and/or decrease a temperature of the heat transfer target 146. FIG. 1 illustrates that the catheter 9 and/or the balloon 3 can warm and/or cool the heat transfer target 146. For example, the balloon 3 can be a warming and/or a cooling balloon and/or the catheter 9 can be a warming and/or a cooling catheter. For example, FIG. 1 illustrates that the thermal therapy system 33 can be a heat exchange catheter system and/or a heat exchange balloon system. For example, the catheter 9 can be a heat exchange catheter and/or the balloon 3 can be a heat exchange balloon.

FIG. 1 illustrates that the heat transferer 4 (e.g., the catheter 9 and/or the balloon 3) can be inserted into and/or withdrawn from a target site 147. For example, FIG. 1 illustrates that the catheter 9 and/or the balloon 3 can be inserted into the target site 147 as shown by arrow 112 and/or that the catheter 9 and/or the balloon 3 can be withdrawn from the target site 147 as shown by arrow 114. The target site 147 can be, for example, one or multiple organs in the body 152. The target site 147 can be, for example, the space and/or cavity inside one or multiple organs in the body 152. For example, the target site 147 can include the esophagus 5, the stomach 2, the pylorus 65, the duodenum 37, the jejunum 10, any portion along the gastrointestinal tract 110 caudal the jejunum 10, or any combination thereof. The target site 147 can be, for example, the location (e.g., desired location) of the catheter 9 and/or the balloon 3 in the body 152 during heat transfer to and/or from the heat transfer target 146, for example, via the catheter 9 and/or the balloon 3. The heat transfer target 146 can be, for example, the targeted heat transfer location. For example, the heat transfer target 146 can be the stomach 2, the pylorus 65, the duodenum 37, and/or the pancreas 1, and the target site 147 can be the stomach 2, the pylorus 65, the duodenum 37, and/or the jejunum 10.

FIG. 1 illustrates that the balloon 3 can be, for example, a gastric balloon. FIG. 1 illustrates that the balloon 3 can be, for example, a lower gastric balloon. FIG. 1 illustrates that the balloon 3 can be positioned in the stomach 2, inflated in the stomach 2, deflated in the stomach 2, or any combination thereof. The balloon 3 can be secured to the catheter 9. The balloon 3 can be, for example, releasably and/or permanently secured to the catheter 9.

The heat transferer 4, the catheter 9, and/or the balloon 3 can be delivered orally and/or nasally, for example, through the nose 11 and/or the mouth 12. For example, FIG. 1 illustrates that the heat transferer 4, the catheter 9, and/or the balloon 3 can be delivered nasally through the nose 11. The heat transferer 4, the catheter 9 and/or the balloon 3 can pass through the esophagus 5 of the patient.

FIG. 1 illustrates that the thermal therapy system 33 can include a pump 148, a fluid 6, and/or a fluid reservoir 150. FIG. 1 illustrates that the heat exchange system 13 can include the pump 148, the fluid 6, and/or the fluid reservoir 150. The pump 148 can be, for example, a recirculating pump. The fluid 6 can be, for example, a heat transfer fluid. The fluid reservoir 150 hold a volume of the fluid 6. The fluid 6 can be pumped and/or out of the catheter 9 and/or the balloon 3 via the pump 148. The fluid 6 can be pumped through the catheter 9 and/or the balloon 3 via the pump 148. For example, FIG. 1 illustrates that the fluid 6 can be circulated and/or recirculated through the catheter 9 and/or the balloon 3 via the pump 148. FIG. 1 illustrates, for example, that the pump 148 can pump the fluid 6 from the fluid reservoir 150 into the catheter 9 and/or the balloon 3, and/or that the pump 148 can pump the fluid 6 from the catheter 9 and/or the balloon 3 into the fluid reservoir 150. FIG. 1 illustrates, for example, that the thermal therapy system 33 can be a closed loop heat exchange system. The balloon 3 can be inflated, for example, by filling the balloon 3 with fluid 6. FIG. 1 illustrates the balloon 3 in an inflated configuration with a portion of the fluid 6 in the balloon 3. The balloon 3 can be deflated, for example, by removing the fluid 6 from the balloon 3.

FIG. 1 illustrates that the balloon 3 can be conformable to the wall 108 of the stomach 2 (also referred to as the stomach wall 108). For example, the balloon 3 can have a high surface area contact with the wall of the stomach 2.

FIG. 1 illustrates that the catheter 9 can have a catheter tip 7. The catheter tip 7 can be, for example, a distal tip of the catheter 9 and/or of the heat transferer 4. The catheter tip 7 can be attached to and/or integrated with the catheter 9. For example, FIG. 1 illustrates that the catheter tip 7 can be integrated with the catheter 9. The heat transferer 4, the catheter 9, the catheter tip 7, and/or the balloon 3 can be positioned adjacent and/or near the pancreas 1. The balloon 3 can be positioned near a gastric pancreas wall 8. The gastric pancreas wall 8 can be, for example, a portion of the stomach wall 108 that is adjacent, opposing, and/or near the pancreas 1. The fluid 6 can raise and/or lower the temperature of the gastric pancreas wall 8 and/or the pancreas 1. The fluid 6 can transfer heat to and/or withdraw heat from the pancreas 1 and/or the gastric pancreas wall 8.

The fluid 6 can be, for example, a liquid, a gas, a plasma, and/or a solid. The fluid 6 can be, for example, water, saline, oil, fat, synthetic, and/or organic.

The heat transferer 4, the fluid 6, the balloon 3 and/or the catheter 9 can be sterile, clean, unclean, and/or unsterile. The heat transferer 4, the catheter 9, and/or the balloon 3 can be single-use, reusable, cleanable, re-cleanable, sterilizable, and/or re-sterilizable.

Nutrients, medications, sensors, devices and/or tools can be delivered through the heat transferer 4, the catheter 9, and/or the balloon 3. For example, nutrients, medications, sensors, devices and/or tools can exit from the catheter tip 7. The catheter tip 7 can aspirate the stomach 2. Nutrients, medications, sensors, devices, and/or tools can be delivered to the duodenum 37 and/or the jejunum 10. FIG. 1 illustrates that the catheter 9, the balloon 3, and/or the heat transferer 4 can pass through the nose 11. The catheter 9, the balloon 3, and/or the heat transferer 4 can pass through the mouth 12. The catheter 9, the balloon 3, and/or the heat transferer 4 can be connected to (e.g., removably connected to) the heat exchange system 13. The heat exchange system 13 can include, for example, a computer, a user interface, a controller, a control system, the pump 148, and/or a warming and/or cooling system. The heat exchange system 13 can cool and/or remove heat from the fluid 6, the heat exchange system 13 can warm and/or transfer heat to the fluid 6, and/or the heat exchange system 13 can cool and/or remove heat from the fluid 6 and can warm and/or transfer heat to the fluid 6. The catheter 9, the balloon 3, and/or the heat transferer 4 can be connected to (e.g., removably connected to) the cooling system 13 at a connector 14. For example, FIG. 1 illustrates that the proximal end of the catheter 9 can be removably connected to the connector 14. The connector 14 can provide a fluid, optical, and/or electrical coupling between the cooling system 13 and the heat transferer 4, the catheter 9, and/or the balloon 3.

The catheter 9 can be, for example, a tube having zero, one, or multiple lumens. For example, the catheter 9 can have 0-10 or more lumens, including every 1 lumen increment within this range (e.g., 0 lumens, 1 lumen, 2 lumens, 3 lumens, 4 lumens, 5 lumens, 10 lumens). FIGS. 2a-2d illustrate that the catheter 9 can have various cross-sections. The cross-section of the catheter 9 can be constant and/or can vary along the length of the catheter 9. FIGS. 2a-2d illustrate that the lumens can have various cross-sections. The cross-sections of the lumens can be constant and/or can vary along the length of the catheter 9. FIGS. 2a-2d illustrate that the catheter 9 and/or the heat transferer 9 can have a lumen 15, a lumen 16, a lumen 17, and/or a lumen 18 (also referred to as a first lumen 15, a second lumen 16, a third lumen 17, and/or a fourth lumen 18, respectively). FIGS. 2a-2d illustrate that the catheter 9 and/or the heat transferer 4 can have any combination of the first lumen 15, the second lumen 16, the third lumen 17, and/or the fourth lumen 18. The lumens 15, 16, 17, and/or 18 can be heat transfer lumens and/or accessory lumens. For example, the lumens 15 and 16 can be heat transfer lumens and the lumens 17 and 18 can be accessory lumens. For example, the lumen 15 can be a first heat transfer lumen, the lumen 16 can be a second heat transfer lumen, the lumen 17 can be a first accessory lumen, and the lumen 18 can be a second accessory lumen. For example, the lumen 15 can be an inflow lumen and the lumen 16 can be an outflow lumen.

Figure 2A:
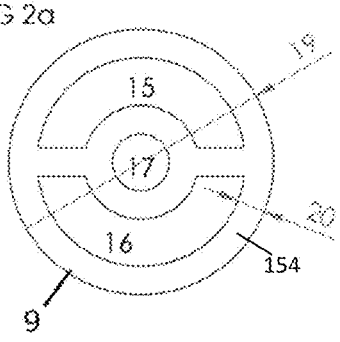
FIGS. 2a-2d illustrate different cross-sections of a catheter.
Figure 2B:
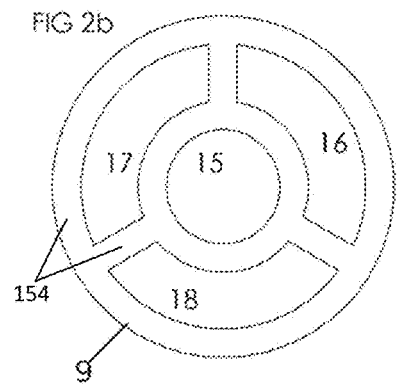
Figure 2C:
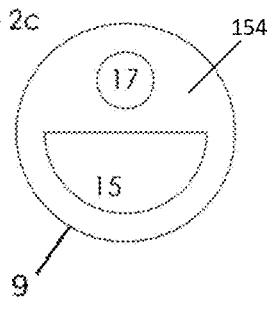

The first lumen 15 and/or the second lumen 16 can transport the fluid 6. For example, the fluid 6 can be transported between the balloon 3 and the heat exchange system 13 through the first lumen 15 and the second lumen 16 in the catheter 9. The fluid 6 can circulate through the catheter 9 and/or the heat transferer 4 in a constant direction; for example, the fluid 6 can flow distally through the first lumen 15 and proximally through the second lumen 16 or vice versa. The fluid 6 can be at different temperatures in the first lumen 15 and/or the second heat transfer lumen 16. For example, FIGS. 2a-2c illustrate that the fluid 6 traveling from the heat exchange system 13 (e.g., from the fluid reservoir 150) to the balloon 3 can travel in the first lumen 15 and can return in the second lumen 16, thereby reducing heat transfer from other portions of the body, such as the esophagus 5. The fluid 6 can flow both proximally and distally through the first lumen 15 and/or the second lumen 16. For example, the fluid 6 can flow distally through the first lumen 15 to inflate the balloon 3, remain in the balloon 3 for a period of time, and then flow proximally through the first lumen 15. The third lumen 17 and/or the fourth lumen 18 can, for example, transport nutrients, medications, sensors, devices and/or tools. The third lumen 17 and/or the fourth lumen 18 can aspirate the stomach 2, the duodenum 37, and/or the jejunum 10. A thickness 20 of a catheter wall 154 can vary at different cross-sections of the catheter 9 and/or within the same cross-section of the catheter 9. The catheter 9 can have a catheter outer diameter 19. The catheter outer diameter 19 can be constant and/or vary along the length of the catheter 9. The cross-section of the catheter 9 can be, for example, circular, square, oval, triangular and/or other geometric shapes. The catheter outer diameter 19 can be continuous and/or non-continuous. The catheter outer diameter 19 can have bumps, divots, grooves, splines and/or ridges.

Figure 3:
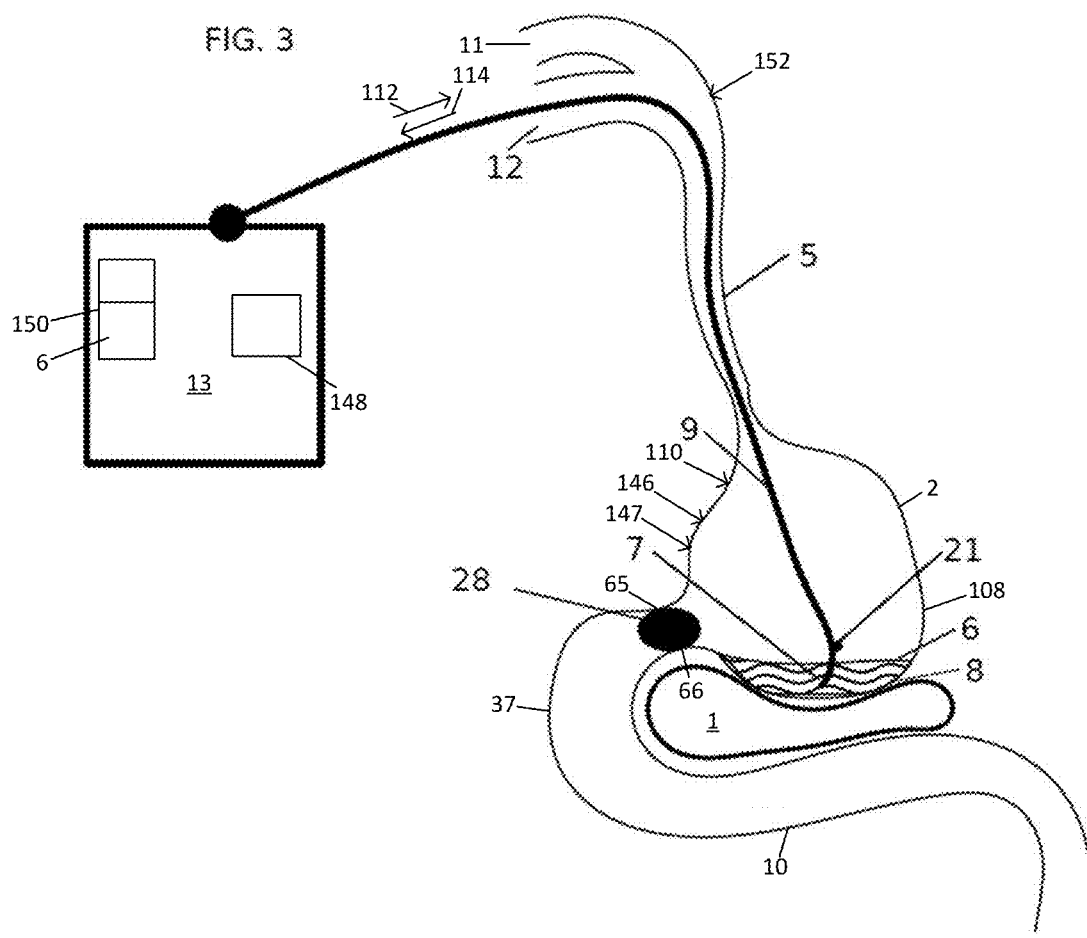
FIG. 3 illustrates a schematic of another embodiment of a thermal therapy system deployed in a patient's digestive system.

FIG. 3 illustrates that the heat transferer 4, the catheter 9, and/or the plug 28 can be delivered orally through the mouth 12. FIG. 3 illustrates that the fluid 6 can be in direct contact with the wall of the stomach 2 and/or the gastric pancreas wall 8. For example, the fluid 6 can be transported through the first lumen 15 and/or the second lumen 16 to the stomach 2. Depending on the orientation of the patient, gravity alone can force the fluid 6 to be adjacent to the gastric pancreas wall 8. The fluid 6 can be naturally occurring fluid present in the stomach 2. For example, the fluid 6 can be gastric acid, gastric juice, stomach acid, blood, and/or abdominal fluid. The fluid 6 can be, for example, compressed gas and/or phase change material. For example, the fluid 6 can be delivered through the catheter 9 in a liquid form and then convert to a gas when it exits the catheter tip 7. When converting from a liquid to a gas, the fluid 6 can absorb energy (e.g., a significant amount of energy), thereby reducing the temperature of the stomach 2, the gastric pancreas wall 8, the pancreas 1, the duodenum 37, and/or the jejunum 10. The catheter tip 7 can be in the stomach 2, the duodenum 37, the jejunum 10, and/or the pancreas 1. The fluid 6 can be, for example, an alcohol, nitrogen, carbon dioxide, a refrigerant (e.g., such as Freon, CFC, HFC, R22, R-290, R-600a, R-717, R-1234, R-744, R-32, R-134a and/or R-410a). The fluid 6 can be stored and/or transported in the catheter 9 at a pressure higher than ambient pressure. The catheter 9 can transfer heat to and/or from the stomach 2, the gastric pancreas wall 8, the pancreas 1, the duodenum 37, and/or the jejunum 10 via a thermoelectric process. For example, the method of heat exchange can include thermoelectric cooling, vapor-compression refrigeration, phase change, carnot cycle refrigeration, reverse rankine refrigeration, evaporative cooling, thermotunnel cooling, magnetic refrigeration, cyclic refrigeration, non-cyclic refrigeration, sortpion cycle, elastocaloric refrigeration, fridget gate, vortex tube, pulse tube refrigeration, thermoacoustics, or any combination thereof. FIG. 3 illustrates that an intestinal plug 28 can be deployed in the target site 147. The intestinal plug 28 can be secured at or near the distal terminal end of the catheter 9 and/or can be disengageable from the catheter 9. The intestinal plug 28 can be delivered through the catheter 9. For example, the intestinal plug 28 can be delivered through the third lumen 17 and/or the fourth lumen 18. The intestinal plug 28 can form an outflow blockage at the interface of stomach 2, the duodenum 37, the jejunum 10, a pyloric sphincter 66 and/or the intestine. The intestinal plug 28 can block fluid from traveling exiting the stomach 2. The intestinal plug 28 can be bioabsorbable. A coating can be delivered to the stomach 2 to alter the rate of absorption and/or adsorption of fluid through the stomach wall 108 and/or the gastric pancreas wall 8. The coating can absorb and/or degrade at a predetermined rate.

The heat transferer 4, catheter 9, the balloon 3, the catheter tip 7, and/or any components passing through the catheter 9 can include zero, one, or multiple sensors 21 (also referred to as the sensor 21 and the sensors 21), for example, 0-10 or more sensors 21, including every 1 sensor increment within this range (e.g., 0 sensors, 1 sensors, 2 sensors, 3 sensors, 10 sensors). The sensors 21 can monitor, for example, temperature, energy, PH, pressure, motion, gravity, orientation, position, electromagnetic waves, magnetism, light, contact, and/or flow rate. The sensors 21 can monitor, for example, the approximate total heat transfer and/or the heat transfer rate from the patient (e.g., the body 152) to the heat transferer 4, the catheter 9, and/or the balloon 3). For example, one or multiple sensors 21 can monitor the temperature of the fluid 6 entering and exiting from the catheter 9, the heat transferer 4, the heat exchange system 13, and/or the balloon 3. The sensors 21 can be connected to the heat exchange system 13. For example, a sensor 21 can be placed in the patient bladder, mouth, nose, skin, dermis, pancreas, jejunum, esophagus, stomach, and/or any other organ, tissue and/or patient fluid. The sensor 21 can monitor the patient for localized and/or generalized hypothermia and/or normathermia. The sensor 21 can monitor the stomach fluid contents, including, but not limited to the stomach fluid acidity.

The sensor 21 can provide an alert to the patient, physicians, nurses and/or other staff. The sensor 21 can determine the orientation of the patient, the fluid 6, the balloon 3, the catheter 9, the heat transferer 4, and/or the catheter tip 7. The sensor 21 can determine if the patient is in an ideal or non-ideal position for efficient localized hypothermia of the pancreas 1. For example, example, the sensor 21 can determine if the balloon 3, the fluid 6 and/or the catheter tip 7 are adjacent to the gastric pancreas wall 8. The patient can move or be moved to improve patient comfort and/or to prevent sores (e.g., pressure ulcers). The patient can move and/or be moved at regular intervals. The heat exchange system 13 can provide manual and/or automatic feedback based on the sensors 21. For example, if the pressure is out of range and/or the patient is not in an ideal therapeutic position, then the balloon 3 can be automatically deflated.

The balloon 3 can be periodically adjusted, moved, inflated and/or deflated. For example, to help prevent pressure ulcers, the balloon 3 can be deflated every 5 minutes, 10 minutes, 15 minutes, 30 minutes, 60 minutes, 90 minutes and/or 120 minutes. The frequency and duration of the inflation/deflation of the balloon 3 can be manually and/or automatically controlled by the heat exchange system 13.

Figure 4A:
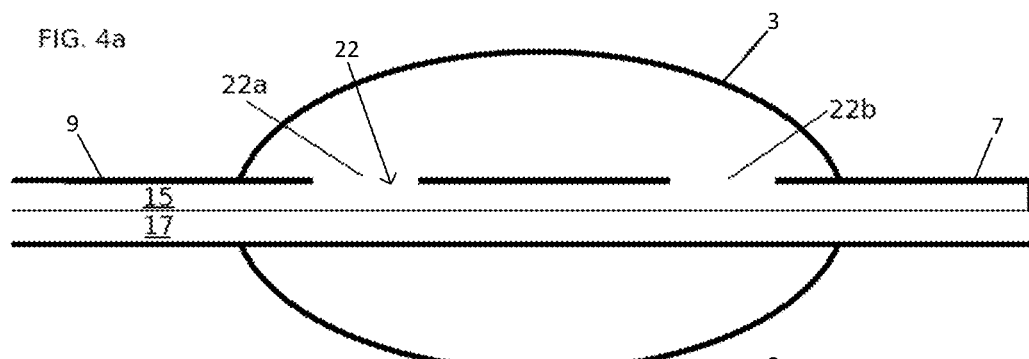
FIGS. 4a and 4b illustrate a cross-section of the distal end of the cooling device with the balloon partially inflated.

FIG. 4a illustrates that the balloon 3 can fluidically communicate with the first lumen 15 through a balloon port 22. The heat transferer 4 and/or the catheter 9 can have multiple balloon ports 22. The multiple balloon ports 22 can allow for improved flow of the fluid 6. For example, multiple balloon ports 22 can provide redundancy, in case one of the balloon ports 22 becomes occluded. For example, multiple balloon ports 22 can provide redundancy, in case one of the balloon ports 22 is occluded.

Figure 4B:
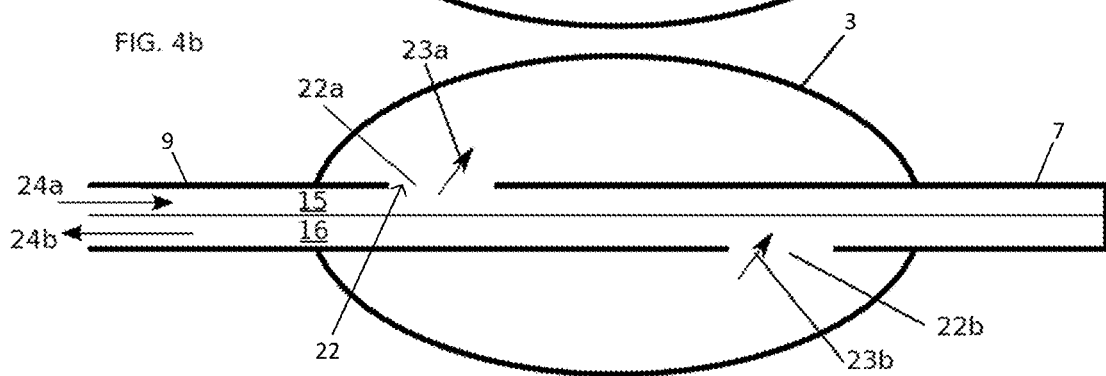

FIG. 4b illustrates that the balloon 3 can fluidically communicate with the first lumen 15 and/or the second lumen 16 through the balloon ports 22. For example the fluid 6 can travel distally from the heat exchange system 13 in a lumen flow direction 24a, the fluid 6 can exit the first lumen 15 through the balloon port 22a in a balloon port flow direction 23a, the fluid 6 can circulate in the balloon 3, the fluid 6 can enter the second lumen 16 through the balloon port 22b in the balloon port flow direction 23b, and the fluid 6 can travel proximally toward the heat exchange system 13 in the lumen flow direction 24b. The fluid 6 can be warmed and/or cooled in the heat exchange system 13 and then travel distally toward the balloon 3.

The balloon 3 can have one or multiple fluids. For example, FIGS. 5a-5b illustrate that the balloon 3 can be filled with the fluid 6 (e.g., a heat transfer fluid) and/or an insulating fluid 25. The insulating fluid 25 can have a lower thermal conductivity than the fluid 6. The insulating fluid 25 can be, for example, a gas, such as air, oxygen and/or nitrogen. The fluid 6 and/or the insulating fluid 25 can travel through the first lumen 15 and/or the second lumen 16. The density of the fluid 6 can be more, less and/or equal to the density of the insulating fluid 25. For example, the fluid 6 can rest on the bottom of the balloon 3 because of gravity. The bottom of the balloon 3 can be adjacent to the gastric pancreas wall 8. The volume of the balloon 3 can be equal to the volume of the insulating fluid 25 and/or the fluid 6 contained within the balloon 3. The heat transfer through the balloon 3 can primarily occur on surfaces in contact with the fluid 6. The configuration illustrated in FIGS. 5a-5b can allow the volume and/or position of the balloon to be adjusted independently of the thermal transfer characteristics and/or the thermal transfer surface of the balloon 3. For example, the balloon 3 can be securely positioned in the stomach 2 and/or can contact multiple surfaces of the stomach 2 while providing localized warming and/or cooling to a small portion of the stomach 2.

FIG. 5a illustrates that the balloon 3 can have fluidically separated compartments or volumes (e.g., a first compartment can receive the insulating fluid 25, and a second compartment can receive the fluid 6), and/or the heat transferer 4 (e.g., the catheter 9) can have one or more balloons 3 (e.g., which can receive the fluid 6 and/or the insulating fluid 25) and one or more insulating balloons (e.g., which can receive the insulating fluid) adjacent to the balloons 3.

FIG. 5b illustrates that an insulating gastric balloon 26 can be inside and/or outside of the balloon 3. The insulating balloon 26 can be in fluid communication with the first lumen 15 via the balloon port 22a. The balloon 3 can be in fluid communication with the second lumen 16 via the balloon port 22b. The insulating balloon 26 can be filled with the insulating fluid 25.

The heat transfer rate of the heat transferer 4, the catheter 9, and/or the balloon 3 can be controlled, for example, using various methods. The thermal conductivity of the fluid 6 can be adjusted. The volume of the fluid 6, the volume of the balloon 3, and/or the portion of the balloon 3 in contact with the gastric pancreas wall 8 can be adjusted. The temperature of the fluid 6 exiting the heat exchange system 13 can be adjusted. The flow rate of the fluid 6 traveling through the catheter 9, the heat transferer 4, and/or the balloon 3 can be adjusted.

FIG. 6 illustrates that the pancreas temperature can be reduced by periodically pulsing the fluid 6 proximally and distally through the catheter 9. The fluid 6 can be warmed and/or cooled by the heat exchange system 13. The cold fluid 6 can travel through the catheter 9 and/or inflate the balloon 3. The cold fluid 6 can increase in temperature as it removes energy from the gastric pancreas wall 8 and/or the pancreas 1. The fluid 6 can be removed from the balloon 3 and/or the stomach 2 periodically. The frequency of cycling the fluid 6 can be based on time, temperature and/or other parameters. With every cycle, the temperature of the pancreas 1 can decrease until a steady-state equilibrium is reached.

FIG. 7 illustrates that the catheter 9 and/or the heat transferer 4 can have or be attached to a gastric positioning mechanism 27. The gastric positioning mechanism 27 can be a mechanical structure. The gastric positioning mechanism 27 can be deployed alongside a cooling membrane and/or the balloon 3. The gastric positioning mechanism 27 can ensure that the catheter 9, the catheter tip 7 and/or the balloon 3 are properly positioned relative to the gastric pancreas wall 8. The gastric positioning mechanism 27 can be a soft stent, a spiral, a balloon, and/or a mesh. The gastric positioning mechanism 27 can be delivered with a small outside diameter and then expanded when in the stomach 2. The gastric positioning mechanism 27 can be a bioabsorbable and/or biodegradable material. The gastric positioning mechanism 27 can brace against the cardia, fundus, corpus of the stomach, pyloric atrium, pyloric canal, or any combination thereof. The catheter 9, the heat transferer 4, the catheter tip 7, the balloon 3 and/or the insulating gastric balloon 26 can include a marker 29 and/or multiple markers 29. The marker 29 can aid visualization via ultrasound, CT, X-RAY, MRI and/or other imaging modalities. The marker 29 can be magnetic. For example, sensor 21 can determine the absolute and/or relative position of the marker 29. The marker 29 can allow an operator to adjust the position of catheter 9, the heat transferer 4, the catheter tip 7, the balloon 3, and/or the insulating gastric balloon 26 via an external magnet and/or magnetic field. The heat exchange system 13, the catheter 9, the heat transferer 4, the catheter tip 7, the balloon 3, and/or the insulating gastric balloon 26 can have a relief valve 30. The relief valve 30 can provide a pressure relief mechanism for the first lumen 15 and/or the second lumen 16. If the pressure in the balloon 3 reaches above a threshold, the excess fluid can exit out of the relief valve 30. For example, the fluid 6 can exit the relief valve 30 if the stomach 2 contracts and compresses the balloon 3 (e.g., this can inhibit and/or prevent damage to the heat transferer 4, the catheter 9, and/or the patient). The set point for the relief valve 30 can be fixed and/or adjustable. The relief valve 30 can be controlled by the heat exchange system 13.

FIG. 8 illustrates that the heat transferer 4 and/or the catheter 9 can have one or multiple insulating ports 31. The insulating port 31 can allow the insulating fluid 25 to pass along the outside of the catheter 9. The insulating fluid 25 can be warm and/or room temperature. The insulating fluid 25 can be in contact with the stomach 2, the esophagus 5, the mouth 12, the nose 11, and/or other patient tissue. The insulating ports 31 can be at various positions along the catheter 9. A balloon can be positioned over the catheter 9 to have the insulating fluid 25. The outside diameter 19 of the heat transferer 4 and/or the catheter 9 can have an insulating material, including but not limited to, aerogel, air, foam, rubber, gas, vacuum, wood, and/or polymers. The insulating fluid 25 and the fluid 6 can travel through the first lumen and/or the second lumen 16. For example, the fluid 6 (e.g., wamr and/or cold fluid 6) can be delivered distally to fill the balloon 3 through the first lumen 15, then the insulating fluid 25 can be delivered through the first lumen 15 to remove the cold fluid 6 from other sections of the catheter 9 (e.g., thereby reducing heat transfer to other organs, such as the esophagus 5). An external or internal warming system (e.g., the external pad 32) can be applied to the patient. For example, blankets can be placed over the blanket to prevent generalized hypothermia.

FIG. 9 illustrates that the heat transferer 4 and/or the catheter 9 can be delivered transabdominally and/or laparoscopically. The catheter tip 7 can be inserted directly into the pancreas 1. The fluid 6 can be delivered directly to the pancreas 1, the peritoneal cavity and/or other tissue. A compressed gas can be delivered to the pancreas 1 and can cool the pancreas 1 as it evaporates. FIG. 9 illustrates that the thermal therapy system 33 can include an external pad 32. FIG. 9 illustrates that the external pad 32 can be positioned on the patient. One or multiple external pads 32 can be positioned on the patient. The external pad 32 can include the sensors 21. The external pad 32 can provide heating and/or cooling of the patient. The external pad 32 can have magnets and/or imaging to help position the heat transferer 4.

Figure 10:
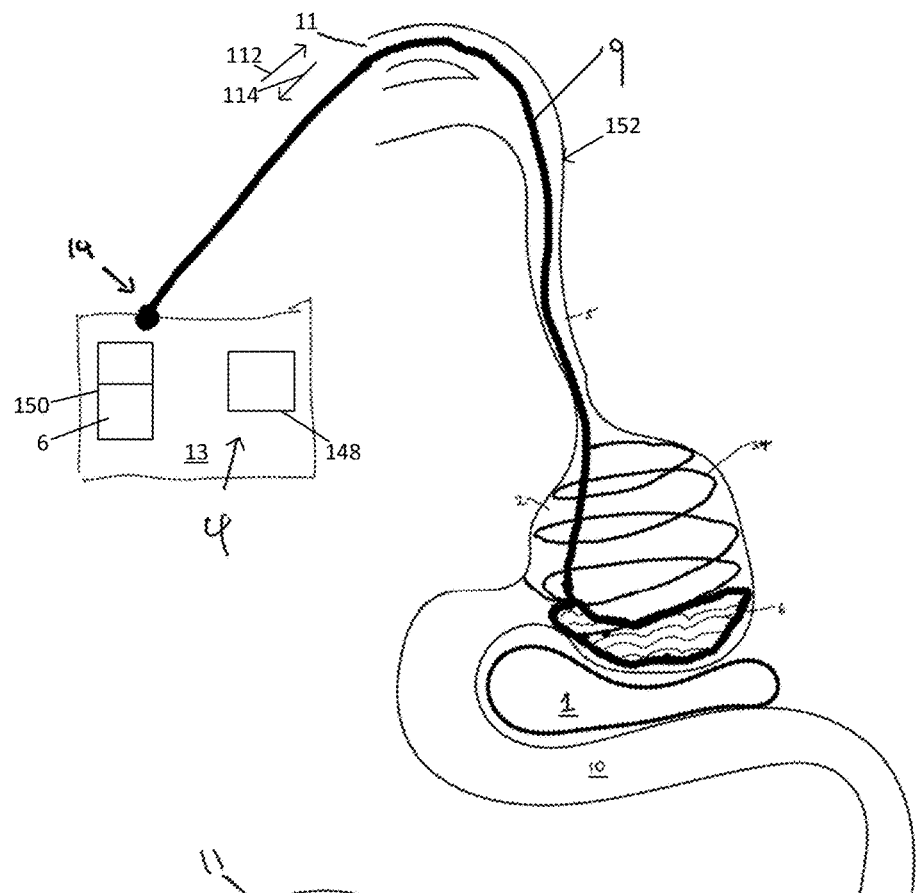
FIG. 10 illustrates a mechanical structure that can position and/or fix the cooling balloon at the stomach wall adjacent to the pancreas

FIG. 10 illustrates that the gastric positioning mechanism can be or can have a fixation mechanism 34 that can position and/or fix the heat transferer 4 and/or the catheter 9 in the stomach 2. The fixation mechanism 34 can be a mechanical structure, such as a resilient coil. The fixation mechanism 34 can position and/or fix the balloon 3 at the gastric pancreas wall 8. The fixation mechanism 34 can brace against the cardia, fundus, corpus, pyloric atrium, pyloric canal, or any combination thereof.

Figure 11:
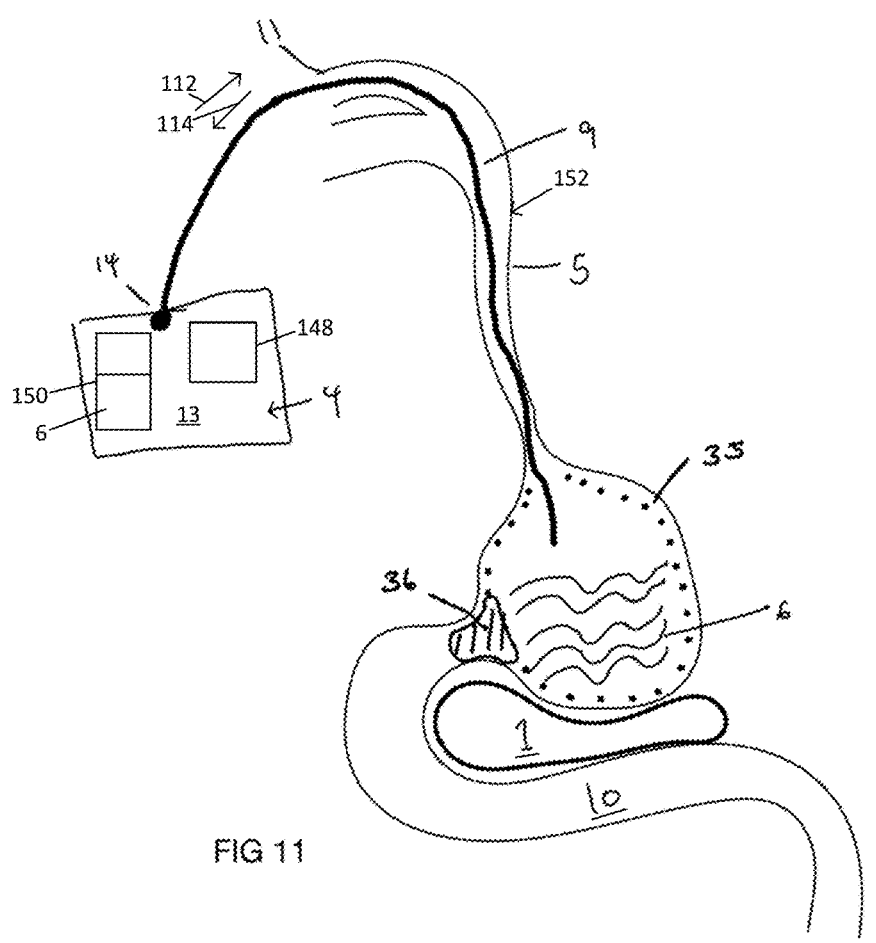
FIG. 11 illustrates a pyloric plug in place to prevent cooling fluid from draining into duodenum and illustrates an impermeable and/or semi-permeable membrane and/or coating deposited on the stomach wall that can prevent and/or slow fluid absorption into the stomach wall.

FIG. 11 illustrates that an impermeable membrane 35 can be deployed in the stomach 2. The impermeable membrane 35 can be a permeable, semi-permeable and/or impermeable membrane and/or coating. The impermeable membrane 35 can be dissolvable and/or resorbable. A pylorus plug 36 can be deposited in the stomach 2. The pylorus plug 36 can be positioned to prevent cooling fluid from draining into the duodenum and/or the jejunum 10. The impermeable membrane 35 can prevent and/or slow fluid absorption into the wall of the stomach 2.

FIG. 12 illustrates that target temperatures of the pancreas can be achieved within a simulated pancreas (using bovine tissue) using a chilled fluid circulating in a cooling balloon placed inside of the simulated stomach (using bovine stomach tissue) in a body temperature (37C) water bath.

Figure 13A:
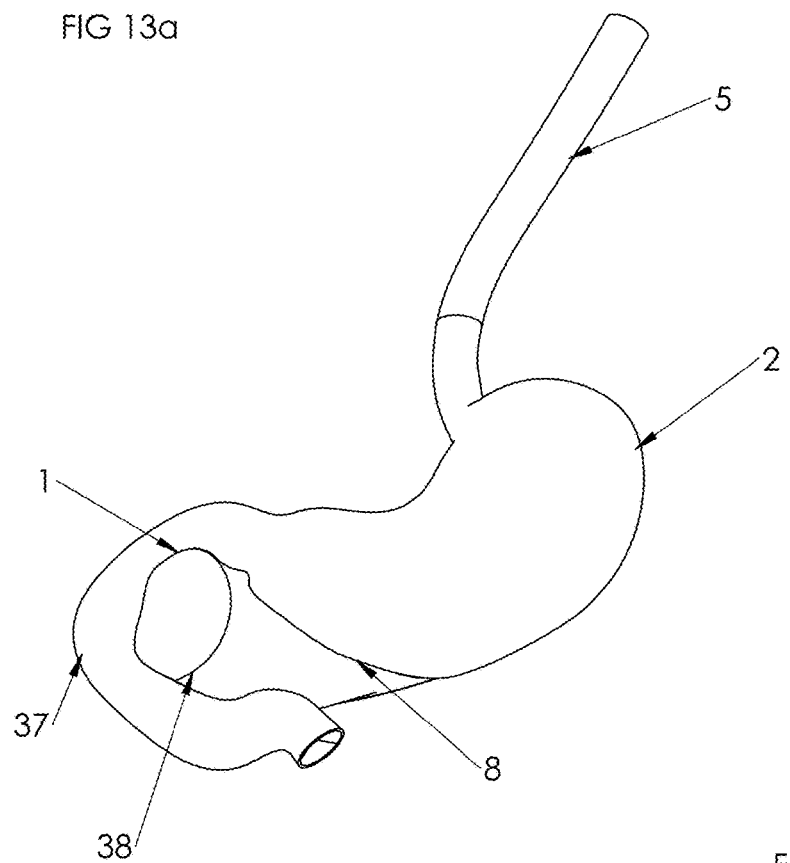
FIGS. 13a and 13b illustrate the stomach and pancreas in two different isometric views.
Figure 13B:
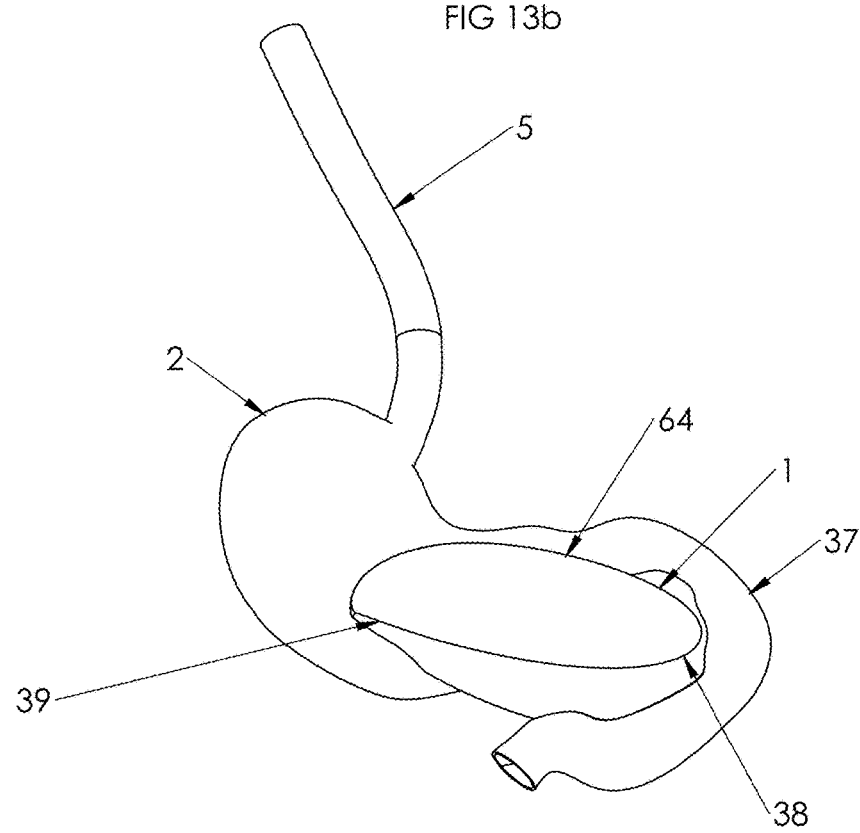

FIGS. 13a and 13b illustrate that the esophagus 5 can extend to the stomach 2, followed by a pylorus 65 and then to a duodenum 37. The pancreas 1 can be in direct and/or indirect contact with the stomach 2 and/or the duodenum 37. The pancreas 1 can be divided into different regions including, but not limited to, a pancreas head 38, a pancreas body 64, and/or a pancreas tail 39. The pancreas tail 39 can have direct and/or indirect contact with the stomach 2. The pancreas head 38 can have direct and/or indirect contact with the stomach 2, the pylorus 65 and/or the duodenum 37.

Figure 14A:
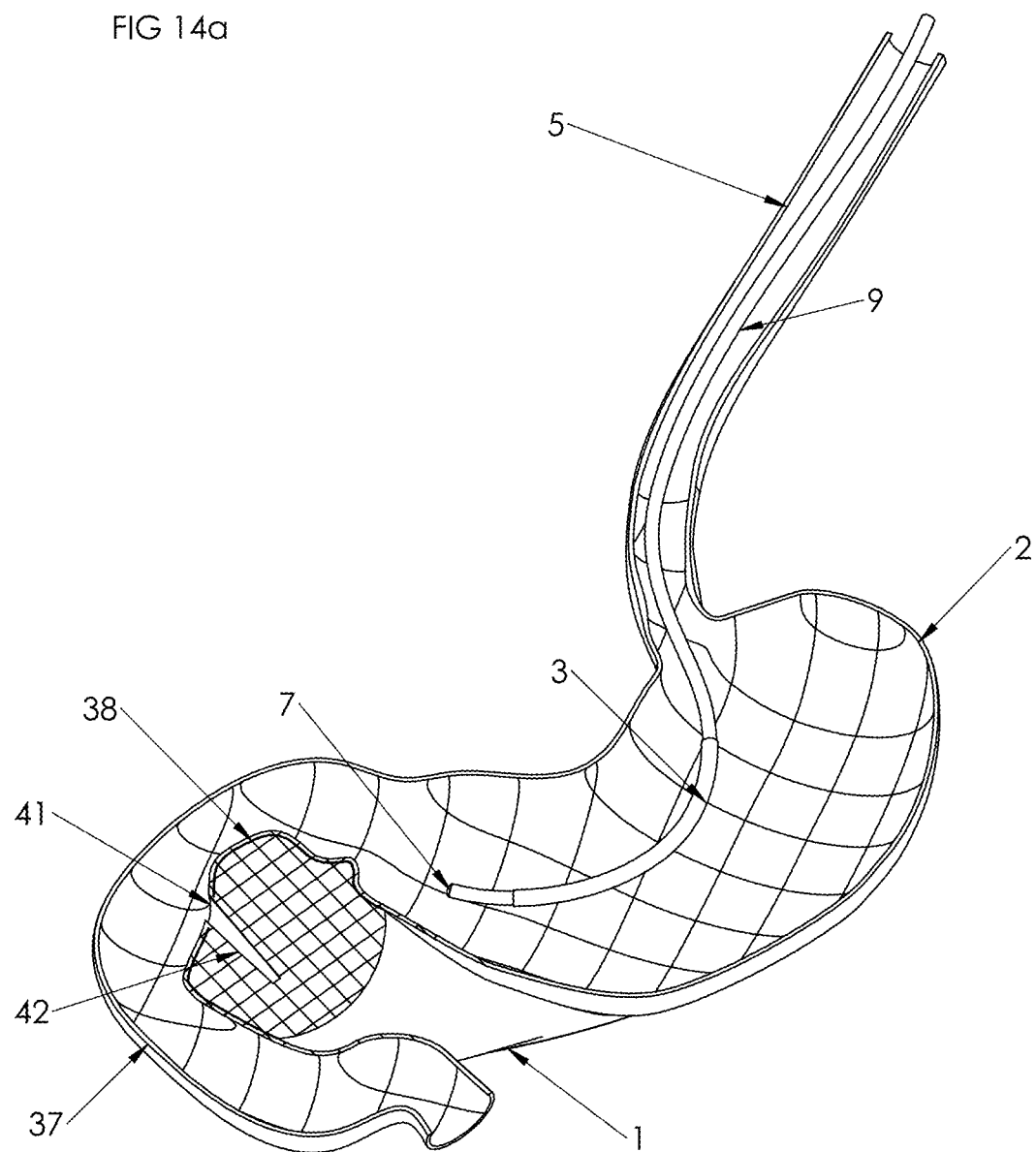
FIGS. 14a and 14b illustrate the stomach and pancreas in an isometric view with the anterior half removed.
Figure 14B:
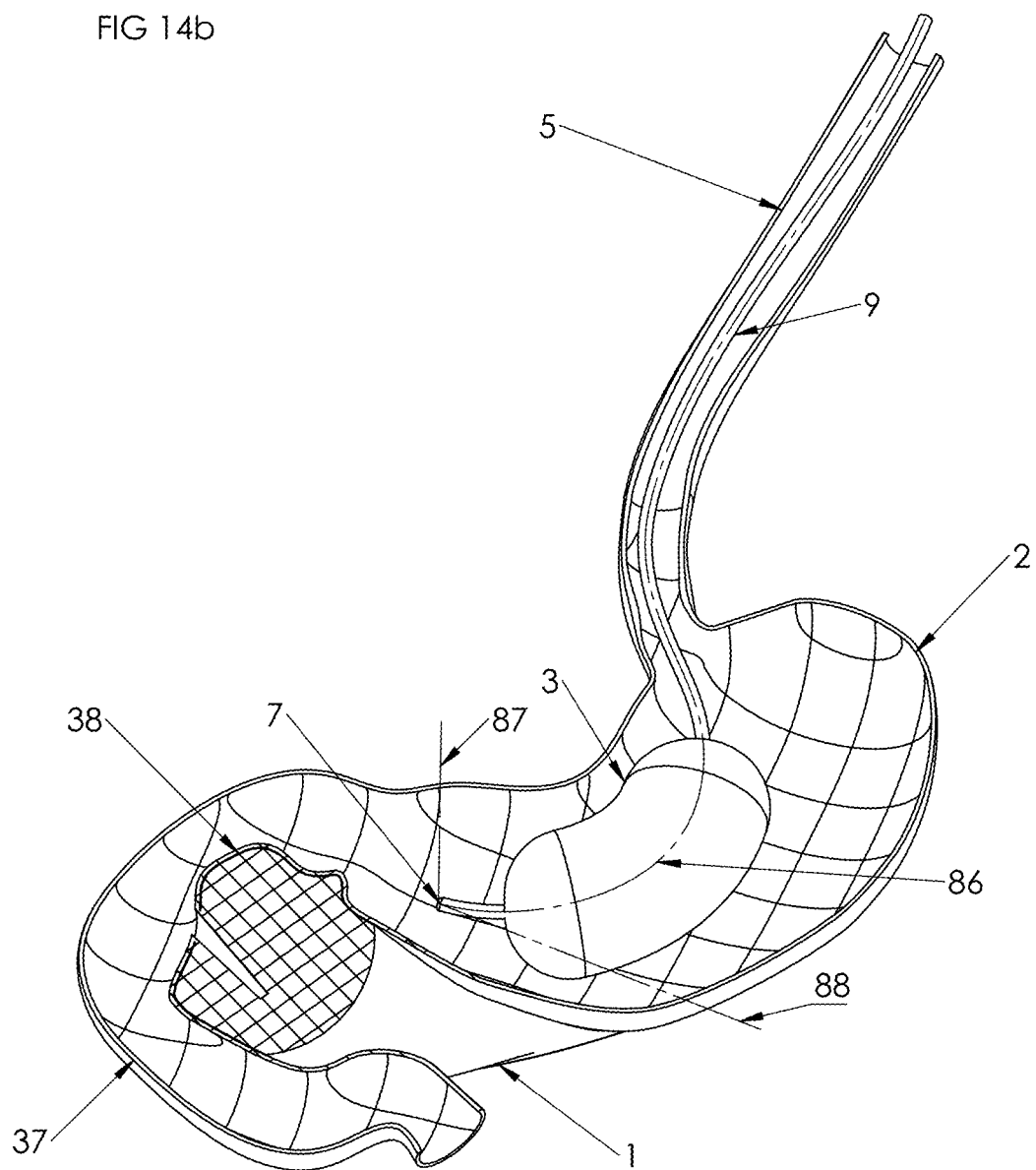

FIGS. 14a and 14b illustrate that the balloon 3 can be elastic. The balloon 3 can be connected to the catheter 9. The balloon 3 can be an extruded tube made from a polymer, elastomer and/or rubber. For example, the balloon 3 can be a thin-walled extruded silicone tube. The balloon 3 can have approximately the same outer diameter as the catheter 9 in the deflated configuration illustrated in FIG. 14a. The balloon 3 can be inflated with the fluid 6. The balloon 3 can be inflated to a low pressure that can adapt and/or conform to the stomach 2. The peristaltic motion and/or motility of the stomach 2 can manipulate and/or move the balloon 3. For example, the stomach contractions can urge and/or force the balloon 3 toward the pylorus 65. The catheter tip 7 can remain in the stomach 2, the esophagus 5, the pylorus 65 and/or the duodenum 37. The catheter tip 7 can have a port for aspiration, decompression, feeding and/or inserting instruments. The catheter tip 7 can be introduced and/or positioned over a guidewire. The balloon 3 can be secured to the catheter 9 with adhesive, ultrasonic welding, heat shrink tubing, metal bands and/or reflow melting. The balloon 3 can be inserted into and/or removed from the esophagus 5 and/or the stomach 2 in the deflated configuration illustrated in FIG. 14a. The balloon 3 can be inflated into the inflated configuration illustrated in FIG. 14b. A catheter axis 86 can run alongside and/or concentric with the catheter 9. A Sagittal axis 87 (also known as the anteroposterior axis) can run from front to back through the center of the body. For example, when a person performs a cartwheel they are rotating about the sagittal axis 87. A frontal axis 88 can run from left to right through the center of the body. For example, when a person performs a somersault they rotate around the frontal axis 88. The dimensions of the balloon 3 can be shorter and/or longer across these various axes. For example, the balloon 3 can be longer along the frontal axis 88 than the sagittal axis 87.

Figure 15B:
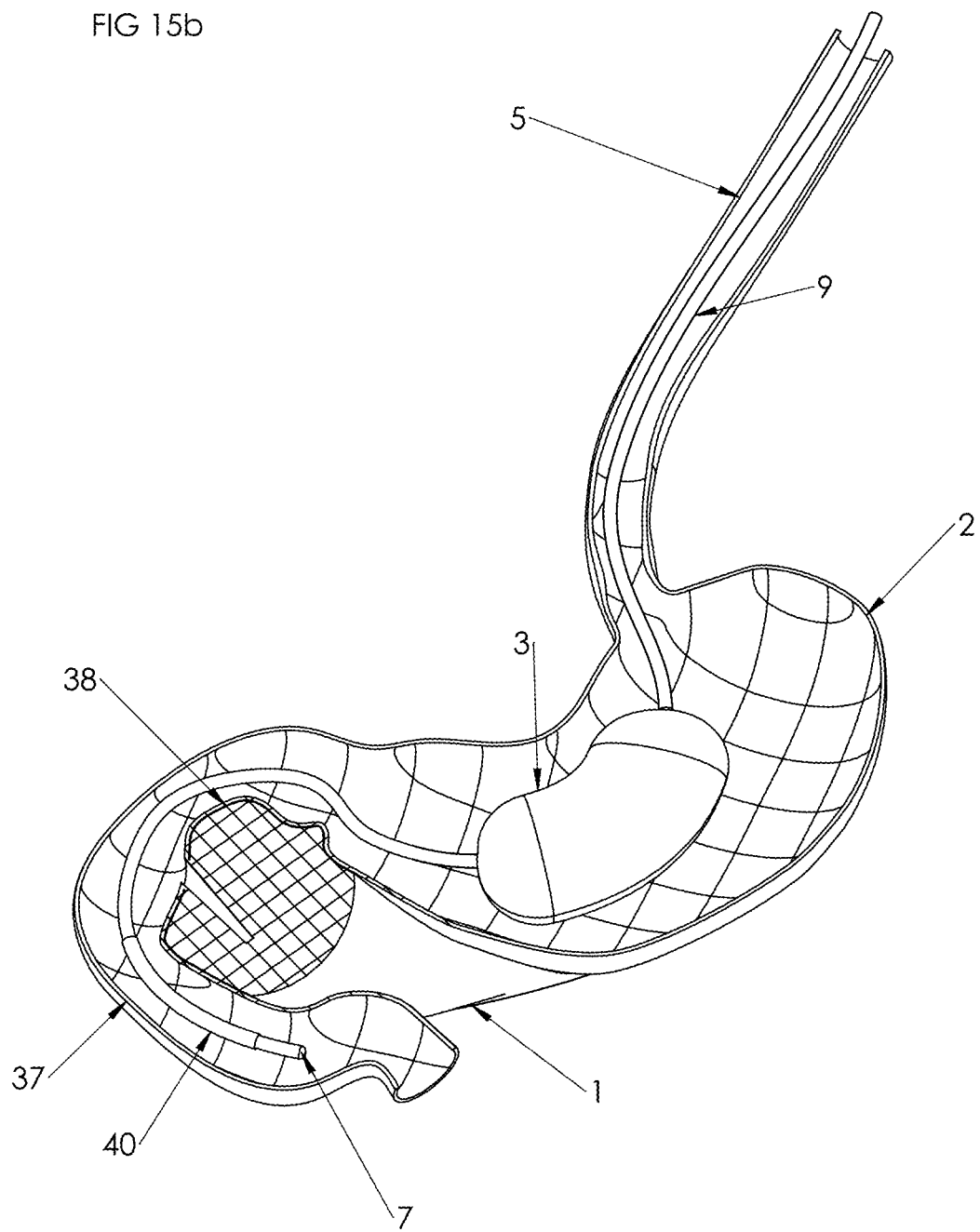
Figure 15C:
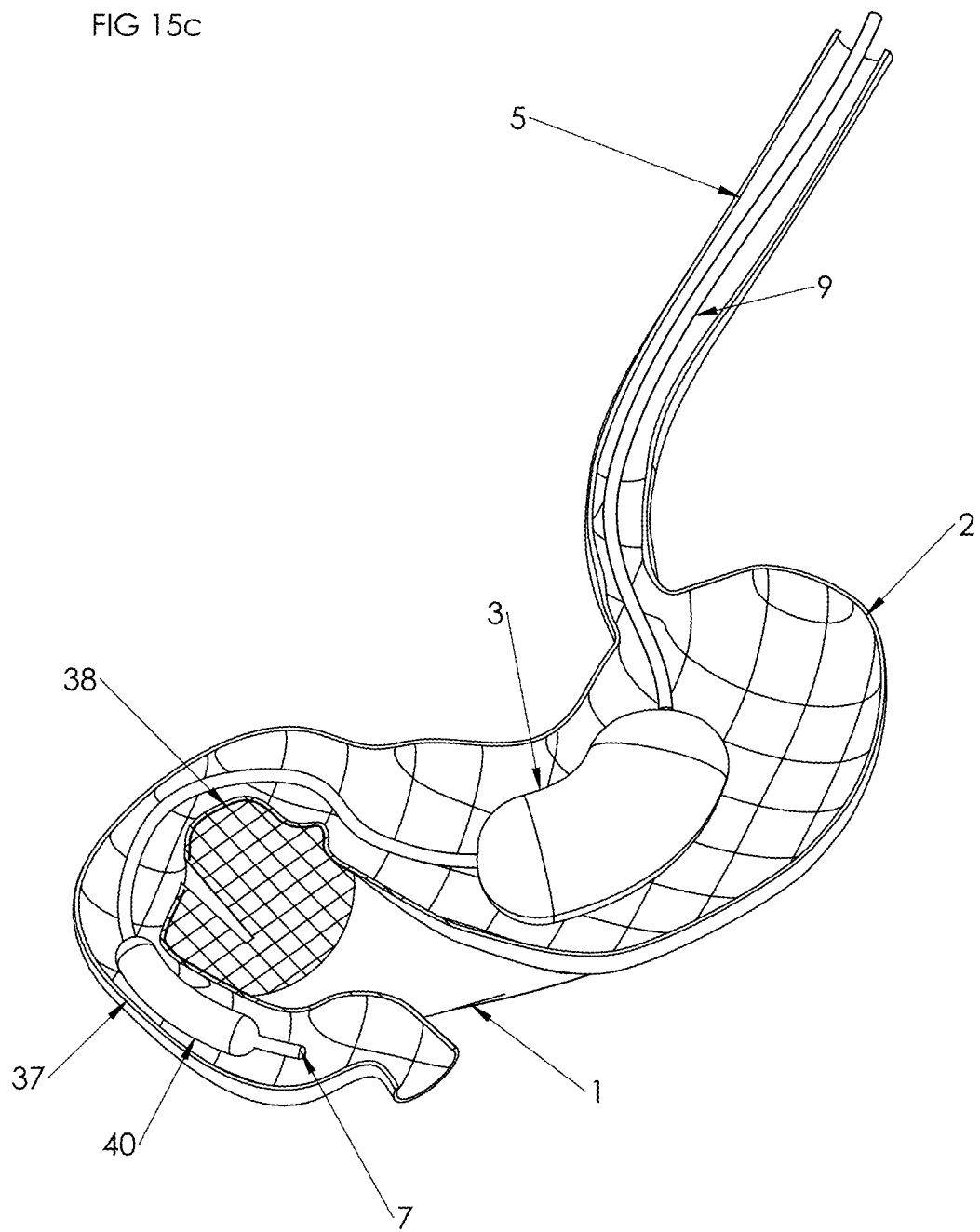

FIGS. 15a-15c illustrate that the balloon 3 can be inelastic. For example, the balloon 3 can be made from a polymer that is flexible but not designed to stretch. For example, the balloon 3 can be made from PET, LDPE, HDPE, mylar and/or nylon. The balloon 3 can be filled to a volume lower than its maximum capacity. A duodenal device 40 can be an elastic and/or inelastic balloon secured to the catheter 9. The duodenal device 40 can act as a reservoir for the balloon 3. For example, if external pressure compresses the balloon 3 (e.g., peristalsis, motility, vomiting, etc.) then the fluid 6 can move from the balloon 3 to the duodenal device 40. The duodenal device 40 can serve as a damper to help regulate, maintain and/or control the volume and/or pressure of the balloon 3. The duodenal device 40 can cycle between a deflated configuration illustrated in FIG. 15b and an inflated configuration illustrated in FIG. 15c. The duodenal device 40 can help to cool and/or warm the pancreas 1, the pylorus 65 and/or the duodenum 37. The duodenal device 40 can help to cool and/or warm the pancreas head 38. The balloon 3 can help to cool and/or warm the stomach 2 and/or the pancreas 1. The catheter 9, the balloon 3 and/or the duodenal device 40 can help to cool and/or heat a core body temperature and/or specific organs in a body.

Figure 16A:
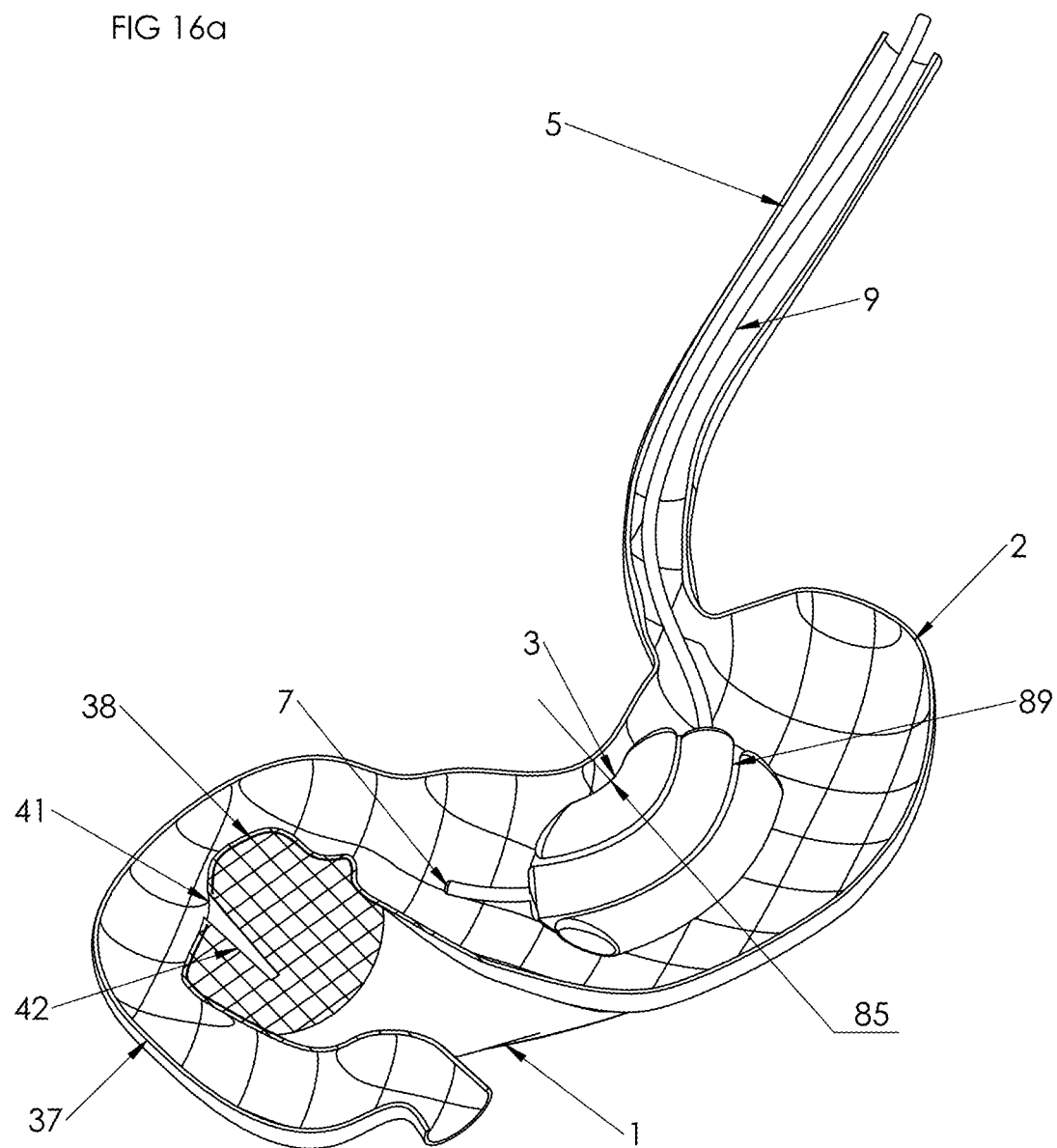
Figure 16C:
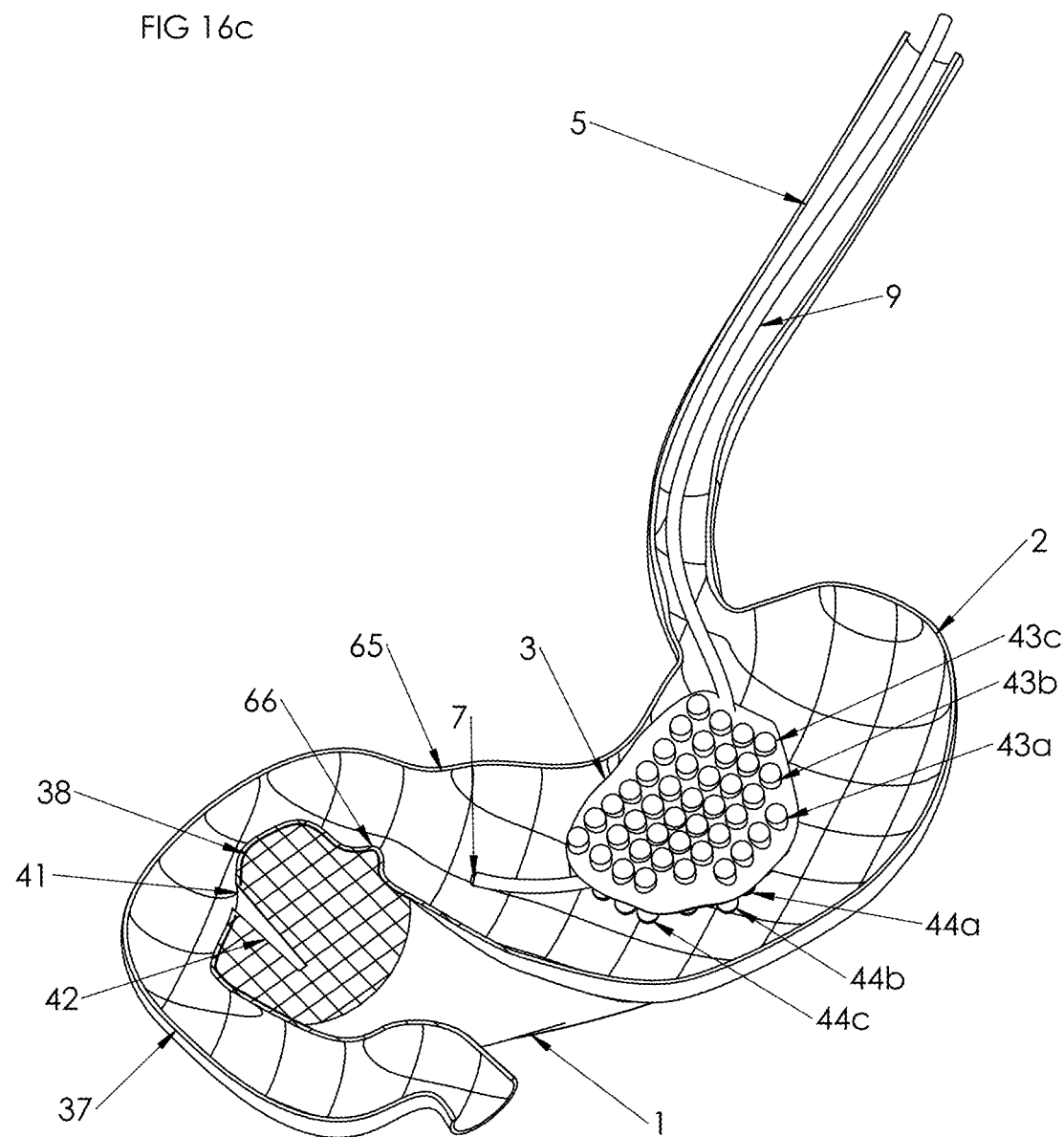

FIGS. 16a, 16b and 16c illustrate that the balloon 3 can be an inelastic structure that inflates. The balloon 3 can be divided into lobes 89 with bonded zones that can be bonded by heat, or chemically (example ultrasonic welding, ultrasonic welding, heat bonding), mechanically (thread, staples, between polymer sheets to form lobes. The lobes are fluidly connected to the catheter to allow circulation of fluids. The bonded zones can form channels that allow flexibility in one or more directions. FIG. 16c illustrates that the bonded zones can surround a lobe 89a allowing for flexibility in all directions. Spacing between bonded sections can determine height of expansion of the lobes limiting height or thickness of the balloon limits expansion or pressure on the stomach towards the anterior-posterior direction.

FIGS. 16b and 16c illustrate two layers of lobes or inflation zones. The anterior layer 43 can be inflated with gas or lower temperature fluid compared to the layer 44 closest to the posterior wall of the stomach. This lower temperature zone helps isolate cooling to the anterior wall of the stomach adjacent to the pancreas and to insulate the posterior wall of the stomach. The outer edges of the balloon can be marked with radio-opaque or echogenic markers to indicate complete inflation or full deployment of the balloon. The catheter tip 7 can remain in the stomach 2, the esophagus 5, the pylorus 65 and/or the duodenum 37. The catheter tip 7 can have a port for aspiration, decompression, feeding and/or inserting instruments. The catheter tip 7 can be introduced and/or positioned over a guidewire.

A balloon radius of curvature 85 can be the same and/or vary over the length of the balloon 3 and/or the catheter 9. The balloon radius of curvature 85 can be inverted. The balloon radius of curvature 85 can be greater than approximately 0.5 in (1.3 cm), yet more narrowly greater than approximately 1 in (2.5 cm), yet more narrowly greater than approximately 2 in (5.1 cm), yet more narrowly greater than approximately 3 in (7.6 cm), yet more narrowly greater than approximately 5 in (12.7 cm), yet more narrowly greater than approximately 7 in (17.8 cm), yet more narrowly greater than approximately 10 in (25.4 cm), yet more narrowly greater than approximately 15 in (38.1 cm) and/or yet more narrowly greater than approximately 20 in (50.8 cm). The balloon radius of curvature 85 can be less than approximately 20 in (50.8 cm), yet more narrowly less than approximately 15 in (38.1 cm), yet more narrowly less than approximately 10 in (25.4 cm), yet more narrowly less than approximately 7 in (17.8 cm), yet more narrowly less than approximately 5 in (12.7 cm), yet more narrowly less than approximately 3 in (7.6 cm), yet more narrowly less than approximately 2 in (5.1 cm), yet more narrowly less than approximately 1 in (2.5 cm), yet more narrowly less than approximately 0.5 in (1.3 cm).

FIG. 17 illustrates that the catheter 9 can function as a heat transfer device. The catheter 9 can have adequate surface area to provide heat transfer between the stomach 2 and the fluid 6. A physician can insert a predetermined length of the catheter 9 into the stomach 2. The physician can adjust the length of the catheter 9 located in the stomach 2 to adjust the surface area of the catheter 9 located in the stomach 2 and can thereby control the heat transfer between the heat transferer 4 and the stomach 2. The catheter 9 can be fixed and/or move with respect to the stomach 2. For example, peristalsis and/or motility can move the catheter 9. The catheter 9 can cool the wall of the stomach 2 directly and/or indirectly. For example, the catheter 9, the balloon 3 and/or the heat transferer 4 can cool the gastric juices and/or fluid located in the stomach 2. The catheter 9 can include a catheter barb 45. The catheter 9 can include multiple of the catheter barbs 45. The catheter barbs 45 can be cilia like flaps on the catheter 9. The catheter barbs 45 can be integral to the catheter 9 and/or a separate component from the catheter 9. The catheter barbs 45 can help guide the catheter 9 into the duodenum 37 and/or the pylorus 65. The catheter barbs 45 can help retain the catheter 9 in the duodenum 37 and/or the pylorus 65. A given cross-section of the catheter 9 can include zero, one and/or multiple of the catheter barb 45. The catheter barb 45 can be provide greater axial friction and/or resistance in one direction. For example, the force to push and/or pull the catheter 9 and/or the catheter barb 45 distally can be less than the force to push and/or pull the catheter 9 and/or the catheter barb 45 proximally. The catheter barbs 45 can self-advance the catheter 9 into the duodenum 37. The duodenal device 40 can be a weight. For example, additional weight at and/or near the catheter tip 7 can help to guide and/or urge the catheter 9 into the duodenum 37 and/or the pylorus 65. For example, additional weight at and/or near the catheter tip 7 can help to retain and/or maintain the catheter 9 in the duodenum 37 and/or the pylorus 65. The duodenal device 40 can help to guide and/or urge the catheter 9 into the duodenum 37 and/or the pylorus 65. The duodenal device 40 can help to retain and/or maintain the catheter 9 in the duodenum 37 and/or the pylorus 65. The duodenal device 40 can be a balloon. The duodenal device 40 can be inflated to increase friction between the heat transferer 4 and an organ (e.g., the duodenum 37). The duodenal device 40 can be inflated after it has passed through the pyloric sphincter 66 and/or the pylorus 65. For example, if the duodenal device 40 is expanded after it has passed through the pyloric sphincter 66 and/or the pylorus 65 then it can help to keep the catheter tip 7 in the duodenum 37. The duodenal device 40 can be a braid and/or a flexible material that can adjust its diameter based on its length. For example, contracting the axial length of the duodenal device 40 can increase its radial diameter. The catheter barbs 45 can be retractable and/or extendable.

Figure 18:
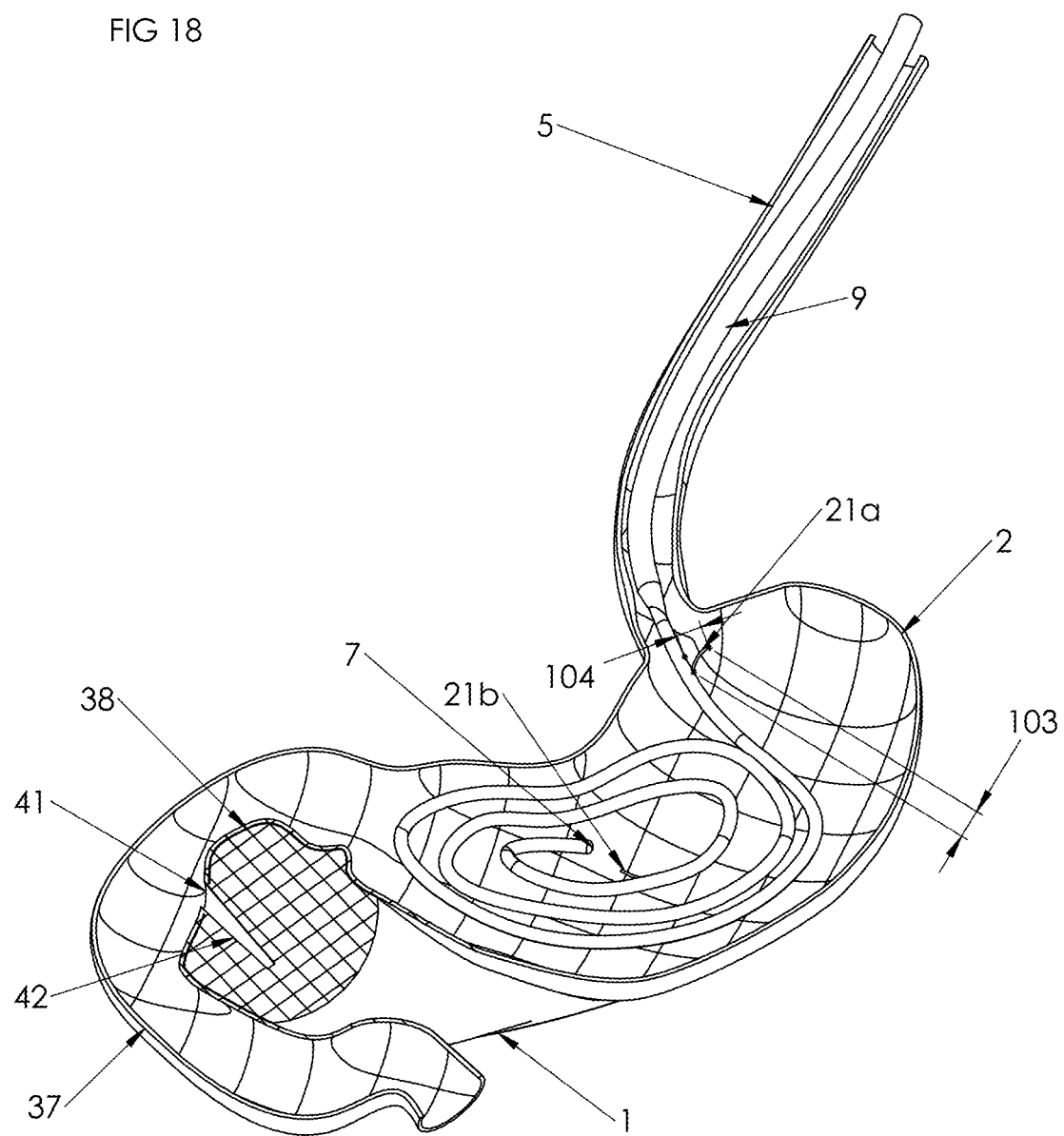
FIG. 18 illustrates the stomach and pancreas in an isometric view with the anterior half removed.

FIG. 18 illustrates that the catheter 9 can have a spiral shape and/or profile. For example, a section of the catheter 9 can be heat set and/or formed into a spiral shape. An additional material and/or component can be used to create and/or adjust the shape of the catheter 9. For example, the catheter 9 can be manufactured with two materials with different coefficients of thermal expansion; for example, when the catheter 9 is exposed to body temperature and/or the temperature from the fluid 6 it can alter its shape and/or profile. A wire (e.g., metal and/or plastic) can be inserted into a lumen of the catheter 9 to create the spiral shape and/or to straighten the catheter 9. For example, during insertion and/or removal it can be desirable to have the catheter 9 approximately straight. The wire can be shaped like a spiral and remain in the catheter 9 to help maintain the spiral shape. The wire can be secured to the catheter tip 7 and then pulled, torqued, twisted and/or pushed relative to the catheter 9 to adjust the shape of the catheter 9. For example, if the wire is off-axis and pulled taught, it can curl the catheter 9 into a spiral shape. The wire can be made from a shape memory alloy (e.g., nitinol) that can adjust its shape based on temperature. A lumen of the catheter 9 can be placed under high or low pressure to force the catheter to form a spiral shape. The catheter 9 can include one and/or multiple of the sensor 21. The sensor 21a can be different than the sensor 21b. The sensor 21 can measure temperature, pressure, flow, pH, sound, enzymes, proteins, biologic activity and/or motion. The sensor 21 may extend outside of the body of the catheter 9 by a sensor length 103. The sensor 21 may extend at various angles away from the catheter 9, therefore the sensor length 103 may be less than, equal to and/or greater than a sensor radial length 104. The sensor radial length 104 may be the minimum distance from the sensor 21 to the body of the catheter 9. The sensor radial length 104 and/or the sensor length 103 may change and/or be adjusted. For example, the sensor 21 may be adhered to the body of the catheter 9 with a dissolvable and/or releasable adhesive, heat shrink, glue and/or mechanism. For example, changes in temperature, acidity and/or pressure may release the tip of the sensor 21 from the body of the catheter 9.

Figure 19:
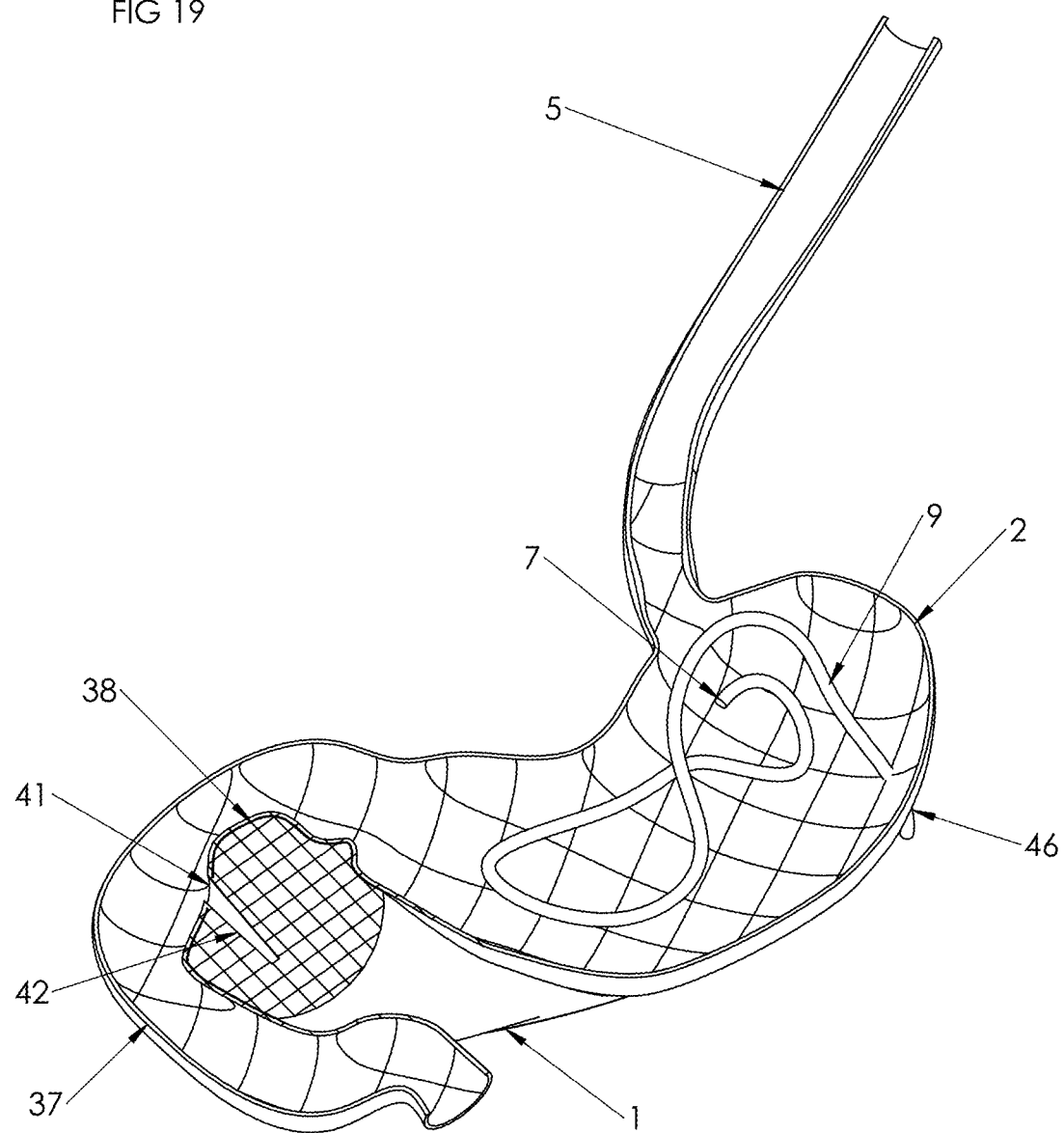
FIG. 19 illustrates the stomach and pancreas in an isometric view with the anterior half removed.

FIG. 19 illustrates that the catheter 9 can be introduced into the stomach 2 via the wall of the stomach 2. For example, the catheter 9 can be introduced via a percutaneous port 46. The catheter 9 can be introduced via the anterior and/or posterior section of the stomach 2. The catheter 9 can be introduced into the stomach cardia, stomach fundus, stomach body, pylorus 65, duodenum 37 and/or the pyloric sphincter 66.

Figure 20:
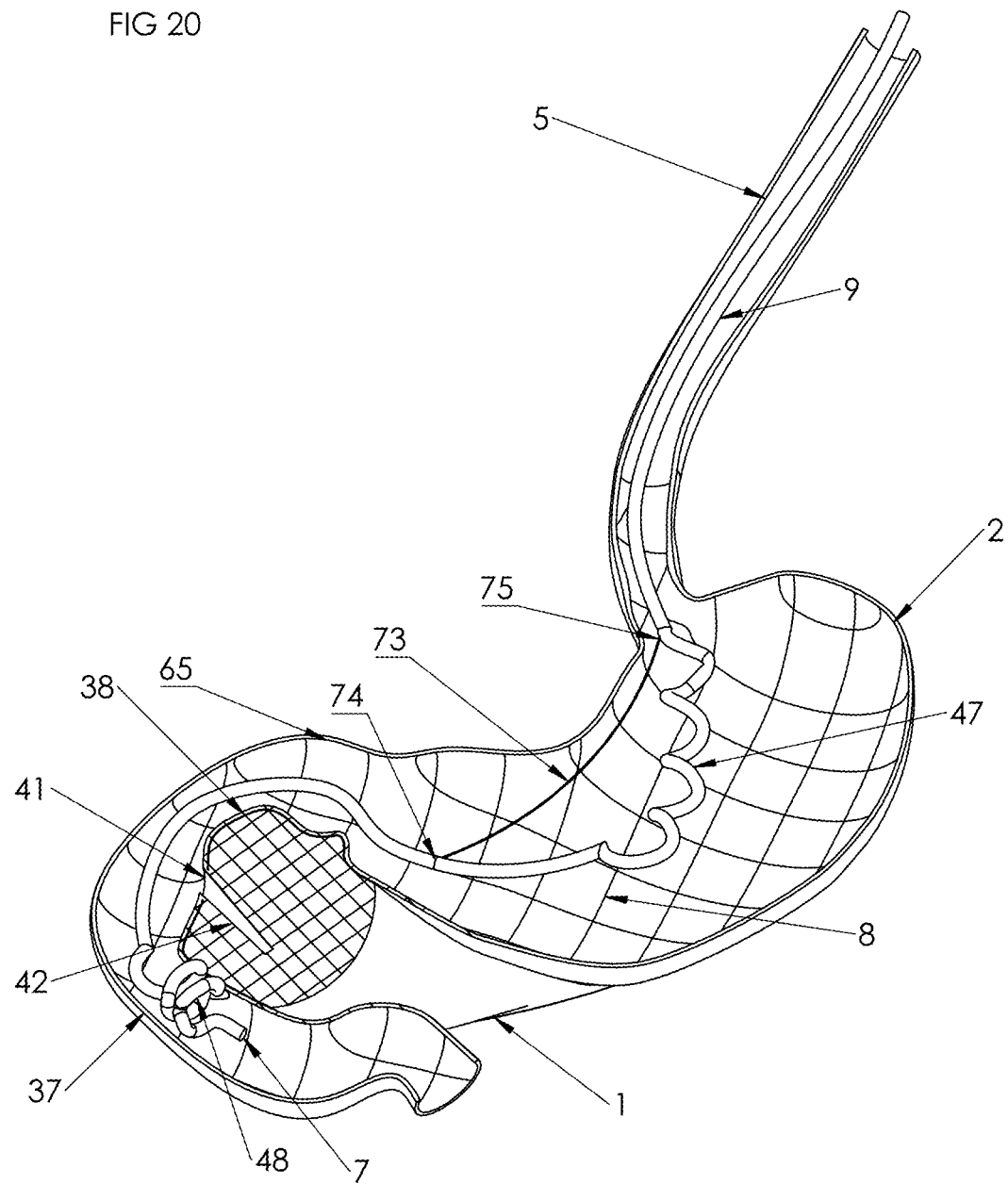
FIG. 20 illustrates the stomach and pancreas in an isometric view with the anterior half removed.

FIG. 20 illustrates that catheter 9 can have one and/or multiple coil and/or helix. For example, a section of the catheter 9 can be heat set and/or formed into a helical shape. An additional material and/or component can be used to create and/or adjust the shape of the catheter 9. For example, the catheter 9 can be manufactured with two materials with different coefficients of thermal expansion; for example, when the catheter 9 is exposed to body temperature and/or the temperature from the fluid 6 it can alter its shape and/or profile. A wire (e.g., metal and/or plastic) can be inserted into a lumen of the catheter 9 to create the helical shape and/or to straighten the catheter 9. For example, during insertion and/or removal it can be desirable to have the catheter 9 approximately straight. The wire can be shaped like a helix and remain in the catheter 9 to help maintain the helical shape. The wire can be secured to the catheter tip 7 and then pulled, torqued, twisted and/or pushed relative to the catheter 9 to adjust the shape of the catheter 9. For example, if the wire is off-axis and pulled taught, it can curl the catheter 9 into a helical shape. The wire can be made from a shape memory alloy (e.g., nitinol) that can adjust its shape based on temperature. A lumen of the catheter 9 can be placed under high or low pressure to force the catheter to form a helical shape. The catheter 9 can have a gastric coil 47 and/or an engager 48. The gastric coil 47 can extend into the duodenum 37. The engager 48 can extend into the stomach 2. The gastric coil 47 can provide additional surface area and/or flexibility. The gastric coil 47 and/or a spiral shape can help prevent the catheter 9 from kinking and/or forming a knot. The engager 48 can help to retain the catheter tip 7 in the duodenum 37. The engager 48 and/or the gastric coil 47 can help increase thermal contact with the fluids and/or tissue. For example, the engager 48 can increase thermal contact with the duodenum 37. The engager 48 and/or the gastric coil 47 can provide some strain relief to counteract and/or resist peristalsis, motility and/or other external forces. The engager 48 can be, for example, a duodenal coil. A tether 73 can be secured to an anchor point 74 on the catheter 9. The tether 73 can run alongside the catheter 9 and/or can enter the catheter 9 at an anchor port 75. The tether 73 can inhibit or prevent a portion of the catheter 9 from passing through the duodenum 37. The tether 73 can ensure that a portion of the catheter 9 does not pass through the duodenum 37. For example, The tether 73 can restrict a section of the catheter 9 proximal to the anchor point 74 from traveling distally into the pylorus 65 and/or the duodenum 37. The tether 73 can be pulled taught relative to the catheter 9 to adjust the maximum distance between the anchor point 74 and the anchor port 75. For example, the distance between the anchor point 74 and the anchor port 75 can be larger during insertion, use and/or removal. For example, the distance between the anchor point 74 and the anchor port 75 can be larger during insertion/removal than once it is in position in the stomach. The tether 73 can pass inside of the first lumen 15, the second lumen 16, the third lumen 17 and/or the fourth lumen 18. The tether 73 can be secured to the catheter 9, the nose 11 and/or the heat transferer 4. For example, once the tether 73 is pulled taught it can be secured to a proximal section of the catheter 9 external to the body. For example, during removal, the tether 73 can be released from the proximal section of the catheter 9 external to the body for easier removal of the catheter 9 from the patient. The tether 73 can be made from a natural and/or synthetic polymer. The tether 73 can be made from metal, plastic and/or ceramic. The proximal section of the tether 73, the catheter 9 and/or the heat transferer 4 can be secured to the patient (e.g., the nose 11, the mouth 12 and/or other points on the patient. The proximal end of the tether can be attached to an actuator. The actuator can create translation of the tether and may have a locking portion that is automatic like a ratchet. Alternately the actuator may be locked into position manually. Deployment of this actuator can ensure and/or can enable consistent tension via maintenance of a constant force (via a spring) or distance adjustment. The actuator can be, for example, a lever, motor, and or wheel. The actuator can have visual indicators for feedback on distance traveled or lock status. The tether 73 can be pulled taut. The tether 73 can, for example, pull the anchor point 74 near and/or adjacent to the anchor port 75. Maintaining the anchor point 74 near and/or adjacent to the anchor port 75 can reduce the risk of knotting and/or migration of the catheter 9. The distance between the anchor point 74 and the anchor port 75 can be approximately equal to the length of the tether between the anchor point 74 and the anchor port 75. The total length of the catheter 9 between the anchor point 74 and the anchor port 75 can be greater than the length of the tether 73 between the anchor point 74 and the anchor port 75. The tether 73 can be, for example, a string. The tether 73 can be, for example, an anchor string.

Figure 21:
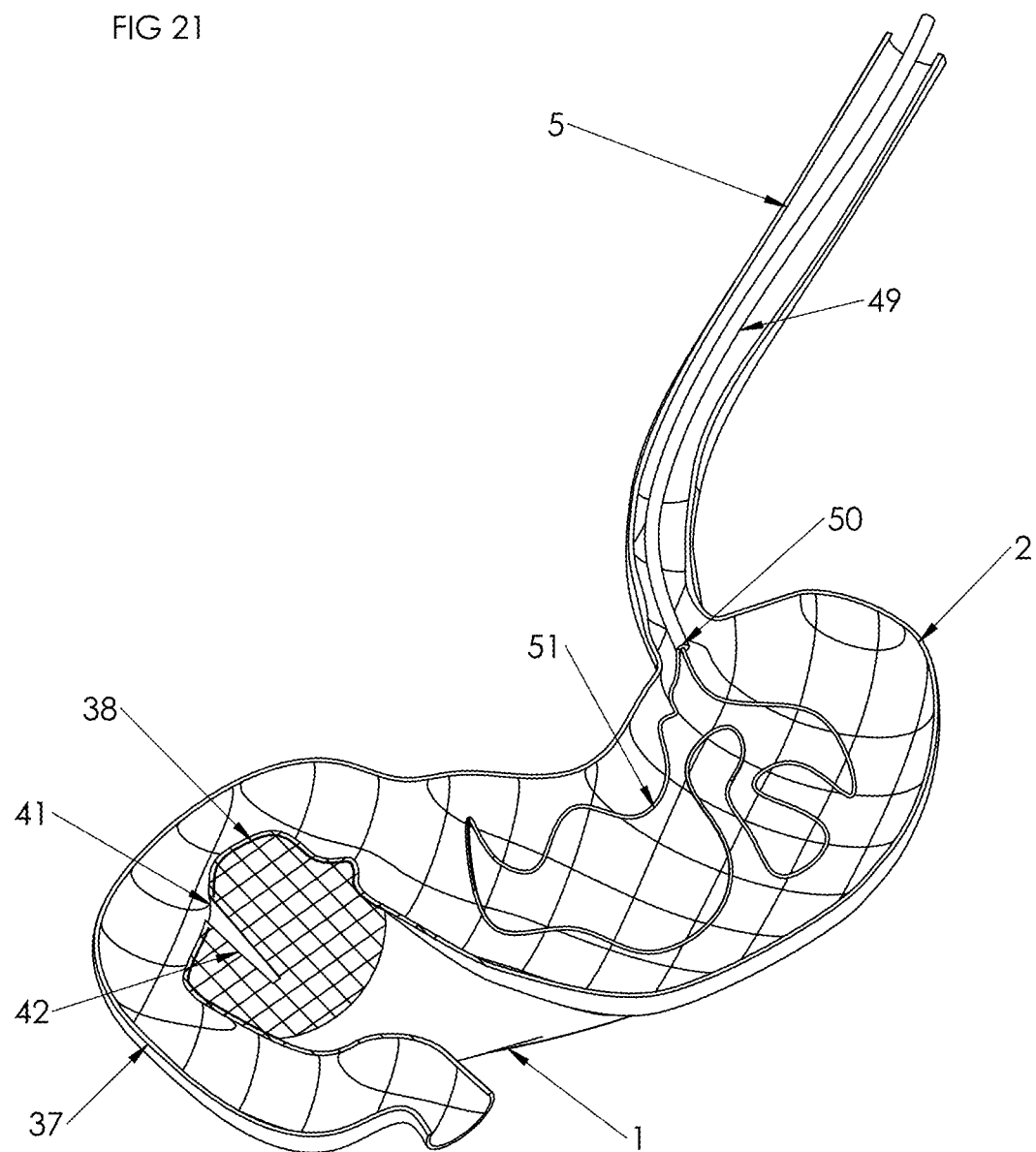
FIG. 21 illustrates the stomach and pancreas in an isometric view with the anterior half removed.

FIG. 21 illustrates that an introducer 49 can be inserted into the esophagus 5 and/or the stomach 2. The introducer 49 can allow easier and/or more controlled placement of the heat transferer 4. The catheter 9 and/or an inner catheter 51 can be introduced through the introducer 49. The introducer 49 can be stiffer than the catheter 9 and/or the inner catheter 51. The introducer 49 can include various features including bend-and-stay, deformability, deflectable guide catheter, sensors, etc. The inner catheter 51 can be a compliant single lumen tube. The inner catheter 51 can provide a high surface area to volume ratio. The fluid 6 can pass through the inner catheter 51. The inner catheter 51 can be the catheter 9. The introducer 49 can provide insulation between the catheter 9 and the tissue and/or organs. For example, the introducer 49 can provide thermal insulation between the catheter 9 and the esophagus 5, the nose 11, the mouth 12 and/or the stomach 2. For example, the introducer 49 can provide thermal insulation between the heat transferer 4 and the esophagus 5, the nose 11, the mouth 12 and/or the stomach 2.

Figure 22:
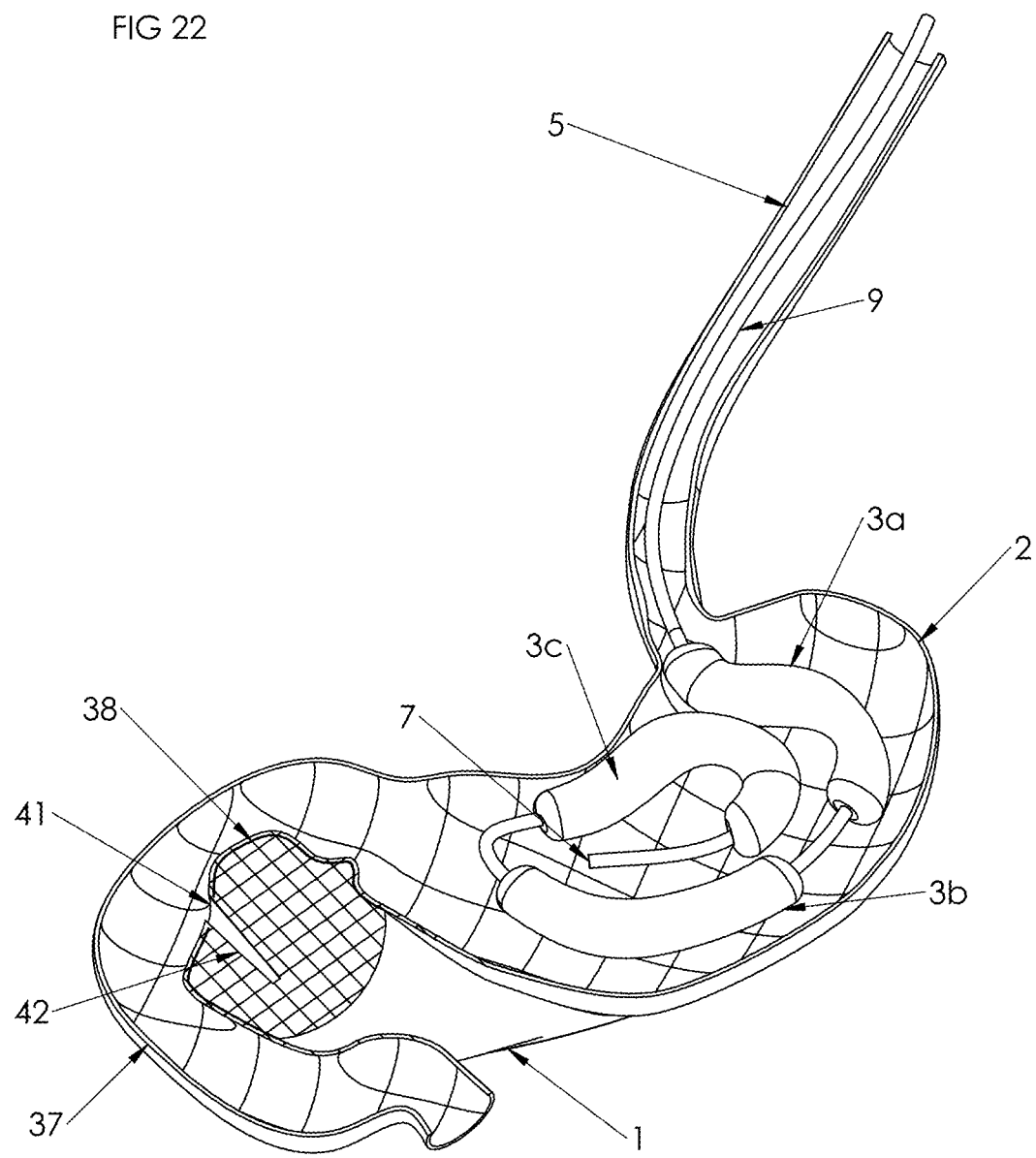
FIG. 22 illustrates the stomach and pancreas in an isometric view with the anterior half removed.

FIG. 22 illustrates that the catheter 9 can have balloons, for example, multiple radially expanding balloons. FIG. 22 illustrates that the balloons can be fluidly coupled to the catheter. The balloons can be elastic, inelastic, or a combination of elastic and inelastic. Multiple balloons in sequence can allow greater flexibility along the axis of the catheter while creating greater surface area for temperature exchange compared to a singular balloon. The inelastic balloon can be produced so that the balloon is limited in diameter and limits volume of the balloon regardless of pressure. Likewise the self-limiting diameter of the inelastic balloon limits radial outward pressure onto the gastric wall. There can be a combination of elastic and inelastic balloons. The inelastic balloons at low pressure can have a wall thickness thin enough so that it can expand and conform to the rugae or curvature of the stomach to allow more intimate contact and greater heat transfer. The same catheter with inelastic balloons can have elastic regions or bellows that can expand for pressure relief within the there is internal or external pressure on the inelastic balloons to maintain integrity of the inelastic balloon material. Any of the cooling balloons can be an extruded tube made from a polymer, elastomer and/or rubber. For example, the balloon 3 can be a thin-walled extruded silicone tube. The balloon 3 can have approximately the same outer diameter as the catheter 9 in the deflated configuration illustrated in FIG. 22. The balloon 3 can be inflated with the fluid 6. The balloon 3 can be inflated to a low pressure that can adapt and/or conform to the stomach 2. The peristaltic motion and/or motility of the stomach 2 can manipulate and/or move the most distal balloon 3. For example, the stomach contractions can urge and/or force the balloon 3 toward the pylorus 65. The catheter tip 7 can remain in the stomach 2, the esophagus 5, the pylorus 65 and/or the duodenum 37. The catheter tip 7 can have a port for aspiration, decompression, feeding and/or inserting instruments. The catheter tip 7 can be introduced and/or positioned over a guidewire. The multiple cooling balloons 3 can be secured to the catheter 9 with adhesive, ultrasonic welding, heat shrink tubing, metal bands and/or reflow melting. The multiple balloon 3 can be inserted into and/or removed from the esophagus 5 and/or the stomach 2 in the deflated configuration illustrated in FIG. 22. The cooling balloon materials 3 can be made from PET, LDPE, HDPE, mylar and/or nylon or elastic materials such as silicone or urethane. The most distal balloon in series can be sized such that peristaltic movement or guided placement via imaging can place it into the duodenum. Such a balloon in the duodenum can serve both to anchor position as well as provide cooling at the duodenum with the intention of cooling the head of the pancreas adjacent to the duodenum. A duodenal device 40 can be an elastic and/or inelastic balloon secured to the catheter 9. The duodenal device 40 can act as a reservoir for the balloon 3.

Figure 23:
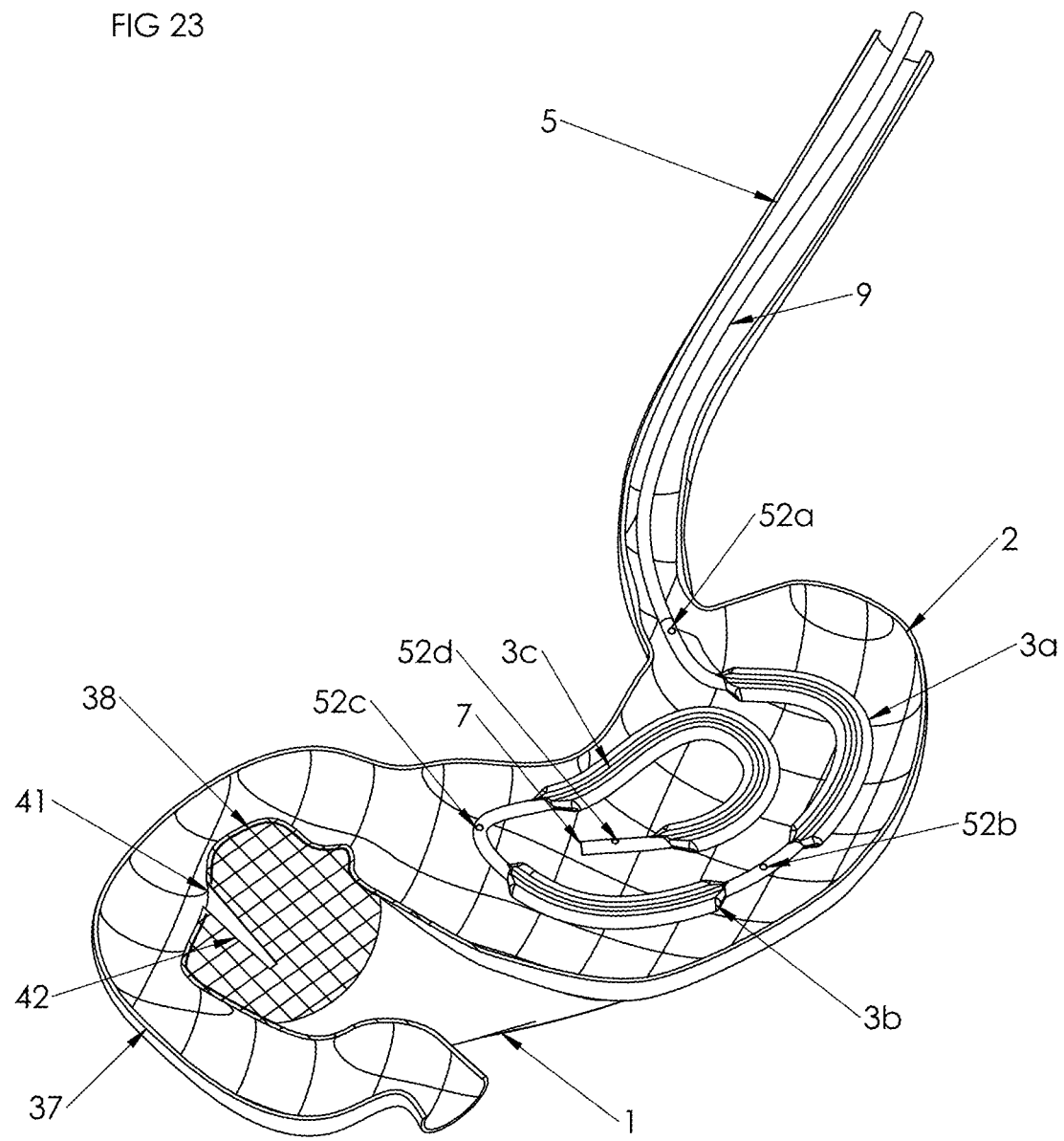
FIG. 23 illustrates the stomach and pancreas in an isometric view with the anterior half removed.

FIG. 23 illustrates that lumens of the catheter 9 can expand. For example, the entire catheter wall 20 and/or a section of the catheter wall 20 can expand under pressure. The expandable catheter wall can be the balloon 3. The expandable catheter wall can allow for increased surface area of the catheter 9 during use. The expandable catheter wall can be in the unexpanded configuration during insertion and/or removal. The expandable catheter wall can include an expandable tube and/or balloon secured concentrically around the catheter 9. The catheter 9 can include a catheter port 52 at the catheter tip 7 and/or along the circumference of the catheter 9. The catheter 9 can include multiple catheter ports 52. The catheter ports 52 can provide distributed access for decompression, feeding, tools and/or sensors. The catheter ports 52 can be connected to the first lumen 15, the second lumen 16, the third lumen 17 and/or the fourth lumen 18. The size and/or diameter of the catheter ports 52 can be the same and/or different.

Figure 24:
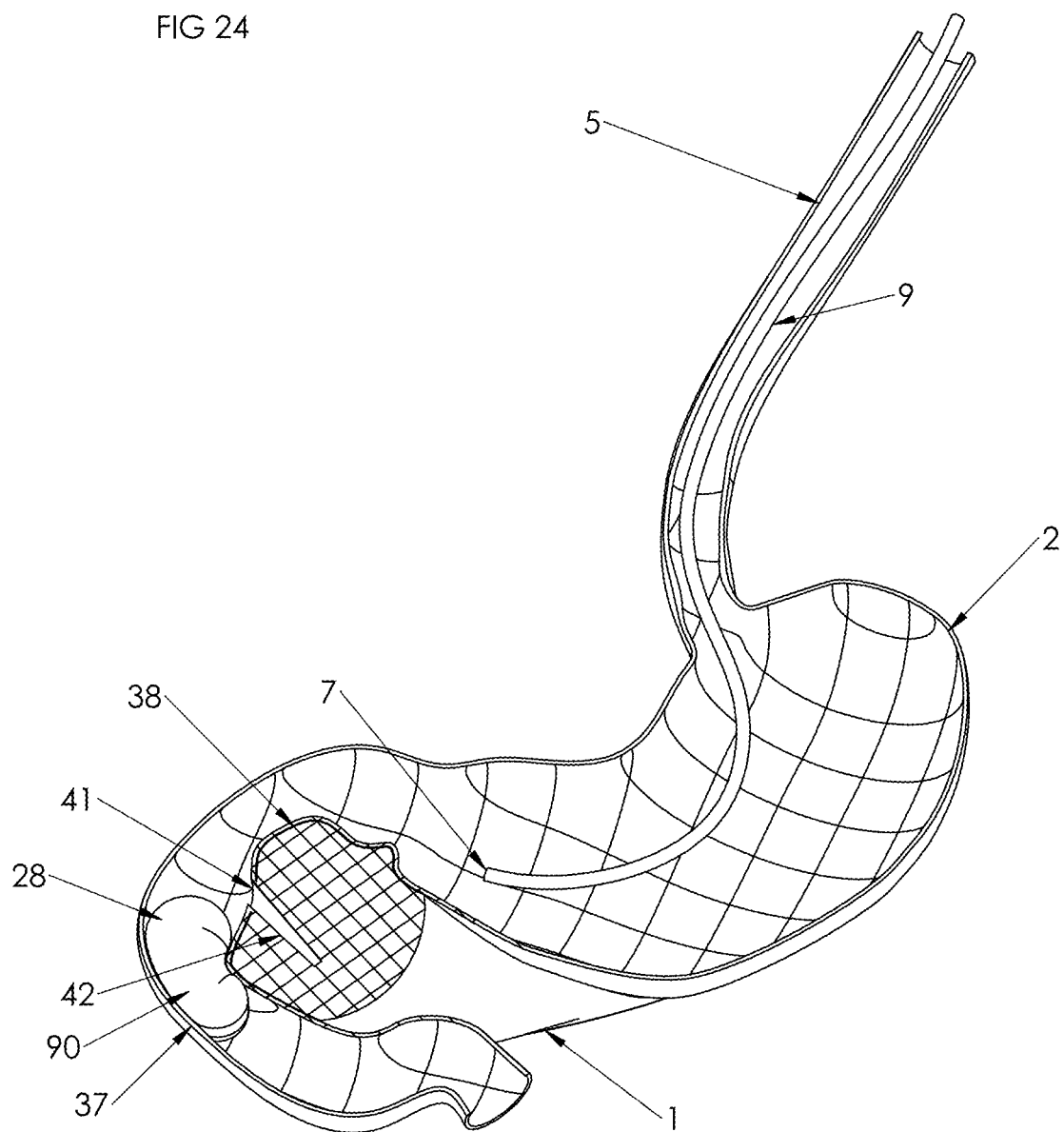
FIG. 24 illustrates the stomach and pancreas in an isometric view with the anterior half removed.

FIG. 24 illustrates an intestine valve 90 at the level of the intestine past the ampulla of vater 41. The intestine valve 90 can be placed endoscopically and anchored by expanding radially or having barb-like retention features. The intestine valve 90 can have barb-like retention features. The intestine valve 90 can be anchored in place by radially expanding the intestine valve 90 and/or by bringing the barb-like retention features into engagement with tissue. The intestine valve 90 can be remotely activated by a signal via an attached wire or wireless through remote control or magnet activation. Cold or warm fluid can be introduced and circulated in the gastric and proximal plugged duodenal region to cool the sections of the stomach and duodenum adjacent to the pancreas when the valve is in the closed position. Cold or warmed fluid can pass into the pancreatic duct via the ampulla of vater 41. The intestine valve 90 can be programmed to open at a set interval or set temperatures via onboard sensors to allow drainage of fluid after the cooling fluid has warmed due to the surrounding structures. The intestine valve 90 can be manually or automatically opened via remote control. Opening of the intestine valve 90 can allow resident fluids such as secretions or ingested food or liquid to pass.

Figure 25:
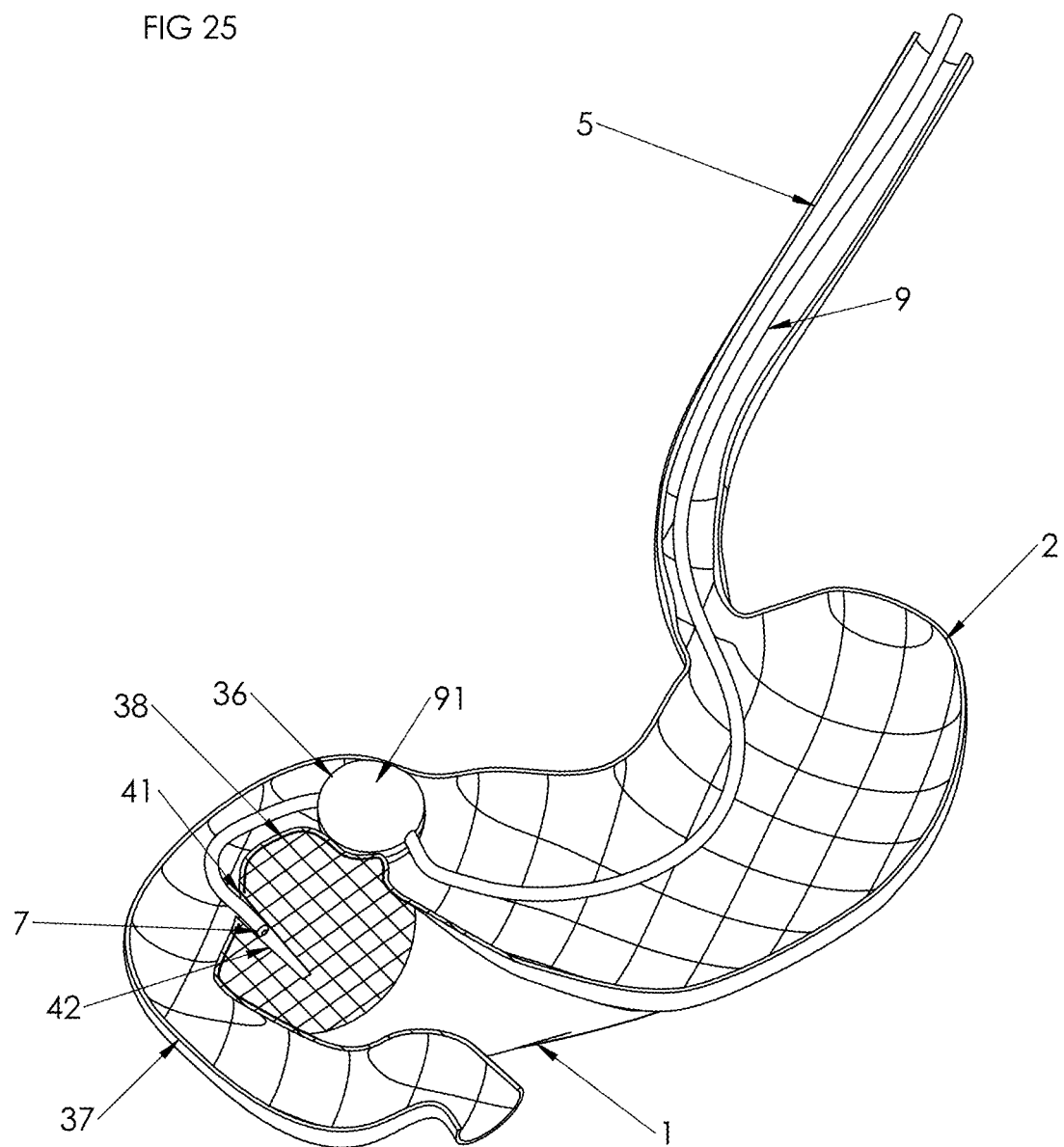
FIG. 25 illustrates the stomach and pancreas in an isometric view with the anterior half removed.

FIG. 25 illustrates a pylorus valve 91 at the level of the pylorus. The pylorus valve 91 can be placed endoscopically and anchored by expanding radially or having barb-like retention features or having a geometry such that it lodges into the pylorus to seal the stomach 2. The pylorus valve 91 can have barb-like retention features. The pylorus valve 91 can be anchored in place by radially expanding the pylorus valve 91 and/or by bringing the barb-like retention features into engagement with tissue. The pylorus valve 91 can be remotely activated by a signal via an attached wire or wireless through remote control or magnet activation. Cold or warm fluid can be introduced and circulated in the gastric region to cool the sections of the stomach 2 adjacent to the pancreas 1 when the pylorus valve 91 is in the closed position. Closure of the pylorus valve 91 controls how much fluid can be absorbed into the by limiting or stopping fluids to pass into the intestine. Once the cool fluid has transferred from the stomach 2 and surrounding organs such that the fluid has warmed, fluid can be evacuated via aspiration and replaced with cold fluids in automatic cycles. A lumen of the catheter 9 with the catheter tip 7 continues past the pylorus valve 91 so that feeding can occur directly into the intestine and bypassing any stimulation of the stomach 2. The pylorus valve 91 can be programmed to open at a set interval or set temperatures via onboard sensors to allow drainage of fluid after the cooling fluid has warmed due to the surrounding structures. The pylorus valve 91 can be manually or automatically opened via remote control. Opening of the pylorus valve 91 can allow resident fluids such as secretions or ingested food or liquid to pass.

Figure 26:
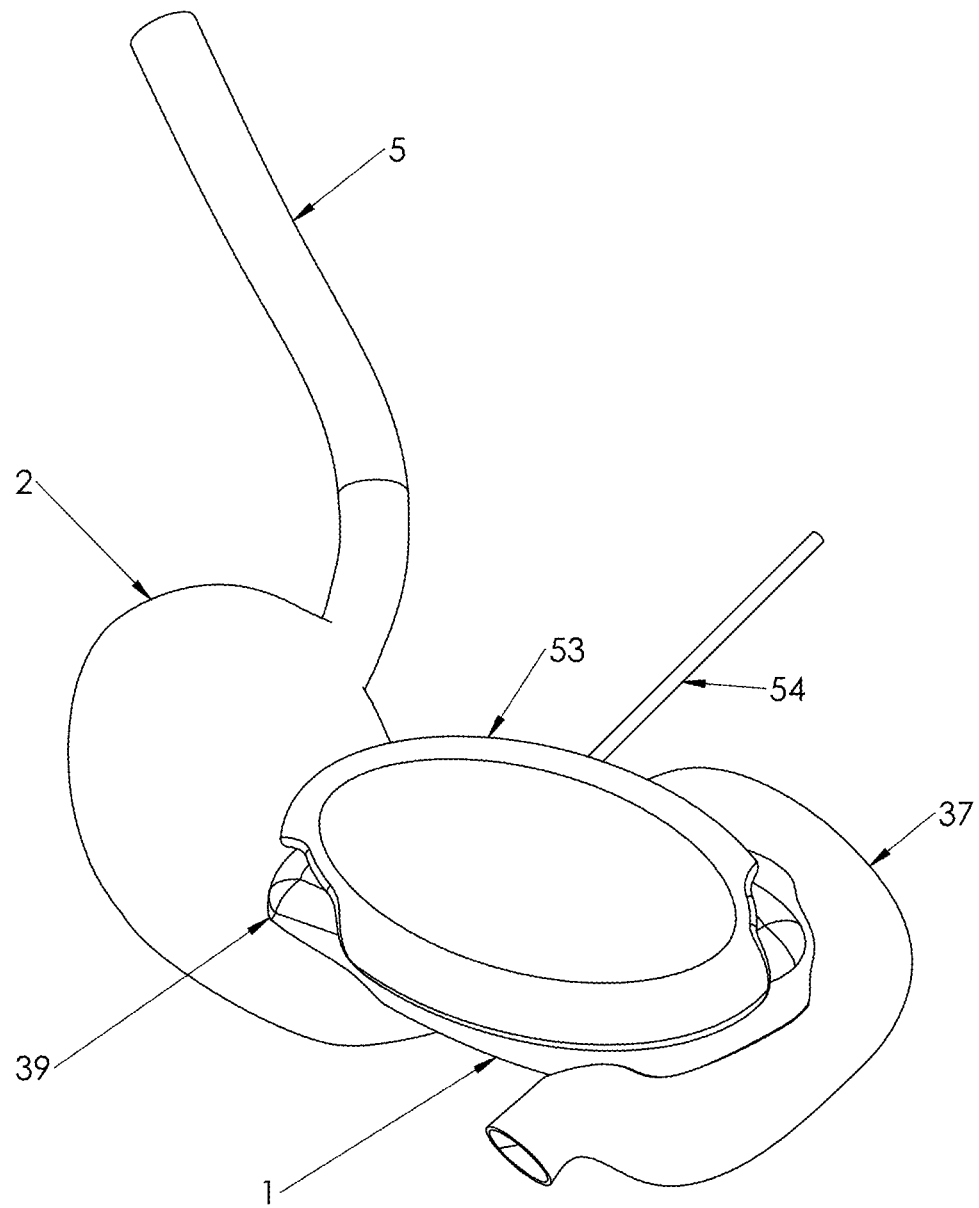
FIG. 26 illustrates the stomach and pancreas in an isometric view.

FIG. 26 illustrates a peritoneal cooling device 53 applied to the outer surface of the pancreas 1. The peritoneal cooling device 53 can be a balloon and/or a catheter. Fluid can be circulated with the peritoneal cooling device 53 via a peritoneal cooling device catheter 54. The peritoneal cooling device 53 can be placed laparoscopically or through direct transabdominal placement.

FIGS. 27a-27f illustrate that the catheter 9 can include various cross-sectional profiles. The cross-section of the catheter 9 can be the same and/or different along its length. FIG. 27a illustrates that the catheter 9 can have circular and/or approximately circular lumens. The diameter and/or area of the first lumen 15, the second lumen 16, the third lumen 17 and/or the fourth lumen 18 can be the same and/or different. FIG. 27b illustrates that the cross-section of the first lumen 15 and/or the second lumen 16 can be non-circular. A circular cross-sectional profile for the third lumen 17 and/or fourth lumen 18 can be desirable for improved passage of tools, sensor, food, tissue and/or other matter. A circular cross-sectional profile for the first lumen 15 and/or the second lumen 16 can allow for higher flow and/or a smaller pressure drop. A non-circular cross-sectional profile for the first lumen 15 and/or the second lumen 16 can allow for a larger hydraulic diameter. A non-circular cross-sectional profile for the first lumen 15 and/or the second lumen 16 can increase thermal transfer through the wall of the catheter 9 by providing a larger surface area in contact with the fluid 6. FIG. 27c illustrates that the cross-sectional profile of the catheter 9 can be non-circular. FIG. 27c illustrates that the wall thickness of the catheter 9 can vary at a given cross-section. A thinner catheter wall 20 can allow for increased thermal transfer through the catheter wall 20. The lumens of the catheter 9 can expand and/or contract under different pressures. For example, under high pressure, the cross-section of the catheter 9 can transform from that illustrated in FIG. 27b to that illustrated in FIG. 27c. The catheter 9 in FIG. 23 can have the cross-section of FIG. 27b and FIG. 27c. The catheter wall 20 can be elastic and/or inelastic. FIG. 27d and FIG. 27e illustrates that the cross-sectional profile of the catheter 9 can maximize thermal transfer through the catheter outer diameter 19. For example, a non-circular profile for the first lumen 15 and/or the second lumen 16 can maximize contact with the external wall of the catheter 9 and thereby can increase thermal transfer through the catheter wall 20. FIG. 27f illustrates that the diameter and/or area of the third lumen 17 can be different than the diameter and/or area of the fourth lumen 18. The third lumen 17 can benefit from a larger diameter if it is being used for aspiration, decompression, feeding and/or passage of tools. The fourth lumen 18 can be beneficial for venting, feeding, sensing and/or for the passage/installation of small tools/sensors. The first lumen 15, the second lumen 16, the third lumen 17 and/or the fourth lumen 18 can spiral around and/or through the catheter 9. The first lumen 15, the second lumen 16, the third lumen 17 and/or the fourth lumen 18 can spiral and/or twist around each other.

FIG. 28a and FIG. 28b illustrate that a tube and/or balloon can be secured concentrically over the catheter 9. The balloon 3 can be secured concentrically over the catheter 9. The catheter 9 in FIG. 23 can have the cross-section of FIG. 28a and FIG. 28b. The balloon 3 can be secured to the catheter 9 at one and/or multiple balloon seal region 55. The balloon seal region 55a and/or 55b can prevent the fluid 6 from transferring between the first lumen 15 and the second lumen 16. The fluid 6 can transfer from the first lumen 15 to the balloon 3 via a catheter hole 65. The catheter hole 65 can be punched, skived, melted, cut, laser-cut, drilled, machined and/or formed into the catheter wall 20. The catheter 9 can have multiple catheter holes 65. For example, the fluid 6 can exit from one of the catheter hole 65 into the balloon 3 and then enter back into the catheter 9 through a second of the catheter hole 65. The first lumen 15 and/or the second lumen 16 can be occluded at certain regions to force the fluid 6 into the balloon 3. The balloon sealing region 55 can secure the balloon 3 to the catheter 9 via adhesive, brazing, heat shrink tubing, springs, melting and/or ultrasonic welding.

FIG. 29 illustrates that the catheter outer diameter 19 can vary over the length of the catheter 9. For example, the catheter outer diameter 19 can be smaller at the nasal region to minimize discomfort and/or heat transfer to the nasal cavity. The catheter outer diameter 19 can be smaller in areas where heat transfer is not desired. For example, the catheter outer diameter 19 can be smaller in the nose 11, the mouth 12, head and/or the esophagus 5. A smaller catheter outer diameter 19 can reduce risk of knotting and/or kinking and/or allow for improved passage, insertion, removal and/or bending. A larger catheter outer diameter 19 can improve heat transfer, increase the heat transfer surface area, reduce risk of knotting and/or kinking. The distal section of the catheter 9 may not have the third lumen 17 and/or the fourth lumen 18. The distal section of the catheter 9 can have a smaller catheter outer diameter 19 if the distal section of the catheter 9 does not have the third lumen 17 and/or the fourth lumen 18. For example, the distal section of the catheter 9 may only have the first lumen 15 and/or the second lumen 16. As another example, the heat the distal section of the catheter 9 can have the first lumen 15 and/or the second lumen 16 but may not have the third lumen 17 and/or the fourth lumen 18).

Figure 30:
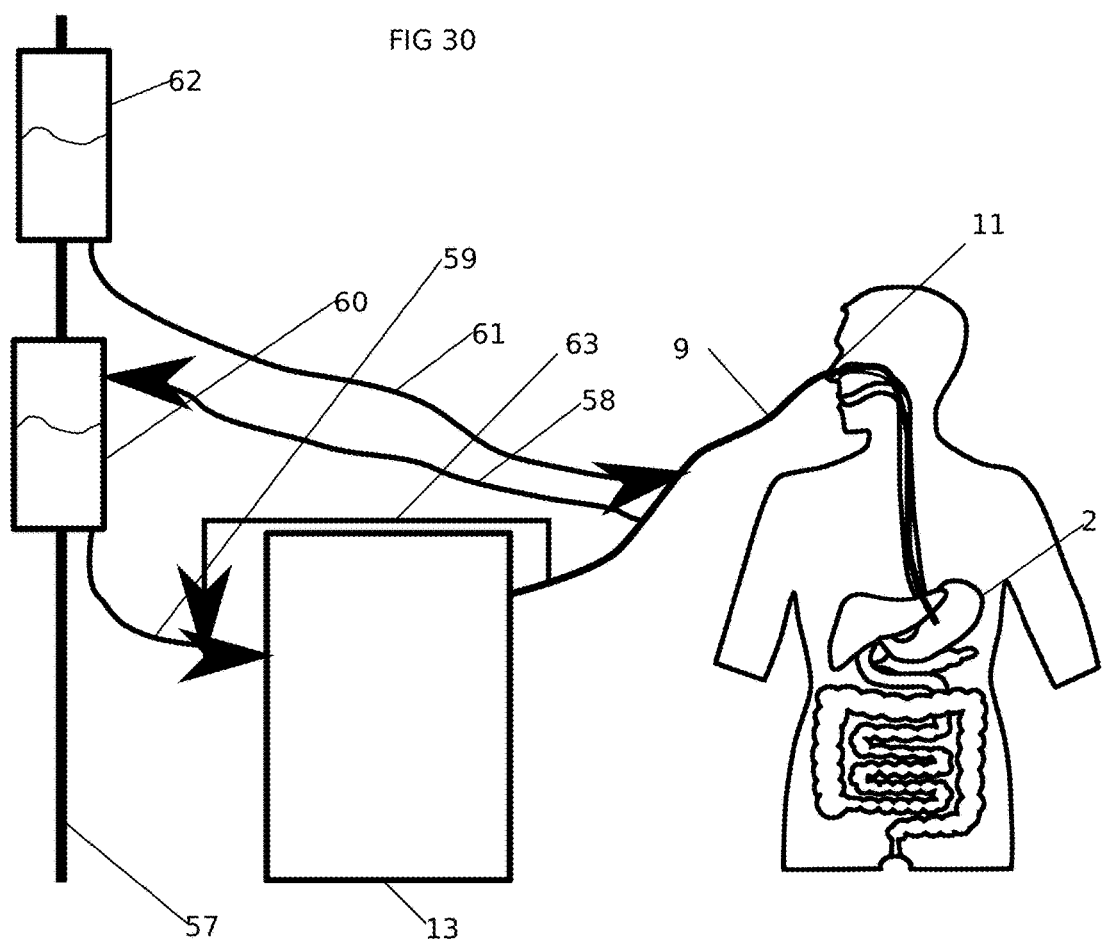
FIGS. 30 and 31 are schematics of a system that can provide thermal transfer to the stomach.

FIG. 30 illustrates that a bypass lumen 63 can allow some of the fluid 6 to pass directly from the output port of the heat exchange system 13 to the return port of the heat exchange system 13 without passing through the heat transferer 4 and/or entering the stomach 2. For example, the heat exchange system 13 can have (e.g., can require) a minimum flow rate which can be higher than can pass through the catheter 9. The bypass lumen 63 can allow the heat exchange system 13 to maintain a sufficiently high flow rate by allowing a portion of the fluid 6 to pass through the catheter 9 and the remainder to pass through the bypass lumen 63. The bypass lumen 63, the heat exchange system 13, the catheter 9 and/or other components can have sensors, pressure relief valves and/or switches to control the flow through the bypass lumen 63. For example, the user can adjust flow of the fluid 6 through the catheter 9 without adjusting the heat exchange system 13. For example, during startup, all of the fluid 6 can pass through the bypass lumen 6 until it is at the appropriate temperature. Once the fluid 6 is at the appropriate temperature, it can then be switched to flow entirely and/or partially through the catheter 9. During an emergency, all of the fluid 6 can flow through the bypass lumen 63 without turning off and/or adjusting the heat exchange system 13. The bypass lumen 63 can provide some damping and/or pressure relief to the catheter 9. An IV pouch 62 can be secured to an IV pole 57. The IV pouch 62 can include saline, nutrients, food, water, medication and/or other material. The contents of the IV pouch 62 can connect to the catheter 9 via an external accessory lumen 61. The external accessory lumen 61 can connect to the third lumen 17 and/or the fourth lumen 18. The flow rate of contents of the IV pouch 62 can be controlled by adjusting the height of the IV pouch 62 relative to the patient. The IV pouch 62 and/or the contents of the IV pouch 62 can be heated and/or cooled before and/or during the procedure. The contents of the IV pouch 62 can provide additional heating and/or cooling of the stomach 2, the pancreas 1, the duodenum 37 and/or other organs of the patient. The flow rate of contents of the IV pouch 62 can be controlled using a metering device, such as a peristaltic pump, drip chamber and/or valve. The return flow of the fluid 6 from the catheter 9 can pass through a return pouch 60 before returning to the heat exchange system 13. For example, fluid 6 can transfer from the catheter 9 to a catheter-pouch return lumen 58 to the return pouch 60 and then to a pouch-cooler return lumen 59. The height of the return pouch 60 relative to the patient and/or the heat exchange system 13 can be adjusted. The height of the return pouch 60 relative to the stomach 2 can impact the pressure of the fluid 6 in the balloon 3 and/or other elements of the heat transferer 4.

Figure 31:
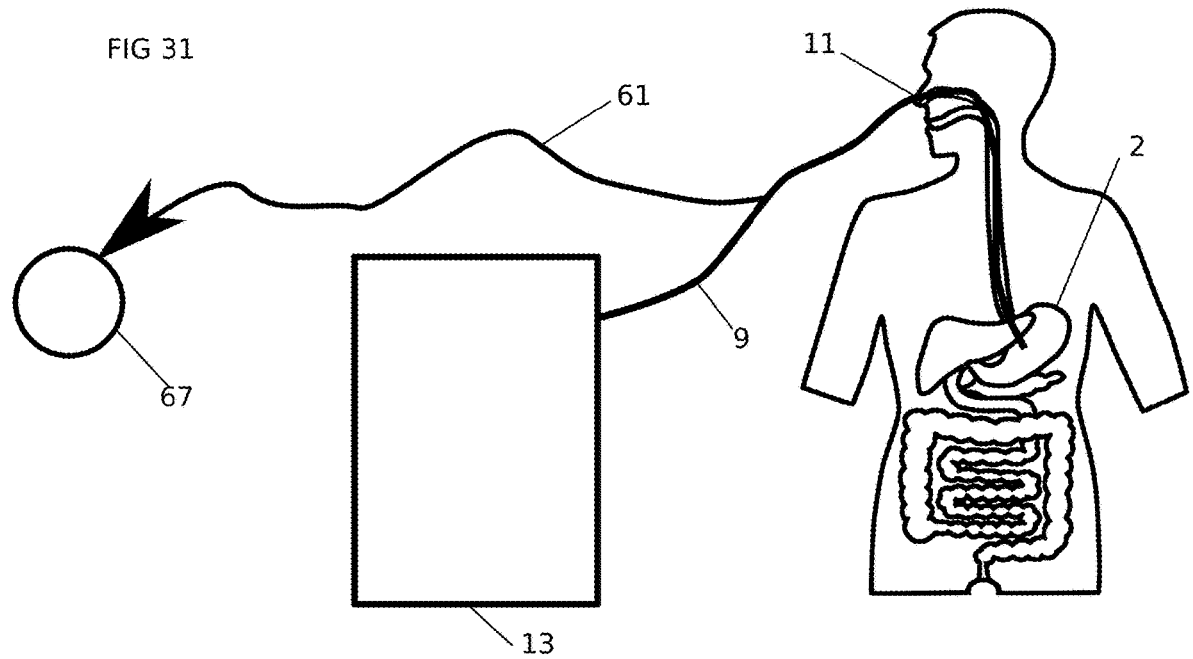

FIG. 31 illustrates that the external accessory lumen can be connected to a vacuum 67. The vacuum 67 can provide aspiration and/or decompression. The vacuum 67 can provide intermittent vacuum and/or pressure. The external accessory lumen 61 can be connected to the vacuum 67, the IV pouch 62 and/or other components/sensors. The heat exchange system 13 can transfer the fluid 6 in a constant direction and/or circuit. The heat exchange system 13 can inject and/or withdraw the fluid 6. For example, the heat exchange system 13 can use a peristaltic pump and/or a syringe pump to inject and/or withdraw the fluid 6. The heat exchange system 13 can heat and/or cool the fluid 6. The heat transferer 4 can heat and/or cool tissue and/or organs. The heat transferer 4, the catheter 9 and/or the balloon 3 can heat and/or cool the stomach 2, the pancreas 1 and/or the duodenum 37.

Figure 32:
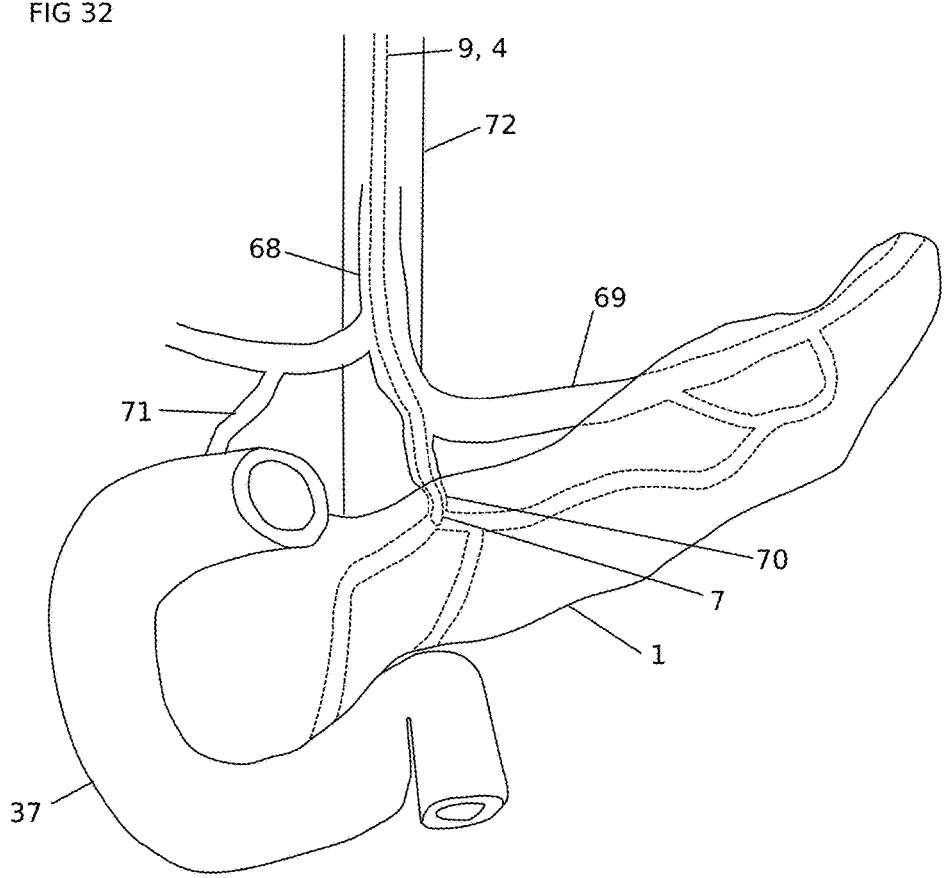
FIG. 32 illustrates an exemplary view of the duodenum and the pancreas, with the catheter passing through an artery.

FIG. 32 illustrates that the catheter 9 and/or the heat transferer 4 can access the pancreas 1 through an artery. For example, the catheter 9 can pass through an aorta 72, a celiac trunk 68, a splenic artery 69, a pancreatic artery 70 and/or a gastroduodenal artery 71. The catheter 9 can provide more efficient and/or localized heat transfer if it is located inside of an artery. For example, the catheter 9 can provide more efficient and/or direct heat transfer to the pancreas 1 by being located inside of the pancreatic artery 70. The catheter 9 can pass through the venous system.

Figure 33:
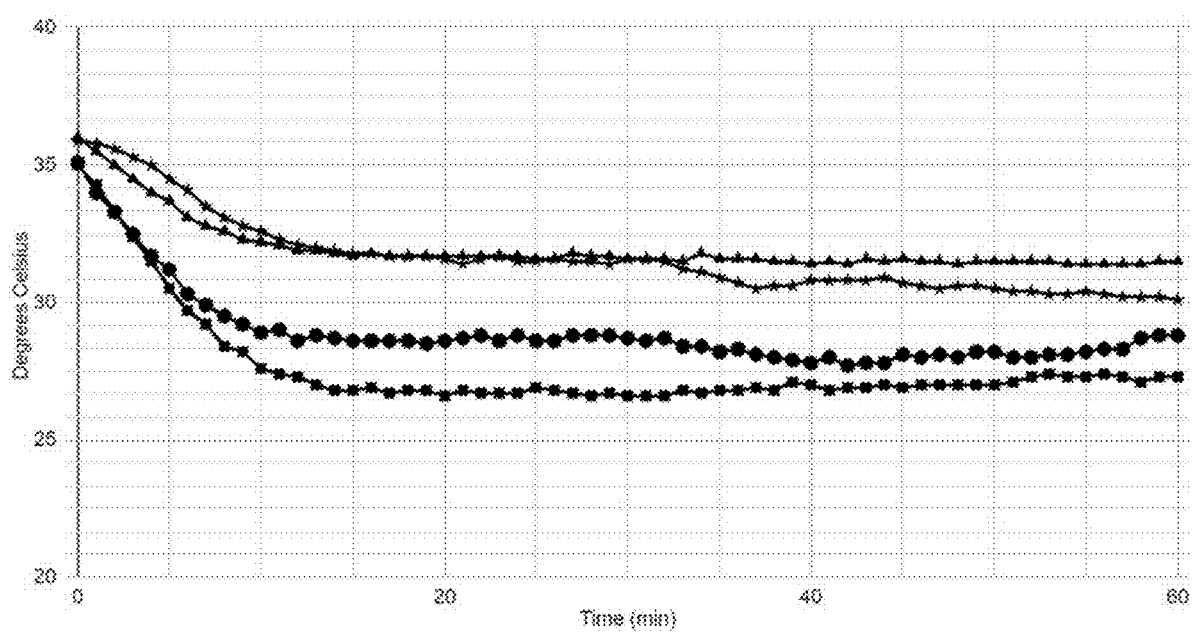
FIG. 33 illustrates data from a simulated localized cooling system

FIG. 33 illustrates that the heat transferer 4 can cool a physical simulation of the stomach 2 and/or the pancreas 1. The model used to obtain the data shown in FIG. 33 included a pliable silicone stomach 2 and pancreas 1 placed in a 37 degree Celsius water bath. Thermocouples were placed at different locations in the pancreas 1. Approximately 90 cm of the catheter 9 was placed inside of the simulated stomach 2 similar to the configuration illustrated in FIG. 18. Approximately 10 mL of fluid was placed inside of the stomach 2 to simulate gastric juices. The catheter 9 was connected to an external recirculating cooling system, with approximately 100 mL/min of 5-15 degree Celsius fluid flowing through the catheter 9. After approximately 30 minutes, a mechanism gently manipulated the stomach 2 to simulate gentle peristalsis and/or motility of the stomach 2. FIG. 33 shows that the thermal therapy system 33 can cool the pancreas 1 in a physical simulation. FIG. 33 shows that gentle peristalsis and/or motility of the stomach 2 can help to average the temperatures of the pancreas 1 (e.g., the second half of the graph has a narrower band of max/min temperatures than the first half). The heat transferer 4 used to obtain the data in FIG. 33 was removing approximately 20-30 Watts of heat at steady state.

Figure 34:
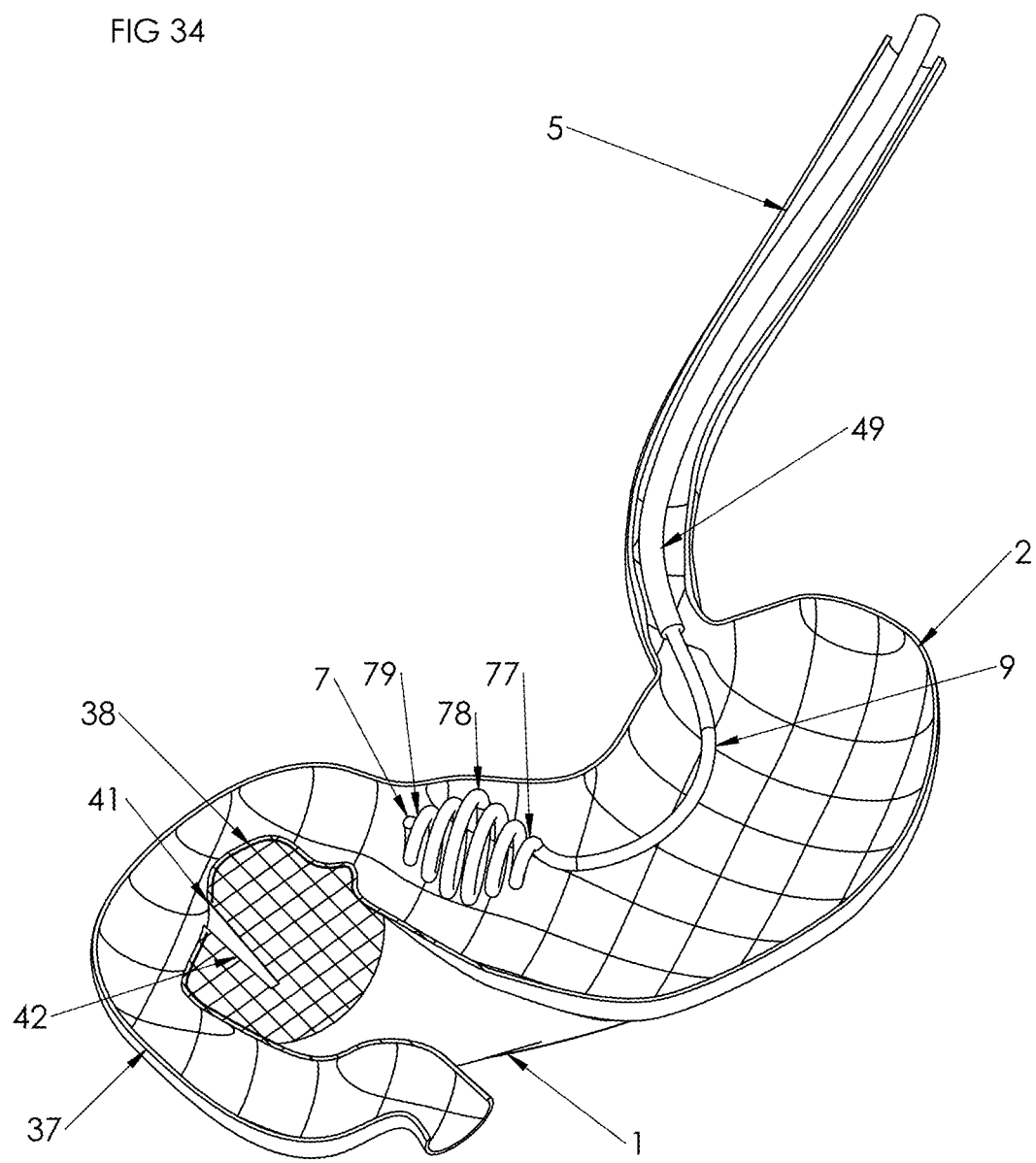
FIG. 34 illustrates the stomach and pancreas in an isometric view with the anterior half removed.

FIG. 34 illustrates a catheter that can be rotated to locate and advance via the catheter tip 7 into the pylorus 65 and into the duodenum 37. The catheter 9 can have a tapered coil distal diameter 79 that can be smaller than the tapered coil maximum diameter 78. The coil diameter at the tapered coil proximal diameter 77 can be less than the tapered coil maximum diameter 78 as it transitions to the helical sections of the catheter 9. The coil diameter at the tapered coil proximal diameter 77 can be less than the tapered coil maximum diameter 78 as it tapers to the helical sections of the catheter 9. At the nose or the narrowest sections of nasal-gastric passage, there can be an introducer 49 or an open ended catheter that can provide a bearing surface for the main cooling catheter 9 when the forward and rotational forces are applied to helical section of the catheter through the pylorus and into the intestine. The introducer can prevent more sensitive portions of the nasal passage from experiencing torque applied to the main heat transfer catheter.

FIGS. 35a-35d illustrate a linear everting catheter with a first catheter 80 that can be connected to a membrane 82 at its distal end. The membrane 82 can be connected to a second catheter 81 and with a seal or connecting port, can have an annulus that responds to hydraulic pressure supplied by fluid, media, or a gas. The hydraulic pressure allows the membrane 82 to evert or roll inside out in a frictionless manner Within the first 80 and second catheter 81, a third catheter can be delivered. The third catheter can have lumens for inflow and outflow of cooling (or heating) media supplied by the external controller, and a lumen for aspiration or delivery of nutritional materials for the patient.

The linear everting catheter can deliver the catheter system through the nasopharynx and into the esophagus 5. The distal end of the first catheter 80 can be positioned at the nostril of the patient and can be hydraulically pressurized by a fluid, media, or gas by an external source. Once pressurized the second catheter 81 can be advanced to allow the membrane 82 to roll through the nasopharynx and into the esophagus 5. Once the membrane 82 and second catheter are fully extended, within the lumen of the second catheter 81 a third catheter can be delivered to supply the catheter cooling system described herein. The hydraulic fluid, media, or gas can supply a passive or active insulation source to protect the patient's nasopharynx from the thermal cooling energy from the third catheter. As an active source of insulation, warming fluid, media, or gas can be introduced within the annulus of the membrane to provide insulation from the cooling energy supplied by the internal third catheter. As a passive source of insulation, the annulus of the linear everting catheter can be filled with air or gas to supply an insulator.

Figure 35A:
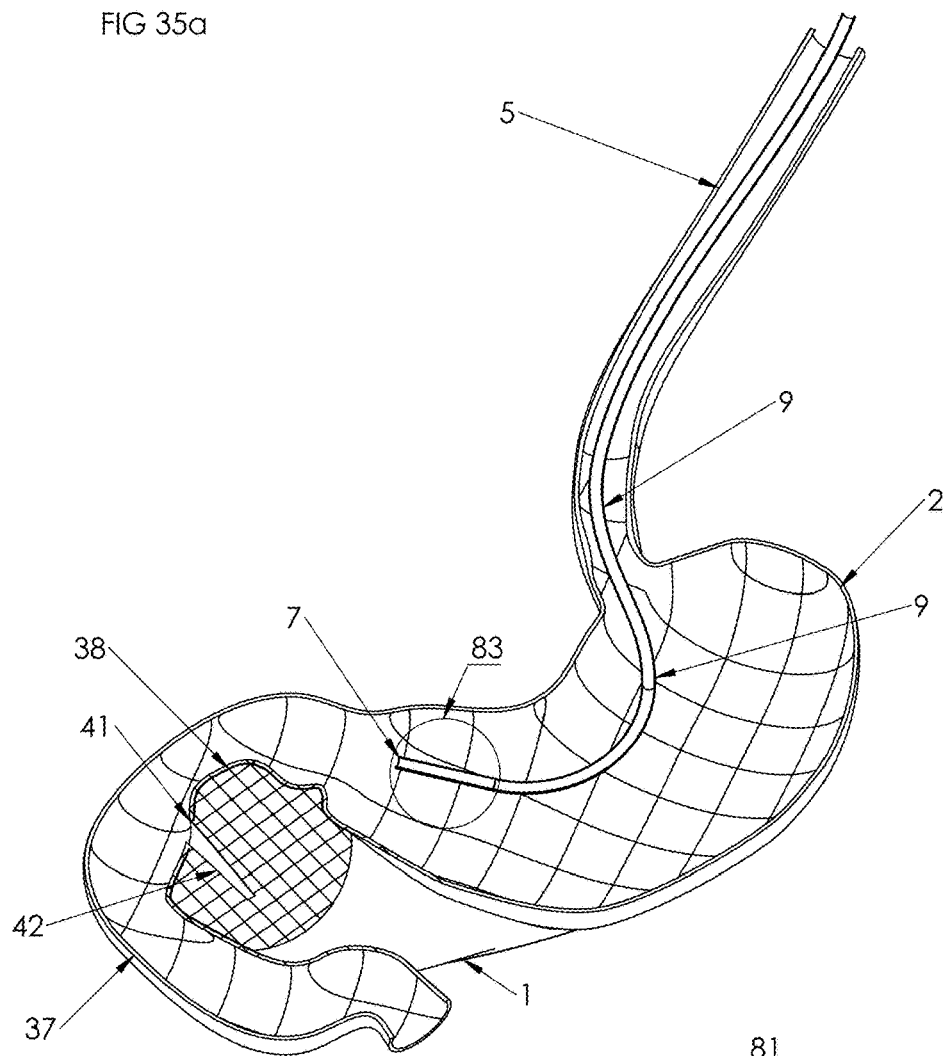
FIGS. 35a-35d illustrate the stomach, the pancreas and a catheter in an isometric view with the anterior half removed.
Figure 35B:
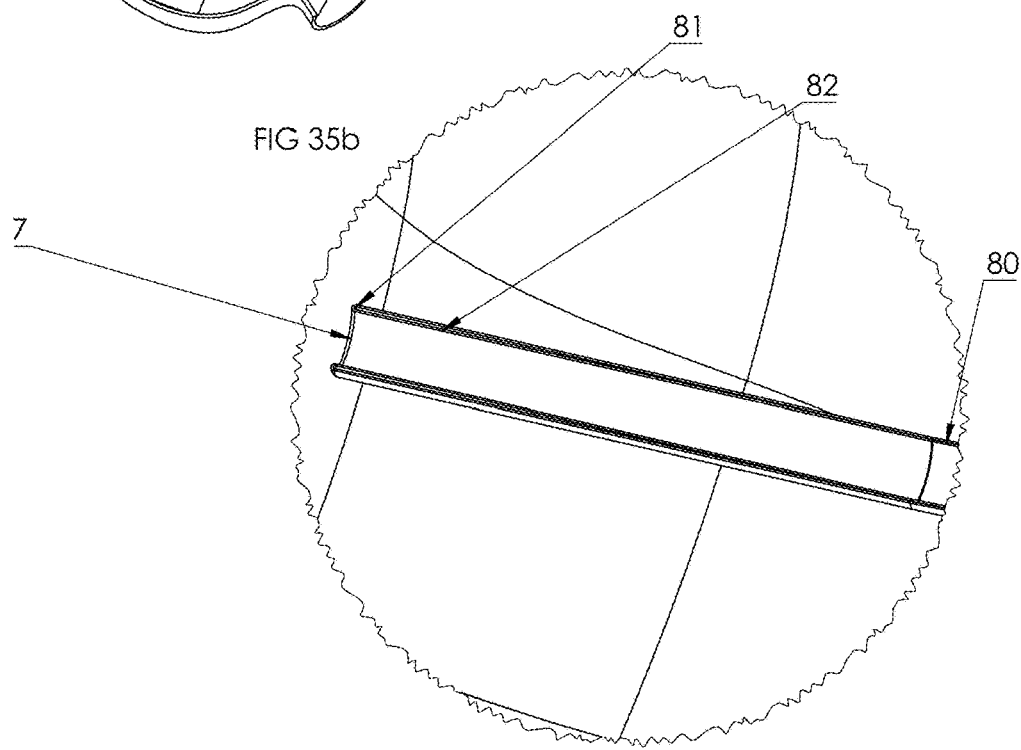
Figure 35C:
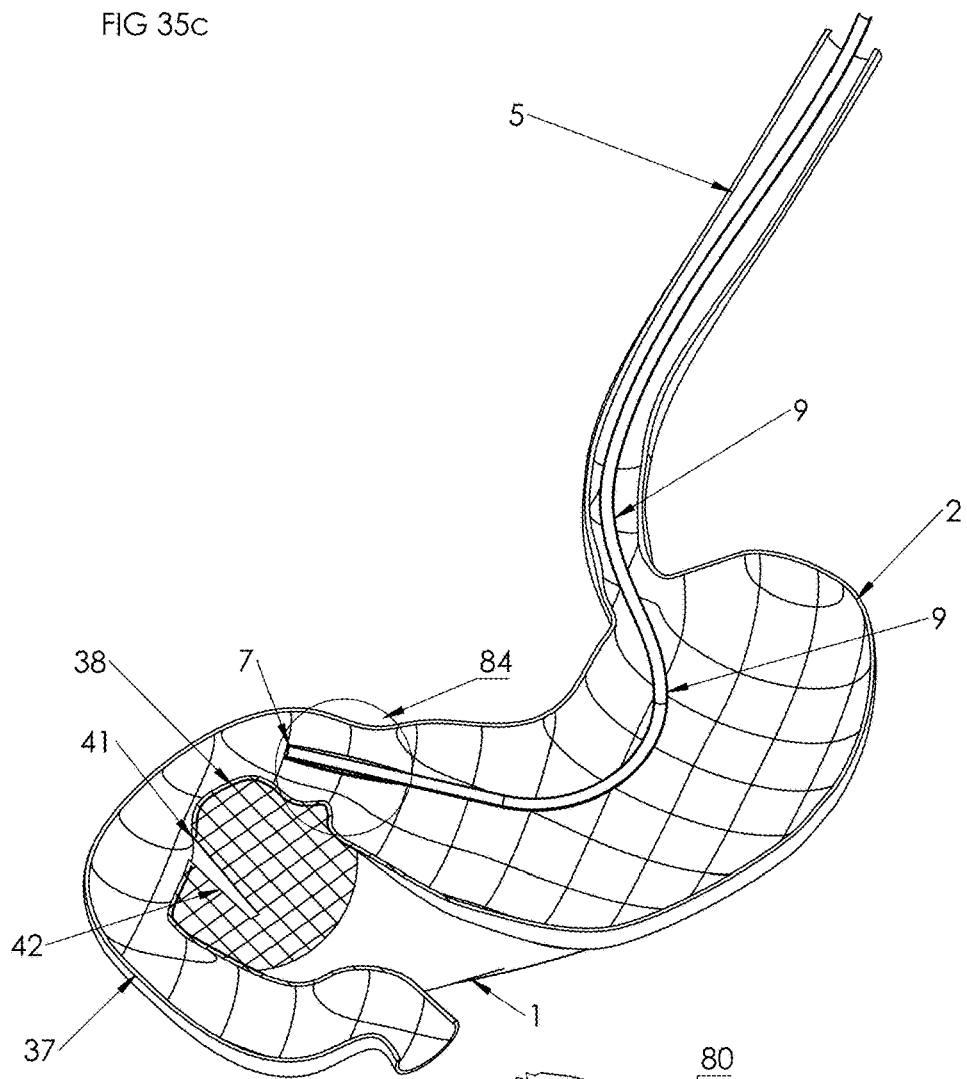

FIG. 35b illustrates that the linear everting catheter can be configured at the distal end of the catheter system once delivered within the patient's stomach. The distal end 7 of the first catheter 80 can be positioned towards the pylorus of the patient. The first catheter 80 can be connected to a membrane 82 that can be connected to a second catheter and upon pressurization by a fluid, media, or gas, the second catheter 81 can be advanced to evert the membrane toward the pylorus. The unrolling action of the membrane 82 can be self-seeking and conformable to intubate the pylorus 65 and advance into and through the duodenum 37. Within the second catheter 81 can be a lumen for a third catheter that can deliver the thermal cooling energy to this location of the anatomy.

The entire catheter system can be configured with both a linear everting delivery system to provide access through the patient's nasopharynx, and a second linear everting delivery system to bring the cooling energy into the duodenum 37 of the patient.

Figure 35D:
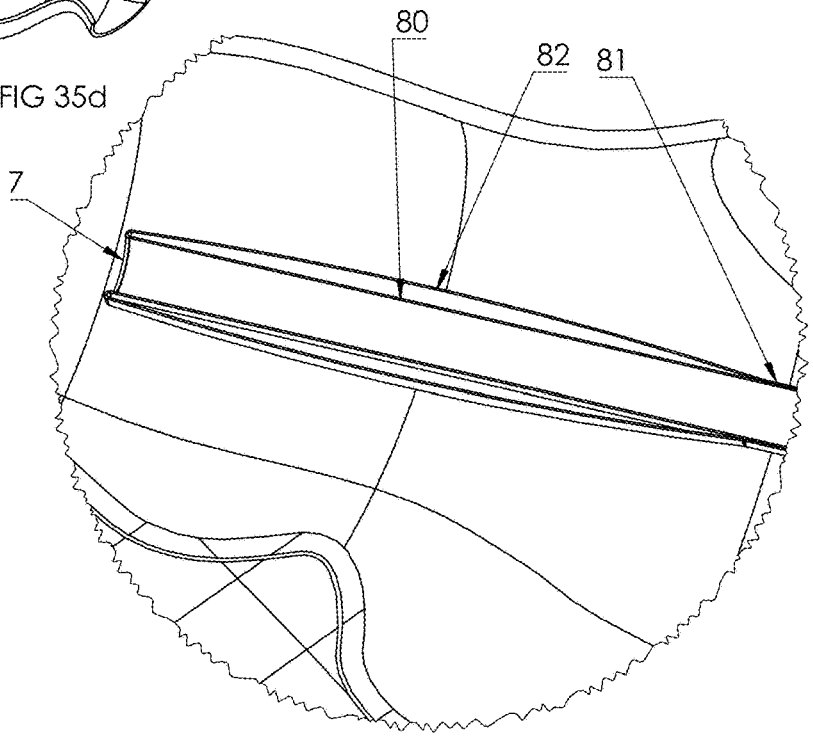

FIG. 35d illustrates that to deliver fluid 6 into the duodenum 37, the membrane 82 can be everted to form two layers that can be always connected at the distal end of the first catheter tip 7 where the inner first catheter 80 layer begins to evert to the second catheter 81 outer layer. The proximal ends of the layers are temporarily locked together by an annular clamp during initial insertion of the catheter to the desired area. Upon reaching the stomach, the annular clamp can be unlocked at the proximal end and the second catheter 81 can slide proximally relative to the first layer 81. Distal movement of the second catheter 81 along the axis on the first catheter 80 causes the distal end of the catheter to advance forward into the stomach past the pylorus 65 and into the duodenum 37. Heat transfer fluid be introduced at the proximal end and can travel between the first catheter 80 and the second catheter 81 to reach the intestine and stomach. Heat transfer fluid can be cycled for constant heat exchange with the tissue surrounding the catheter. The center of the lumen of the first catheter 80 can serve as an aspiration or feeding tube.

FIG. 35d illustrates a linear everting catheter with single layer catheter that can be everted to form two layers that can be always connected at the catheter tip where the first catheter 80 layer begins to evert to the second catheter 81 outer layer. FIG. 35d illustrates that a heat transfer catheter having one or more lumens for a fluid 6 or for feeding and aspiration can be connected to the center of the first catheter 80 inner layer of the linear everting catheter. The proximal ends of the layers are temporarily locked together by an annular clamp during initial insertion of the catheter 9 to the desired area. Upon reaching the stomach, the annular clamp can be unlocked at the proximal end and the outer layer can slide proximally relative to each layer. Distal movement of the outer layer along the axis on the inner layer causes the distal end of the catheter to advance forward into the stomach past the pylorus 65 and into the duodenum 37. After the heat transfer catheter 9 is delivered to the desired location, the first catheter 80 and second catheter 81 at the proximal end can be locked by annular compression to stabilize the position and prevent relative motion.

Figure 36:
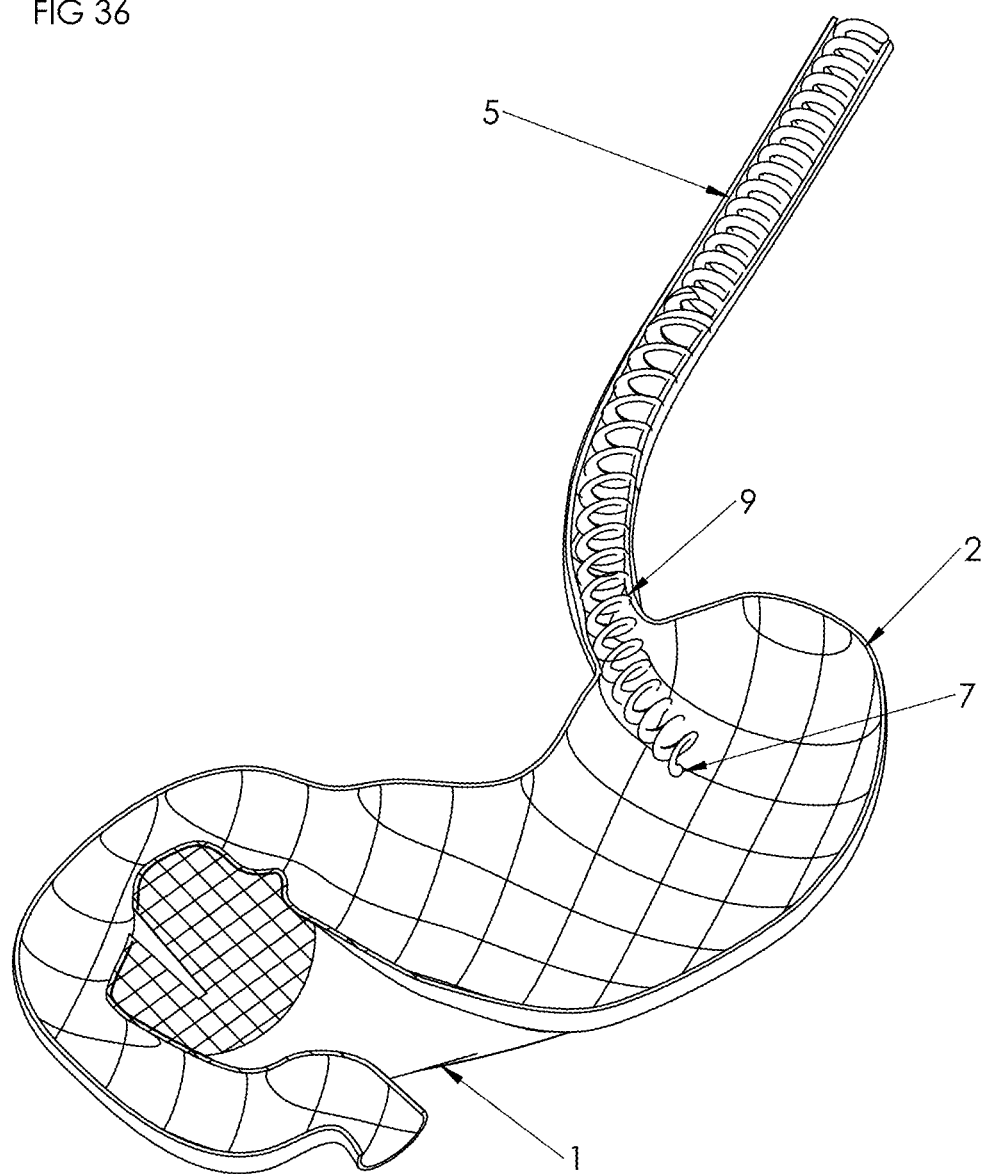
FIG. 36 illustrates the stomach and pancreas in an isometric view with the anterior half removed.

FIG. 36 illustrates that the catheter 9 can be located in the stomach 2 and/or the esophagus 5. The catheter 9 can be coiled to maximize contact with adjacent organs, including but not limited to the esophagus 5. For example, the catheter 9 can be coiled to ensure contact with the esophagus 5 while maintaining radial and/or longitudinal flexibility. The coiled section of the catheter 9 can expand, contract and/or deform to ensure contact with the esophagus 5. The cross-section of the coil can be circular (e.g., it can look like a standard compression and/or extension spring) or it can be another shape (e.g., oval, square, triangular, etc.). A coiled catheter 9 can maximize thermal contact and/or thermal transfer with the esophagus 5. The fluid 6 can circulate within the catheter 9. The first lumen 15 can be oriented on the external circumference of the coil and the second lumen 16 can be oriented on the internal circumference of the coil to maximize heat transfer with the esophagus 5.

Figure 37A:
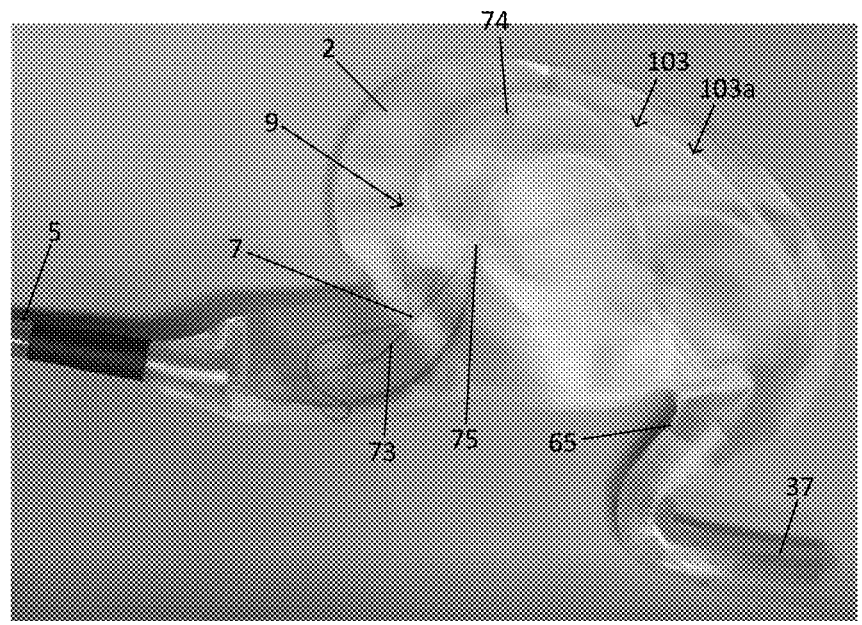
FIG. 37a illustrates a variation of the catheter in the stomach.
Figure 37B:
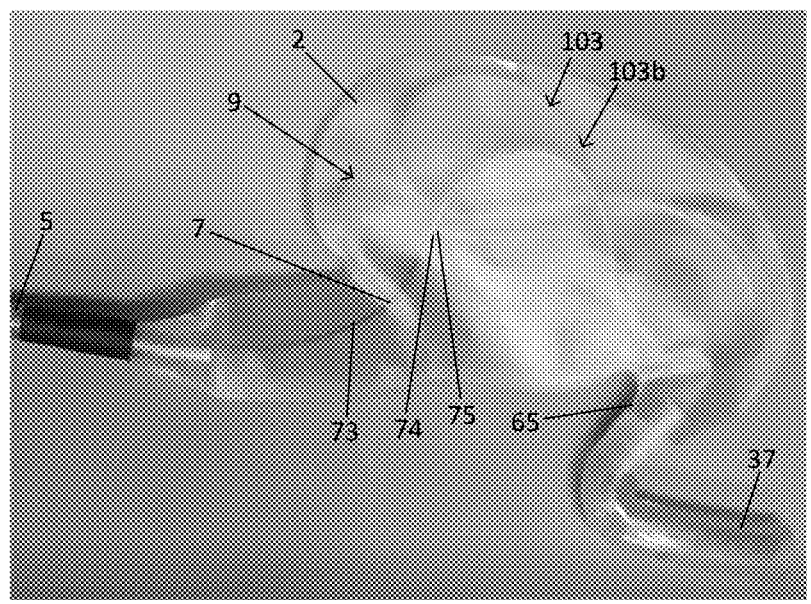
FIG. 37b illustrates a variation of the catheter in the stomach.

FIGS. 37a and 37b illustrate that the catheter 9 can have a lattice shape 103 when the catheter 9 is in a deployed configuration. FIGS. 37a and 37b illustrate that actuating (e.g., withdrawing, pulling) the tether 73 can change the lattice shape 103, for example, from a lattice first shape 103a to a lattice second shape 103b. FIG. 37a illustrates that the catheter 9 can have the lattice first shape 103a before the tether 73 is actuated, for example, when the tether 73 is in a non-actuated position. FIG. 37b illustrates that the catheter 9 can have the lattice second shape 103b after the tether 73 is actuated, for example, when the tether 73 is in an actuated position. The catheter 9 can be deployed with or without the tether 73. The catheter 9 can be deployed with or without actuating the tether 73. For example, the deployed configuration of the catheter 9 in FIG. 37a can be a partially deployed configuration of the catheter 9, and the deployed configuration of the catheter 9 in FIG. 37b can be a fully deployed configuration of the catheter 9. As another example, the deployed configuration of the catheter 9 in FIG. 37a can be a fully deployed configuration of the catheter 9. The catheter 9 may not have a tether (e.g., the tether 73). In such cases, the deployed configuration of the catheter 9 in FIG. 37a can be a fully deployed configuration.

Figure 38:
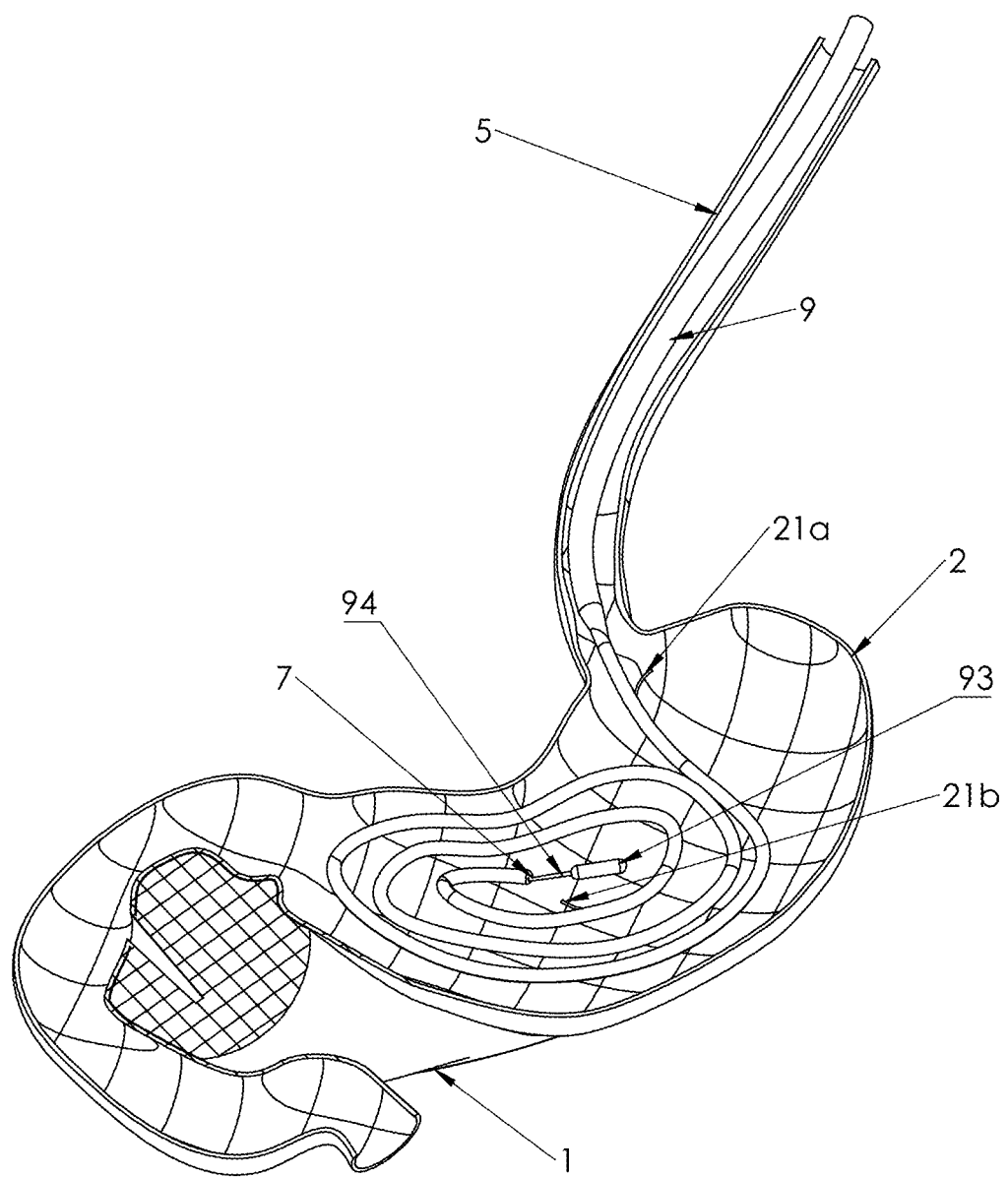
FIG. 38 illustrates a variation of the catheter with a remote sensor

FIG. 38 illustrates that the catheter 9 can have a remote sensor 93. The remote sensor 93 can be integral to the catheter 9 and/or separate to the catheter 9. For example, the remote sensor 93 can be inserted and/or swallowed separately than the catheter 9. For example, the remote sensor 93 can be adhered and/or secured to the catheter 9 during insertion and then may be separated and/or partially detached from the catheter 9 when the device is in the stomach 2. The remote sensor 93 can be tethered to the catheter 9 with a remote sensor tether 94. The remote sensor 93 can communicate wirelessly and/or without wires. The remote sensor 93 can have a battery source and/or a power generation source (e.g., thermo-electric). The remote sensor 93 can be charged and/or powered wirelessly (e.g., induction charging). The remote sensor tether 94 can be optically and/or electrically communicated to the catheter 9. For example, the remote sensor tether 94 can include electrical wires and/or fiberoptic cables. The remote sensor 93 can monitor temperature, pH, stomach motility and/or other key metrics. The remote sensor 93 can include a camera. The remote sensor 93 can monitor different wavelength (e.g., optical, infrared and/or ultraviolet). The remote sensor 93 can measure the temperature of the stomach 2 and/or the gastric pancreas wall 8. The remote sensor 93 can detect if the surrounding media is solid, liquid and/or gas (e.g., by measuring electrical resistance and/or conductivity across two points).

Figure 39A:
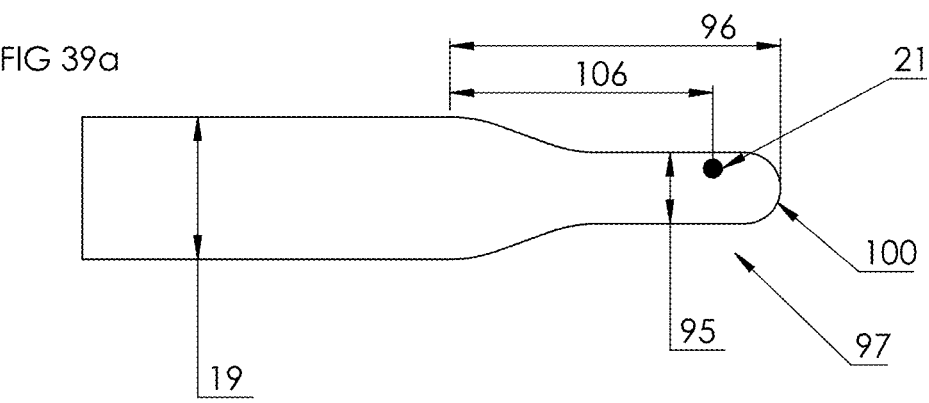
FIG. 39a-39b illustrates a tip of the device with a proboscis.
Figure 39B:
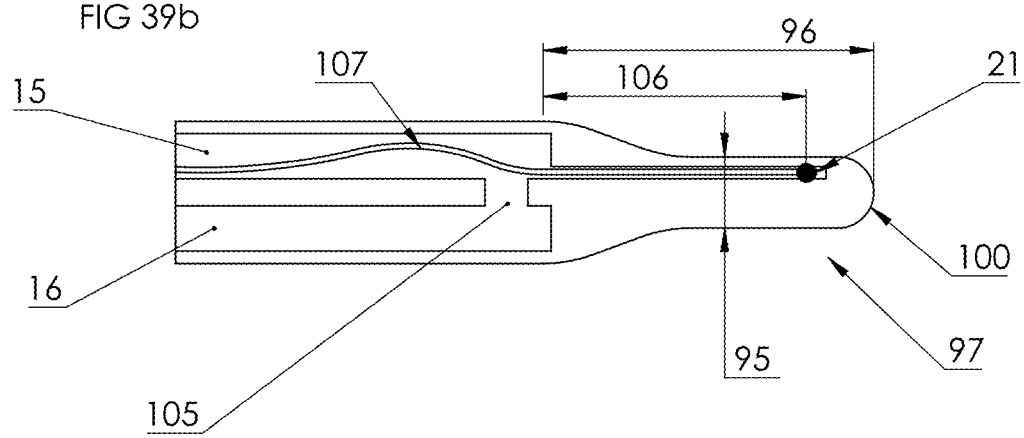

FIGS. 39a and 39b illustrate that the tip of the catheter 9 can feature a proboscis 97. A proboscis diameter 95 can be smaller, larger and/or equal to the catheter OD 19. The stiffness of the proboscis 97 can be the same and/or different than the rest of the catheter 9. For example, the proboscis 97 can provide easier insertion of the catheter 9 into the nose 11 and/or other organs. The proboscis 97 can provide a soft tip to prevent the catheter 9 from irritating the wall of the stomach 2 and/or other organs. The proboscis 97 can prevent the catheter 9 from tunneling into tissue. The proboscis 97 can have a different radiopacity and/or echogenicity than the rest of the catheter 9. For example, the proboscis 97 can include a metal marker band. The proboscis 97 can be denser than the rest of the catheter 9. The catheter 9, the proboscis 97 and/or any portion of the thermal therapy system 33 can include radiopaque additives, such as barium sulfate (i.e., $BaSO_4$). A proboscis length 96 can be approximately 1 cm. The proboscis 97 may have an atraumatic proboscis tip 100. The proboscis tip may be rounded and/or dome shaped. The sensor 21 may be embedded and/or secured to the proboscis 97. For example, the sensor 21 may be a thermistor, thermocouple, RTD and/or another temperature sensor. The sensor 21 may measure pH and/or be a camera. The remote sensor 93 may be the sensor 21. The first lumen 15, the second lumen 16, the third lumen 17 and/or the fourth lumen 18 may and/or may not extend into the proboscis 97. For example, the proboscis 97 may be thermally isolated from the remainder of the catheter 9 so that it can more accurately measure the temperature of the stomach 2. A sensor cable 107 may connect the sensor 21 to an external console, a DAQ, a data acquisition device, the heat exchange system 13, a computer and/or other systems. The sensor cable 107 may be the remote sensor tether 94. The sensor cable 107 may be wires, cables, fiber optics tubes and/or a conduit that can transmit information. The sensor cable 107 may pass through the outside of the catheter 9 and/or through one of the catheter lumens. The catheter 9 may include a merge zone 105. The merge zone 105 may allow the first lumen 15 to fluidly communicate with the second lumen 16. A sensor proboscis length 106 may be less than, equal to and/or greater than the proboscis length 96. The sensor proboscis length may be sufficiently large to minimize heat transfer between the catheter 9 and the sensor 21. For example, The region of the catheter 9 proximal to the merge zone 105 may be warmer and/or cooler than the region distal to the merge zone 105. The sensor 21 may be an infrared temperature sensor.

Figure 40:
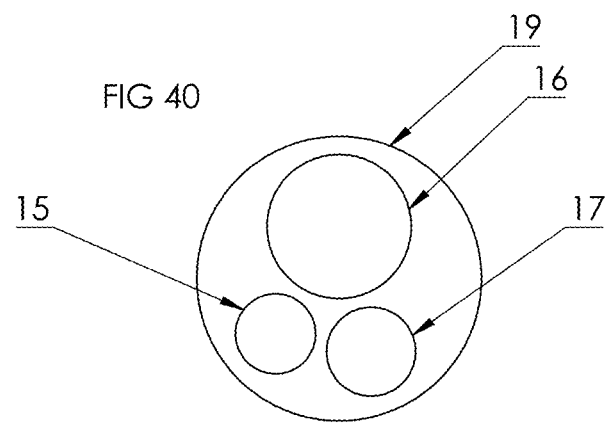
FIG. 40 illustrates a cross-section of the catheter

FIG. 40 illustrates that the diameters of the first lumen 15, the second lumen 16 and/or the third lumen 17 may be the same and/or different. The pressure at the distal tip of the catheter 9 and/or the balloon 3 can be determined by the ratio of the hydraulic diameter of the first lumen 15 and the hydraulic diameter of the second lumen 16. For example, the ratio of the hydraulic diameters of the first lumen 15 and the second lumen 16 can be directly proportional to the pressure drop across the length of the lumens (and therefore the pressure at the balloon 3). It may be desirable to reduce the pressure of the balloon 3 for improved compliance and/or flexibility.

Figure 41:
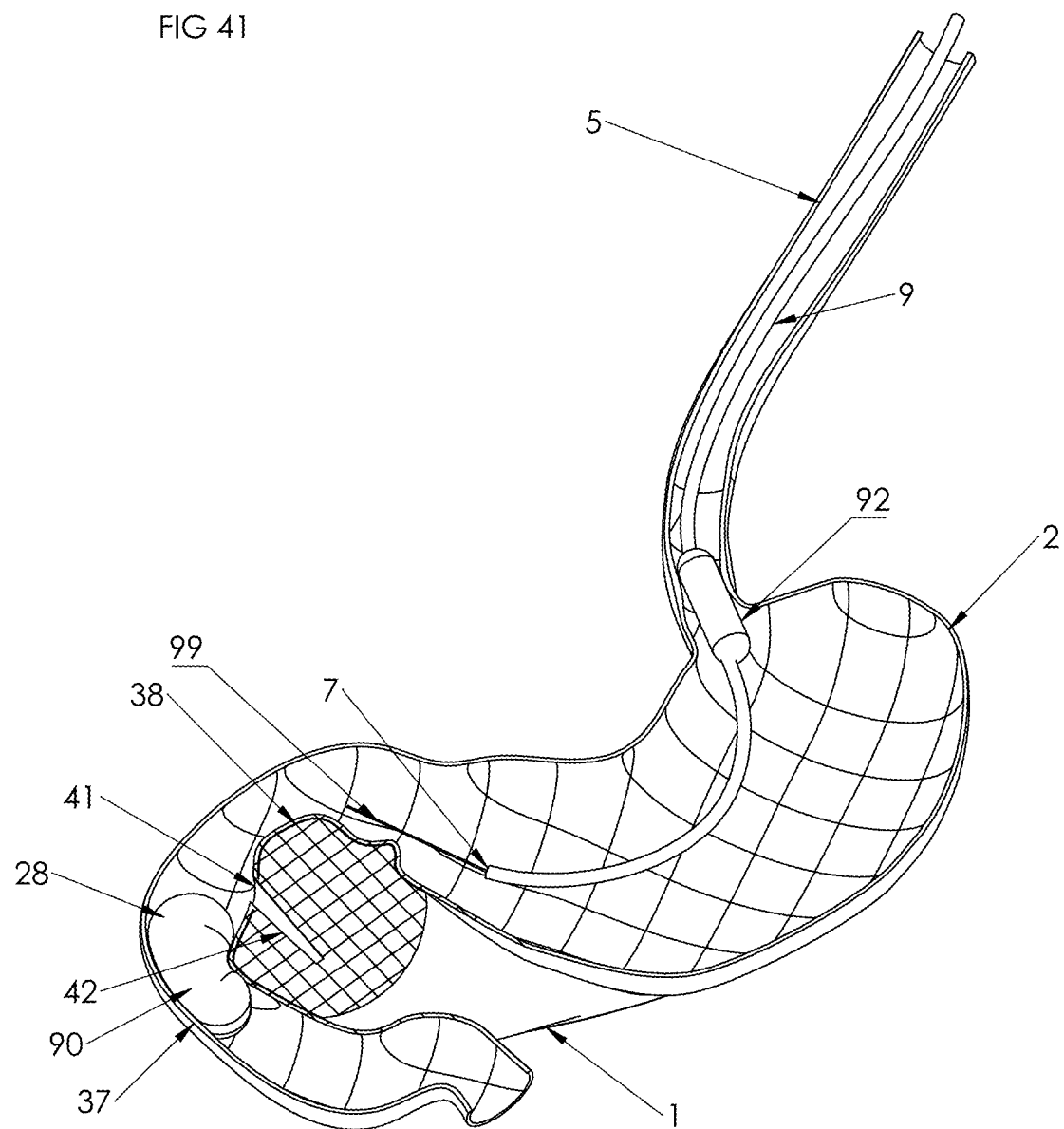
FIG. 41 illustrates a variation of the catheter inserted over a guidewire with an esophageal valve.

FIG. 41 illustrates that the catheter 9 can be introduced over a guidewire 99. The guidewire 99 may pass through the third lumen 17 and/or the fourth lumen 18. The guidewire 99 may be coated with a hydrophilic and/or hydrophobic material. The guidewire 99 may be separate and/or integral to the catheter 9. The thermal therapy system 33 can include an esophageal valve 92. The esophageal valve 92 can control the amount and/or rate of fluid passing from the esophagus 5 to the stomach 2 and/or vice-versa. The catheter 9 may pass through the esophageal valve 92. The catheter 9 may be permanently secured to and/or removable from the esophageal valve 92. The esophageal valve 92 may be an anti-reflux valve. The guidewire 99 can guide the catheter 9 to certain regions (e.g., the pylorus and/or antrum of the stomach 2).

Figure 42:
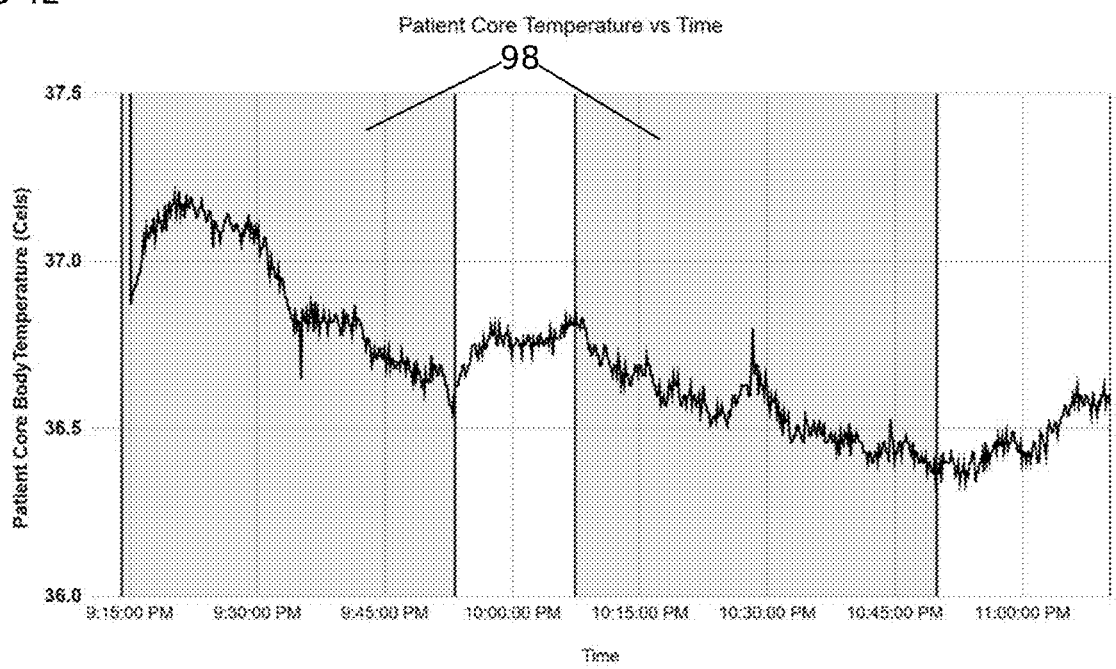
FIG. 42 illustrates how the core body temperature can be impacted using a thermal therapy system.

FIG. 42 illustrates that the thermal therapy system 33 can actively control the core body temperature of a patient. For this study, approximately 75 cm of the catheter 9 was randomly positioned in the stomach (similar to FIG. 18), with a cross-section similar to that shown in FIG. 27b. The core body temperature of the human patient dropped during active cooling periods 98 and rose when the cooling was terminated. Core body temperature was monitored using a zero-heat flux thermometer (3M Bair Hugger™).

Figure 43:
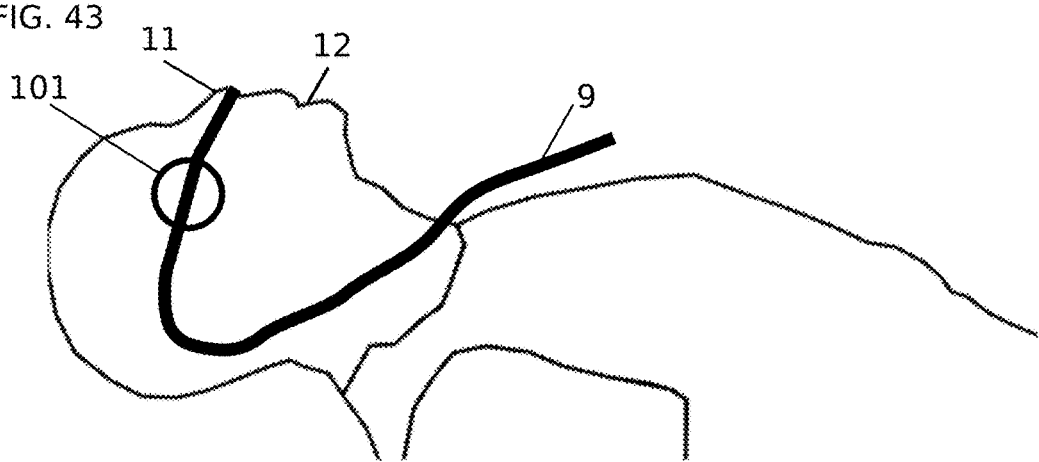
FIG. 43 illustrates a thermal insulation pad on the face of a patient.

FIG. 43 illustrates that an insulation pad 101 may be placed between the catheter 9 and the patient to prevent any discomfort. The insulation pad 101 may be a soft foam. The insulation pad 101 may be permanently secured to the catheter 9 and/or removable. The insulation pad 101 can have adhesive on one surface to adhere the catheter 9 and/or the insulation pad 101 to the patient.

Figure 44:
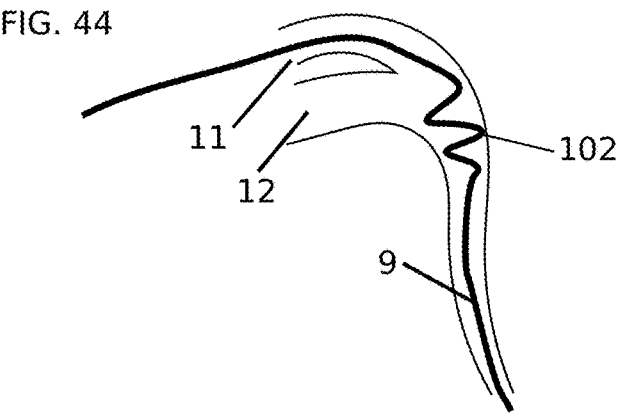
FIG. 44 illustrates a thermal insulation mechanism on the back of the throat.

FIG. 44 illustrates that the catheter 9 may have an insulation coil 102. The insulation coil 102 may be a preformed shape of the catheter 9. The insulation coil 102 may minimize contact between the catheter 9 and the back of the throat and/or other organs. A guidewire 99 can keep the insulation coil 102 straight during insertion into the nose 11. The insulation coil 102 may have foam insulation to minimize thermal transfer between the catheter 9 and the patient.

Figure 45A:
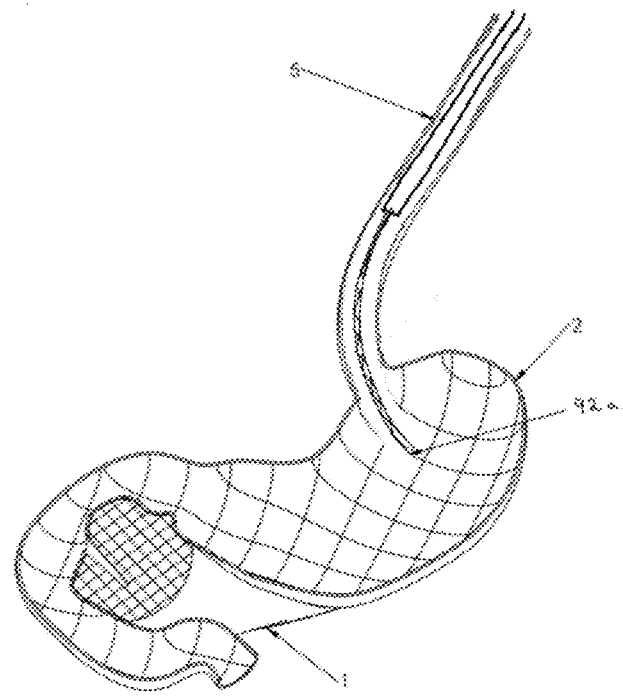
FIGS. 45a and 45b illustrate a variation of the catheter in the stomach with an expandable catheter array.
Figure 45B:
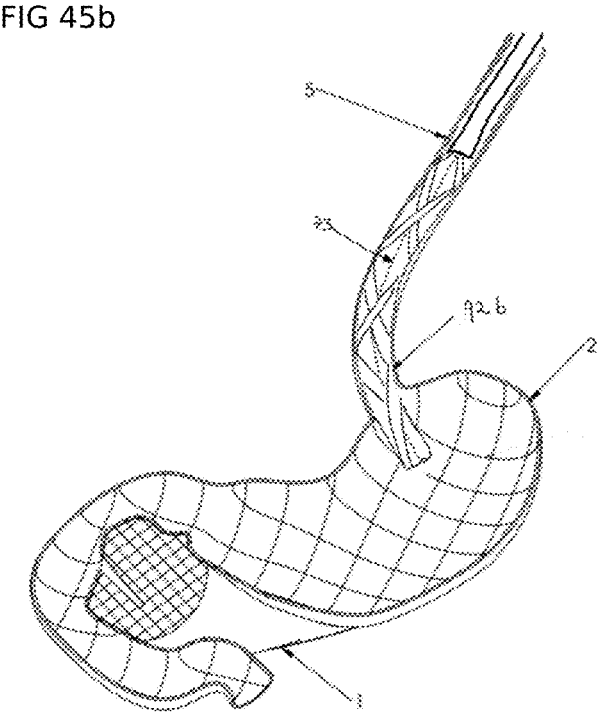

FIGS. 45a and 45b illustrate a variation of the catheter 9 in the stomach 2 with an expandable catheter array.

Figure 46A:
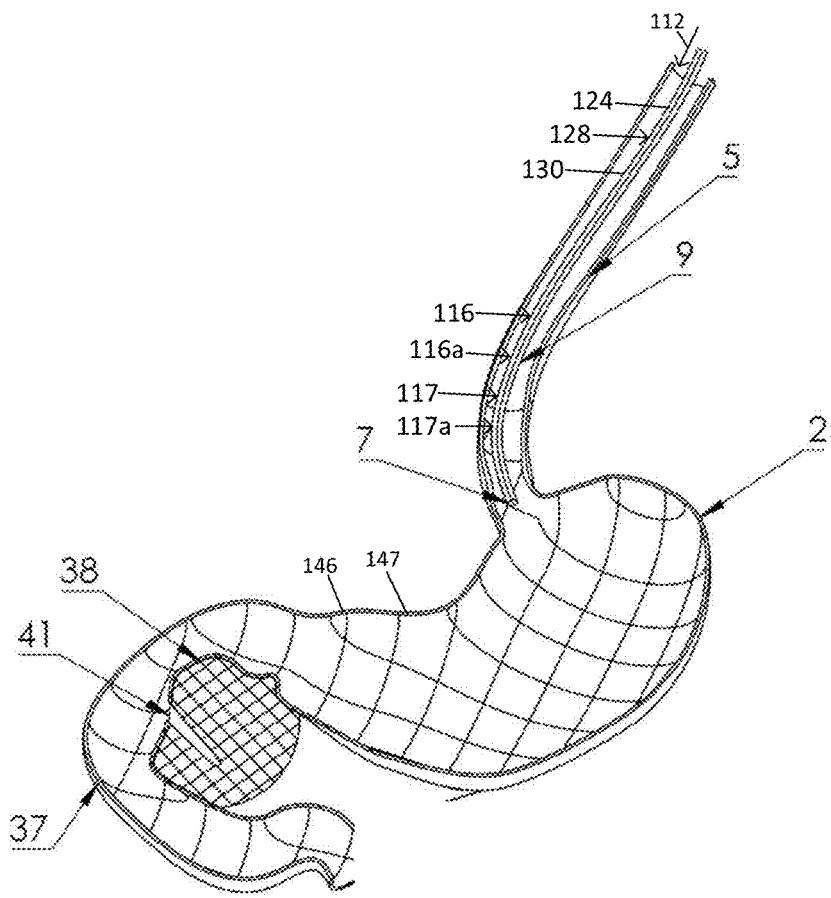
Figure 46B:
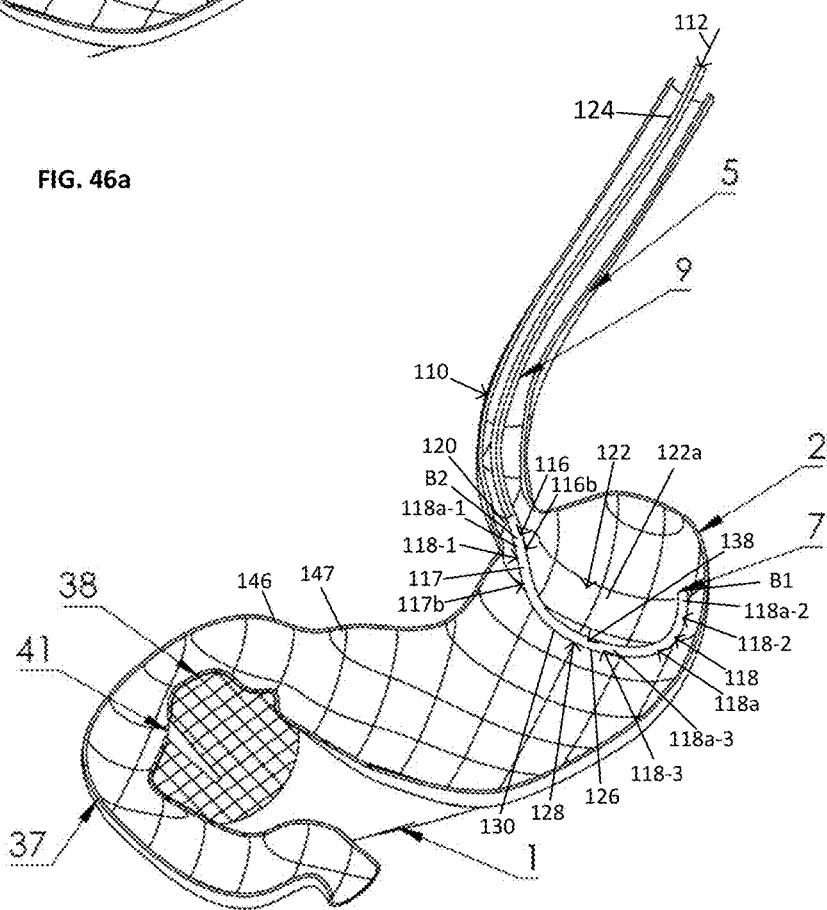
Figure 46C:
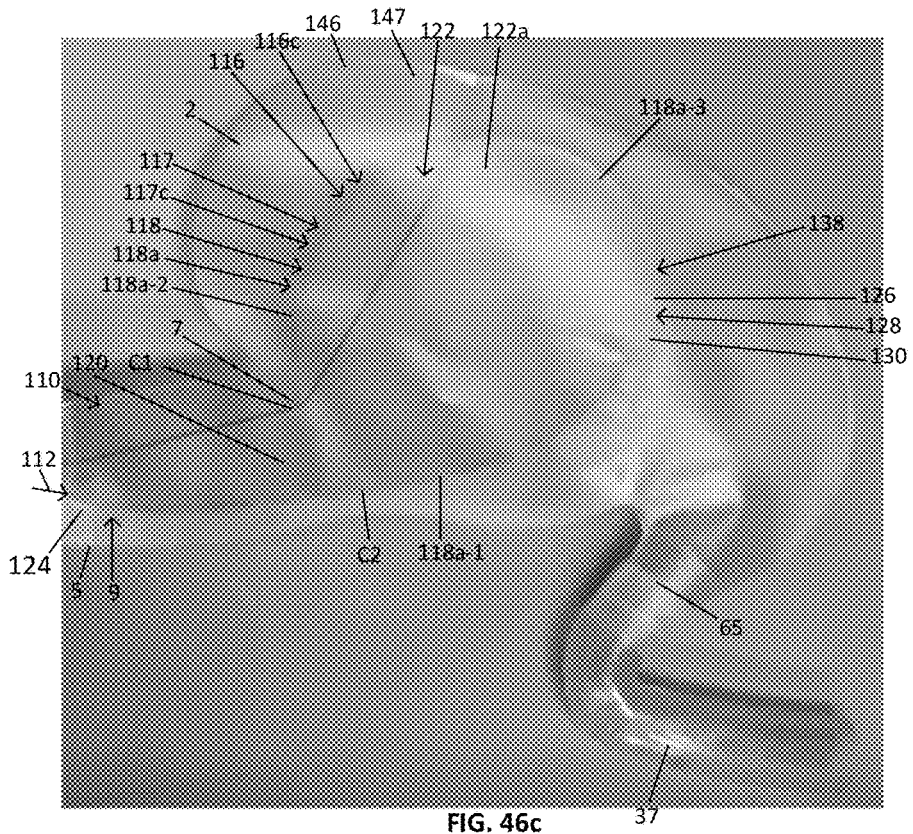
Figure 46D:
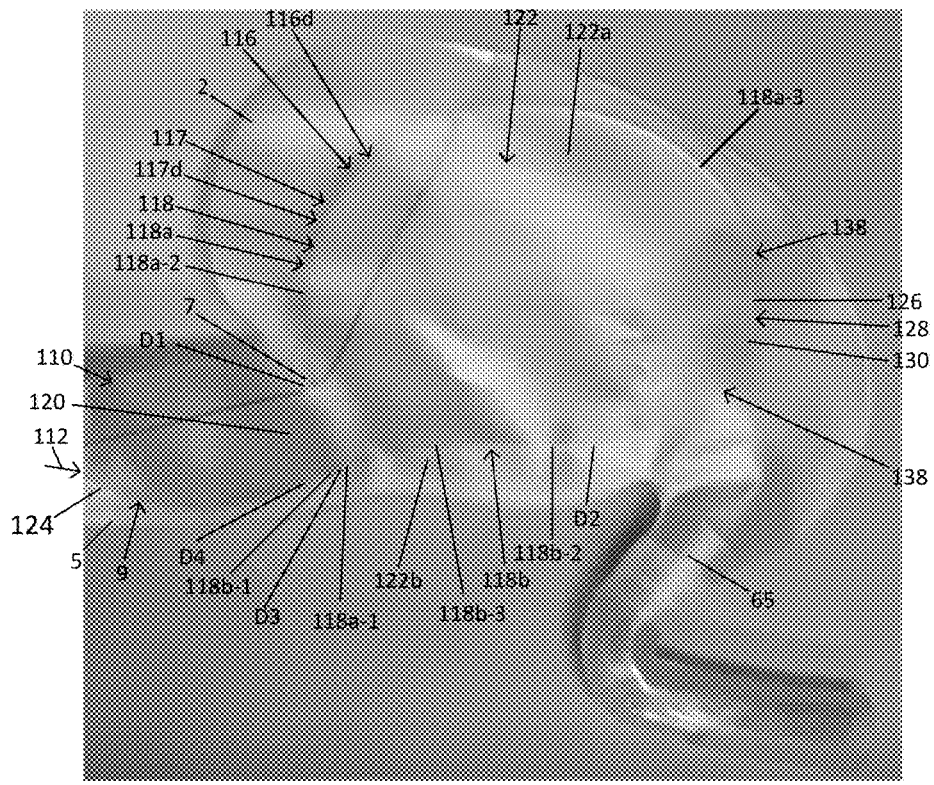
Figure 46E:
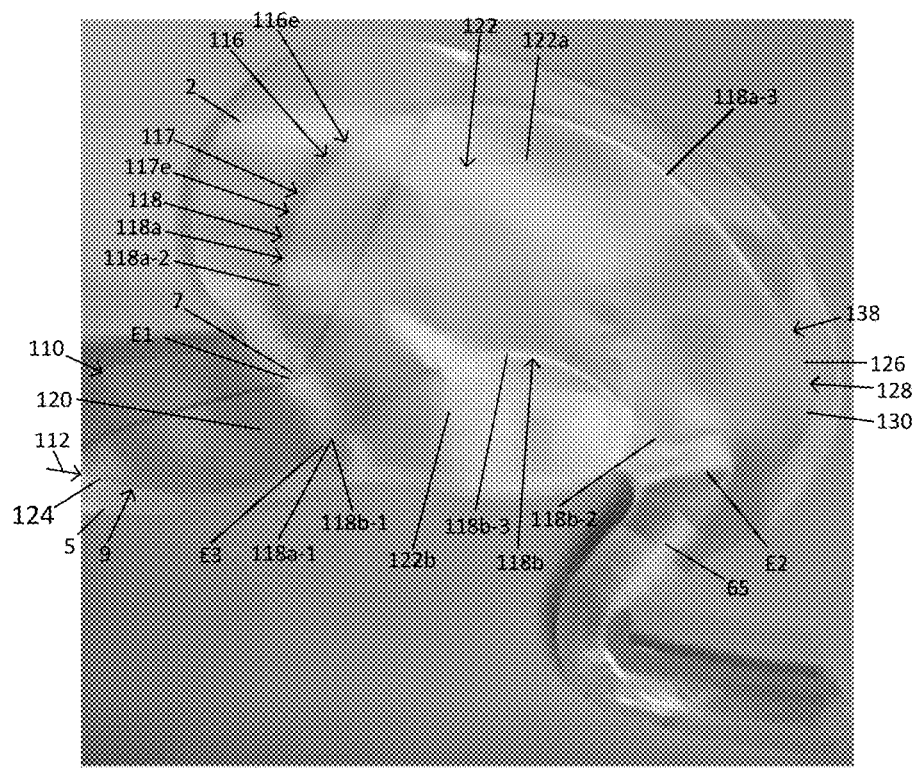
Figure 46F:
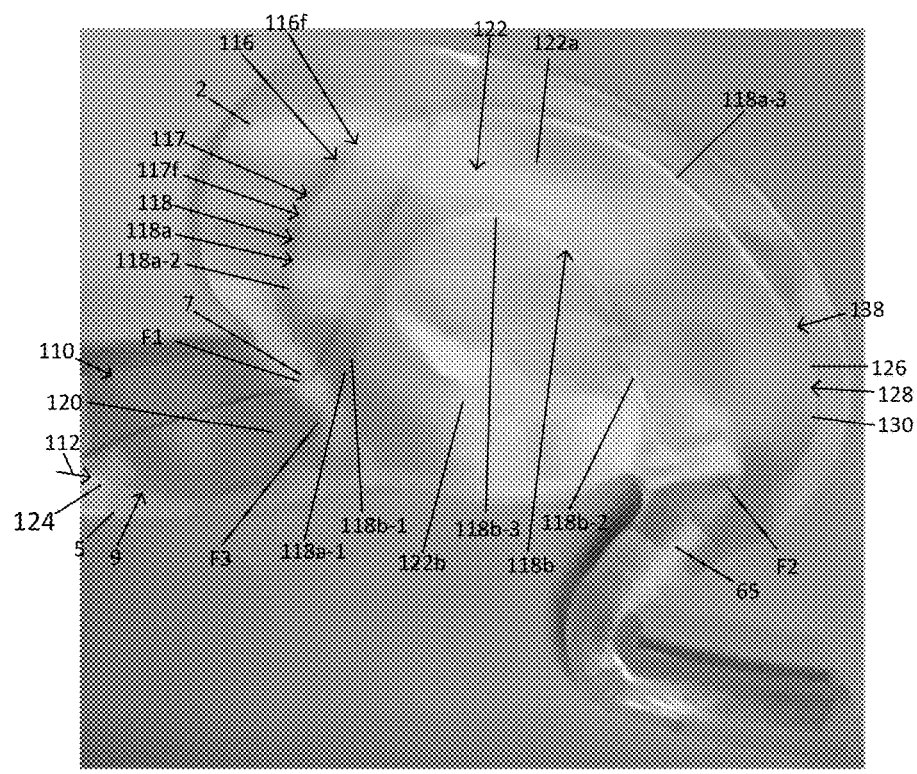
Figure 46G:
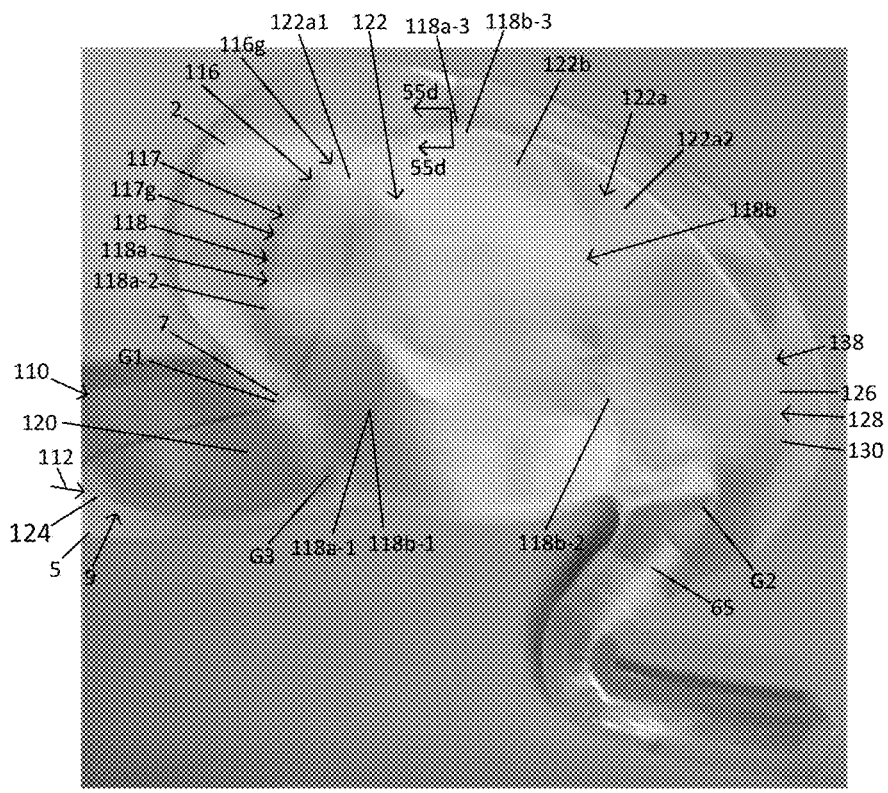
Figure 46H:
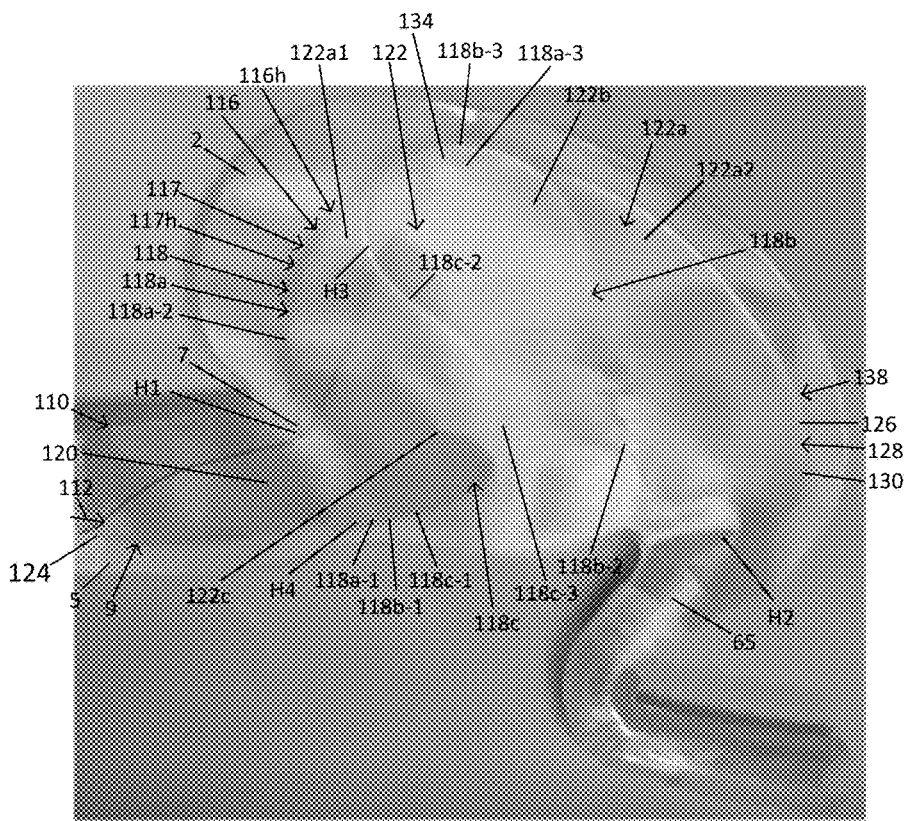
Figure 46I:
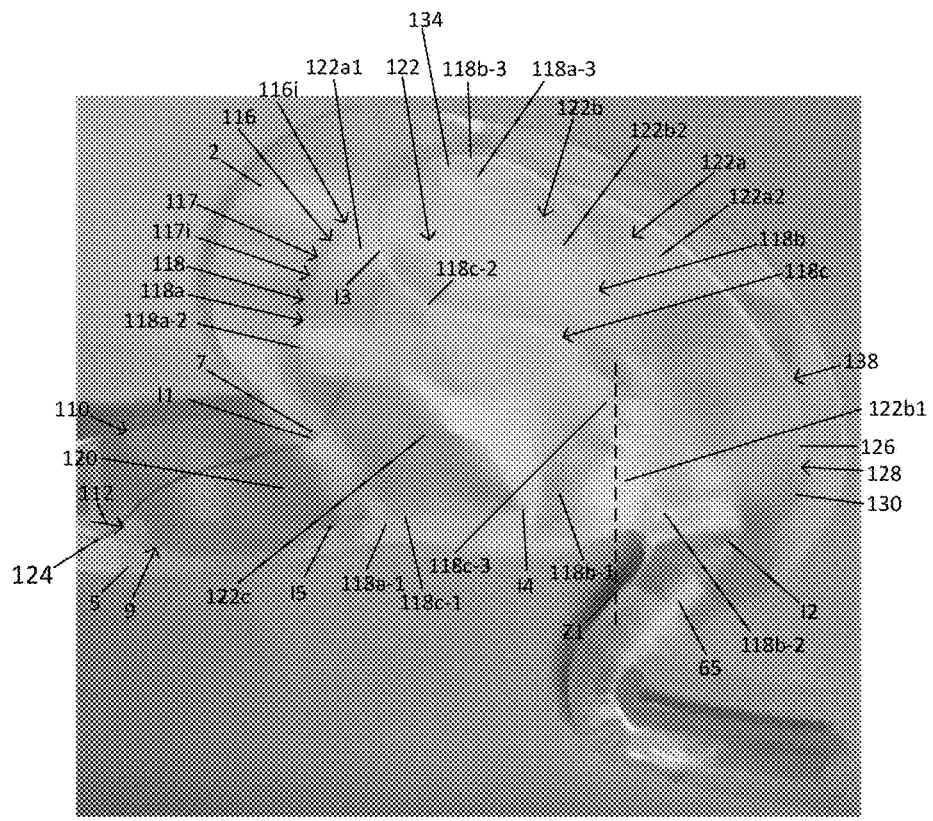
Figure 46J:
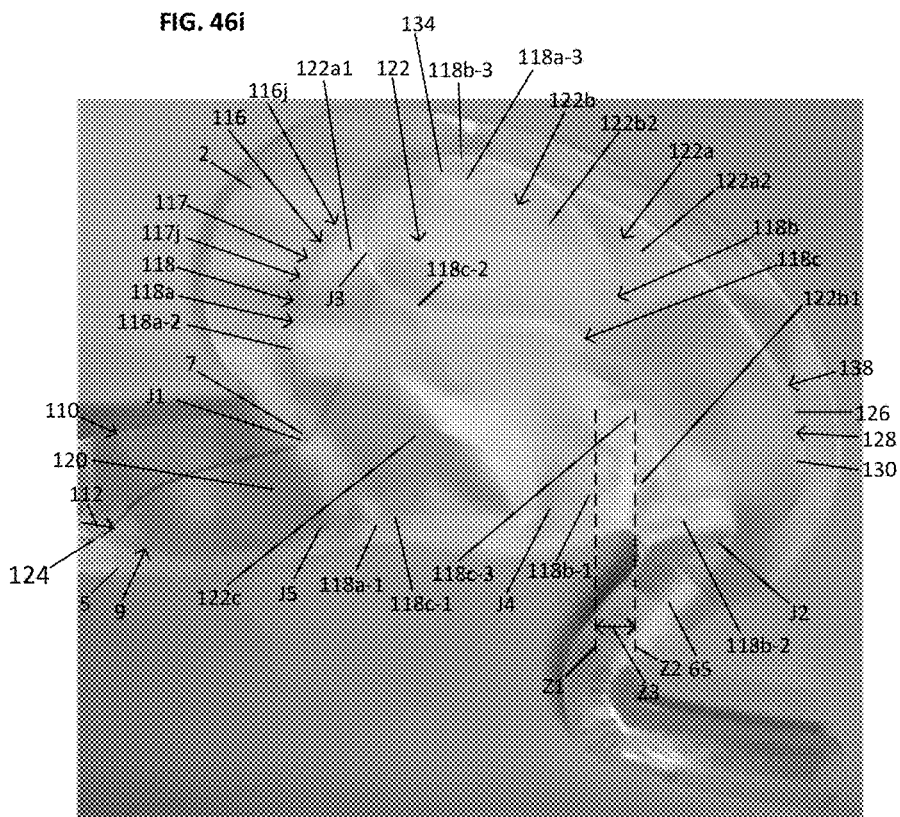
Figures 46K, 46L:
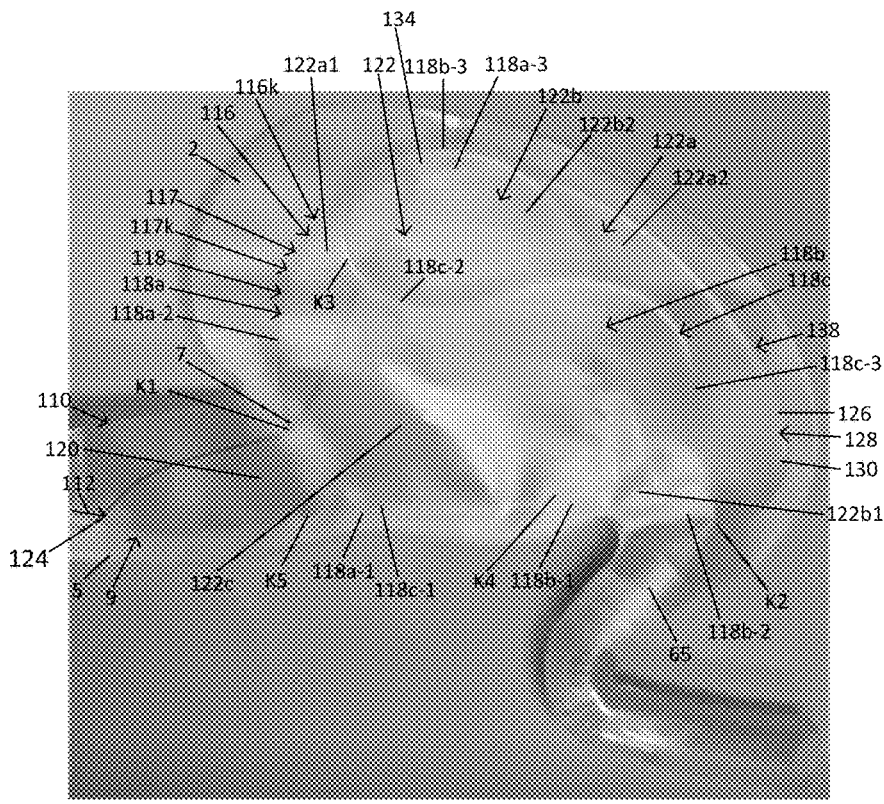
Figure 46M:
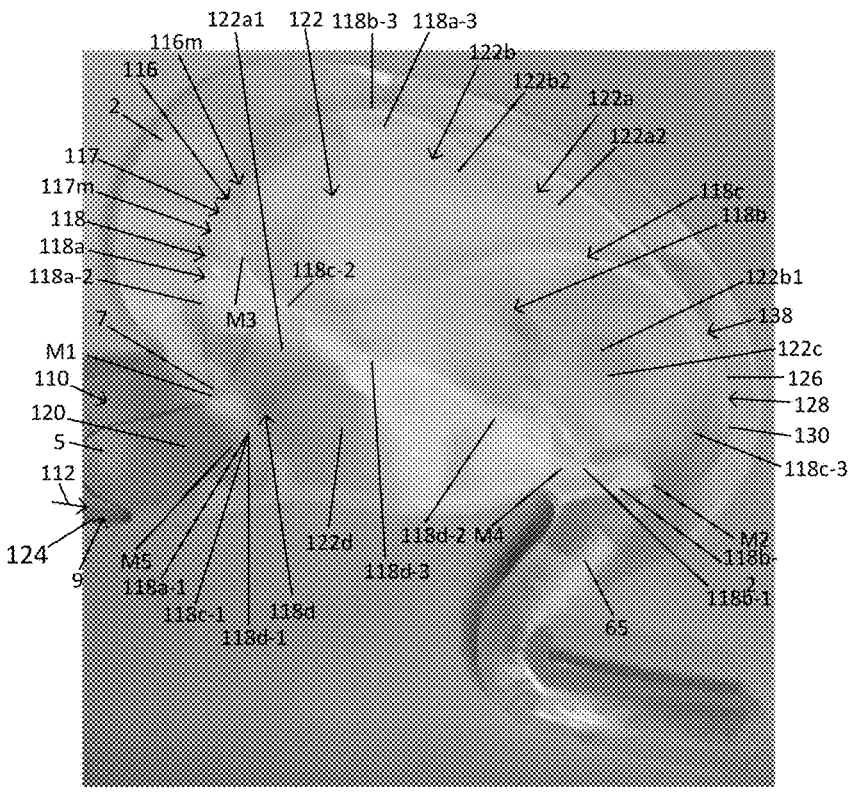
Figure 46N:
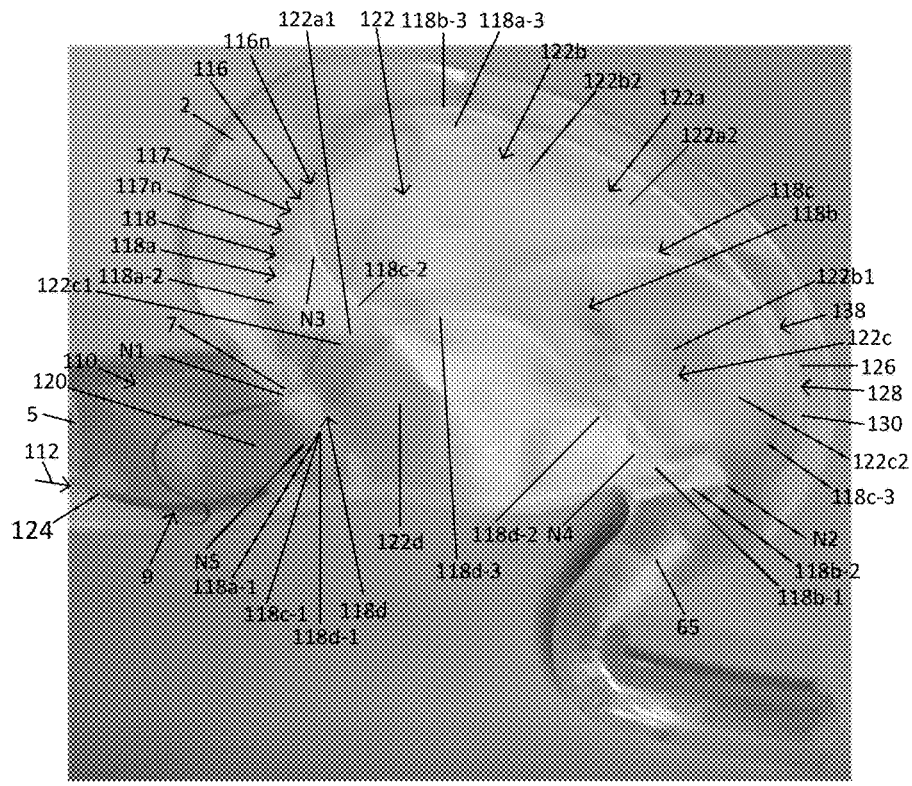
Figure 46O:
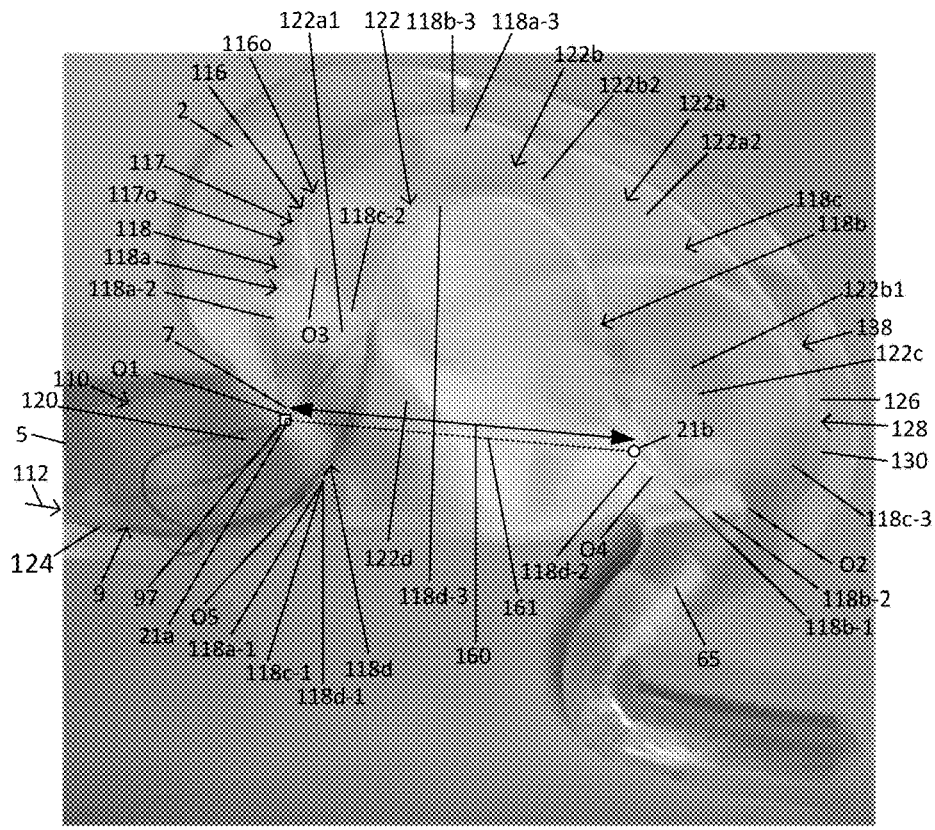
Figure 46P:
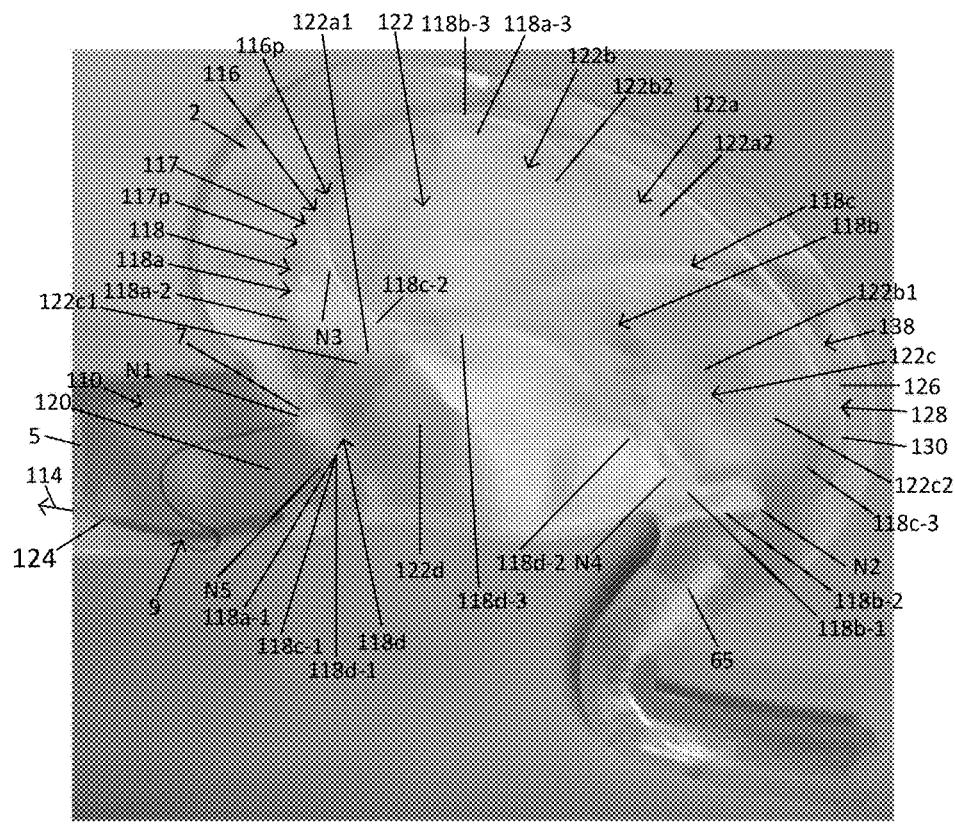
Figure 46Q:
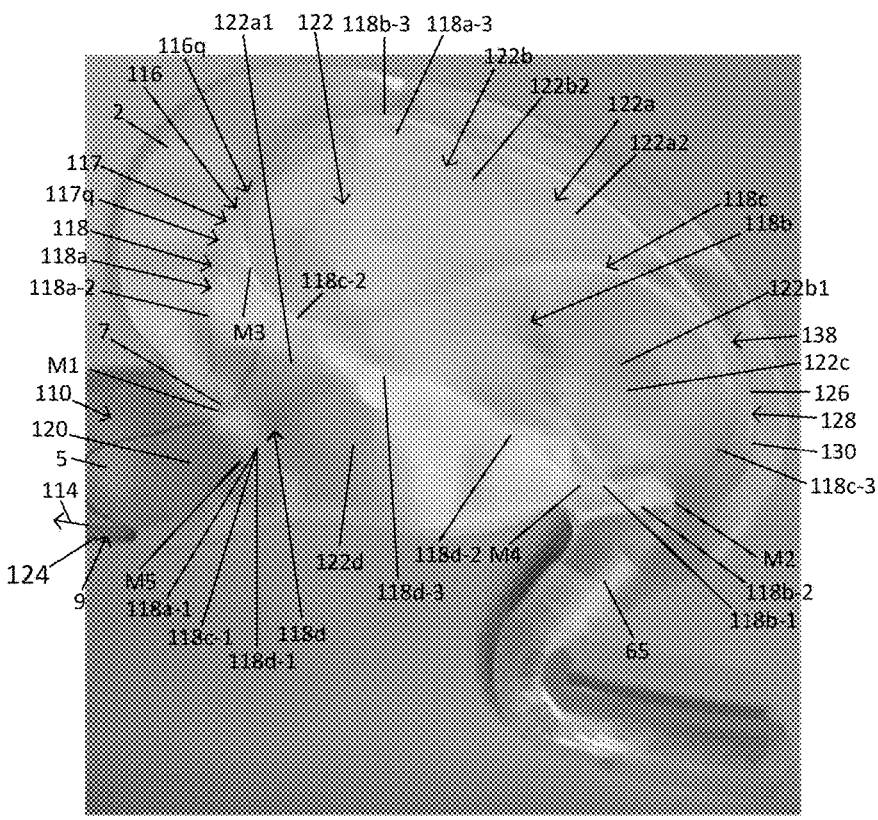
Figure 46R:
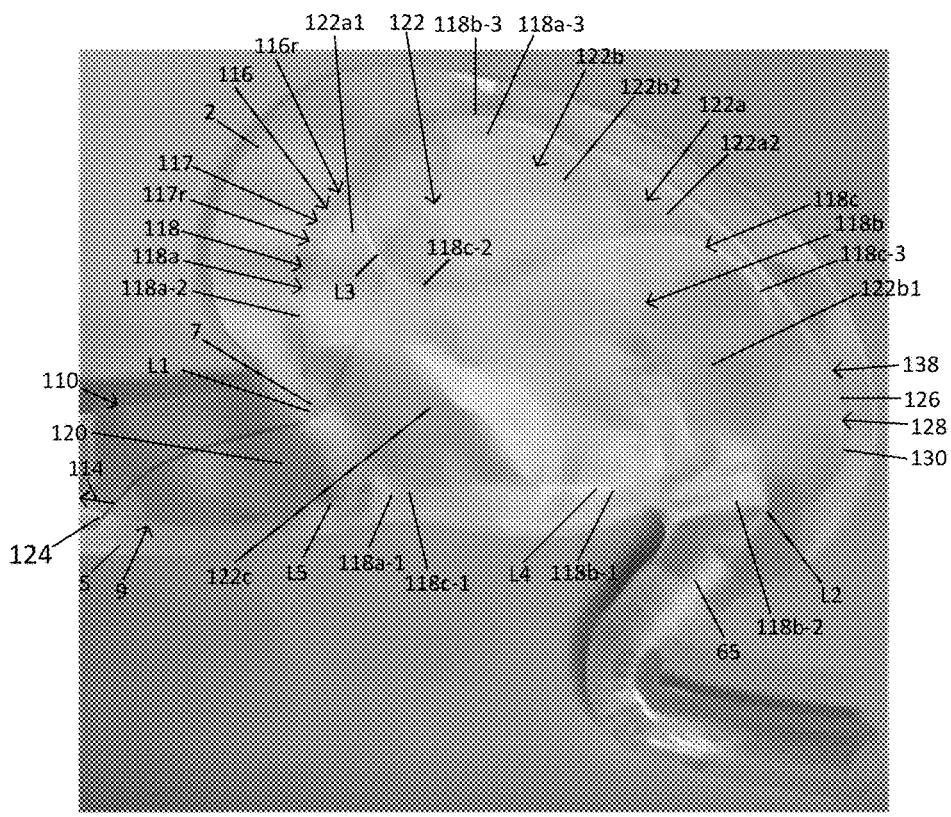
Figure 46S:
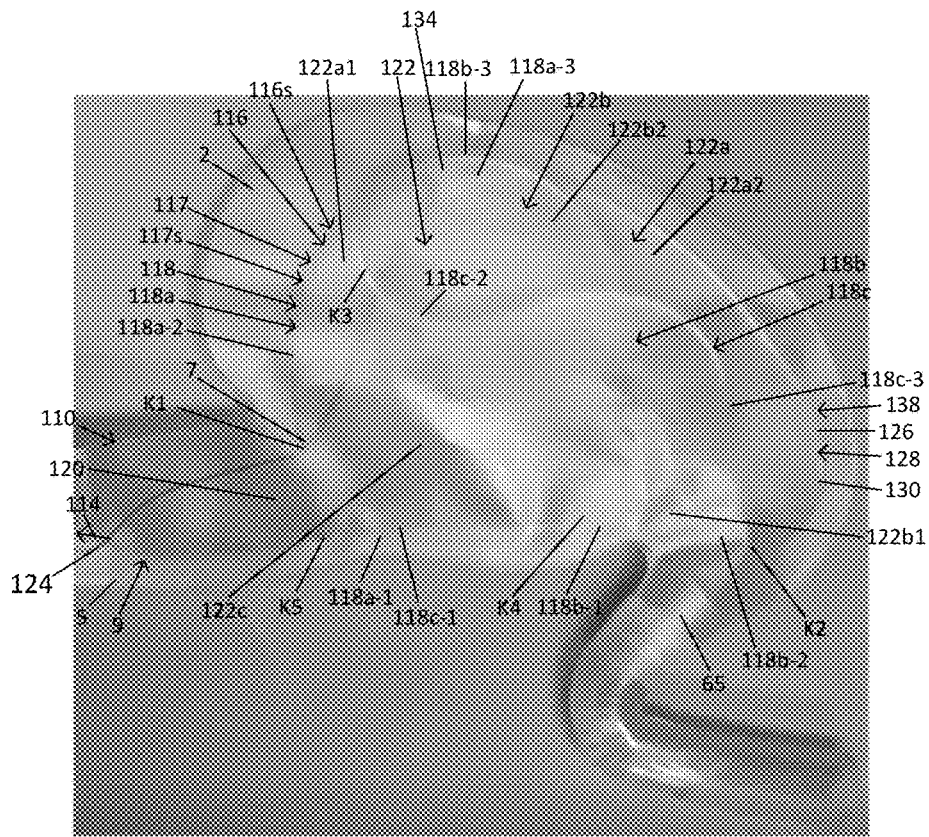
Figure 46T:
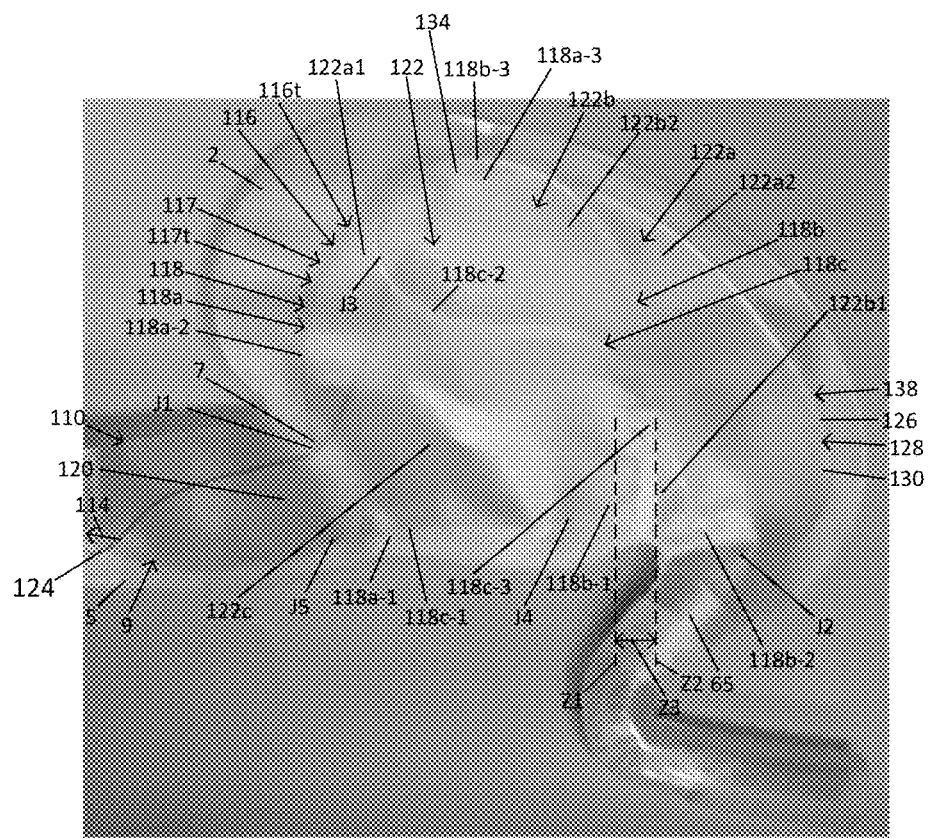
Figure 46U:
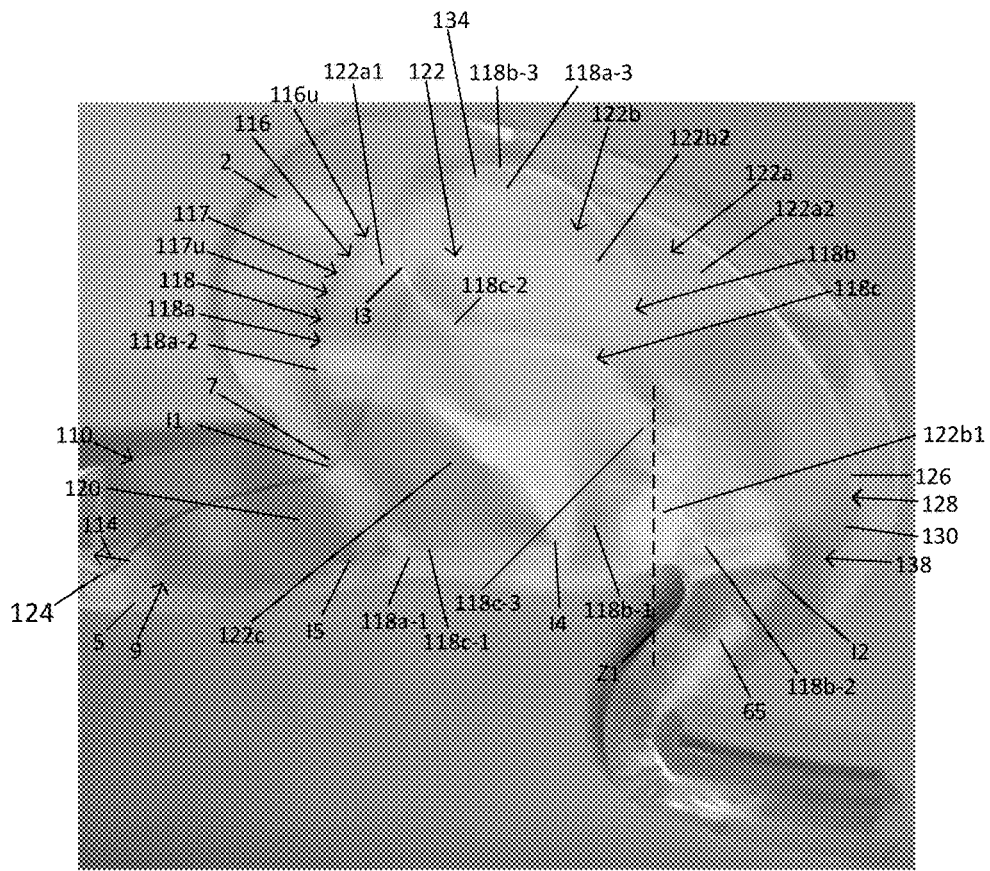
Figure 46V:
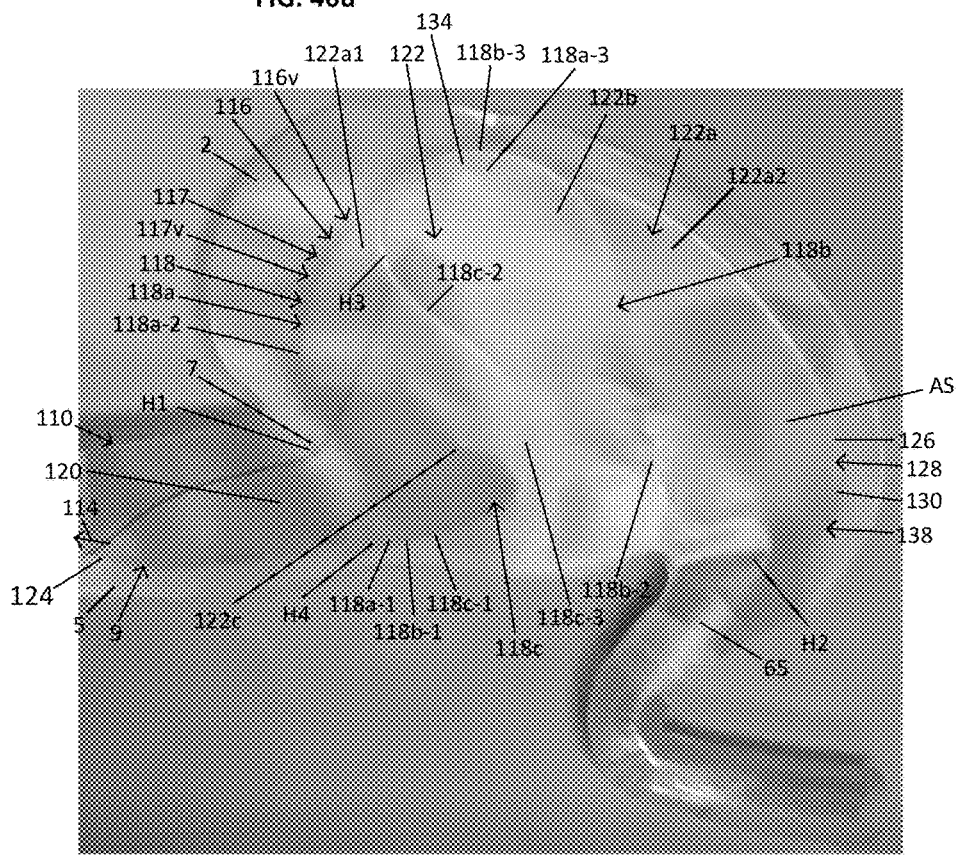
Figure 46W:
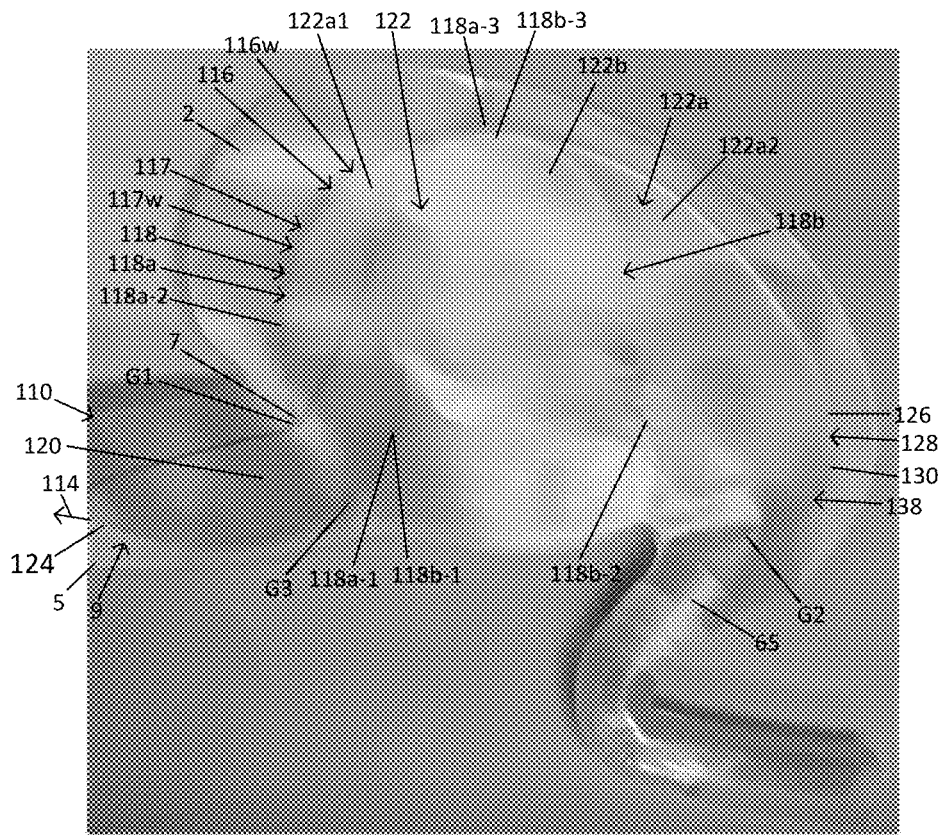
Figure 46X:
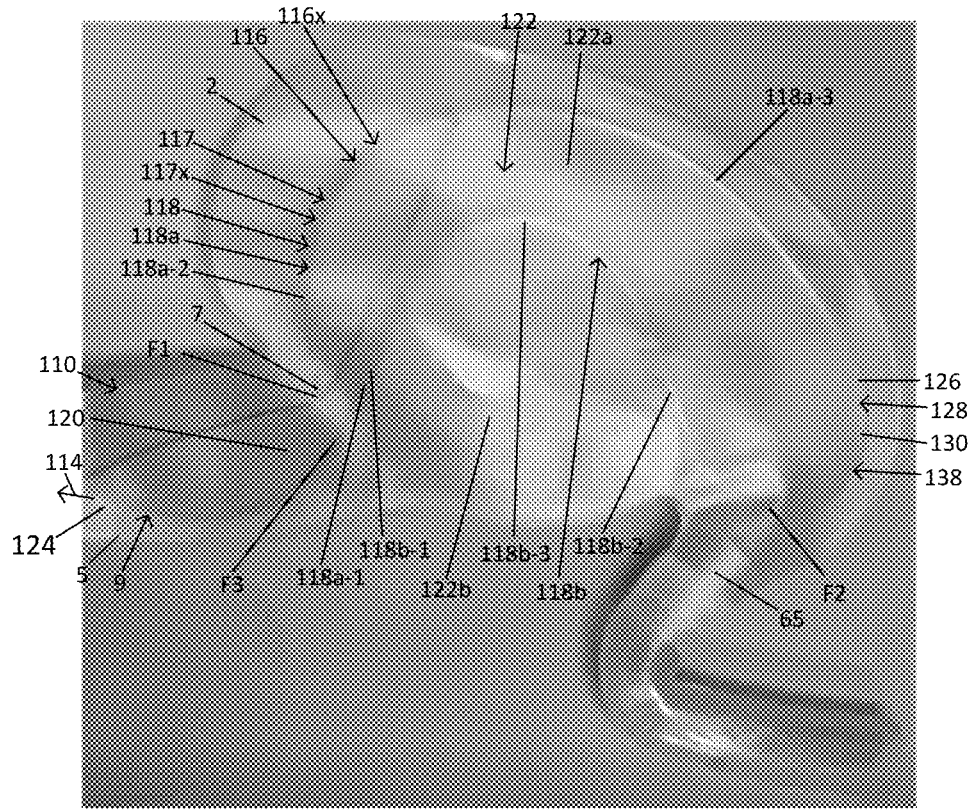
Figure 46Y:
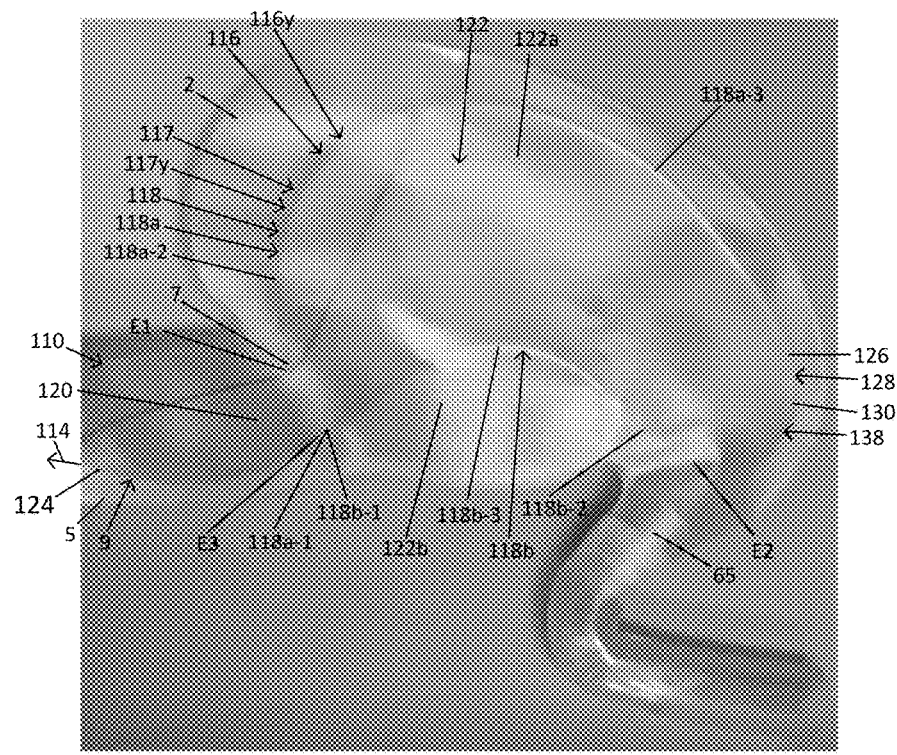
Figure 46Z:
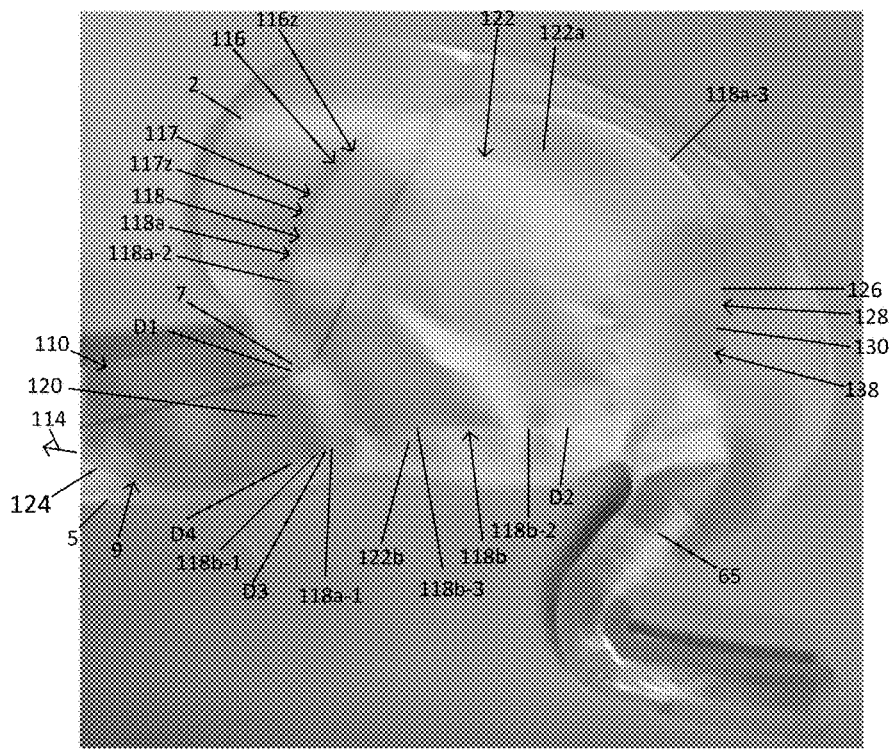

FIGS. 46a-46z3 illustrate that the catheter 9 can be inserted into and/or withdrawn from the body. For example, FIGS. 46a-46z3 illustrate that the catheter 9 can be inserted into and/or withdrawn from the gastrointestinal tract 110. For example, FIGS. 46a-46o illustrate that the catheter 9 can be inserted into the stomach 2 as shown by arrow 112 and FIGS. 46o-46z3 illustrate that the catheter 9 can be removed from the stomach 2 as shown by arrow 114. The insertion direction as shown by arrow 112 can be, for example, opposite the withdrawal direction as shown by 114. FIGS. 46a-46z3 illustrate that the catheter 9 can be introduced into and/or removed from the stomach 2, for example, through the esophagus 5. FIGS. 46a-46z3 illustrate that the target site 147 can be, for example, the stomach 2.

The catheter 9 can have one or multiple configurations 116 in the body, for example, in the gastrointestinal tract 110. The catheter 9 can be formed into the configurations 116, for example, during insertion of the catheter 9 into the body and/or during withdrawal of the catheter 9 from the body. The catheter 9 can be formed into the configurations 116, for example, by inserting the catheter 9 into the body and/or by withdrawing the catheter 9 from the body. Each one of the configurations 116 can include, for example, an arrangement of the catheter 9 inside the body (e.g., inside the gastrointestinal tract 110). For example, FIGS. 46a-46z3 illustrate twenty-nine configurations 116 that the catheter 9 can have in the body, for example, during insertion into and/or withdrawal from the gastrointestinal tract 110, including, for example, configurations 116a-116z3 or any combination thereof. For example, FIGS. 46a and 46z3 illustrate that configurations 116a and 116z3 can correspond to arrangements that the catheter 9 can have in the esophagus 5, and FIGS. 46b-46z2 illustrate that configurations 116b-116z2 can correspond to arrangements that the catheter 9 can have in the stomach 2. The configurations 116a-116z3 can be, for example, a first configuration through a twenty-ninth configuration 116a-116z3, respectively, that the catheter 9 can form during insertion of the catheter 9 into the body and/or withdrawal of the catheter 9 from the body.

The catheter 9 can transfer heat to and/or from the body (e.g., to and/or from the heat transfer target 146) when the catheter 9 is in the body, including, for example, when the catheter 9 is in any of the configurations 116 (e.g., the configurations 116a-116z3 in FIGS. 46a-46z3). Any of the configurations 116 can be, for example, an operational state (also referred to as an operational configuration) of the catheter 9. When the catheter 9 is in an operational configuration (e.g., in one of the configurations 116 or any combination thereof), the catheter 9 can transfer heat to and/or from the body, for example, by pumping a fluid through a lumen in the catheter 9. The fluid can be, for example, the fluid 6, and the lumen can be, for example, the lumen 15 and/or the lumen 16. For example, FIGS. 46a-46z3 illustrate that the catheter 9 can have the lumen 15 and the lumen 16, that the lumen 15 can be an inflow lumen, and that the lumen 16 can be an outflow lumen. FIGS. 46a-46z3 illustrate, for example, that configurations 116a-116z3 can each be an operational configuration of the catheter 9.

Each configuration 116 of the catheter 9 can be a partially deployed configuration and/or a fully deployed configuration of the catheter 9. For example, FIGS. 46a-46z3 illustrate that the configurations 116a-116n and 116p-116z3 can be partially deployed configurations of the catheter 9 and that the configuration 116o can be a fully deployed configuration of the catheter 9. As another example, any of the configurations 116 (e.g., configurations 116a-116z3) can be a fully deployed configuration. For example, when the configuration 116f is the fully deployed configuration, the catheter 9 can be inserted into the body to form the configuration 116f and then the catheter 9 can be withdrawn from the body without ever having formed configurations 116g-116o. When the catheter 9 is in a partially deployed configuration (e.g., configurations 116a-116z3), the catheter 9 can transfer heat to and/or from the body, for example, by pumping the fluid 6 through the lumen 15 and the lumen 16. When the catheter 9 is in a fully deployed configuration (e.g., configurations 116a-116z3), the catheter 9 can transfer heat to and/or from the body, for example, by pumping the fluid 6 through the lumen 15 and/or the lumen 16.

The configurations 116 formed by the catheter 9 during withdrawal of the catheter 9 from the body can be the same as or different than the configurations 116 formed by the catheter 9 during insertion of the catheter 9 into the body. FIGS. 46a-46z3 illustrate, for example, that the configurations 116 formed by the catheter 9 during withdrawal (e.g., configurations 116o-116z3) can be the same as the configurations 116 formed by the catheter 9 during insertion (e.g., configurations 116a-116o). For example, FIGS. 46a-46z3 illustrate that the configurations 116p-116z3 can be the same as the configurations 116n-116a, respectively (e.g., the sixteenth configuration 116p can be the same as the fourteenth configuration 116n, the twenty-seventh configuration 116z1 can be the same as the third configuration 116c). As another example, the configurations 116 formed by the catheter 9 during withdrawal of the catheter 9 from the body can be different from the configurations 116 formed by the catheter 9 during insertion of the catheter 9 into the body.

The catheter 9 can be formed into one or more of the configurations 116 in the target site 147, for example, before, during, and/or after passing (e.g., pumping) a fluid through a lumen in the catheter 9. The catheter 9 can be formed into a configuration 116 in the target site 147, for example, before, during, and/or after passing (e.g., pumping) a fluid through the first lumen 15 and/or the second lumen 16 in the catheter 9. For example, FIGS. 46a-46o illustrate that the catheter 9 can be formed into configurations 116a-116o before passing the fluid 6 through the first lumen 15 and/or the second lumen 16, and FIGS. 46p-46z3 illustrate that the catheter 9 can be formed into configurations 116p-116z3 after passing (e.g., pumping) the fluid 6 through the first lumen 15 and/or the second lumen 16.

Passing a fluid through the catheter 9 may or may not change the configuration 116 of the catheter 9. For example, FIGS. 46a-46z3 illustrate that passing a fluid through the catheter 9 (e.g., through an inflow lumen and/or an outflow lumen in the catheter 9) may not change the configuration 116 of the catheter 9. The configurations 116 can remain constant before, during, and/or after a fluid is passed (e.g., pumped) through the catheter 9. For example, FIGS. 46a-46z3 illustrate that the configurations 116 (e.g., configurations 116a-116z3) can remain constant before, during, and after a fluid is passed (e.g., pumped) through the catheter 9.

The catheter 9 can be formed into one or more configurations 116 in the gastrointestinal tract 110, for example, by inserting the catheter 9 into the gastrointestinal tract 110 and/or by withdrawing the catheter 9 from the gastrointestinal tract 110. For example, the catheter 9 can be formed into one or more configurations 116 in the gastrointestinal tract 110 by inserting the catheter 9 into the stomach 2 and/or a portion of the gastrointestinal tract 110 caudal the stomach 2 (e.g., into the duodenum 27) and/or by withdrawing the catheter 9 from the stomach 2 and/or a portion of the gastrointestinal tract 110 caudal the stomach 2 (e.g., from the duodenum 37), or any combination thereof.

The catheter 9 can form one or multiple shapes 117 (also referred to as catheter shapes 117) in the body, for example, as the catheter 9 is inserted into the body and/or as the catheter 9 is withdrawn from the body. Each shape 117 can be, for example, an arrangement of the catheter 9 inside the body. Each shape 117 can be defined, for example, by the path that the catheter 9 has in the body. For example, each shape 117 can include the path that the catheter 9 traces through the body, for example, through the gastrointestinal tract 110 (e.g., through the stomach 2, the pylorus 65, and/or the duodenum 37). Each configuration 116 of the catheter 9 can include a catheter shape 117. Each shape 117 can correspond to a configuration 116 of the catheter 9. For example, FIGS. 46a-46z3 illustrate that configurations 116a-116z3 can include and/or correspond to shapes 117a-117z3, respectively, such that the shapes 117a-117z3 can be the arrangement of the catheter 9 when the catheter 9 is in configurations 116a-116z3, respectively. For example, FIGS. 46a-46z3 illustrate that the catheter 9 can have twenty-nine shapes 117 that the catheter 9 can have in the body, for example, during insertion into and/or withdrawal from the gastrointestinal tract 110, including, for example, shapes 117a-117z3 or any combination thereof. For example, FIGS. 46a and 46z3 illustrate that shapes 117a and 117z3 can be the shapes (e.g., the paths) that the catheter 9 can have in the esophagus 5, and FIGS. 46b-46z2 illustrate that shapes 117*b*-117*z*2 can be the shapes (e.g., the paths) that the catheter 9 can have in the stomach 2. The shapes 117*a*-117*z*3 can be, for example, a first shape through a twenty-ninth shape 117*a*-117*z*3, respectively, that the catheter 9 can have during insertion of the catheter 9 into the body and/or withdrawal of the catheter 9 from the body.

The catheter shape 117 in each configuration 116 can depend, for example, on the length of the catheter 9 in the gastrointestinal tract 110 (e.g., in the stomach 2, in the pylorus 65, and/or in the duodenum 37), the entry angle of the catheter 9 into the stomach 2 (e.g., from the esophagus 5), the entry angle of the catheter 9 into the duodenum 37 (e.g., from the stomach 2), the stiffness of the catheter 9, the diameter of the catheter 9, the size of the stomach 2, the size of the duodenum 37, the size of organs adjacent the stomach 2 (e.g., the pancreas), the size of the organs adjacent the duodenum 37 (e.g., the pancreas), or any combination thereof. For example, based on these factors, a given length of the catheter 9 inserted into the stomach 2 (e.g., 100 cm of the catheter 9, 150 cm of the catheter 9, 200 cm of the catheter) can form various configurations 116 having various shapes 117 in the stomach 2. For example, FIGS. 46*a*-46*z*3 illustrate that the catheter 9 can have shapes 117*a*-117*z*3 in the stomach 2 as 30 cm-300 cm is inserted, or more narrowly, as 30 cm-150 cm is inserted, including every 1 cm increment within these ranges. As another example, because of these factors, inserting the same length (e.g., 100 cm, 150 cm, 200 cm) of the same catheter 9 (e.g., either literally the same catheter 9 or two different catheters 9 that are the same make and model) into the same stomach 2 on two different occasions can result in forming the catheter 9 into two different configurations 116 and/or can result in forming the catheter 9 into two identical configurations 116. The catheter 9 can have, for example, a 1.0 cm-3.0 cm minimum bend radius, including every 0.1 cm increment within this range (e.g., 1.0 cm, 1.5 cm, 1.6 cm, 2.5 cm). The stiffness of the catheter 9 can be quantified, for example, as the force needed to bend the catheter 9. The axial force to bend the catheter 9 can be, for example, greater than 2.0 Newtons-6.0 Newtons, including every 0.1 Newton increment within this range (e.g., greater than 2.0N, greater than 3.0N, greater than 4.0N, greater than 4.5N, greater than 4.8N, greater than 5.0N, greater than 6.0N). The axial force to bend the catheter 9 can be, for example, 2.0 Newtons-6.0 Newtons, including every 0.1 Newton increment within this range (e.g., 2.0N, 3.0N, 4.0N, 4.5N, 4.8N, 5.0N, 6.0N).

The shapes 117 formed by the catheter 9 during withdrawal of the catheter 9 from the body can be the same as or different than the shapes 117 formed by the catheter 9 during insertion of the catheter 9 into the body. FIGS. 46*a*-46*z*3 illustrate, for example, that the shapes 117 formed by the catheter 9 during withdrawal (e.g., shapes 117*o*-117*z*3) can be the same as the shapes 117 formed by the catheter 9 during insertion (e.g., shapes 117*a*-117*o*). For example, FIGS. 46*a*-46*z*3 illustrate that the shapes 117*p*-117*z*3 can be the same as the shapes 117*n*-117*a*, respectively (e.g., the sixteenth shape 117*p* can be the same as the fourteenth shape 117*n*, the twenty-seventh shape 117*z*1 can be the same as the third shape 117*c*). As another example, the shapes 117 formed by the catheter 9 during withdrawal of the catheter 9 from the body can be different from the shapes 117 formed by the catheter 9 during insertion of the catheter 9 into the body.

The shape 117 of the catheter 9 in each configuration 116 can include, for example, one or more straight sections of the catheter 9 and/or one or more curved sections of the catheter 9.

The catheter shape 117 in a deployed configuration (e.g., the configurations 116) can include, for example, one or more loops 118 formed by the catheter 9. The catheter 9 can have, for example, 1-30 or more loops 118 in a deployed configuration (e.g., the configurations 116), including every 1 loop increment within this range (e.g., 1 loop, 2 loops, 3 loops, 4 loops, 5 loops, 10 loops, 40 loops). The one or more straight sections of the catheter 9 and/or one or more curved sections of the catheter 9 can define the one or more loops 118. For example, FIGS. 46*a*-46*z*3 illustrate that the catheter 9 can have 1-4 or more loops 118 in a deployed configuration (e.g., configurations 116), including, for example, a loop 118*a*, a loop 118*b*, a loop 118*c*, a loop 118*d*, or any combination thereof. The loops 118*a*-118*d* can be, for example, a first loop through a fourth loop (e.g., a first loop 118*a*, a second loop 118*b*, a third loop 118*c*, a fourth loop 118*d*).

Each of the loops 118 can have a loop first end 118-1, a loop second end 118-2, and a loop head 118-3.

FIGS. 46*a*-46*z*3 illustrate, for example, that the loop 118*a* can have a loop first end 118*a*-1, a loop second end 118*a*-2, and a loop head 118*a*-3. The loop first end 118*a*-1, the loop second end 118*a*-2, and the loop head 118*a*-3 can be, for example, a first loop first end 118*a*-1, a first loop second end 118*a*-2, and a first loop head 118*a*-3, respectively.

FIGS. 46*a*-46*z*3 illustrate, for example, that the loop 118*b* can have a loop first end 118*b*-1, a loop second end 118*b*-2, and a loop head 118*b*-3. The loop first end 118*b*-1, the loop second end 118*b*-2, and the loop head 118*b*-3 can be, for example, a second loop first end 118*b*-1, a second loop second end 118*b*-2, and a second loop head 118*b*-3, respectively.

FIGS. 46*a*-46*z*3 illustrate, for example, that the loop 118*c* can have a loop first end 118*c*-1, a loop second end 118*c*-2, and a loop head 118*c*-3. The loop first end 118*c*-1, the loop second end 118*c*-2, and the loop head 118*c*-3 can be, for example, a third loop first end 118*c*-1, a third loop second end 118*c*-2, and a third loop head 118*c*-3, respectively.

FIGS. 46*a*-46*z*3 illustrate, for example, that the loop 118*d* can have a loop first end 118*d*-1, a loop second end 118*d*-2, and a loop head 118*d*-3. The loop first end 118*d*-1, the loop second end 118*d*-2, and the loop head 118*d*-3 can be, for example, a fourth loop first end 118*d*-1, a fourth loop second end 118*d*-2, and a fourth loop head 118*d*-3, respectively.

The loop first end 118-1 can be, for example, a first longitudinal end of the loop 118 along the catheter 9 (e.g., along the center longitudinal axis of the catheter 9). The loop second end 118-2 can be, for example, a second longitudinal end of the loop 118 along the catheter 9 (e.g., along the center longitudinal axis of the catheter 9). The loop first end 118-1 and/or the loop second end 118-2 can form a base of the loop 118 (also referred to as the loop base). The loop base can be, for example, the base of the loop first end 118-1, the base of the loop second end 118-2, a straight axis that connects the base of the loop first end 118-1 and the base of the loop second end 118-2, the location where the loop first end 118-1 and the loop second end 118-2 cross each other, or any combination thereof. The loop head 118-3 can be between the loop first end 118-1 and the loop second end 118-2. For example, the loop head 118-3 can be a middle portion of the loop 118 (e.g., of the catheter 9) between the loop first end 118-1 and the loop second end 118-2. As another example, the loop head 118-3 can include a portion of the loop first end 118-1 and a portion of the loop second end 118-2. The loop head 118-3 can be opposite (e.g., diametrically opposite) the base of the loop 118. The loop head 118-3 can have a loop apex. As another example, the loop head 118-3 can be the loop apex. The loop apex can be the midpoint along the catheter 9 between the loop first end 118-1 and the loop second end 118-2 and/or the loop apex can be the farthest point along the loop 118 as measured along a straight line from the loop base to the loop apex. The loop apex can, for example, divide the loop 118 into a first half and a second half (e.g., into two equal or non-equal halves). The first half of the loop 118 can include, for example, the loop first end 118-1 and/or a portion (e.g., half) of the loop head 118-3. The second half of the loop 118 can include, for example, the loop second end 118-2 and/or a portion (e.g., half) of the loop head 118-3. The loop head 118-3 can connect the loop first end 118-1 and the loop second 118-2 to each other. As another example, when the loop head 118-3 is considered the loop apex (e.g., as opposed to another section of the of the catheter 9), the loop first end 118-1 and the loop second end 118-2 can meet at the loop head 118-3 (e.g., at the loop apex). The loops 118 can be symmetrical or asymmetrical about a straight axis that intersects the loop base and the loop head 118-3 (e.g., the loop apex). The loop first end 118-1 can be shorter, longer, or the same length as the loop second end 118-2. The loop second end 118-2 can be shorter, longer, or the same length as the loop first end 118-1.

The loop first end 118-1, the loop second end 118-2, and the loop head 118-3 for each loop 118 can be, for example, different sections of the catheter 9 along the length of the catheter 9. Different loops 118 can include the same and/or different sections of the catheter 9. A loop 118 can include the same and/or different sections of the catheter 9 as another loop 118. For example, a first loop (e.g., loop 118*a*) can include the same and/or different sections of the catheter as a second loop (e.g., loop 118*b*, 118*c*, and/or 118*d*). As another example, a first loop (e.g., loop 118*b*) can include the same and/or different sections of the catheter as a second loop (e.g., loop 118*a*, 118*c*, or 118*d*). The loop first end 118-1, the loop second end 118-2, and the loop head 118-3 can have relative positions to each other along the length of the catheter 9. For example, FIGS. 46*a*-46*z*3 illustrate that the loop first end 118-1 can be proximal the loop second end 118-2 and the loop head 118-3 along the length of the catheter 9, that the loop second end 118-2 can be distal the loop first end 118-1 and the loop head 118-3 along the length of the catheter 9, and the loop head 118-3 can be distal the loop first end 118-1 and proximal the loop second end 118-2 along the length of the catheter 9.

Each loop 118 can be, for example, a closed loop or an open loop (e.g., one or more of the loops 118 can be an open loop and one or more of the loops 118 can be a closed loop). An open loop can be, for example, a loop 118 that has a loop first end 118-1 that is separated from a loop second end 118-2 by a gap. A closed loop can be, for example, a loop 118 that has a loop first end 118-1 that crosses a loop second end 118-2 or vice versa. The loop first end 118-1 and the loop second end 118-2 of a closed loop may or may not contact each other.

The catheter shape 117 in a deployed configuration (e.g., the configurations 116) can include, for example, one or more cells 122. The catheter 9 can have, for example, 1-30 or more cells 122 in a deployed configuration (e.g., the configurations 116), including every 1 cell increment within this range (e.g., 1 cell, 2 cells, 3 cells, 4 cells, 5 cells, 10 cells, 30 cells). The one or more straight sections of the catheter 9 and/or one or more curved sections of the catheter 9 can define the one or more cells 122. For example, the loops 118 can define the cells 122. The cells 122 can be defined by an external surface of the catheter 9. The boundary of the cells 122 can be the catheter 9, for example, an exterior surface of the catheter 9. The cells 122 can be, for example, the spaces, openings, holes, and/or through holes between sections of the catheter 9 when the catheter is in a deployed configuration (e.g., the configurations 116). For example, FIGS. 46*a*-46*z*3 illustrate that the catheter 9 can have 1-4 or more cells 122 in a deployed configuration (e.g., configurations 116), including, for example, a cell 122*a*, a cell 122*b*, a cell 122*c*, a cell 122*d*, or any combination thereof. The cells 122*a*-122*d* can be, for example, a first cell through a fourth cell (e.g., a first cell 122*a*, a second cell 122*b*, a third cell 122*c*, a fourth cell 122*d*). Each cell 122 can be, for example, a closed cell or an open cell. An open cell can be, for example, the cell 122 of an open loop. A closed cell can be, for example, the cell 122 of a closed loop.

The catheter 9 can be formed into the catheter shapes 117, for example, into the loops 118, in the gastrointestinal tract 110, for example, by inserting the catheter 9 into the gastrointestinal tract 110 and/or by withdrawing the catheter 9 from the gastrointestinal tract 110. For example, the catheter 9 can be formed into one or more shapes 117, for example, into one or more loops 118, in the gastrointestinal tract 110 by inserting the catheter 9 into the stomach 2 and/or a portion of the gastrointestinal tract 110 caudal the stomach 2 (e.g., into the pylorus 65 and/or the duodenum 27) and/or by withdrawing the catheter 9 from the stomach 2 and/or a portion of the gastrointestinal tract 110 caudal the stomach 2 (e.g., from the pylorus 65 and/or the duodenum 37), or any combination thereof.

As the catheter 9 is inserted into the gastrointestinal tract 110, the catheter 9 can engage with, can be pushed against, and/or can be constrained by a wall of the gastrointestinal tract 110 which can, for example, cause the catheter 9 to form bends, form loops (e.g., loops 118), fold over itself, cross over itself, contact itself, or any combination thereof to form the configurations 116 having shapes 117. The wall of the gastrointestinal tract 110 can include, for example, one or more walls of the stomach 2, one or more walls of the pylorus 65, one or more walls of the duodenum 37, one or more walls of the gastrointestinal tract 110 caudal the duodenum 37, or any combination thereof. FIGS. 46*a*-46*o* illustrate, for example, that the catheter 9 can progressively form more elaborate configurations 116 having more elaborate shapes 117 as the catheter 9 is progressively inserted into the stomach 2 (e.g., through the esophagus 5). FIGS. 46*a*-46*o* illustrate, for example, that the loops 118 can be progressively formed by more proximal portions of the catheter.

As the catheter 9 is withdrawn from the gastrointestinal tract 110, the catheter 9 can straighten and/or become less curved which can, for example, cause the catheter 9 to unravel, unwind, uncoil, uncurl, unfold, and/or unbend to form the configurations 116 having shapes 117. As the catheter 9 is withdrawn from the gastrointestinal tract 110, the loops 118 can collapse (e.g., unravel, unwind, uncoil, uncurl, unfold, and/or unbend). FIGS. 46*o*-46*z*3 illustrate, for example, that the catheter 9 can progressively form less elaborate configurations 116 having less elaborate shapes 117 as the catheter 9 is progressively withdrawn from the stomach 2 (e.g., through the esophagus 5).

The loops 118 and the cells 122 can be formed by inserting the catheter 9 into and/or withdrawing the catheter 9 from the target site 147 (e.g., stomach 2, the pylorus 65, the duodenum 37, and/or a portion of the gastrointestinal tract 110 caudal the duodenum 37).

The loops 118 can change size and/or shape in the target site 147. For example, the size (e.g., the perimeter, length, width, and/or height) of the loops 118 can increase and/or decrease as the catheter 9 is inserted into the target site 147.

The loops 118 can have a perimeter (also referred to as a loop perimeter). The loop perimeter can be measured, for example, along a center longitudinal axis of the catheter 9 from the loop first end 118-1 to the loop second end 118-2. The loop perimeter can be, for example, 5.0 cm-80.0 cm, including every 0.5 cm increment within this range (e.g., 5.0 cm, 9.5 cm, 15.0 cm, 30.0 cm, 50.0 cm, 80.0 cm). The loop perimeter can be, for example, greater than 9.0-70.0 cm, including every 0.5 cm increment within this range (e.g., greater than 5.0 cm, 9.5 cm, 15.0 cm, 30.0 cm, 50.0 cm, 80.0 cm). The loop perimeter can be, for example, less than 80.0 cm. The loop perimeter can be, for example, greater than the lesser curvature of the stomach 2 and/or greater than the greater curvature of the stomach 2. FIGS. 46a-46z3 illustrate that the size (e.g., perimeter) of the loops 118 can increase and decrease in the target site 147. FIGS. 46a-46z3 illustrate, for example, that at least one of the loops 118 (e.g., the loop 118a) can have a perimeter greater than 9.5 cm. FIGS. 46a-46z3 illustrate that the shape of a loop 118 can change, for example, as the sections that form the loop 118 (e.g., that form the loop first end 118-1, the loop second end 118-2, and/or the loop head 118-3) straighten and/or form bends and/or curves as the catheter 9 is inserted into and/or withdrawn from the target site 147.

The loops 118 can have a length, a width, and a height (also referred to as a loop length, a loop width, and a loop height).

The length of each loop 118 can be measured along a straight axis (also referred to as a straight line) from the base of the loop 118 to the loop head 118-3 of the loop 118 (e.g., to the apex of the loop 118). The loop length can be, for example, 3.0 cm-40.0 cm, including every 0.5 cm increment within this range (e.g., 3.0 cm, 9.0 cm, 15.0 cm, 30.0 cm, 40.0 cm). The loop length can be, for example, greater than 3.0-30.0 cm, including every 0.5 cm increment within this range (e.g., greater than 3.0 cm, 9.0 cm, 15.0 cm, 30.0 cm). The loop length can be, for example, greater than the lesser curvature of the stomach 2, greater than the greater curvature of the stomach 2, and/or greater than a length of the duodenum 37. For example, the loop length can be greater than 25%-100% of the length of the duodenum 37. For example, when the loop 118 is in both the stomach 2 and the duodenum, the loop length can be greater than the greater curvature of the stomach 2. The loop length can be greater than 3 cm. The loop length can be, for example, less than 20.0 cm-40.0 cm, including every 0.5 cm increment within this range (e.g., less than 20.0 cm, 30.0 cm, 40.0 cm). The loop length can be, for example, less than the width of the widest section of the stomach 2 and/or less than the greater curvature of the stomach 2.

The width of each loop 118 can be measured along a straight axis (also referred to as a straight line) from a point on the loop first end 118-1 of the loop 118 to a point on the loop second end 118-2 of the loop 118. The loop width can be, for example, 3.0 cm-40.0 cm, including every 0.5 cm increment within this range (e.g., 3.0 cm, 9.0 cm, 15.0 cm, 30.0 cm, 40.0 cm). The loop width can be, for example, greater than 3.0-30.0 cm, including every 0.5 cm increment within this range (e.g., greater than 3.0 cm, 9.0 cm, 15.0 cm, 30.0 cm). The loop width can be, for example, greater than the lesser curvature of the stomach 2, greater than the greater curvature of the stomach 2, and/or greater than a width of the duodenum 37. For example, the loop width can be greater than 25%-100% of the width of the duodenum 37. The loop width can be greater than 3 cm. The loop width can be, for example, less than 20.0 cm-40.0 cm, including every 0.5 cm increment within this range (e.g., less than 20.0 cm, 30.0 cm, 40.0 cm). The loop width can be, for example, less than the width of the widest section of the stomach 2 and/or less than the greater curvature of the stomach 2. The loop width can be the same as or different than the loop length.

The height of each loop 118 can be the 1.0-7.0 or more times the diameter of the catheter 9. The height of each loop 118 can be, for example, the height a flat plane that the loop extends through loop first end 118-1, the loop second end 118-2, and the loop head 118-3.

FIGS. 46a-46z3 illustrate that the loops 118 can have various sizes, shapes, and relative positions. FIGS. 46a-46z3 illustrate that some of the loops 118 can be smaller than another one of the loops 118. FIGS. 46a-46z3 illustrate that some of the loops 118 can be larger than another one of the loops 118.

The loops 118 can have one or multiple straight sections and/or curved sections of the catheter 9. The curved sections of the loops 118 can have a constant or a variable radius. Each loop 118 can have the same radius and/or a different radius than another one of the loops.

The loops 118 can change from an open loop to a closed loop inside the target site 147 (e.g., inside the stomach 2, the pylorus 65, and/or the duodenum 37) and/or can change from a closed loop to an open loop inside the target site 147 (e.g., inside the stomach 2, the pylorus 65, and/or the duodenum 37), for example, as the catheter 9 is advanced into the target site 147 and/or as the catheter 9 is withdrawn from the target site 147. A loop 118 can have a closed section and an open section.

Each loop 118 can have the same size as or a different size than another one of the loops 118. A first loop (e.g., one of the loops 118) can have the same size as or a different size than a second loop (e.g., another one of the loops 118).

Each loop 118 can have the same shape as or a different shape than another one of the loops 118. A first loop (e.g., one of the loops 118) can have the same shape as or a different shape than a second loop (e.g., another one of the loops 118). The loops 118 can have, for example, a bulbous shape, an oblong shape, a teardrop shape, an irregular shape, or any combination thereof.

The catheter 9 can be moved relative to the loops 118 in the target site 147, for example, by inserting and/or withdrawing the catheter 9 from the target site 147. For example, FIGS. 46a-46z3 illustrate that catheter 9 inside the target site 147 can be moved (e.g., pushed and/or pulled) relative to the loops 118 which can cause, for example, one or more loops 118 to form and/or unwind. The catheter 9 can be moved into and/or out of contact with the loops 118 in the target site 147. The catheter 9 can be moved against (e.g., slid against) one or more of the loops 118 in the target site 147. The catheter 9 can be pushed and/or pulled into a loop 118 which can cause the loop 118 to move and/or change shape in the target site 147. The catheter 9 can be moved over and/or under one or more of the loops 118 in the target site 147.

The loops 118 can be moved relative to each other in the target site 147, for example, by inserting and/or withdrawing the catheter 9 from the target site 147. For example, FIGS. 46a-46z3 illustrate that the loops 118a-118d can be moved relative to each other in in the target site 147. The loops 118 can be moved into and/or out of contact with each other in the target site 147. The loops 118 can be moved against (e.g., slid against) each other in the target site 147. The loops 118 can be moved toward and/or away from each other in the target site 147. The loops 118 can be moved over and/or under each other in the target site 147.

The cells 122 can change size and/or shape in the target site 147. For example, the size (e.g., the area, length, and/or height) of a cell 122 can increase and/or decrease as the catheter 9 is inserted into the target site 147 (e.g., the stomach 2 and/or the duodenum 37).

The cells 122 can have an area (also referred to as a cell area). The cell area can be the space bounded (e.g., enclosed) by the loops 118. For example, the cell area of the cell 122a can be the area of the space enclosed by the loop 118a. The loop area can be, for example, 7 cm$^2$-300 cm$^2$, including every 1 cm$^2$ increment within this range (e.g., 7 cm$^2$, 50 cm$^2$, 100 cm$^2$, 300 cm$^2$). The loop area can be, for example, greater than 7 cm$^2$-300 cm$^2$, including ever 1 cm$^2$ increment within this range (e.g., greater than 7 cm$^2$, 50 cm$^2$, 100 cm$^2$, 300 cm$^2$). FIGS. 46a-46z3 illustrate that the size of the cells 122 can increase and/or decrease in the target site 147, for example, as the loops 118 increase and/or decrease in size in the target site 147, respectively. FIGS. 46a-46z3 illustrate that the shape of a cell 122 can change, for example, as the shape of the loops 118 change.

The cells 122 can have a length, a width, and a height (also referred to as a cell length, a cell width, and a cell height).

The cell length can be measured along the same axis that the loop length can be measured along. For example, the cell length can be measured along the straight axis from the base of the loop 118 to the loop head 118-3 of the loop 118. The cell length can be the same as or different than the loop length. For example, when the loop length is measured from the base of the loop 118 to an external surface of the loop head 118-3, the cell length can be the same as the loop length. As another example, when the loop length is measured from the base of the loop 118 to a center longitudinal axis of the of the catheter 9 in the loop head 118-3, the cell length can be, for example, the loop length minus the radius or the diameter of the catheter 9.

The cell width can be measured along the same axis that the loop width can be measured along. For example, the cell width can be measured along the straight axis from a point on the loop first end 118-1 of the loop 118 to a point on the loop second end 118-2 of the loop 118. The cell width can be the same as or different than the loop width. For example, when the point on the loop first end 118-1 and the point on the loop second end 118-2 are on an external surface (e.g., a radial inner surface of the loop 118), the cell width can be the same as the loop width. As another example, when the point on the loop first end 118-1 and the point on the loop second end 118-2 are on a center longitudinal axis of the of the catheter 9, the cell width can be, for example, the loop width minus the diameter of the catheter 9.

The cell height can be, for example, the same as the loop height.

FIGS. 46a-46z3 illustrate that the cells 122 can have various sizes, shapes, and relative positions. FIGS. 46a-46z3 illustrate that some of the cells 122 can be smaller than another one of the cells 122. FIGS. 46a-46z3 illustrate that some of the cells 122 can be larger than another one of the cells 122.

The cells 122 can change from an open cell to a closed cell inside the target site 147 (e.g., inside the stomach 2, the pylorus 65, and/or the duodenum 37) and/or can change from a closed cell to an open cell inside the target site 147 (e.g., inside the stomach 2, the pylorus 65, and/or the duodenum 37), for example, as the catheter 9 is advanced into the target site 147 and/or as the catheter 9 is withdrawn from the target site 147. The loops 118 can define open and/or closed cells 122. For example, open loops 118 can define open cells 122 and closed loops 122 can define open cells 122. As another example, loops 118 in which the loop first end 118-1 and the loop second end 118-2 cross each other can define one or more open cells 122 and one or more closed cells 122 (e.g., the tip of the loop 118 can define a closed cell 122 and the base of the loop 118 can define an open cell 122).

Each cell 122 can have the same size as or a different size than another one of the cells 122. A first cell (e.g., one of the cells 122) can have the same size as or a different size than a second cell (e.g., another one of the cells 122).

Each cell 122 can have the same shape as or a different shape than another one of the cells 122. A first cell (e.g., one of the cells 122) can have the same shape as or a different shape than a second cell (e.g., another one of the cells 122). The cells 122 can have, for example, a bulbous shape, an oblong shape, a teardrop shape, an irregular shape, or any combination thereof.

The cells 122 can be aligned with each other, can be offset with each other, can overlap each other, or any combination thereof. For example, FIGS. 46a-46z3 illustrate that the cells 122 can be offset with each other and/or can overlap each other. Each of the cells 122 can have a cell central axis that extends through a center cell 122. When two cells 122 are aligned with each other, the central axis of the two cells 122 can be aligned with (e.g., coincident with) each other such that the catheter 9 can have a helical shape. When two cells 122 are offset with each other, the central axis of the two cells 122 can be offset from each other. For example, when two cells 122 are offset with each other, the central axis of the two cells 122 can be separated by a gap (also referred to as the cell axis gap). The central axes of the cells 122 can extend through the cells 122 at an angle perpendicular to the face of the of the cell. The cell axis gap between the cell central axis of a first cell (e.g., one of the cells 122) and the cell central axis of a second cell (e.g., another one of the cells 122) can be, for example, 1 cm-40 cm or more, including every 1 cm increment within this range (e.g., 1 cm, 5 cm, 10 cm, 20 cm, 40 cm). The cell axis gap can be, for example, greater than 1 cm-40 cm, including every 1 cm increment within this range (e.g., greater than 1 cm, 3 cm, 4 cm, 5 cm, 40 cm). The cell axis gap can be greater than the lesser curvature of the stomach 2 and/or greater than the greater curvature of the stomach 2. One or more of the cell central axes can be parallel with another cell central axis. One or more of the cell central axes can be at an angle (e.g., less than 180 degrees) relative to another cell central axis. The cells 122 can be separated from each other by gaps between loops and/or the cells 122 can overlap each other.

The cells 122 can be moved relative to each other (e.g., over and/or under each other) in the target site 147, for example, by inserting and/or withdrawing the catheter 9 from the target site 147. The cells 122 can be moved into and/or out of alignment with each other in the target site 147. The cells 122 can be moved from first offset positions to second offset positions. The cells 122 may or may not be moved into and/or out of alignment with each other.

The catheter 9 (e.g., a portion of one of the loops 118) can be moved across one or more of the cells 122. The portion of the catheter 9 that extends across the cell 122 can partially occlude (also referred to as partially obstruct) the cell 122. The cells 122 can be obstructed and/or unobstructed by moving the catheter 9 over a cell 122 and/or by moving the catheter 9 away from the cell 122, respectively. Moving the catheter 9 across a cell 122 can, for example, split the cell 122 into two or more subcells.

FIGS. 46a-46z3 illustrate that the catheter 9 (e.g., the loops 118) and/or the cells 122 can have various arrangements and orientations in the target site 147, for example, relative to a flow path through the target site 147 and/or one or more walls of the target site 147. For example, the flow path through the stomach 2 can be along a path having a curved axis that does not contact the stomach wall 108 from a gastroesophageal junction 120 of the gastrointestinal tract 110, through the stomach 2, to the pylorus 65. FIGS. 46a-46z3 illustrate that when the catheter 9 is in a deployed configuration (e.g., a configuration 116), the catheter 9 can obstruct a center of the flow path through the target site 147 (e.g., the flow path that extends through the stomach 2, the pylorus 65, and/or the duodenum 37). FIGS. 46a-46z3 illustrate that when the catheter 9 is in a deployed configuration (e.g., a configuration 116), the catheter 9 can extend across a center of the flow path through the target site 147 (e.g., the flow path that extends through the stomach 2, the pylorus 65, and/or the duodenum 37). When the catheter 9 is in a deployed configuration, the catheter 9 (e.g., the loops 118) can contact an anterior wall of the stomach 2, a posterior wall of the stomach 2, a superior wall of the stomach 2, an inferior wall of the stomach 2, a lateral wall of the stomach 2, a proximal wall of the stomach 2, a distal wall of the stomach 2, or any combination thereof. When the catheter 9 is in a deployed configuration, the cells 122 can face the anterior wall of the stomach 2, the posterior wall of the stomach 2, the superior wall of the stomach 2, the inferior wall of the stomach 2, the lateral wall of the stomach 2, the proximal wall of the stomach 2, the distal wall of the stomach 2, or any combination thereof. For example, FIGS. 46a-46z3 illustrate that the cells 122 can face the anterior wall of the stomach 2 and the posterior wall of the stomach 2. The cell central axis of the cells 122 can be at an angle of 70 degrees-110 degrees relative to a longitudinal axis of the flow path through the target site 147 (e.g., relative to a flow path along having a curved axis from a gastroesophageal junction 120 of the gastrointestinal tract 110 to the pylorus 65), including every 1 degree increment within this range (e.g., 70 degrees, 90 degrees, 110 degrees). For example, the cells 122 can be perpendicular to the flow path through the target site 147.

The loops 118 and/or the cells 122 can be formed and/or collapsed in the target site 147 in any order. For example, FIGS. 46a-46o illustrate that the loops 118 (e.g., 118a, 118b, 118c, and/or 118d) can be formed in the order shown and FIGS. 46o-46z3 illustrate that the loops 118 (e.g., 118a, 118b, 118c, and/or 118d) can be collapsed in the order shown. A loop 118 can be considered to collapse, for example, when the size (e.g., the perimeter) of the loop 118 decreases, the loop length of the loop 118 decreases, the loop width of the loop 118 decreases, the loop height of the loop 118 decreases, or any combination thereof. The loops 118 can be collapsed, for example, by withdrawing the catheter 9 from the target site 147. The loops 118 and/or the cells 122 can be formed and/or collapsed in the target site 147 in any order, for example, sequentially and/or simultaneously. For example, FIGS. 46a-46c illustrate that during a first phase of loop formation, the loop 118a can be formed before the loop 118b, and FIGS. 46d-46f illustrate that during a second phase of loop formation, the loop 118a and the loop 118b can be formed simultaneously. As another example, FIGS. 46x-46z illustrate that during a first phase of loop collapse, the loop 118a and the loop 118b can simultaneously collapse, and FIGS. 46d-46f illustrate that during a second phase of loop collapse, the loop 118a can be collapsed after the loop 118 is collapsed.

FIGS. 46a-46z3 illustrate that the catheter 9 can be packed into and/or unpacked from a target site 147 in the body such that the catheter 9 crisscrosses and/or extends across the target site 147 in multiple directions. FIGS. 46a-46z3 illustrate that the target site 147 can be the stomach 2. The catheter 9 can be packed into a target site 147 by inserting the catheter 9 into the target site 147. The catheter 9 can be unpacked from the target site 147 by withdrawing the catheter 9 from the target site 147.

FIGS. 46a-46z3 illustrate that when the catheter 9 is in a deployed configuration (e.g., a configuration 116), the catheter 9 can define a mesh having cells (e.g., cells 122), a lattice structure having cells (e.g., cells 122), a matting having cells (e.g., cells 122), a path (e.g., a tortuous path) defining cells (e.g., cells 122) and nodes (e.g., the nodes can be where the catheter 9 crosses over itself—the catheter 9 may or may not contact itself at the nodes), a meandering path defining cells (e.g., cells 122), a serpentine path defining cells (e.g., cells 122), a scaffold having cells (e.g., cells 122), a 3D structure having cells (e.g., cells 122), an amorphous 3D structure having cells (e.g., cells 122), an arrangement having cells (e.g., cells 122), a web having cells (e.g., cells 122), a network having cells (e.g., cells 122), a labyrinth having cells (e.g., cells 122), a patchwork of sections of the catheter 9 that can crisscross each other, a tangled structure, a coil, a coiled structure, or any combination thereof. For example, FIGS. 46a-46z3 illustrate that the catheter 9 can form a coil 138 inside the target site 147 such that the catheter 9 winds back and forth in multiple directions across (e.g., longitudinally across and/or transversely across) the target site 147. FIGS. 46a-46z3 illustrate, for example, that the catheter 9 can extend across the target site 147 in multiple directions and/or zigzag across the target site 147.

The catheter 9 can have a total length 124 (also referred to as the total catheter total length 124). The catheter total length 124 can be, for example, 100 cm-900 cm or more, including every 1 cm increment within this range (e.g., 100 cm, 200 cm, 300 cm, 500 cm, 900 cm). The total length 124 can be, for example, the total length of the catheter 9 from a proximal end of the catheter 9 to a distal end of the catheter 9. The total length 124 can be, for example, the total length of the catheter 9 from a proximal end of the catheter 9 to the catheter tip 7. The total length 124 can be, for example, the total length of the catheter 9 from a proximal terminal end of the catheter 9 to a distal terminal end of the catheter 9 (e.g., to a distal terminal end of the catheter tip 7). For example, total length 124 can be, for example, the total length of the catheter 9 from the connector 14 to a distal terminal end of the catheter 9. As another example, the total length 124 can be, for example, the total length of the catheter 9 from a handle of the catheter 9 to a distal terminal end of the catheter 9 (e.g., to a distal terminal end of the catheter tip 7).

A length 126 of the catheter 9 (also referred to as the catheter length 126) can be inserted into and/or removed from the target site 147. The length 126 of the catheter 9 can be a portion of the total length 124 of the catheter. The catheter length 126 can be, for example, 20 cm-600 cm, 20 cm-300 cm, 30 cm-300 cm, 50 cm-300 cm, 70 cm-300 cm, or 110 cm-300 cm, including every 1 cm increment within these ranges (e.g., 20 cm, 30 cm, 40 cm, 50 cm, 60 cm, 100 cm, 110 cm, 150 cm, 300 cm, 600 cm). The length 126 can be, for example, 5%-90% of the total length 124, including every 1% increment within this range (e.g., 5%, 10%, 50%, 90%). The length 126 can be, for example, 10% or more, 20% or more 30% or more, 40% or more, 50% or more, 60% or more, and/or 70% or more of the total length 124. The length 126 of the catheter 9 in the target site 147 can include a distal portion of the catheter 9. For example, 50% or less of the total length 124 can be in the target site 147. As another example, the length 126 of the catheter 9 in the target site 147 can include a proximal portion of the catheter 9 and a distal portion of the catheter 9. For example, greater than 50% of the total length 124 can be in the target site 147. For example, the catheter 9 can have a midpoint between the proximal terminal end of the catheter 9 and the distal terminal end of the catheter 9. The proximal portion of the catheter 9 can be the portion of the catheter 9 proximal the midpoint and the distal portion of the catheter 9 can be the portion of the catheter 9 distal the midpoint such that the proximal portion of the catheter 9 and the distal portion of the catheter 9 can have the same length (e.g., 50% of the total length 124).

Different lengths (e.g., any length 126) of the catheter 9 can be introduced into and/or removed from the target site 147. The length 126 of the catheter 9 in the target site 147 can be increased and/or decreased. For example, more and/or less length of the catheter 9 can be introduced and/or removed depending on the size of the target site 147 (e.g., the stomach 2 and/or the duodenum 37) and/or other organs (e.g., the duodenum 37 and/or the pancreas 1). The length 126 of the catheter 9 in the target site 147 can be adjusted, for example, before, during, and/or after transferring heat to and/or from the catheter 9 (e.g., before, after, and/or while passing the fluid 6 through the catheter 9). For example, the catheter length 126 in the target site 147 can be increased and/or decreased. Adjusting the length of the catheter 9 in the target site 147 can, for example, impact the surface area of the catheter 9 that contacts the stomach 2 and/or impact the total heat transfer to the stomach 2 and/or other organs. FIGS. 46a-46o illustrate, for example, that increasing the length 126 of the catheter 9 in the target site 147 can increase the surface area of the catheter 9 inside the target site 147 and can increase the total heat transfer to and/or from the stomach 2 and/or other organs. FIGS. 46o-46z3 illustrate, for example, that decreasing the length 126 of the catheter 9 in the stomach 2 can decrease the surface area of the catheter 9 inside the stomach 2 and can decrease the total heat transfer to and/or from the stomach 2 and/or other organs. The configuration 116 and the shape 117 of the catheter 9 can be changed, for example, by increasing and/or decreasing the length 126 of the catheter 9 in the target site 147. For example, the configuration 116 and the shape 117 of the catheter 9 can be changed from a first configuration and a first shape (e.g., any configuration 116 and shape 117) to a second configuration and a second shape (e.g., any configuration 116 and shape 117), for example, by increasing and/or decreasing the length 126 of the catheter 9 in the target site 147. For example, any of the configurations 116 and shapes 117 in FIGS. 46a-46z3 can be a first configuration and a first shape, respectively, and any of the configurations 116 and shapes 117 in FIGS. 46a-46z3 can be a second configuration and a second shape, respectively. For example, FIGS. 46a-46z3 that the arrangement and/or path (e.g., the shape 117) that the catheter 9 can have in the target site 147 can depend on the length of the catheter 9 that is in the target site 147. FIGS. 46a-46z3 illustrate that the arrangement and/or path (e.g., the shape 117) of the catheter 9 can change, for example, as the catheter 9 is inserted into and/or withdrawn from the target site 147. FIGS. 46a-46z3 illustrate, for example, that the arrangement and/or path (e.g., the shape 117) of the catheter 9 can be changed by increasing and/or decreasing the length 126 of the catheter 9 in the target site 147.

The catheter 9 can have one or multiple heat transfer regions 128, for example, 1-30 or more heat transfer regions 128, including every 1 heat transfer region increment within this range (e.g., 1 heat transfer region, 2 heat transfer regions, 30 heat transfer regions). One or more portions of the catheter 9 can be a heat transfer region 128. One or more portions of the catheter 9 can have a heat transfer region 128. The heat transfer region 128 can be a length (e.g., a section) of the catheter 9. The heat transfer region 128 can be a continuous length of the catheter 9. For example, the heat transfer region 128 can be a length of the catheter 9, for example, the length 126 and/or the total length 124. For example, the portion of the catheter 9 in the target site 147 can be a heat transfer region 128 and/or the entire length of the catheter 9 can be a heat transfer region 128. As another example, the heat transfer region 128 can be, for example, 50%-100% of a length (e.g., the catheter length 126) of the catheter 9 positionable in the target site 147. As another example, when the catheter 9 is in a deployed configuration (e.g., a configuration 116), the heat transfer region 128 can be, for example, 50%-100% of a length (e.g., the catheter length 126) of the catheter 9 in the target site 147 (e.g., in the stomach 2 and/or in the duodenum 37). As another example, when the catheter 9 is in a deployed configuration (e.g., a configuration 116), the heat transfer region 128 can be, for example, 50%-100% of a length (e.g., the catheter length 126) of the catheter 9 inside the body (e.g., inside the mouth, a nasal passageway, a nasal cavity, the esophagus 5, the stomach 2, the pylorus 65, the duodenum 37, the jejunum 10, or any combination thereof). FIGS. 46a-46z3 illustrate, for example, that the heat transfer region 128 can extend continuously along a length (e.g., the length 126) of the catheter 9. FIGS. 46a-46z3 illustrate that the heat transfer region 128 can be the catheter 9, for example, a length of the catheter 9 (e.g., the length 126 of the catheter 9). The heat transfer regions 128 can be, for example, one or more lengths (e.g., one or more sections) of the catheter 9. The heat transfer regions 128 can be integrated with and/or attached to each other. The heat transfer regions 128 can be, for example, the loops 118. Each loop 118 in a configuration 116 can be a different heat transfer region 128 or a different portion of the same heat transfer region 128. For example, FIGS. 46a-46z3 illustrate that each loop 118 in a configuration 116 can be a different portion of the same heat transfer region 128.

The heat transfer regions 128 can have a length 130 (also referred to as the heat transfer region length 130). The length 130 can be, for example, 10% or more, 20% or more 30% or more, 40% or more, 50% or more, 60% or more, and/or 70% or more of the length 126 and/or the total length 124. The length 130 can be the same as or different than the catheter length 126 and/or the total length 124. For example, the portion of the catheter 9 having the length 126 can be a heat transfer region 128 (e.g., a continuous heat transfer region) such that the configurations 116 and the shapes 117 of the catheter 9 can be the configurations and shapes of the heat transfer region 128. For example, the heat transfer region 128 can be formed into the configurations 116 having shapes 117. Each loop 118 of a shape 117 can be a different heat transfer region 128 (e.g., the perimeter of each loop 118 can be the length of each heat transfer region 128) and/or can be different portions of the same heat transfer region 128 (e.g., the portion of the catheter having the length 126 can be the heat transfer region 126). A ratio of the length 130 to a length of the target site 147) can be, for example, 1.5 to 20.0.

The path (e.g., the shape 117) of the heat transfer region 128 in the target site 147 can vary. For example, FIGS. 46a-46z3 that the path (e.g., the shape 117) that the heat transfer region 128 can have in the target site 147 can depend on the length 130 of the heat transfer region 128 that is in the target site 147. FIGS. 46a-46z3 illustrate that the path (e.g., the shape 117) of the heat transfer region 128 can change, for example, as the catheter 9 is inserted into and/or withdrawn from the target site 147. FIGS. 46a-46z3 illustrate, for example, that the path (e.g., the shape 117) can be changed by increasing and/or decreasing the length 126 of the catheter 9 in the target site 147.

When the catheter 9 is in a deployed configuration (e.g., a configuration 116), the heat transfer region 128 can be proximal and/or distal the catheter tip 7. For example, FIGS. 46a-46z3 illustrate that the heat transfer region 128 can be proximal the catheter tip 7. When the catheter 9 is in a deployed configuration, the heat transfer region 128 can be proximal and/or distal a distal terminal end of the catheter 9. For example, FIGS. 46a-46z3 illustrate that the heat transfer region 128 can be proximal the distal terminal end of the catheter 9. FIGS. 46a-46z3 illustrate that the heat transfer region 128 can extend proximally away from the catheter tip 7. As another example, the heat transfer region 128 can extend proximally away from the catheter tip 7 and/or distally away from the catheter tip 7. The heat transfer region 128 can be between a distal end of the catheter 9 and a proximal end of the catheter 9 along the length of the catheter 9. The heat transfer region 128 can be between a distal terminal end of the catheter 9 and a proximal terminal end of the catheter 9 along the length of the catheter 9.

The heat transfer region 128 can be, for example, any portion of the catheter 9 that has a lumen (e.g., the lumen 15 and/or the lumen 16). For example, the heat transfer region 128 can be any portion of the catheter that has an inflow lumen and/or an outflow lumen (e.g., the lumen 15 and/or the lumen 16). The distal terminal end of the heat transfer region 128 can be, for example, the merge zone 105 of the inflow lumen and the outflow lumen. The merge zone 105 can be inside the catheter 9, for example, inside a distal end of the catheter 9. The merge zone 105 can be inside the distal end of the catheter (e.g., inside the catheter tip 7), for example, 0.10 cm-10.00 cm proximal the distal terminal end of the catheter 9, including every 0.10 cm increment within this range (e.g., 0.10 cm, 1.00 cm, 2.00 cm, 5.00 cm, 10.00 cm). The heat transfer region 128 can terminate anywhere along the length of the catheter 9. For example, the heat transfer region 128 can terminate, for example, where the inflow lumen and the outflow lumen merge (e.g., at the merge zone 105).

The catheter 9 (e.g., the heat transfer region 128) can transfer heat when a fluid (e.g., the fluid 6) is in the catheter 9. For example, the catheter 9 (e.g., the heat transfer region 128) can transfer heat to and/or from the body when a fluid is pumped through a lumen in the catheter 9, for example, through an inflow lumen and an outflow lumen (e.g., the lumen 15 and the lumen 16). For example, when a fluid is 2 in the catheter 9 (e.g., in the heat transfer region 128) and the fluid has a temperature greater than or less than the surrounding tissue, heat can be transferred to and/or from the fluid through the catheter wall to and/or from the surrounding tissue. When a fluid is in the catheter 9 (e.g., in the heat transfer region 128) and the fluid has a temperature greater than or less than the surrounding tissue, the fluid can emit and/or absorb heat, for example, through the wall of the catheter 9. The catheter 9 can emit and/or absorb heat.

The catheter 9 can have one or more heat transfer zones 132 (also referred to as heating zones 132). The heat transfer zones 132 can extend from the one or more heat transfer regions 128. The heat transfer zone 132 can be, for example, a space adjacent the catheter 9. The heat transfer zone 132 can extend (e.g., radially extend) away from the catheter 9. For example, the heat transfer zone 132 can have a cylindrical shape (e.g., a hollow cylindrical shape) that extends along a length of the catheter 9 (e.g., the total length 124, the length 126, and/or the length of the heat transfer region 128). The catheter 9 can extend through the heat transfer zone 132. For example, the catheter 9 can extend through a longitudinal center of the of the heat transfer zone 132. The heat transfer zone 132 can extend, for example, a distance 132d (e.g., a radius) of 1 cm-10 cm or more away (e.g., radially away) from the catheter 9, for example, as measured from a center longitudinal axis Ac of the catheter 9 or from the exterior surface of the catheter 9, including every 1 cm increment within this range (e.g., 1 cm, 2 cm 5 cm, 10 cm).

The heat transfer zone 132 of different lengths (also referred to as sections) of the catheter 9 can overlap with each other. For example, when the catheter is in a configuration 116, a first heating zone of a first length of the heat transfer region 128 can overlap a second heating zone of a second length of the heat transfer region 128. The first heating zone can be the heating zone 132 of any first length of the catheter 9 and the second heating zone can be the heating zone 132 of any second length of the catheter 9. For example, the first heating zone can be a heating zone 132 that can extend from the loop first end 118-1 to the loop second end 118-1 of one of the loops 118 (e.g., the loop 118a) and the second heating zone can be a heating zone 132 that can extend from the loop first end 118-1 to the loop second end 118-1 of another one of the loops 118 (e.g., the loop 118b, 118c, or 118d). As another example, the first heating zone can be the heating zone 132 that can extend from one of the loops 118 (e.g., loop 118a) and the second heating zone can be the heating zone 132 that can extend from another one of the loops 118 (e.g., loop 118b, 118c, or 118d). As yet another example, the first heating zone can be a heating zone 132 that can extend from the loop first end 118-1 to the loop second end 118-1 of one of the loops 118 (e.g., the loop 118a) and the second heating zone can be a heating zone 132 that can extend from the loop second end 118-2 of the same or a different loop 118 (e.g., the loop 118a, 118b, 118c, or 118d).

The catheter 9 can have various configurations 116 and/or shapes 117 in the target site 147. For example, the catheter 9 can have the configurations 116 and the shapes 117 shown in FIGS. 46a-58b. The catheter 9 can have various positions relative to itself, the target site 147, and the surrounding organs. For example, the catheter 9 can have the various positions relative to itself, the target site 147, and the surrounding organs shown in FIGS. 46a-58b. The loops 118 can have various relative positions to each other. For example, the loops 118 can have the relative positions between each other shown in FIGS. 46a-58b. The loops 118 can have various sizes and/or shapes. For example, the loops 118 can have the sizes and/or shapes shown in FIGS. 46a-58b. The cells 122 can have various sizes, shapes, and/or relative positions. For example, the cells 122 can have the sizes, shapes, and/or relative positions shown in FIGS. 46a-58b.

In FIGS. 46b-46z2, reference points B1-B2, C1-C2, D1-D4, E1-E3, F1-F3, G1-G3, H1-H4, I1-I5, J1-J5, K1-K5, L1-L5, M1-M5, N1-N5, O1-O5 are provided to assist in the identification of different sections of the catheter 9 and to assist in the description of the shapes 117 (e.g., shapes 117a-117z3) and/or the loops 118 that the catheter 9 can have. The reference points are used, for example, to refer to different sections of the catheter 9. The different sections can be integral with each other and/or attached to each other. For example, the different sections of the catheter 9 can be sections of a single length of the catheter 9 (e.g., sections of the total length 124 of the catheter 9). Reference points B1, C1, D1, E1, D1, E1, F1, G1, H1, I1, J1, K1, L1, M1, N1, and O1 can mark, for example, the distal terminal end of the catheter 9 and/or the distal terminal end of the heat transfer region 128. Reference points B2, C2, D3, E3, F3, G3, H4, I5, J5, K5, L5, M5 N5, and O5 can mark, for example, the location that catheter 9 enters the target site 147.

FIGS. 46a-46o illustrate that when the catheter 9 is in the first through the fifteenth configuration 116a-116o, the catheter 9 can have the first through the fifteenth the shape 117a-117o, respectively. FIGS. 46a-46o illustrate that the catheter 9 can change from the first to through the fifteenth configuration 116a-116o by inserting the catheter 9 into the target site 147. FIGS. 46o-46z3 illustrate that when the catheter 9 is in the fifteenth through the twenty-ninth configuration 116o-116z3, the catheter 9 can have the fifteenth through the twenty-ninth shape 117o-117z3, respectively. FIGS. 46a-46z3 illustrate that the catheter 9 can change from the fifteenth to the twenty-ninth configuration 116o-116z3 by withdrawing the catheter 9 from the target site 147.

FIG. 46a illustrates that when the catheter tip 7 is in the esophagus 5, the catheter 9 may not have a loop 118. As another example, when the catheter tip 7 is in the esophagus 5, the catheter 9 can have loops that can expand upon entry into the target site 147 and/or when the loops are inflated.

FIG. 46b illustrates that the first loop 118a can be formed by section B1-B2 of the of the catheter 9. The length of section B1-B2 of the catheter 9 can be, for example, the length 126.

FIG. 46c illustrates that the first loop 118a can be formed by section C1-C2 of the of the catheter 9. The length of section C1-C2 of the catheter 9 can be, for example, the length 126. FIG. 46c illustrates that the size (e.g., the perimeter) of the first loop 118a can be larger when the catheter 9 is in the third configuration 116c than when the catheter 9 is in the second configuration 116b. FIG. 46c illustrates that the gap between the first loop first end 118a-1 and the first loop second end 118a-2 can be smaller when the catheter 9 is in the third configuration 116c than when the catheter 9 is in the second configuration 116b. FIG. 46c illustrates that the catheter tip 7 can be in a different position in the target site 147 when the catheter 9 is in the third configuration 116c than when the catheter 9 is in the second configuration 116b. For example, FIG. 46c illustrates that the catheter tip 7 can be closer to a superior portion of the stomach 2 and/or to the gastroesophageal junction 120 when the catheter 9 is in the third configuration 116c than when the catheter 9 is in the second configuration 116b.

FIG. 46d illustrates that the first loop 118a can be formed by section D1-D3 of the of the catheter 9 and that the second loop 118b can be formed by section D2-D4 of the catheter 9. The length of section D1-D3 of the catheter 9 can be, for example, the length 126. The length of section D2-D4 can be, for example, less than the length of section D1-D3. FIG. 46d illustrates that section D3-D4 of the second loop 118b can be in the esophagus 5 and that section D2-D3 of the second loop 118b can be in the target site 147. FIG. 46d illustrates that the same section of the catheter 9 can define multiple loops 118. For example, FIG. 46d illustrates that section D2-D3 of the catheter 9 can be a section of the first loop 118a and a section of the second loop 118b. FIG. 46d illustrates, for example, that the second loop 118b can be formed from a section (e.g., section D2-D3) of the first loop 118a. FIG. 46d illustrates that the size (e.g., the perimeter) of the first loop 118a can be larger when the catheter 9 is in the fourth configuration 116d than when the catheter 9 is in the third configuration 116c. FIG. 46d illustrates that the gap between the first loop first end 118a-1 and the first loop second end 118a-2 can be smaller when the catheter 9 is in the fourth configuration 116d than when the catheter 9 is in the third configuration 116b. FIG. 46d illustrates that when the catheter 9 is in the fourth configuration 116d, the catheter tip 7 can be in the same position in the target site 147 as when the catheter 9 is in the third configuration 116c.

FIG. 46e illustrates that the first loop 118a can be formed by section E1-E3 of the of the catheter 9 and that the second loop 118b can be formed by section E2-E3 of the catheter 9. The length of section E1-E3 of the catheter 9 can be, for example, the length 126. The length of section E2-E3 can be, for example, less than the length of section E1-E3. FIG. 46e illustrates that the size (e.g., the perimeter) of the first loop 118a and/or the second loop 118b can be larger when the catheter 9 is in the fifth configuration 116e than when the catheter 9 is in the fourth configuration 116d. FIG. 46e illustrates that the second loop 118b can be closer to the catheter tip 7 when the catheter 9 is in the fifth configuration 116e than when the catheter 9 is in the fourth configuration 116d. FIG. 46e illustrates that the second loop 118b (e.g., the second loop head 118b-3) can be closer to the first loop 118a (e.g., to the first loop first end 118a-1 and/or to the first loop head 118a-3) when the catheter 9 is in the fifth configuration 116e than when the catheter 9 is in the fourth configuration 116d. FIG. 46d illustrates that when the catheter 9 is in the fifth configuration 116e, the catheter tip 7 can be in the same position in the target site 147 as when the catheter 9 is in the fourth configuration 116d. FIG. 46e illustrates that the gap between the first loop first end 118a-1 and the first loop second end 118a-2 can be smaller when the catheter 9 is in the fifth configuration 116e (e.g., the gap between reference points E1 and E3) than when the catheter 9 is in the fourth configuration 116d (e.g., the gap between reference points D1 and D3).

FIG. 46f illustrates that the first loop 118a can be formed by section F1-F3 of the of the catheter 9 and that the second loop 118b can be formed by section F2-F3 of the catheter 9. The length of section F1-F3 of the catheter 9 can be, for example, the length 126. The length of section F2-F3 can be, for example, less than the length of section F1-F3. FIG. 46f illustrates that the size (e.g., the perimeter) of the first loop 118a and/or the second loop 118b can be larger when the catheter 9 is in the sixth configuration 116f than when the catheter 9 is in the fifth configuration 116e. FIG. 46f illustrates that the second loop 118b (e.g., the second loop head 118b-3) can be closer to the first loop 118a (e.g., to the first loop first end 118a-1 and/or to the first loop head 118a-3) when the catheter 9 is in the sixth configuration 116f than when the catheter 9 is in the fifth configuration 116e.

FIG. 46g illustrates that the first loop 118a can be formed by section G1-G3 of the of the catheter 9 and that the second loop 118b can be formed by section G2-G3 of the catheter 9. The length of section G1-G3 of the catheter 9 can be, for example, the length 126. The length of section G2-G3 can be, for example, less than the length of section G1-G3. FIG. 46g illustrates that the size (e.g., the perimeter) of the first loop 118a and/or the second loop 118b can be larger when the catheter 9 is in the seventh configuration 116g than when the catheter 9 is in the sixth configuration 116f. FIG. 46g illustrates that the second loop 118b (e.g., the second loop head 118b-3) can be closer to the first loop 118a (e.g., to the first loop first end 118a-1 and/or to the first loop head 118a-3) when the catheter 9 is in the seventh configuration 116g than when the catheter 9 is in the sixth configuration 116f. FIGS. 46d-46g illustrate that increasing the length of the catheter 9 in the target site 147 (e.g., the stomach 2) can move the second loop 118b toward the first loop 118a. FIGS. 46f-46g illustrate that increasing the length of the catheter 9 in the target site 147 (e.g., the stomach 2) can move the second loop 118b across (e.g., over or under) the first loop 118a. FIGS. 46f-46g illustrate that increasing the length of the catheter 9 in the target site 147 can pinch the first loop 118a closed which can split the first cell 122a into subcells, for example, a first subcell 122a1 and a second subcell 122a2. FIG. 46g illustrates that the first subcell 122a1 can be an open cell and that the second subcell 122a2 can be a closed cell. FIG. 46g illustrates, for example, that the second cell 122b can be between the first subcell 122a1 and the second subcell 122a2. FIGS. 46d-46f illustrate that increasing the length of the catheter 9 in the target site 147 (e.g., the stomach 2) can move the second loop 118b (e.g., the second loop first end 118b-1) toward the catheter tip 7. FIGS. 46f-46g illustrate that increasing the length of the catheter 9 in the target site 147 (e.g., the stomach 2) can move the second loop 118b (e.g., the second loop first end 118b-1) away from the catheter tip 7.

FIG. 46h illustrates that the first loop 118a can be formed by section H1-H4 of the of the catheter 9, that the second loop 118b can be formed by section H2-H4 of the catheter 9, and that the third loop 118c can be formed by section H3-H4 of the catheter 9. The length of section H1-H4 of the catheter 9 can be, for example, the length 126. The length of sections H2-H4 and H3-H4 can be, for example, less than the length of section H1-H4. FIG. 46h illustrates that the size (e.g., the perimeter) of the third loop 118c can be larger when the catheter 9 is in the eighth configuration 116h than when the catheter 9 is in the seventh configuration 116g. FIG. 46h illustrates that the third loop 118c can be farther from the gastroesophageal junction 120 when the catheter 9 is in the eighth configuration 116h than when the catheter 9 is in the seventh configuration 116g. FIG. 46h illustrates that the same section of the catheter 9 can define multiple loops 118. For example, FIG. 46h illustrates that section H3-H4 of the catheter 9 can be a section of the second loop 118b and a section of the third loop 118c. FIG. 46h illustrates that the first loop 118 can extend back and forth across the target site 147. For example, FIG. 46h illustrates that the first loop first end 118a-1 can extend back and forth across the target site 147. FIG. 46h illustrates that a portion of the first loop 118a can extend across (e.g., over or under) the second cell 122b. FIG. 46h illustrates that the portion of the first loop 118a that extends across the second cell 122b can partially obstruct the second cell 122b. FIG. 46h illustrates that the second loop 118b can extend across (e.g., over or under) the first loop 118a such that a cell 134 can be created between the first loop 118a and the second loop 118b. FIG. 46h illustrates that a first section of the catheter 9 (e.g., the second loop head 118b-3) can extend across a second section of the catheter 9 (e.g., the first loop second end 118a-2 and/or the first loop head 118-3) at two locations, for example, at opposite ends of the cell 134. FIG. 46h illustrates that the cell 134 can be created, for example, between a radial outer surface of the first loop 118a and a radial inner surface of the second loop 118b.

FIG. 46i illustrates that the first loop 118a can be formed by section I1-I5 of the of the catheter 9, that the second loop 118b can be formed by section I2-I4 of the catheter 9, and that the third loop 118c can be formed by section I3-I5 of the catheter 9. The length of section I1-I5 of the catheter 9 can be, for example, the length 126. The length of sections I2-I4 and I3-I5 can be, for example, less than the length of section I1-I5. FIG. 46i illustrates that the size (e.g., the perimeter) of the third loop 118c can be larger when the catheter 9 is in the ninth configuration 116i than when the catheter 9 is in the eighth configuration 116h. FIGS. 46h-46i illustrate that increasing the length of the catheter 9 in the target site 147 can pinch the second loop 118b closed which can split the second cell 122b into subcells, for example, a first subcell 122b1 and a second subcell 122b2. FIG. 46i illustrates that the first subcell 122b1 can be an open cell and that the second subcell 122b2 can be a closed cell. FIG. 46i illustrates, for example, that a first section of the catheter 9 (e.g., the second loop first end 118b-1 and/or the third loop head 118c-3) can be adjacent to and/or in contact with a second section of the catheter 9 (e.g., second loop second end 118b-2) at a location Z1. FIGS. 46h-46i illustrate, for example, that increasing the length of the catheter 9 in the target site 147 can cause a first section of the catheter 9 (e.g., the second loop first end 118b-1 and/or the third loop head 118c-3) to move adjacent to and/or in contact with a second section of the catheter 9 (e.g., second loop second end 118b-2) at the first location Z1.

FIG. 46j illustrates that the first loop 118a can be formed by section J1-J5 of the of the catheter 9, that the second loop 118b can be formed by section J2-J4 of the catheter 9, and that the third loop 118c can be formed by section J3-J5 of the catheter 9. The length of section J1-J5 of the catheter 9 can be, for example, the length 126. The length of sections J2-J4 and J3-J5 can be, for example, less than the length of section J1-J5. FIG. 46j illustrates that the size (e.g., the perimeter) of the third loop 118c can be larger when the catheter 9 is in the tenth configuration 116j than when the catheter 9 is in the ninth configuration 116i. FIGS. 46i-46j illustrate that increasing the length of the catheter 9 in the target site can cause a first section of the catheter 9 (e.g., the second loop first end 118b-1 and/or the third loop head 118c-3) to move (e.g., push) a second section of the catheter 9 (e.g., second loop second end 118b-2) from the first location Z1 to a second location Z2. FIG. 46j illustrates that location Z2 can be farther from the esophagus 5 and/or closer to the pylorus 65 by a distance Z3. The distance Z3 can be, for example, 1 cm-5 cm or more, including every 1 cm increment within this range (e.g., 1 cm, 2 cm, 3 cm, 5 cm). FIGS. 46i-46j illustrate, for example, that a first section of the catheter 9 (e.g., the second loop first end 118b-1 and/or the third loop head 118c-3) can deform a second section of the catheter 9 (e.g., second loop second end 118b-2), for example, by the first section moving into the second section as the catheter 9 is packed into the target site 147. FIGS. 46i-46j illustrate, for example, that the second section of the catheter 9 (e.g., second loop second end 118b-2) can resist movement of the first section of the catheter 9 (e.g., the second loop first end 118b-1 and/or the third loop head 118c-3) into the target site 147 as the catheter 9 is packed into (e.g., inserted into) the target site 147.

FIG. 46k illustrates that the first loop 118a can be formed by section K1-K5 of the of the catheter 9, that the second loop 118b can be formed by section K2-K4 of the catheter 9, and that the third loop 118c can be formed by section K3-K5 of the catheter 9. The length of section K1-K5 of the catheter 9 can be, for example, the length 126. The length of sections K2-K4 and K3-K5 can be, for example, less than the length of section K1-K5. FIG. 46*k* illustrates that the size (e.g., the perimeter) of the third loop 118*c* can be larger when the catheter 9 is in the eleventh configuration 116*k* than when the catheter 9 is in the tenth configuration 116*j*. FIG. 46*k* illustrates that a portion of the second loop 118*b* (e.g., the second loop second end 118*b*-2) can extend across the third cell 122*c*. FIG. 46*k* illustrates that the portion of the second loop 118*b* that extends across the third cell 122*c* can partially obstruct the third cell 122*c*. FIG. 46*k* illustrates that a first section of the catheter 9 (e.g., the second loop first end 118*b*-1 and/or the third loop head 118*c*-3) can extend across (e.g., over or under) a second section of the catheter 9 (e.g., second loop second end 118*b*-2) at two locations. FIG. 46*k* illustrates that the third cell 122*c* can overlap with the first cell 122*a* (e.g., with the second subcell 122*a*2).

FIG. 46*l* illustrates that the first loop 118*a* can be formed by section L1-L5 of the of the catheter 9, that the second loop 118*b* can be formed by section L2-L4 of the catheter 9, and that the third loop 118*c* can be formed by section L3-L5 of the catheter 9. The length of section L1-L5 of the catheter 9 can be, for example, the length 126. The length of sections L2-L4 and L3-L5 can be, for example, less than the length of section L1-L5. FIG. 46*l* illustrates that more of the third cell 122*c* can overlap with the first cell 122*a* (e.g., with the second subcell 122*a*2) when the catheter 9 is in the twelfth configuration 116*l* than when the catheter 9 is in the eleventh configuration 116*k*. FIG. 46*l* illustrates that a first section of the catheter 9 (e.g., the second loop first end 118*b*-1 and/or the third loop head 118*c*-3) can be adjacent to and/or in contact with a second section of the catheter 9 (e.g., the first loop head 118*a*-3). FIGS. 46*k*-46*l* illustrate, for example, that increasing the length of the catheter 9 in the target site 147 can cause a first section of the catheter 9 (e.g., the second loop first end 118*b*-1 and/or the third loop head 118*c*-3) to move adjacent to and/or in contact with a second section of the catheter 9 (e.g., the first loop head 118*a*-3). FIGS. 46*h*-46*l* illustrate that increasing the length of the catheter 9 in the target site 147 (e.g., the stomach 2) can move the third loop 118*c* toward a boundary of the shape 117.

FIG. 46*m* illustrates that the first loop 118*a* can be formed by section M1-M5 of the of the catheter 9, that the second loop 118*b* can be formed by section M2-M4 of the catheter 9, that the third loop 118*c* can be formed by section M3-M5 of the catheter 9, and that the fourth loop 118*d* can be formed by section M4-M5. The length of section M1-M5 of the catheter 9 can be, for example, the length 126. The length of sections M2-M4, M3-M5, and M4-M5 can be, for example, less than the length of section M1-M5. FIG. 46*m* illustrates that more of the third cell 122*c* can overlap with the first cell 122*a* (e.g., with the second subcell 122*a*2) when the catheter 9 is in the thirteenth configuration 116*m* than when the catheter 9 is in the twelfth configuration 116*l*. FIG. 46*m* illustrates that the second loop 118*b* and the third loop 118*c* can define an infinity shape. For example, FIG. 46*m* illustrates that section M2-M4 of the catheter 9 can include the infinity shape.

FIG. 46*n* illustrates that the first loop 118*a* can be formed by section N1-N5 of the of the catheter 9, that the second loop 118*b* can be formed by section N2-N4 of the catheter 9, that the third loop 118*c* can be formed by section N3-N5 of the catheter 9, and that the fourth loop 118*d* can be formed by section N4-N5. The length of section N1-N5 of the catheter 9 can be, for example, the length 126. The length of sections N2-N4, N3-N5, and N4-N5 can be, for example, less than the length of section N1-N5. FIG. 46*n* illustrates that the size (e.g., the perimeter) of the fourth loop 118*d* can be larger when the catheter 9 is in the fourteenth configuration 116*n* than when the catheter 9 is in the thirteenth configuration 116*m*. FIGS. 46*m*-46*n* illustrate that increasing the length of the catheter 9 in the target site 147 can pinch the third loop 118*c* closed which can split the third cell 122*c* into subcells, for example, a first subcell 122*c*1 and a second subcell 122*c*2. FIG. 46*n* illustrates that the first subcell 122*c*1 can be an open cell and that the second subcell 122*c*2 can be a closed cell. FIG. 46*n* illustrates, for example, that a first section of the catheter 9 (e.g., the third loop first end 118*c*-1 and/or the fourth loop head 118*d*-3) can be adjacent to and/or in contact with a second section of the catheter 9 (e.g., the third loop second end 118*c*-2). FIGS. 46*m*-46*n* illustrate, for example, that increasing the length of the catheter 9 in the target site 147 can cause a first section of the catheter 9 (e.g., the third loop first end 118*c*-1 and/or the fourth loop head 118*d*-3) to move adjacent to and/or in contact with a second section of the catheter 9 (e.g., the third loop second end 118*c*-2).

FIG. 46*o* illustrates that the first loop 118*a* can be formed by section O1-O5 of the of the catheter 9, that the second loop 118*b* can be formed by section O2-O4 of the catheter 9, that the third loop 118*c* can be formed by section O3-O5 of the catheter 9, and that the fourth loop 118*d* can be formed by section O4-O5. The length of section O1-O5 of the catheter 9 can be, for example, the length 126. FIG. 46*o* illustrates, for example, that the length 126 can be 110 cm. The length of sections O2-O4, O3-O5, and O4-O5 can be, for example, less than the length of section O1-O5. FIG. 46*o* illustrates that the size (e.g., the perimeter) of the fourth loop 118*c* can be larger when the catheter 9 is in the fifteenth configuration 116*o* than when the catheter 9 is in the fourteenth configuration 116*n*. FIG. 46*o* illustrates that a first section of the catheter (e.g., the third loop first end 118*c*-1 and/or the fourth loop head end 118*d*-3) can extend across the second cell 122*b*. FIG. 46*o* illustrates that the portion of the catheter 9 that extends across the second cell 122*b* can partially obstruct the second cell 122*b*. FIG. 46*o* illustrates that a first section of the catheter (e.g., the third loop first end 118*c*-1 and/or the fourth loop head end 118*d*-3) can extend across (e.g., over or under) a second section of the catheter 9 (e.g., the third loop second end 118*c*-2) at two locations. FIG. 46*o* illustrates that the fourth cell 122*d* can overlap with the second cell 122*b* (e.g., with the second subcell 122*b*2). FIGS. 46*a*-46*o* illustrate that the first loop 118*a* can include the second loop 118*b*, the third loop 118*c*, and the fourth loop 114*b*.

The loops 118 can be formed proximal and/or distal the catheter tip 7 in the target site 147. For example, FIGS. 46*a*-46*z*3 illustrate that the loops 118 can be formed distal the catheter tip 7 in the target site 147. For example, FIGS. 46*a*-46*z*3 illustrate that the loops 118 (e.g., the second loop 118*b*, the third loop 118*c*, and the fourth loop 118*d*) can be formed between the catheter tip 7 and the pylorus 65.

FIGS. 46*o*-46*z*3 illustrate that the catheter 9 can be withdrawn from the target site 147. FIGS. 46*o*-46*z*3 illustrate that the loops 118 can be collapsed in and/or removed from the target site 147. FIGS. 46*o*-46*z*3 illustrate that collapsing the loops 118 can include straightening the loop 118, decreasing the curve of a loop, decreasing the perimeter of the loop 118, decreasing the loop length of the loops 118, decreasing the width of the loops 118, decreasing the height of the loops 118, or any combination thereof. FIGS. 46*a*-46*z*3 illustrate that the loops 118 can be collapsed in the target site 147 by withdrawing the catheter 9 from the target site 147.

FIGS. 46a-46o illustrate that the catheter 9 can form a coil (e.g., the coil 138) in the target site 147, for example, by inserting the catheter 9 into the target site 147. FIGS. 46a-46o illustrate, for example, that the coil 138 (e.g., the length 126 of the catheter 9 in the target site 147) can become more tangled, can become larger, can extend across the target site 147 more times, and/or can become more dense (e.g., more of the catheter 9 per unit of volume of the target site 147 such as more of the catheter per 1 cm³ of the target site 147) as the catheter 9 is inserted into the target site 147. FIGS. 46a-46z3 illustrate that the catheter 9 can form (e.g., progressively form) the coil 138. FIGS. 46o-46z3 illustrate, for example, that the coil 138 can become less tangled, decrease in size, extend across the target site 147 less times, and/or become less dense in the target site 147 as the catheter 9 is withdrawn from the target site 147. FIGS. 46o-46z3 illustrate that the catheter 9 can uncoil (e.g., progressively uncoil) as the catheter 9 is withdrawn from the target site 147. FIGS. 46o-46z3 illustrate, for example, that the coil 138 can uncoil (e.g., progressively uncoil) in the target site 147 as the catheter 9 is withdrawn from the target site 147.

FIGS. 46a-46z3 illustrate that when the catheter 9 is in a deployed configuration (e.g., a configuration 116), the heat transfer region 128 can be in the stomach 2 and the esophagus 5.

FIGS. 47a-47i illustrate that the catheter 9 can be inserted into and/or removed from the stomach 2. FIGS. 47a-47i illustrate that various lengths of the catheter 9 (e.g., the length 126 shown in FIGS. 47b-47h) can be introduced into and/or removed from the stomach 2. FIGS. 47a-47i illustrate various configurations 116 and shapes 117 that the catheter 9 can have. The configurations 116 and shapes 117 in FIGS. 47a-47i can be, for example, different than the configurations 116 and shapes 117 in FIGS. 46a-46z3. FIGS. 47a-47i illustrate, for example, that when the catheter 9 is in a first through a ninth configuration 116a-116i, the catheter 9 can have the first through the ninth shape 117a-117i, respectively. As another example, the catheter 9 in the target site 147 can have any combination of the loops 118 and/or cells 122 shown in FIGS. 46b-46z2 and 47b-47i.

FIGS. 47a-47e illustrate that the catheter 9 can be inserted into the target site 147 as shown by arrow 112.

FIG. 47a illustrates that when the catheter tip 7 is in the esophagus 5, the catheter 9 may not have the loops 118.

Figure 47B:
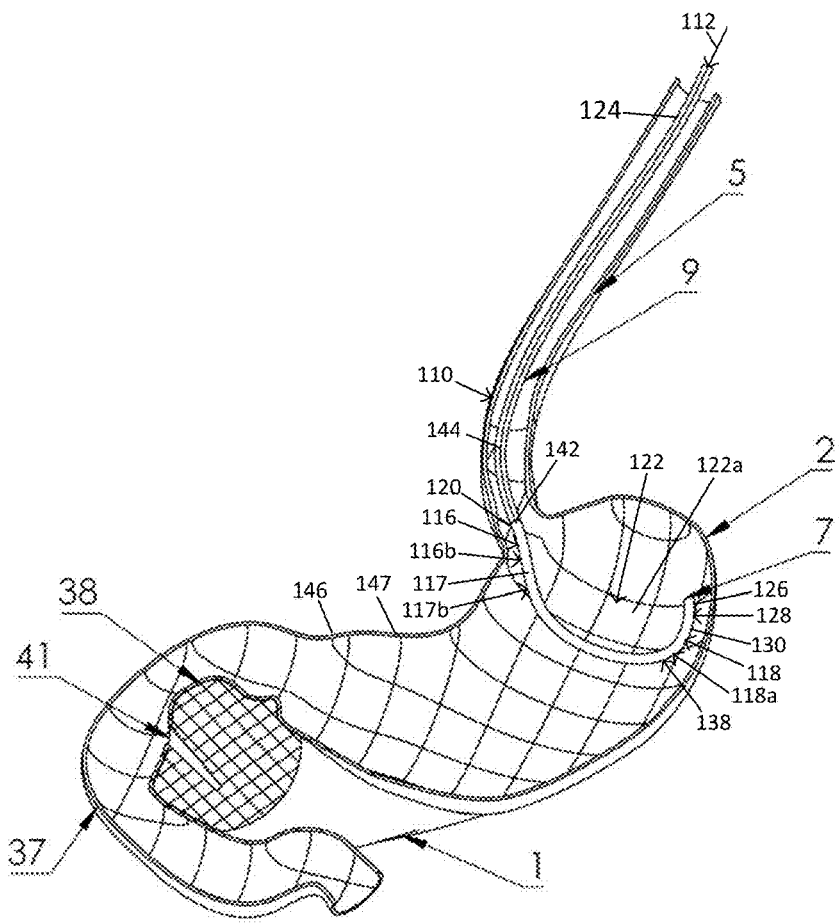

FIG. 47b illustrates that the first loop 118a can be an open loop. FIG. 47b illustrates that in the configuration 116 shown, the length 126 can be, for example, 15 cm-40 cm (e.g., 25 cm).

Figure 47C:
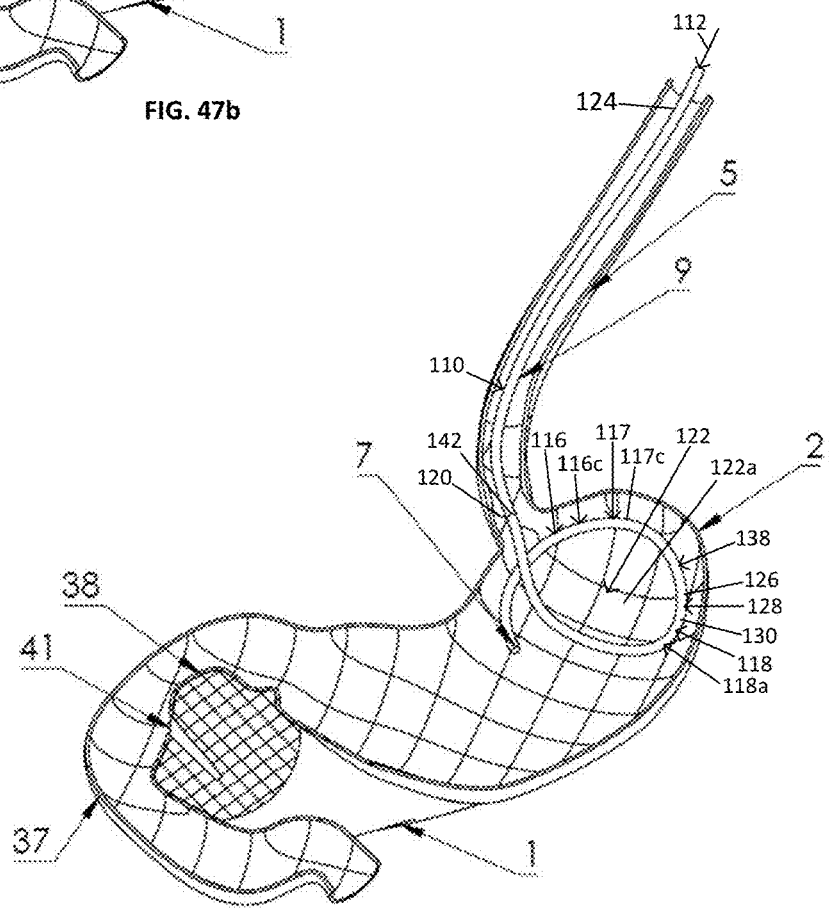

FIG. 47c illustrates that the first loop 118a can be a closed loop. FIGS. 47b-47c illustrate that the first loop 118 can be changed from an open loop to a closed loop, for example, by inserting the catheter 9 into the target site 147. FIGS. 47b-47c illustrate that the size (e.g., the perimeter) of the first loop 118a can be larger when the catheter 9 is in the third configuration 116c than when the catheter 9 is in the second configuration 116b. FIG. 47c illustrates that in the configuration 116 shown, the length 126 can be, for example, 20 cm-90 cm (e.g., 50 cm).

Figure 47D:
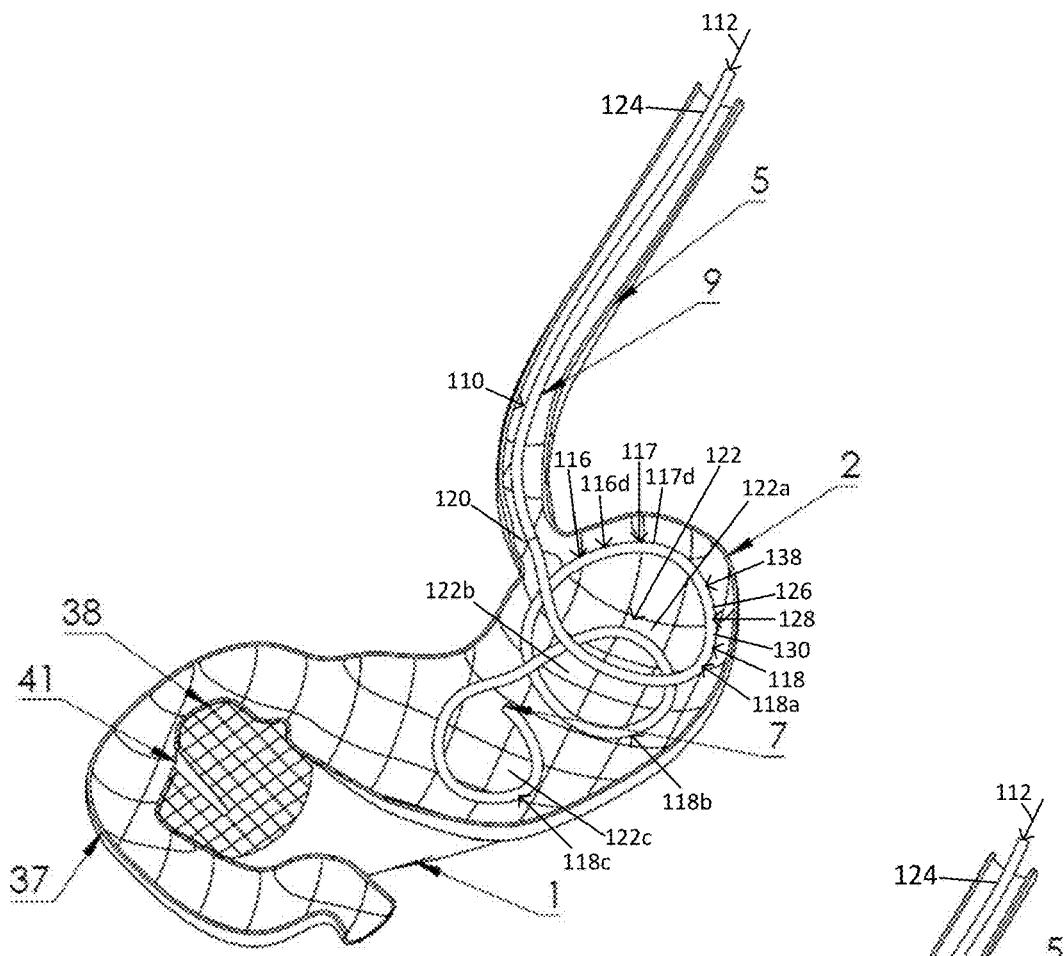

FIG. 47d illustrates that the first loop 118a and the second loop 118b can be closed loops and that the third loop 118c can be an open loop. FIG. 47d illustrates that the first loop 118a can overlap with the second loop 118b. FIG. 47d illustrates that the second loop 118b can overlap with the first loop 118a. FIG. 47d illustrates that a portion of the second loop 118b can be posterior to the first loop 118a. FIG. 47d illustrates that the first cell 122a and the second cell 122b can overlap and be offset from each other. For example, FIG. 47d illustrates that an inferior portion of the first cell 122b can overlap with (e.g., be aligned with) a superior portion of the second cell 122b. FIG. 47d illustrates that in the configuration 116 shown, the length 126 can be, for example, 70 cm-200 cm (e.g., 80 cm).

Figure 47E:
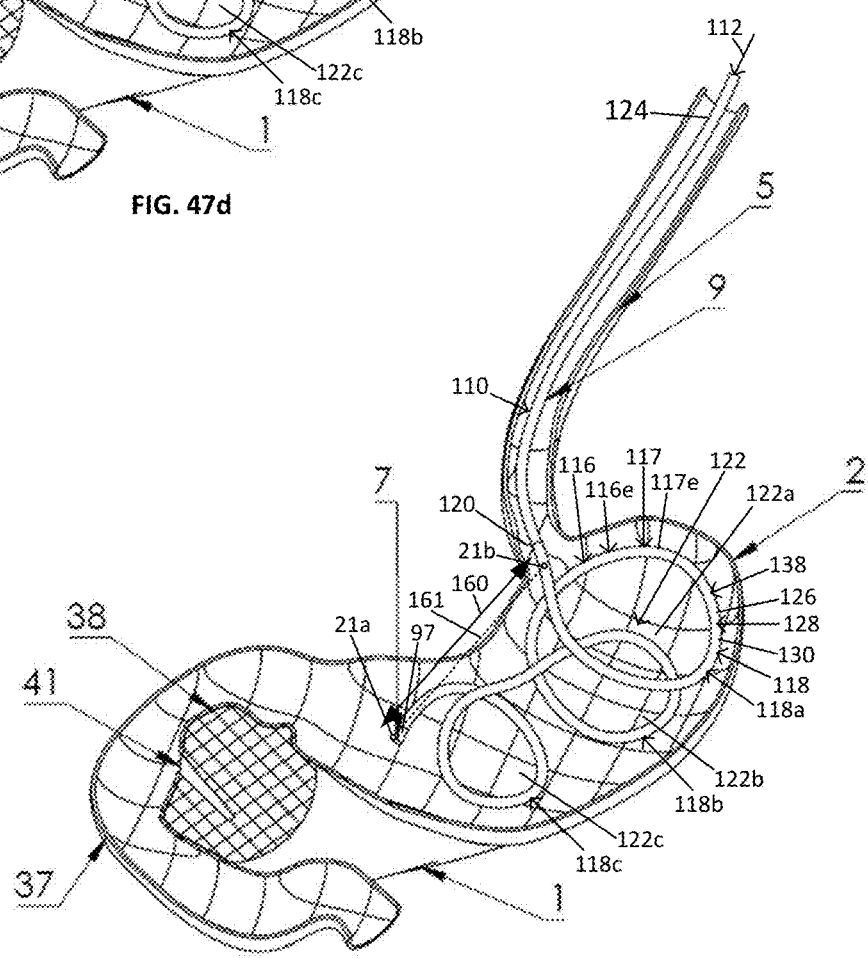
Figure 47F:
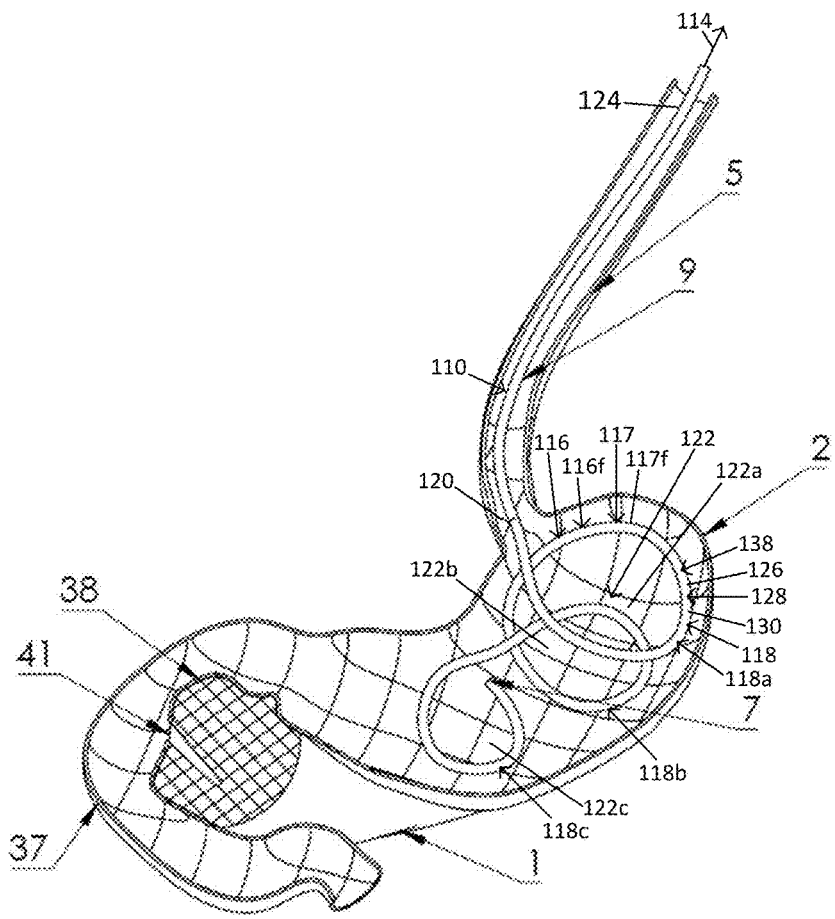
Figure 47G:
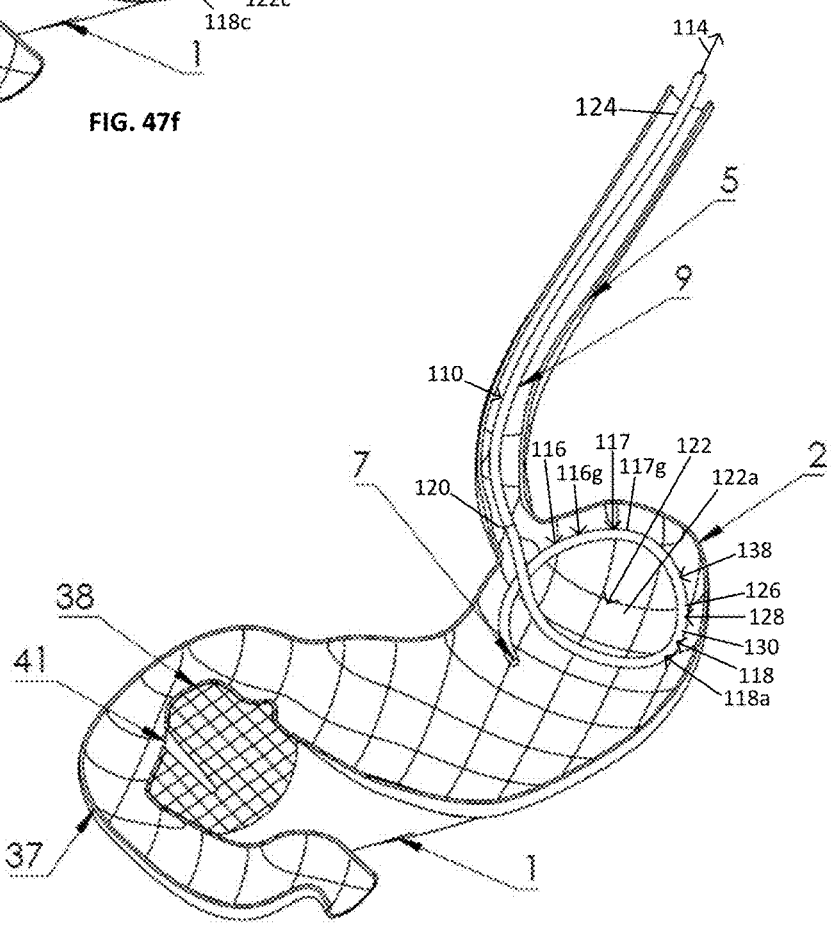
Figure 47H:
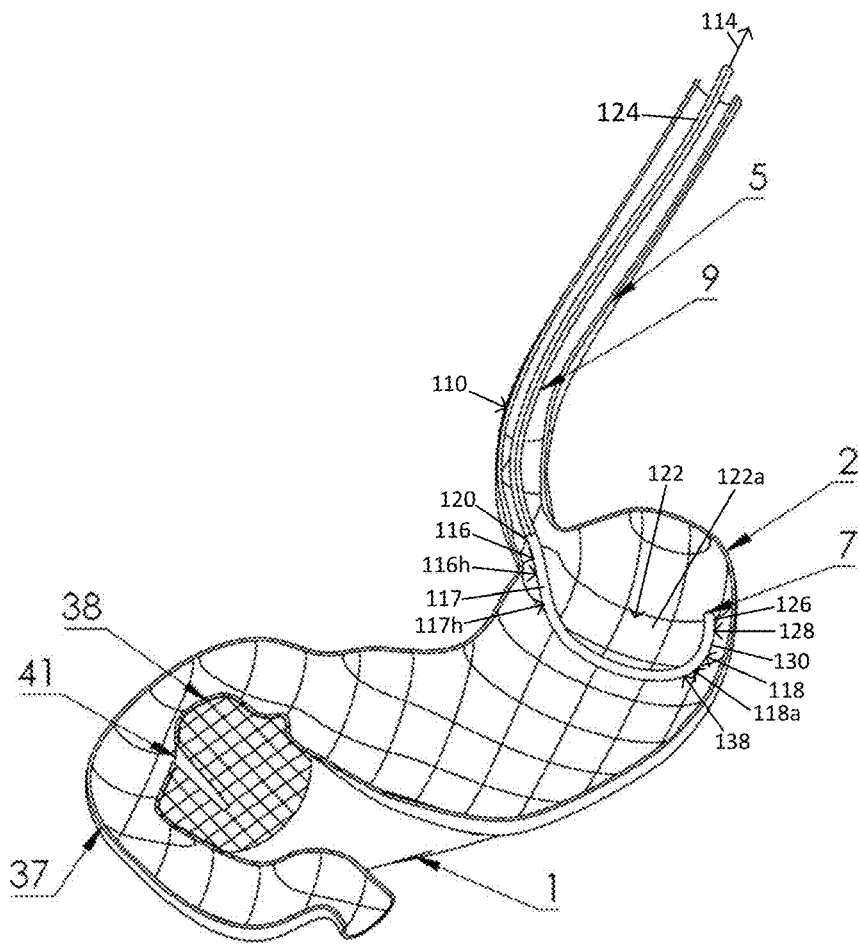
Figure 47I:
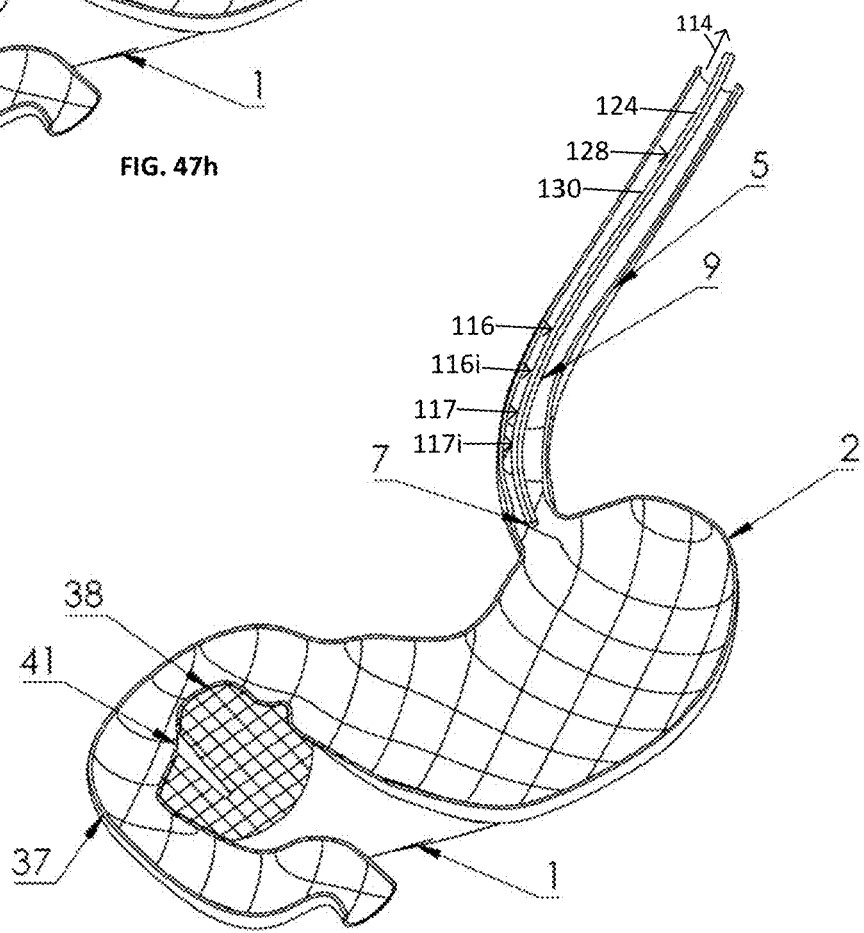

FIG. 47e illustrates that the first loop 118a, the second loop 118b, and the third loop 118c can be closed loops. FIGS. 47d-47e illustrate that the third loop 118 can be changed from an open loop to a closed loop, for example, by inserting the catheter 9 into the target site 147. FIGS. 47d-47e illustrate that the size (e.g., the perimeter) of the third loop 118c can be larger when the catheter 9 is in the fifth configuration 116e than when the catheter 9 is in the fourth configuration 116d. FIGS. 47d-47e illustrate that the size (e.g., the perimeter) of the second third loop 118c can be increased and/or decreased independently of the size of the first loop 118 and/or of the second loop 118b. FIG. 47e illustrates that in the configuration 116 shown, the length 126 can be, for example, 80 cm-180 cm (e.g., 90 cm).

FIGS. 47d-47e illustrates that a distal loop (e.g., the second loop 118b and/or the third loop 118c) can be formed in the target site 147 after a proximal loop (e.g., the first loop 118a) loop is formed in the target site 147. FIG. 47e illustrates that a distal cell (e.g., the second cell 122b and/or the third cell 122c) can be formed in the target site 147 after a proximal cell (e.g., the first cell 122a) is formed in the target site 147.

FIGS. 47a-47e illustrate that the loops 118 and the cells 122 can be formed by inserting the catheter 9 into the target site 147. The loops 118 can be formed in the target site 147 in any order, for example, sequentially and/or simultaneously. For example, FIGS. 47a-47e illustrate that the first loop 118a, the second loop 118b, and the third loop 118c can be sequentially formed. For example, FIGS. 47a-47e illustrate that the first loop 118a can be formed in the target site 147, then the second loop 118b can be formed in the target site 147, and then the third loop 118c can be formed in the target site 147. For example, FIGS. 47a-47e illustrate that the second loop 118b can be formed after the first loop 118a is formed and that the third loop 118c can be formed after the first loop 118a and/or the second loop 118b are formed.

FIGS. 47a-47e illustrate, for example, that during a first phase of loop formation, the loop 118a can be formed, that during a second phase of loop formation, the loop 118b can be formed, and that during a third phase of loop formation, the loop 118c can be formed. The first phase of loop formation can be before the second phase of loop formation. The second phase of loop formation can be after the first phase of loop formation. The third phase of loop formation can be after the second phase of loop formation. While the second loop 118b is being formed (e.g., during the second phase of loop formation), the first loop 118a can have a constant size and/or shape. As another example, while the second loop 118b is being formed (e.g., during the second phase of loop formation), the size (e.g., perimeter) of the first loop 118a can increase and/or decrease, the shape of the first loop 118a can change, or any combination thereof. While the third loop 118c is being formed (e.g., during the third phase of loop formation), the first loop 118a and/or the second loop 118b can have a constant size and/or shape. As another example, while the third loop 118c is being formed (e.g., during the third phase of loop formation), the size (e.g., perimeter) of the first loop 118a and/or the second loop 118b can increase and/or decrease, the shape of the first loop 118a and/or the second loop 118b can change, or any combination thereof.

FIGS. 47a-47e illustrate that different sections of the catheter 9 can form different loops 118 at different times and/or at different stages of loop formation. For example, FIGS. 47a-47e illustrate that when the catheter 9 is in the third configuration 116c, a first section of the catheter 9 can form the first loop 118a, and that when the catheter 9 is in the fourth configuration 116d, the first section of the catheter 9 can form the third loop 118c and a second section of the catheter 9 can form the first loop 118a. As another example, FIGS. 47a-47e illustrate that when the catheter 9 is in the third configuration 116c, a first section of the catheter 9 can form the first loop 118a, and that when the catheter 9 is in the fifth configuration 116e, the first section of the catheter 9 can form the third loop 118c and a second section of the catheter 9 can form the first loop 118a. The first section of the catheter 9 can have the same length when the catheter 9 is in the third configuration 116c, the fourth configuration 116d, and the fifth configuration 116e. FIGS. 47a-47e illustrate that the first section of the catheter 9 can be distal the second section of the catheter along the length of the catheter 9. FIGS. 47a-47e illustrate, for example, that the first section of the catheter 9 can be a distal end of the catheter 9. FIGS. 47a-47e illustrate, for example, that the first section of the catheter 9 can have the catheter tip 7. As yet another example, during the first phase of loop formation, a first section of the catheter 9 can form the first loop 118a, during the second phase of loop formation, the first section of the catheter 9 can form the second loop 118b and a second section of the catheter 9 can form the first loop 118a, during the third phase of loop formation, the first section of the catheter 9 can form the third loop 118c, the second section of the catheter 9 can form the second loop 118b, and a third section of the catheter 9 can form the first loop 118a. FIGS. 47a-47e illustrate, for example, that the catheter tip 7 can trace out the path of the catheter 9 in the target site 147 as the catheter 9 is inserted into the target site 147. FIGS. 47a-47e illustrate, for example, that one or more sections of the catheter 9 proximal the catheter tip 7 can follow the path of a distal section (e.g., the distal tip 7) through the target site 147 as the catheter 9 is advanced into the target site 147 (e.g., proximal sections of the catheter 9 can follow the path of distal sections of the catheter 9 in the target site 147 as the catheter 9 is inserted into the target site 147). For example, FIGS. 47a-47e illustrate that the second loop 118b can be formed distal the first loop 118a and that the third loop 118c can be formed distal the first loop 118a and the second loop 118b. FIGS. 47a-47e illustrate, for example, that when the catheter 9 is in the fourth configuration 116d and the fifth configuration 116e, the third loop 118c can be the distal most loop along the catheter 9 in the target site 147 and the first loop 118a can be the proximal most loop along the catheter 9 in the target site 147. FIGS. 47d and 47e illustrate, for example, that when the catheter 9 is in the fourth configuration 116d and the fifth configuration 116e, the first loop 118a can be proximal the second loop 118b and the third loop 118c in the target site 147 and the second loop 118b can be proximal the third loop 118c in the target site 147.

FIGS. 47e-47i illustrate that the catheter 9 can be withdrawn from the target site 147 as shown by arrow 114. FIGS. 47e-47i illustrate that the loops 118 can be collapsed in and/or removed from the target site 147. FIGS. 47e-47i illustrate that collapsing the loops 118 can include straightening the loop 118, decreasing the curve of a loop, decreasing the perimeter of the loop 118, decreasing the loop length of the loops 118, decreasing the width of the loops 118, decreasing the height of the loops 118, or any combination thereof. FIGS. 47e-47i illustrate that the loops 118 can be collapsed in the target site 147 by withdrawing the catheter 9 from the target site 147 as shown by arrow 114. FIGS. 47e-47i illustrate, for example, that the catheter 9 can straighten and/or become less curved in the target site 147 as the catheter 9 is withdrawn (e.g., pulled) from the target site 147 into the esophagus 5.

The loops 118 can be collapsed in and/or removed from the target site 147 in any order, for example, sequentially and/or simultaneously. For example, FIGS. 47e-47i illustrate that the first loop 118a, the second loop 118b, and the third loop 118c can be sequentially collapsed and/or sequentially removed from the target site 147. FIGS. 47e-47i illustrate, for example, that the first loop 118a, the second loop 118b, and the third loop 118c can be removed from the target site 147 as they are collapsing (e.g., as they are decreasing in size). For example, FIGS. 47e-47i illustrate that the first loop 118a can be collapsed and removed from the target site 147, then the second loop 118b can be collapsed and removed from the target site 147, and then the third loop 118c can be collapsed and removed from the target site 147. For example, FIGS. 47e-47i illustrate that the second loop 118b can be collapsed and removed from the target site 147 after the first loop 118a is collapsed and removed from the target site 147 and that the third loop 118c can be collapsed and removed from the target site 147 after the first loop 118a and the second loop 118b are collapsed and removed from the target site 147. FIGS. 47e-47i illustrate that the loops 118 can be collapsed independently from one another as the catheter 9 is withdrawn from the target site 147, starting with the proximal most loop (e.g., the loop 118a) and ending with the distal most loop (e.g., the loop 118c). FIGS. 47e-47i illustrate that as the first loop 118a is being collapsed and removed from the target site 147, the second loop 118b and the third loop 118c can move (e.g., be pulled) toward the gastroesophageal junction 120. FIGS. 47e-47i illustrate that as the second loop 118b is being collapsed and removed from the target site 147, the third loop 118c can move (e.g., be pulled) toward the gastroesophageal junction 120.

FIGS. 47e-47i illustrate, for example, that during a first phase of catheter removal, the section of the catheter 9 defining the first loop 118a can be removed from the target site 147, that during a second phase of catheter removal, the section of the catheter 9 defining the second loop 118b can be removed from the target site 147, and that during a third phase of catheter removal, the section of the catheter 9 defining the third loop 118c can be removed from the target site 147. During the first phase of catheter removal, the first loop 118a can collapse in the target site 147. During the second phase of catheter removal, the second loop 118b can collapse in the target site 147. During the third phase of catheter removal, the third loop 118c can collapse in the target site 147. As another example, the first loop 118a, the second loop 118b, and/or the third loop 118c can be removed from the target site 147 without collapsing, for example, if the size of the first loop 118a, the second loop 118b, and/or the third loop 118c is smaller than the passageway through the esophagus 5. The first phase of catheter removal can be before the second phase of catheter removal. The second phase of catheter removal can be after the first phase of catheter removal. The third phase of catheter removal can be after the second phase of catheter removal. While the first loop 118a is being removed (e.g., during the first phase of catheter removal), the second loop 118b and/or the third loop 118c can have a constant size and/or shape. As another example, while the first loop 118a is being removed (e.g., during the first phase of catheter removal), the size (e.g., perimeter) of the second loop 118b and/or the third loop 118c can increase and/or decrease, the shape of the second loop 118b and/or the third loop 118c can change, or any combination thereof. While the second loop 118b is being removed (e.g., during the second phase of catheter removal), the third loop 118c can have a constant size and/or shape. As another example, while the second loop 118b is being removed (e.g., during the second phase of catheter removal), the size (e.g., perimeter) of the third loop 118c can increase and/or decrease, the shape of the third loop 118c can change, or any combination thereof. FIGS. 47e-47i illustrate, for example, that one or more distal sections of the catheter 9 can follow the path of a proximal section through the target site 147 as the catheter 9 is withdrawn from the target site 147 (e.g., distal sections of the catheter 9 can follow the path of proximal sections of the catheter 9 in the target site 147 as the catheter 9 is inserted into the target site 147).

FIGS. 47a-47e illustrate that the catheter 9 can form a coil (e.g., the coil 138) in the target site 147, for example, by inserting the catheter 9 into the target site 147. FIGS. 47e-47i illustrate that the coil 138 can uncoil (e.g., progressively uncoil) in the target site 147 as the catheter 9 is withdrawn from the target site 147.

FIGS. 47a-47i illustrate, for example, that the configurations 116 formed by the catheter 9 during withdrawal can be the same as the configurations 116 formed by the catheter 9 during insertion. As another example, the configurations 116 formed by the catheter 9 during withdrawal of the catheter 9 from the body can be different from the configurations 116 formed by the catheter 9 during insertion of the catheter 9 into the body.

FIGS. 48a-48i illustrate that the catheter 9 can be inserted into and/or removed from the stomach 2. FIGS. 48a-48i illustrate that various lengths of the catheter 9 (e.g., the length 126 shown in FIGS. 48b-48h) can be introduced into and/or removed from the stomach 2. FIGS. 48a-48i illustrate various configurations 116 and shapes 117 that the catheter 9 can have. The configurations 116 and shapes 117 in FIGS. 48a-48i can be, for example, different than the configurations 116 and shapes 117 in FIGS. 46a-46z3. FIGS. 48a-48i illustrate, for example, that when the catheter 9 is in a first through a ninth configuration 116a-116i, the catheter 9 can have the first through the ninth shape 117a-117i, respectively.

FIGS. 48a-48i illustrate the same configurations 116 and shapes 117 as FIGS. 47a-47i but illustrate that the loops 118 can be formed differently and/or can be collapsed and/or removed in a different order. For example, FIGS. 48a-48e illustrate that the coil 138 can have a preset shape. For example, FIGS. 48a-48i illustrate that the catheter 9 and/or the guidewire 99 can have a preset shape in the shape of the coil 138. FIGS. 48a-48i illustrate that the coil 138 can be, for example, a loose coil (e.g., a coil with loops 118 and/or cells 122 offset from each other). FIGS. 48a-48i illustrate various shapes 117 of the coil 138. As the catheter 9 is inserted into the target site 147, the catheter 9 can be biased to form the preset shape (e.g., of the coil 138) such that the catheter 9 can, for example, automatically form the preset shape upon insertion into the target site 147 once the catheter 9 is no longer constrained by the esophagus 5. As another example, as the guidewire 99 is withdrawn from the catheter 9 as shown by arrow 111, the catheter 9 can be biased to form the preset shape (e.g., the shape of the coil 138) such that the catheter can, for example, automatically form the present shape upon withdrawal of the guidewire 99 from the catheter 9 in the target site 147. The catheter 9 can form the loops 118 and the cells 122 by forming the preset shape in the target site 147. The preset shape can have the loops 118 and the cells 122. The preset shape can be, for example, the shapes in FIGS. 48b-48h. The catheter 9 can form the present shape in the target site 147, for example, as the catheter 9 enters the target site 147 and/or as the guidewire 99 is withdrawn from the catheter 9 in the target site 147. The guidewire 99 can be removed and/or introduced to the catheter 9 to adjust the shape of the catheter 9 in the target site 147.

Figure 48A:
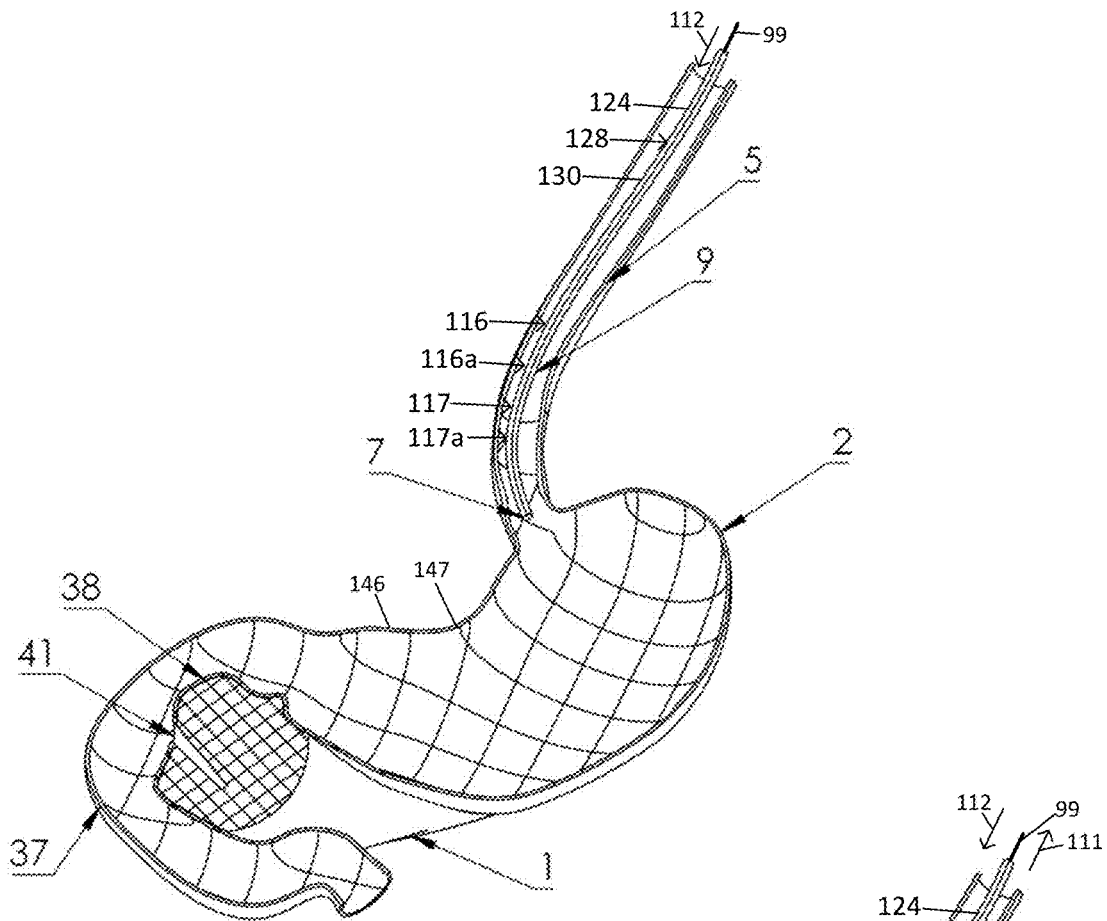
FIGS. 48a-48i illustrate the stomach, duodenum, and pancreas in an isometric view with the anterior half removed.
Figure 48B:
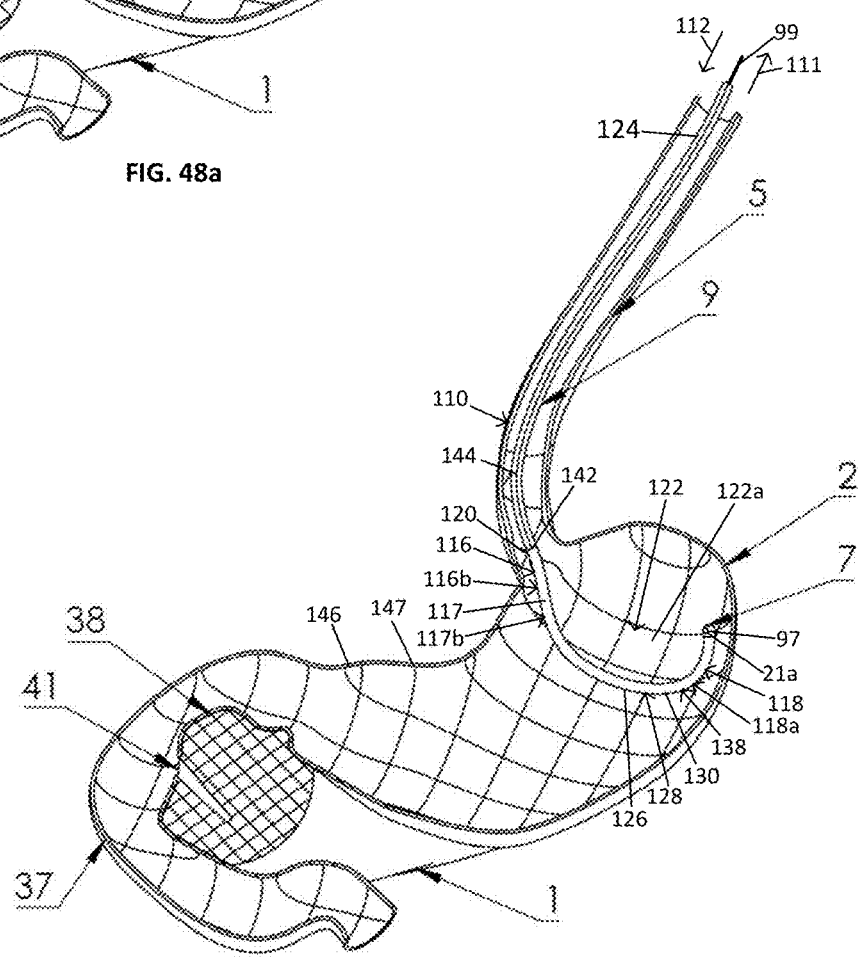
Figure 48C:
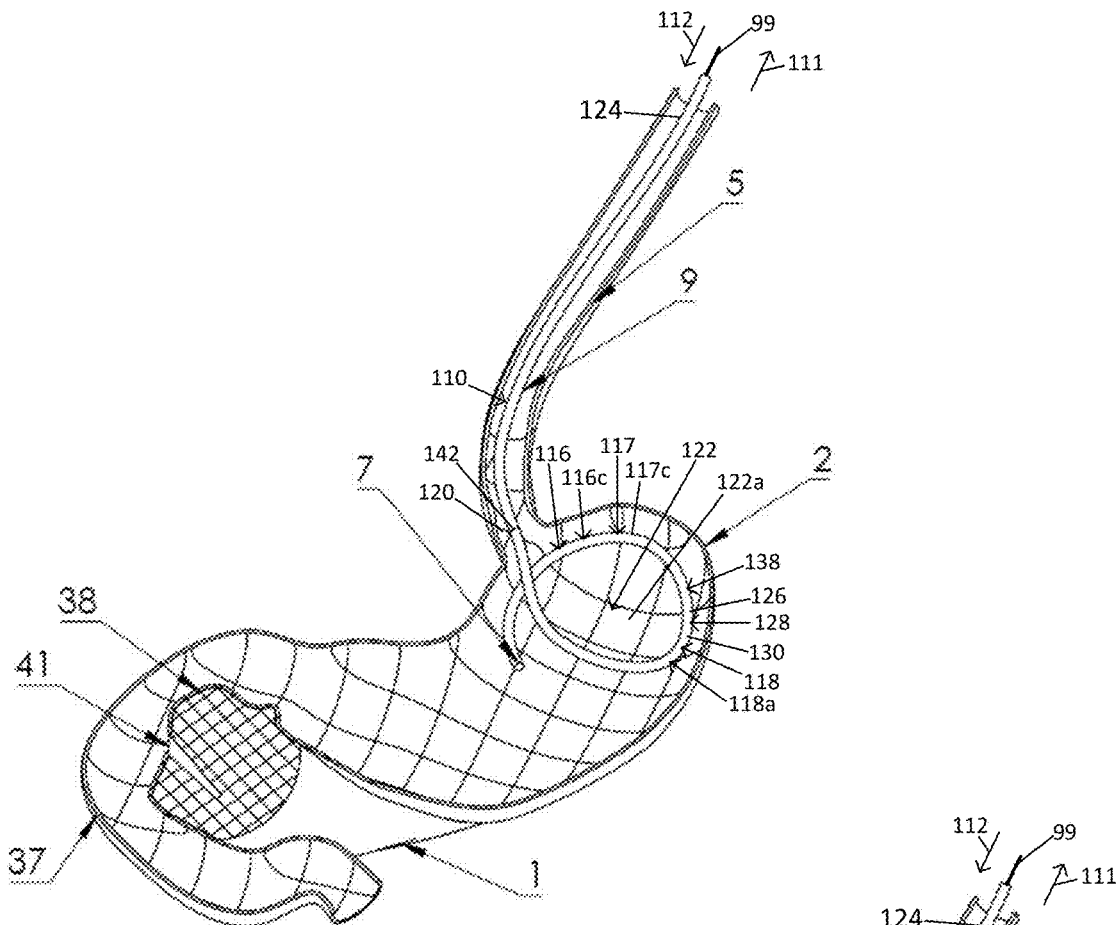
Figure 48D:
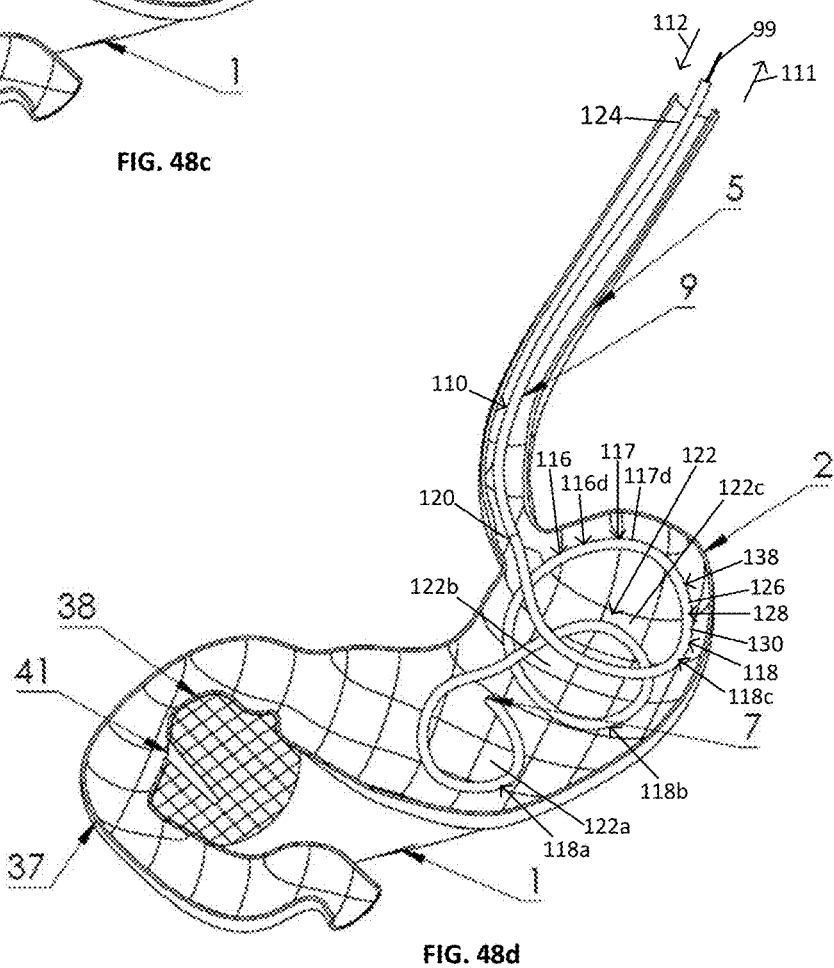
Figure 48E:
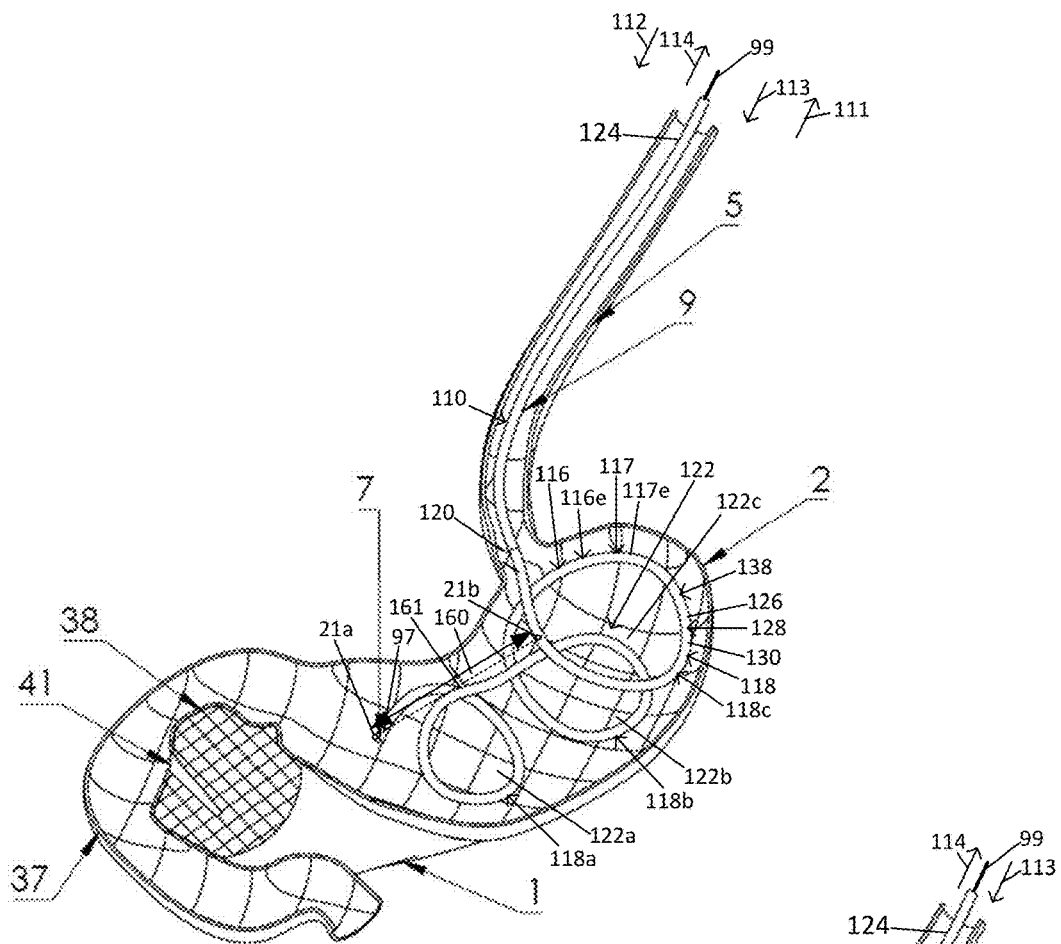
Figure 48F:
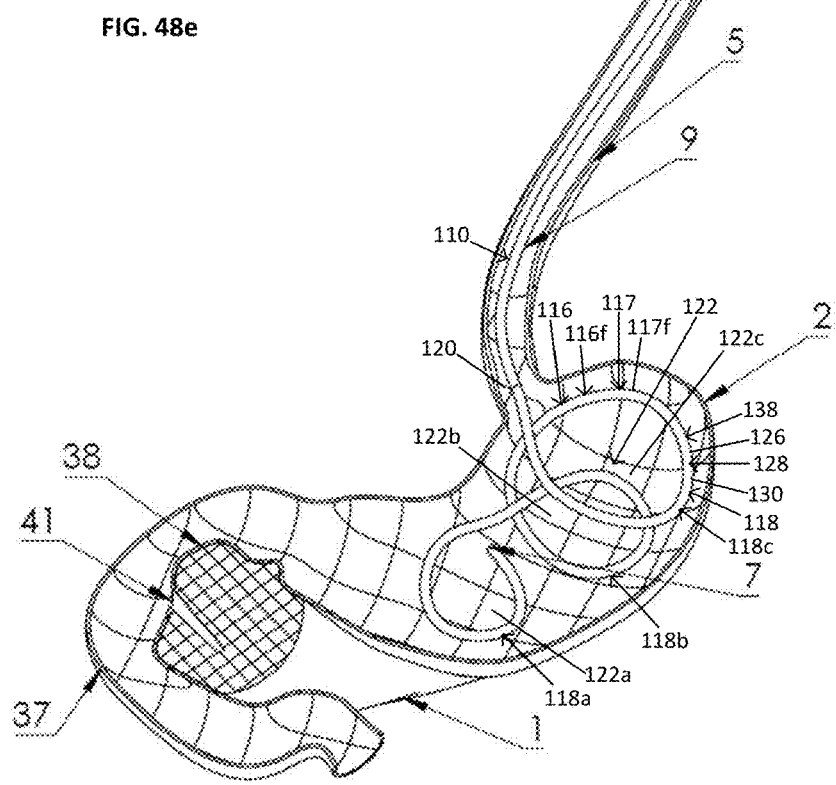
Figure 48G:
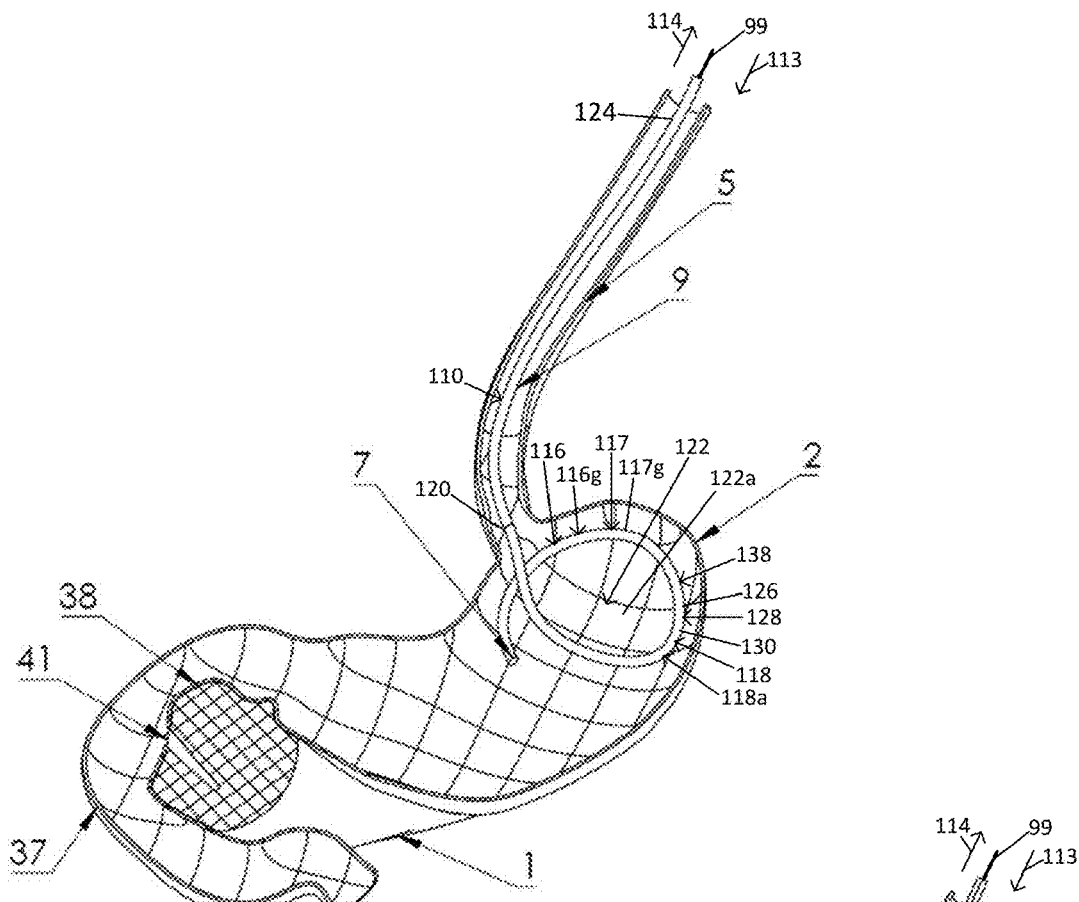
Figure 48H:
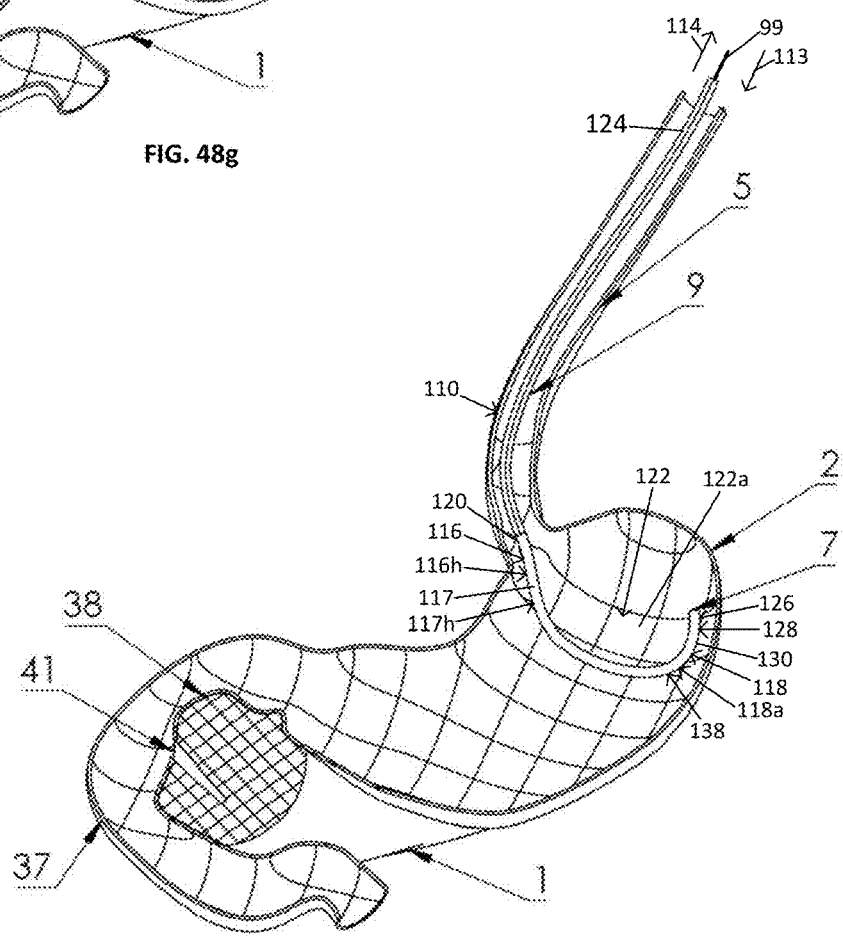
Figure 48I:
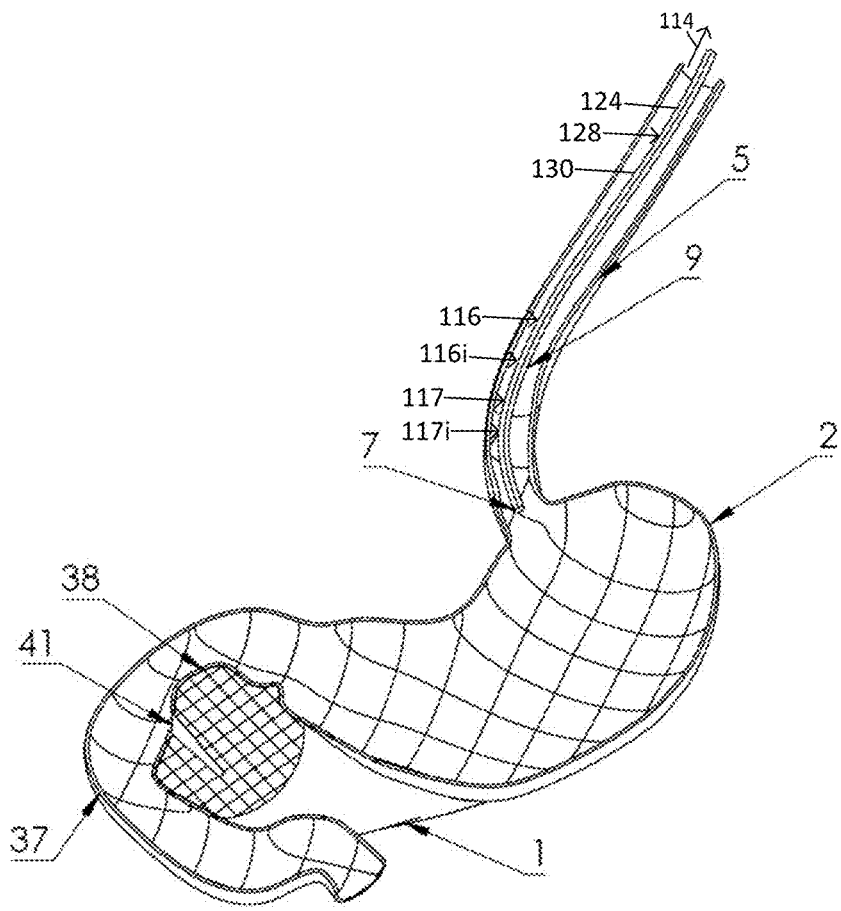

FIGS. 48a-48e illustrate that the first loop 118a can be formed by a section of the catheter 9 that is distal the sections of the catheter that form the second loop 118b and the third loop 118c, respectively. FIGS. 48a-48e illustrate that the second loop 118b can be formed by a section of the catheter 9 that is distal the section of the catheter 9 that forms the third loop 118c. FIGS. 48d and 48e illustrate, for example, that when the catheter 9 is in the fourth configuration 116d and the fifth configuration 116e, the first loop 118a can be distal the second loop 118b and the third loop 118c along the length 126 of the catheter 9 and the second loop 118b can be distal the third loop 118c along the length 126 of the catheter 9. FIGS. 48a-48e illustrate, for example, that when the catheter 9 is in the fourth configuration 116d and the fifth configuration 116e, the first loop 118a can be the distal most loop along the catheter 9 in the target site 147 and the third loop 118c can be the proximal most loop along the catheter 9 in the target site 147. FIGS. 48d and 48e illustrate, for example, that when the catheter 9 is in the fourth configuration 116d and the fifth configuration 116e, the first loop 118a can be distal the second loop 118b and the third loop 118c in the target site 147 and the second loop 118b can be distal the third loop 118c in the target site 147.

FIGS. 48a-48e illustrate that the loops 118 and the cells 122 can be formed by inserting the catheter 9 into the target site 147 and/or by withdrawing the guidewire 99 from the catheter 9. The loops 118 can be formed in the target site 147 in any order, for example, sequentially and/or simultaneously. For example, FIGS. 48a-48e illustrate that the first loop 118a, the second loop 118b, and the third loop 118c can be sequentially formed. For example, FIGS. 48a-48e illustrate that the first loop 118a can be formed in the target site 147, then the second loop 118b can be formed in the target site 147, and then the third loop 118c can be formed in the target site 147. For example, FIGS. 48a-48e illustrate that the second loop 118b can be formed after the first loop 118a is formed and that the third loop 118c can be formed after the first loop 118a and/or the second loop 118b are formed.

FIGS. 48a-48e illustrate, for example, that during a first phase of loop formation, the loop 118a can be formed, that during a second phase of loop formation, the loop 118b can be formed, and that during a third phase of loop formation, the loop 118c can be formed. The first phase of loop formation can be before the second phase of loop formation. The second phase of loop formation can be after the first phase of loop formation. The third phase of loop formation can be after the second phase of loop formation. While the second loop 118b is being formed (e.g., during the second phase of loop formation), the first loop 118a can have a constant size and/or shape. As another example, while the second loop 118b is being formed (e.g., during the second phase of loop formation), the size (e.g., perimeter) of the first loop 118a can increase and/or decrease, the shape of the first loop 118a can change, or any combination thereof. While the third loop 118c is being formed (e.g., during the third phase of loop formation), the first loop 118a and/or the second loop 118b can have a constant size and/or shape. As another example, while the third loop 118c is being formed (e.g., during the third phase of loop formation), the size (e.g., perimeter) of the first loop 118a and/or the second loop 118b can increase and/or decrease, the shape of the first loop 118a and/or the second loop 118b can change, or any combination thereof.

FIGS. 48a-48e illustrate that different sections of the catheter 9 can form the loops 118 at different times and/or at different stages of loop formation. For example, FIGS. 48a-48e illustrate that when the catheter 9 is in the third configuration 116c, a first section of the catheter 9 can form the first loop 118a, and that when the catheter 9 is in the fourth configuration 116d and the fifth configuration 116e, the first section of the catheter 9 can form the first loop 118a, a second section of the catheter 9 can form the second loop 118b, and a third section of the catheter 9 can form the third loop 118c.

FIGS. 48e-48i illustrate that the catheter 9 can be withdrawn from the target site 147. FIGS. 48e-48i illustrate that the loops 118 can be collapsed in and/or removed from the target site 147. FIGS. 48e-48i illustrate that collapsing the loops 118 can include straightening the loop 118, decreasing the curve of a loop, decreasing the perimeter of the loop 118, decreasing the loop length of the loops 118, decreasing the width of the loops 118, decreasing the height of the loops 118, or any combination thereof. FIGS. 48e-48i illustrate that the loops 118 can be collapsed in the target site 147 by withdrawing the catheter 9 from the target site 147, by inserting the guidewire 99 through the catheter 9 into the esophagus 5 and/or into the target site 147 and withdrawing the catheter 9 out of the target site 147 over the guidewire 99, or by any combination thereof. The catheter 9 can straighten and/or become less curved in the target site 147 as the catheter 9 is withdrawn (e.g., pulled) into the esophagus 5 as shown by arrow 114, as the guidewire 99 is inserted into the catheter 9 as shown by arrow 113, and/or as the catheter 9 is withdrawn (e.g. pulled) onto the guidewire 99 as shown by arrow 114.

The loops 118 can be collapsed in and/or removed from the target site 147 in any order, for example, sequentially and/or simultaneously. For example, FIGS. 48e-48i illustrate that the third loop 118c, the second loop 118b, and the first loop 118a can be sequentially collapsed and/or sequentially removed from the target site 147. FIGS. 48e-48i illustrate, for example, that the third loop 118c, the second loop 118b, and the first loop 118a can be removed from the target site 147 as they are collapsing (e.g., as they are decreasing in size). For example, FIGS. 48e-48i illustrate that the third loop 118c can be collapsed and removed from the target site 147, then the second loop 118b can be collapsed and removed from the target site 147, and then the first loop 118a can be collapsed and removed from the target site 147. For example, FIGS. 48e-48i illustrate that the second loop 118b can be collapsed and removed from the target site 147 after the third loop 118c is collapsed and removed from the target site 147 and that the first loop 118a can be collapsed and removed from the target site 147 after the second loop 118b and the third loop 118c are collapsed and removed from the target site 147. FIGS. 48e-48i illustrate that the loops 118 can be collapsed independently from one another as the catheter 9 is withdrawn from the target site 147, starting with the proximal most loop (e.g., the loop 118c) and ending with the distal most loop (e.g., the loop 118a). FIGS. 48e-48i illustrate that as the third loop 118c is being collapsed and removed from the target site 147, the second loop 118b and the first loop 118a can move (e.g., be pulled) toward the gastroesophageal junction 120. FIGS. 48e-48i illustrate that as the second loop 118b is being collapsed and removed from the target site 147, the first loop 118a can move (e.g., be pulled) toward the gastroesophageal junction 120.

FIGS. 48e-48i illustrate, for example, that during a first phase of catheter removal, the section of the catheter 9 defining the third loop 118c can be removed from the target site 147, that during a second phase of catheter removal, the section of the catheter 9 defining the second loop 118b can be removed from the target site 147, and that during a third phase of catheter removal, the section of the catheter 9 defining the first loop 118a can be removed from the target site 147. During the first phase of catheter removal, the third loop 118c can collapse in the target site 147. During the second phase of catheter removal, the second loop 118b can collapse in the target site 147. During the third phase of catheter removal, the first loop 118a can collapse in the target site 147. As another example, the third loop 118c, the second loop 118b, and/or the first loop 118c can be removed from the target site 147 without collapsing. The first phase of catheter removal can be before the second phase of catheter removal. The second phase of catheter removal can be after the first phase of catheter removal. The third phase of catheter removal can be after the second phase of catheter removal. While the third loop 118c is being removed (e.g., during the first phase of catheter removal), the second loop 118b and/or the first loop 118a can have a constant size and/or shape. As another example, while the third loop 118c is being removed (e.g., during the first phase of catheter removal), the size (e.g., perimeter) of the second loop 118b and/or the first loop 118a can increase and/or decrease, the shape of the second loop 118b and/or the third loop 118c can change, or any combination thereof. While the second loop 118b is being removed (e.g., during the second phase of catheter removal), the first loop 118a can have a constant size and/or shape. As another example, while the second loop 118b is being removed (e.g., during the second phase of catheter removal), the size (e.g., perimeter) of the first loop 118a can increase and/or decrease, the shape of the third loop 118c can change, or any combination thereof.

FIGS. 48a-48i illustrate, for example, that the configurations 116 formed by the catheter 9 during withdrawal can be the same as the configurations 116 formed by the catheter 9 during insertion. As another example, the configurations 116 formed by the catheter 9 during withdrawal of the catheter 9 from the body can be different from the configurations 116 formed by the catheter 9 during insertion of the catheter 9 into the body.

FIGS. 49a-49i illustrate that the catheter 9 can be inserted into and/or removed from the stomach 2 and/or the duodenum 37. FIGS. 49a-49i illustrate, for example, that the target site 147 can be the stomach 2 and/or duodenum 37. FIGS. 49a-49i illustrate that various lengths of the catheter 9 (e.g., the length 126 shown in FIGS. 49b-49h) can be introduced into and/or removed from the stomach 2 and/or the duodenum 37. FIGS. 49a-49i illustrate various configurations 116 and shapes 117 that the catheter 9 can have. FIGS. 49a-49i illustrate, for example, that when the catheter 9 is in a first through a ninth configuration 116a-116i, the catheter 9 can have the first through the ninth shape 117a-117i, respectively.

Figure 49A:
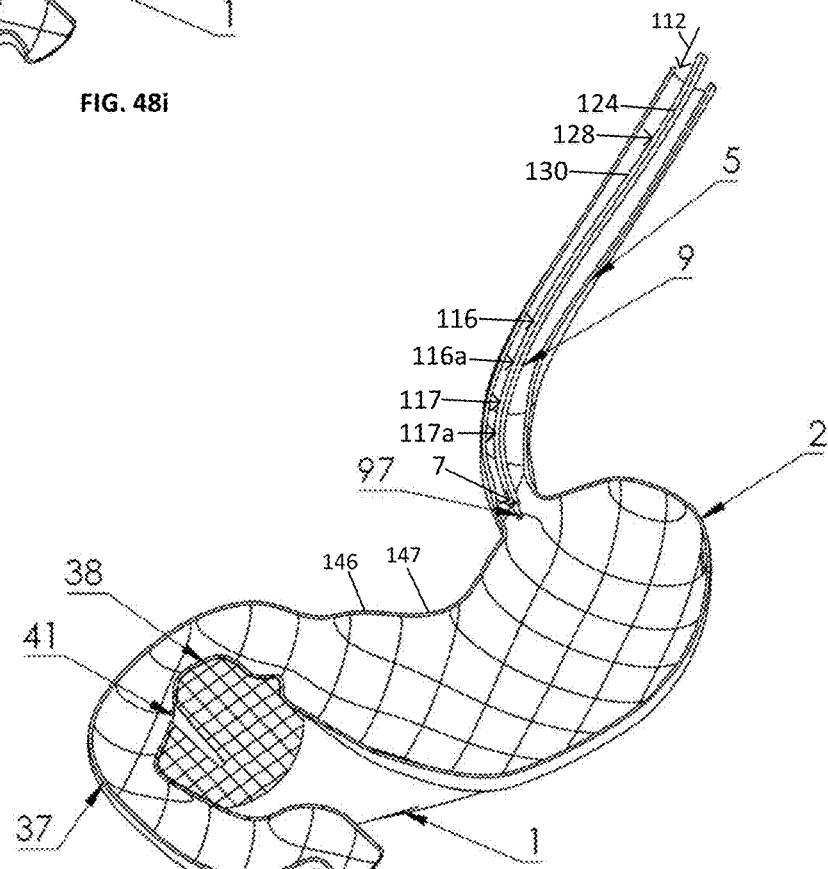
FIGS. 49a-49i illustrate the stomach, duodenum, and pancreas in an isometric view with the anterior half removed.
Figure 49B:
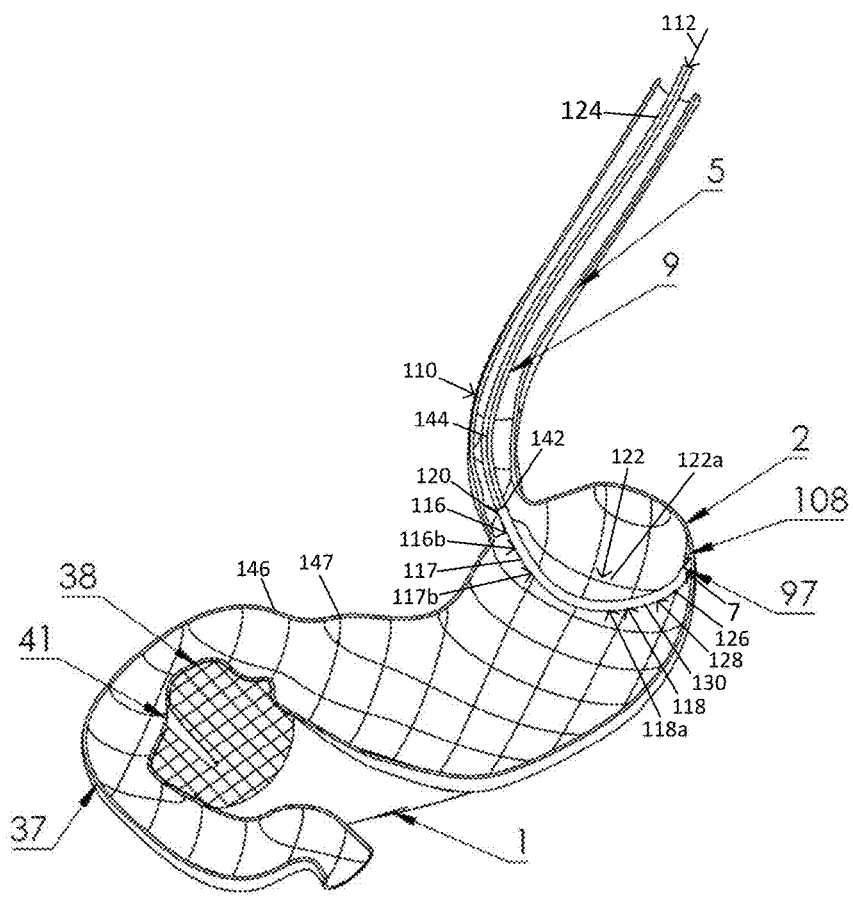
Figure 49C:
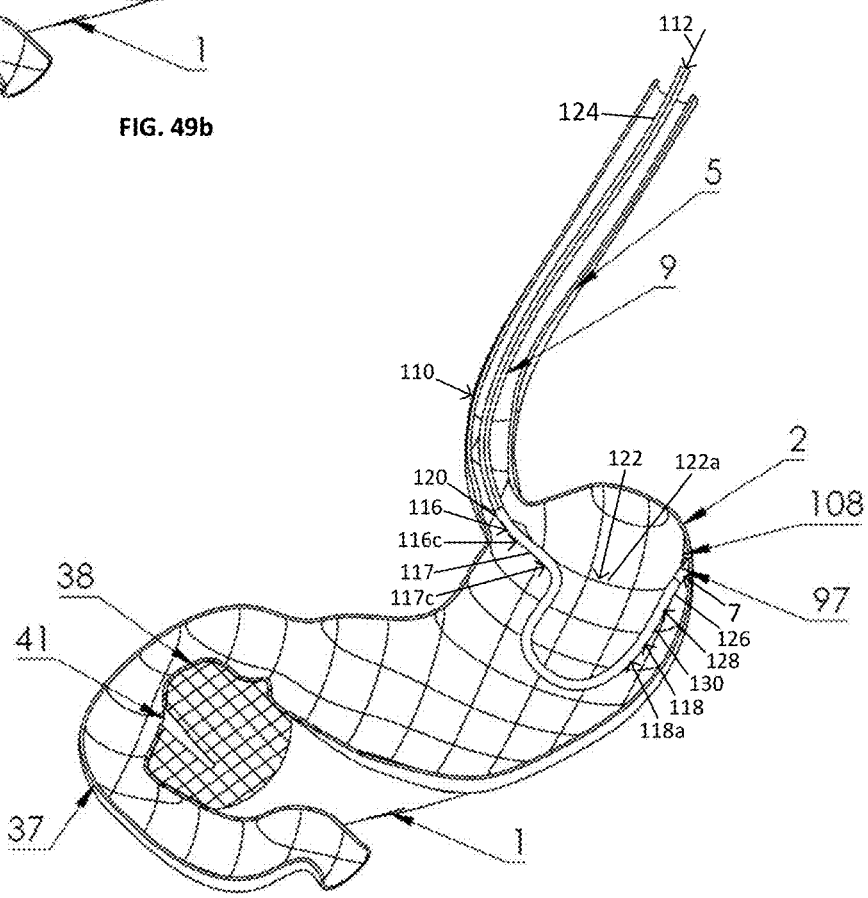
Figure 49D:
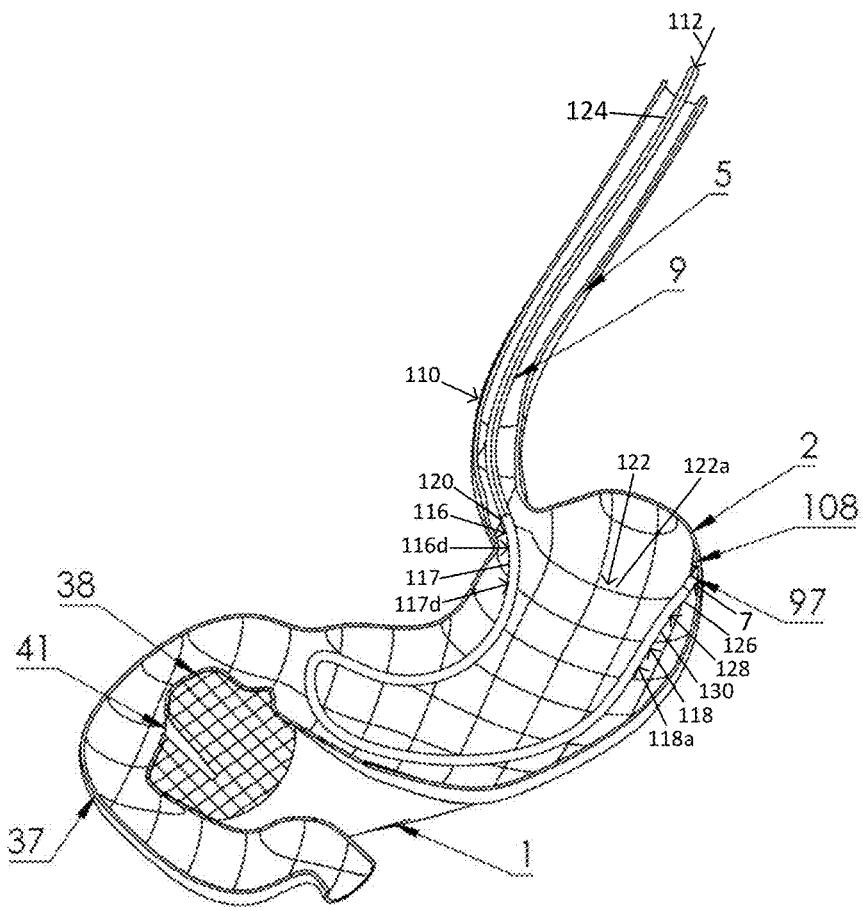
Figure 49E:
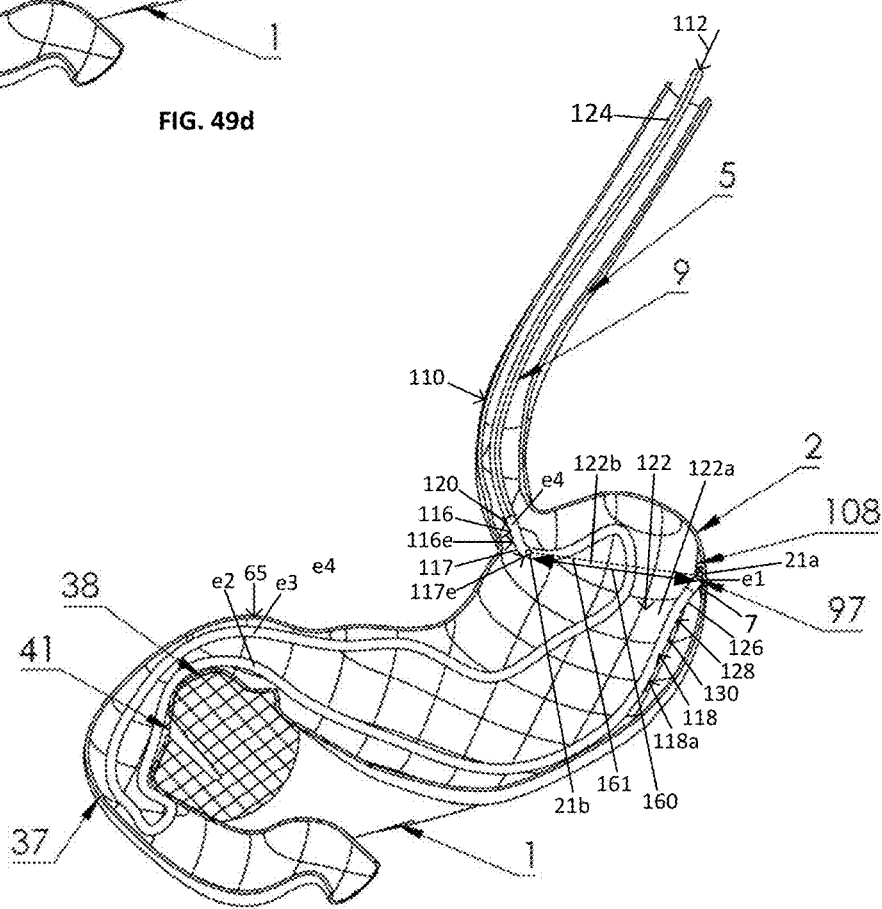

The catheter tip 7 and/or the proboscis 97 can be moved into and/or out of contact with the stomach 2, the duodenum 37, and/or another organ. For example, FIGS. 49a-49i illustrate that the proboscis 97 can be moved into and out of contact with the stomach 2. For example, FIGS. 49a-49b illustrate that the proboscis 97 can be moved into contact with the stomach 2 during insertion and FIGS. 49h-49i illustrate that the proboscis 97 can be moved out of contact with the stomach 2 during withdrawal. FIGS. 49a-49b illustrate, for example, that the proboscis 97 can be moved into contact with the stomach 2 by advancing the catheter 9 in the stomach 2 as shown by arrow 112 and FIGS. 49h-49i illustrate, for example, that the proboscis 97 can be moved out of contact with the stomach 2 by withdrawing the catheter 9 from the stomach 2 as shown by arrow 114. The proboscis 97 may or may not contact a wall of the stomach 2 when the catheter 9 is in a deployed configuration (e.g., a configuration 116). For example, FIGS. 49b-49h illustrate that the proboscis 97 can contact the stomach wall 108 when the catheter 9 is in a deployed configuration (e.g., the configurations 116b-116h).

The catheter tip 7 and/or the proboscis 97 can be permanently and/or temporarily engaged with a wall of the stomach 2, the duodenum 37, and/or another other organ. The stomach wall 108 can include a naturally occurring feature in the stomach 2, including, for example, a gastric ruga, gastric rugae, an ulcer, or any combination thereof. FIGS. 49b-49h illustrate that the proboscis 97 can be permanently and/or temporarily engageable with the stomach wall 108, for example, with a gastric ruga, gastric rugae, an ulcer, or any combination thereof. The proboscis 97 can, for example, releasably anchor and/or releasably engage the distal end of the catheter 9 (e.g., the catheter tip 7) to the stomach wall 108 when the catheter 9 is in the stomach 2. The catheter 9 can, for example, be releasably anchored and/or releasably engaged to the stomach wall 108 via the proboscis 97 via friction between the proboscis 97 and the stomach wall 108, via the proboscis 97 being wedged between two gastric rugae (e.g., between two adjacent gastric rugae), or any combination thereof. The catheter 9 can be unanchored and/or disengaged from the stomach wall 108, for example, by moving (e.g., pulling) the proboscis 97 away from the stomach wall 108 by withdrawing the catheter 9 from the stomach 2 as shown by arrow 114.

FIGS. 49a-49b illustrate that as the catheter 9 is introduced into the stomach 2, the proboscis 97 can become engaged with (e.g., can be moved into contact with) the stomach wall 108. When the proboscis 97 is engaged with the stomach wall 108, the proboscis 97 can remain engaged with (e.g., can remain in contact with) the stomach wall 108, can disengage from (e.g., can move out of contact with) the stomach wall 108, can re-engage with the stomach wall 108, or any combination thereof while the catheter 9 is advanced into the stomach 2, while the catheter 9 is withdrawn from the stomach 2, and/or while the catheter 9 migrates in the stomach 2 and/or in the duodenum 37. FIGS. 49d-49e illustrate that the natural stomach motility and/or peristalsis of the stomach 2 can cause the catheter 9 to migrate in the stomach 2 and/or in the duodenum 37. FIGS. 49a-49e illustrate that movement and/or deployment of the catheter 9 can include insertion of the catheter 9 into the stomach 2 and/or the duodenum 37, migration of the catheter 9 in the stomach 2 and/or the duodenum 37, withdrawal of the catheter 9 from the stomach 2 and/or the duodenum 37, or any combination thereof. The proboscis 97 can move and/or remain in a fixed position relative to the stomach wall 108 as the catheter 9 moves in the stomach 2 and/or in the duodenum 37, for example, during insertion, withdrawal, and/or migration of the catheter 9. The proboscis 97 can, for example, move and/or remain in a fixed position relative to the stomach wall 108 while the catheter 9 is advanced into the stomach 2, while the catheter 9 is forced into and/or migrates into the duodenum 37, while the catheter 9 is withdrawn from the stomach 2, while the catheter 9 is withdrawn from the duodenum 37, or any combination thereof. For example, FIGS. 49b-49h illustrate that the proboscis 97 can remain in a fixed position relative to the stomach wall 108 while the catheter 9 is advanced into the stomach 2, while the catheter 9 migrates into the duodenum 37, while the catheter 9 is withdrawn from the stomach 2, and while the catheter 9 is withdrawn from the duodenum 37.

The proboscis 97 can move 0.00-5.0 cm or more away from the engaged position (e.g., the engaged position shown in FIG. 49b) in any direction along the stomach wall 108, in any direction away from the stomach wall 108 (e.g., perpendicularly away), in any direction toward the stomach wall 108 (e.g., perpendicularly toward), or any combination thereof while the catheter 9 is advanced into the stomach 2, while the catheter 9 is forced into and/or migrates into the duodenum 37, while the catheter 9 is withdrawn from the stomach 2, while the catheter 9 is withdrawn from the duodenum 37, or any combination thereof, including every 0.1 cm increment within this range (e.g., 0.0 cm, 0.1 cm, 1.0 cm, 2.0 cm, 3.0 cm, 5.0 cm). A 0.0 cm movement of the proboscis 97 can correspond to the proboscis 97 remaining stationary relative to the stomach wall 108. For example, FIGS. 49b-49h illustrate that the proboscis 97 can remain stationary (e.g., 0.0 cm movement) relative to the stomach wall 108 while the catheter 9 is advanced into the stomach 2, while the catheter 9 is forced into and/or migrates into the duodenum 37, while the catheter 9 is withdrawn from the stomach 2, while the catheter 9 is withdrawn from the duodenum 37, or any combination thereof. FIGS. 49h-49i illustrate that the catheter 9 can become disengaged from (e.g., can be moved out of contact with) the stomach wall 108. FIGS. 49h-49i illustrate, for example, that the proboscis 97 can be disengaged from the stomach wall 108 by withdrawing the catheter 9 from the stomach 2. Withdrawing the catheter 9 from the stomach 2 can, for example, include pulling the proboscis 97 away from the stomach wall 108 toward the gastroesophageal junction 120.

The proboscis 97 and/or the catheter tip 7 may or may not pivot on the stomach wall 108 once the proboscis 97 and/or the catheter tip 7 contacts the stomach wall 108. For example, FIGS. 49b-49h illustrate that the proboscis 97 and the catheter tip 7 may not pivot on the stomach wall 108 when the proboscis 97 is in contact with the stomach wall 108. As another example, the catheter tip 7 can pivot on the stomach wall 108 when the proboscis 97 is in contact with the stomach wall 108.

The proboscis 97 may or may not be forced into (e.g., pressed into) contact with the stomach wall 108 during insertion of the catheter 9 into the stomach 2. For example, FIGS. 49a-49b illustrate that the proboscis 97 can be forced into the stomach wall 108 during insertion of the catheter 9 into the stomach 2. When the proboscis 97 is pressed into the stomach wall 108 during insertion into the stomach 2, the proboscis 97 can inhibit and/or prevent the catheter tip 7 from tunneling into and/or through the stomach wall 108, for example, by deflecting. For example, FIGS. 49b-49c illustrate that the proboscis 97 can be flexible and/or can be a flexible tip that can deform (e.g., bend) when pushed into the stomach wall 108.

FIGS. 49d-49e illustrate that the catheter 9 can enter the duodenum 37. The insertion of the catheter 9 into the stomach 2 can force the catheter 9 to enter the duodenum 37, the natural stomach motility and/or peristalsis can urge and/or force the catheter 9 to enter the duodenum 37 and/or the intestine caudal the duodenum 37, or any combination thereof. The catheter 9 can, for example, migrate into the duodenum 37 from the stomach 2 through the pylorus 65 by the natural motility and/or peristalsis of the stomach 2. For example, FIGS. 49d-49e illustrate that the insertion of the catheter 9 into the stomach 2 can force the catheter 9 to enter the duodenum 37. As another example, FIGS. 49*d*-49*e* illustrate that the natural stomach motility and/or peristalsis can urge and/or force the catheter 9 to enter the duodenum 37. As yet another example, FIGS. 49*d*-49*e* illustrate that the insertion of the catheter 9 into the stomach 2 can force the catheter 9 to enter the duodenum 37 and the natural stomach motility and/or peristalsis can urge and/or force the catheter 9 to enter the duodenum 37.

The catheter 9 and/or the catheter tip 7 can enter the duodenum before, during, and/or after passing (e.g., pumping) a fluid (e.g., the fluid 6) through a lumen in the catheter 9. For example, FIGS. 49*d*-49*e* illustrate that the catheter 7 can migrate into the duodenum 37 while the fluid 6 is being pumped (e.g., recirculated) through an inflow lumen and an outflow lumen in the catheter 9.

The catheter 9 can enter the duodenum 37 before, during, and/or after the catheter tip 7 enters the stomach 2. For example, FIGS. 49*a*-49*e* illustrate that the catheter 9 can enter the duodenum 37 after the catheter tip 7 enters the stomach 2. The catheter 9 can enter the duodenum 37 when the catheter tip 7 is in the stomach 2, in the esophagus 5, in the pylorus 65, in the duodenum 37, and/or outside the body. For example, FIGS. 49*a*-49*e* illustrate that the catheter 9 can enter the duodenum 37 when the catheter tip 7 is in the stomach 2. The catheter 9 can enter the duodenum 37 before, during, and/or after the proboscis 97 enters the stomach 2. For example, FIGS. 49*a*-49*e* illustrate that the catheter 9 can enter the duodenum 37 after the proboscis 97 enters the stomach 2. The catheter 9 can enter the duodenum 37 when the proboscis 97 is in the stomach 2, in the esophagus 5, in the pylorus 65, in the duodenum 37, and/or outside the body. For example, FIGS. 49*a*-49*e* illustrate that the catheter 9 can enter the duodenum 37 when the proboscis 97 is in the stomach 2. The catheter 9 can enter the duodenum 37 before, during, and/or after the catheter tip 7 and/or the proboscis 97 becomes engaged with the stomach wall 108. For example, FIGS. 49*a*-49*e* illustrate that the catheter 9 can enter the duodenum 37 after the proboscis 97 is pushed into engagement with (e.g., into contact with) the stomach wall 108. The catheter 9 can enter the duodenum 37 while the catheter tip 7 and/or the proboscis 97 are engaged with the stomach wall 108 (e.g., when the catheter tip 7 and/or the proboscis 97 is in contact with the stomach wall 108) and/or while the catheter tip 7 and/or the proboscis 97 are disengaged from the stomach wall 108 (e.g., when the catheter tip 7 and/or the proboscis 97 is not in contact with the stomach wall 108). For example, FIGS. 49*a*-49*e* illustrate that the catheter 9 can enter the duodenum 37 while the proboscis 97 is engaged with (e.g., in contact with) the stomach wall 108. The catheter tip 7 may or may not remain in the stomach 2 during insertion and/or migration of the catheter 9. For example, FIGS. 49*a*-49*e* illustrate that the catheter tip 7 can remain in the stomach 2 during insertion and/or migration of the catheter 9.

The catheter 9 can enter the duodenum 37 when at least 10 cm-150 cm or more of the catheter 9 is in the stomach 2, including every 1 cm increment within this range (e.g., at least 10 cm, at least 30 cm, at least 40 cm, at least 70 cm, at least 100 cm). For example, FIGS. 49*a*-49*e* illustrate that the catheter 9 can enter the duodenum 37 when at least 30 cm of the catheter 9 is in the stomach 2.

Figure 49F:
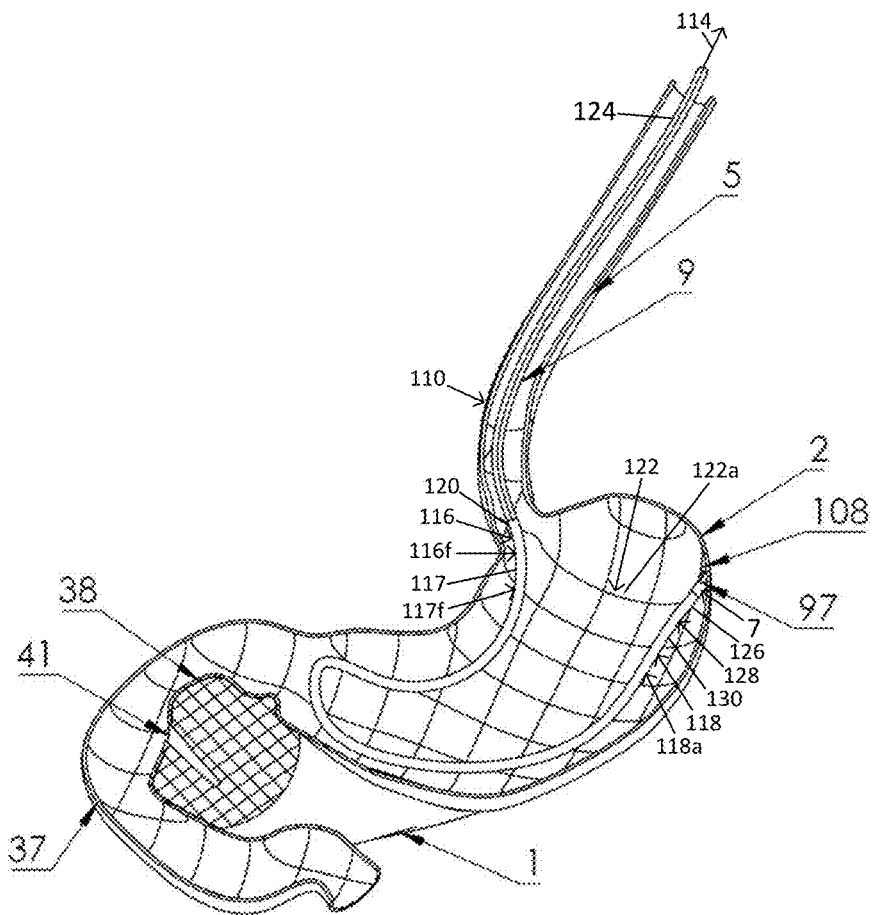
Figure 49G:
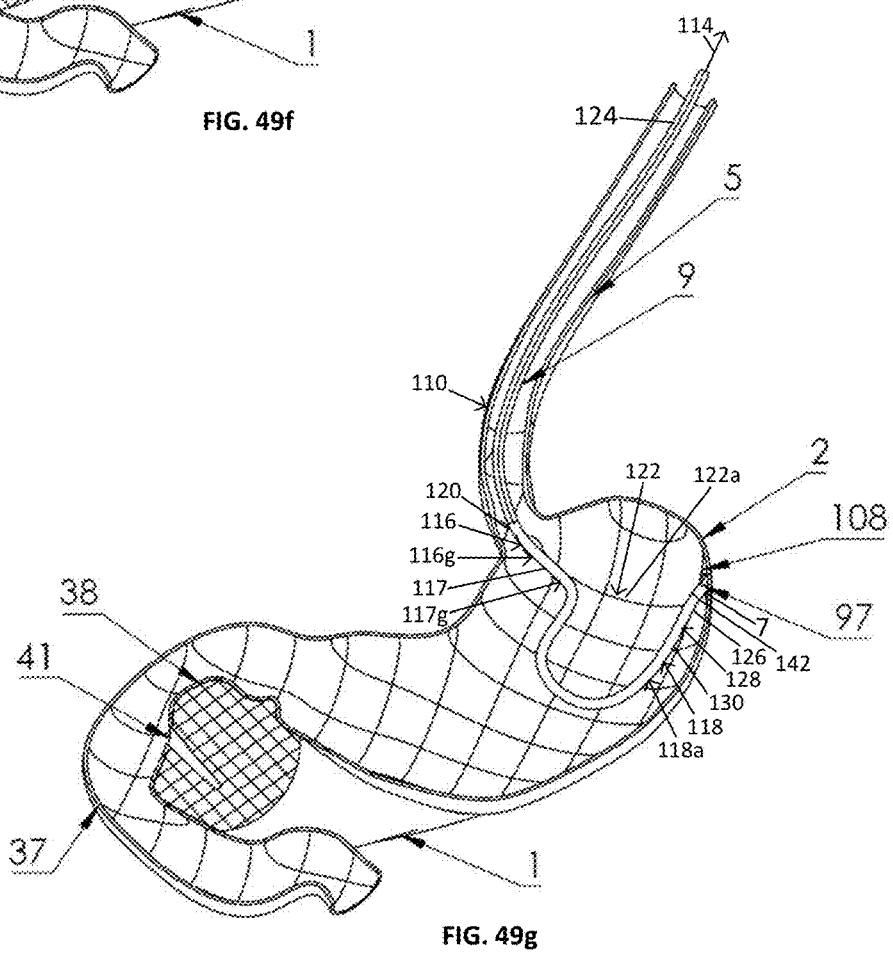
Figure 49H:
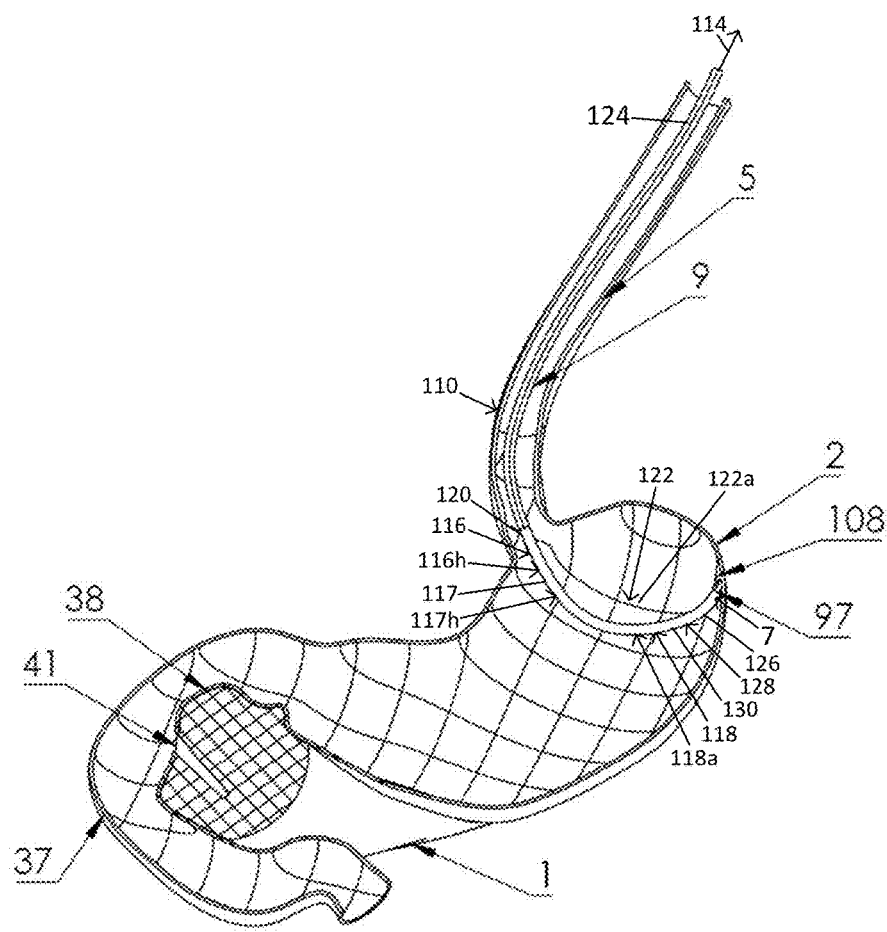
Figure 49I:
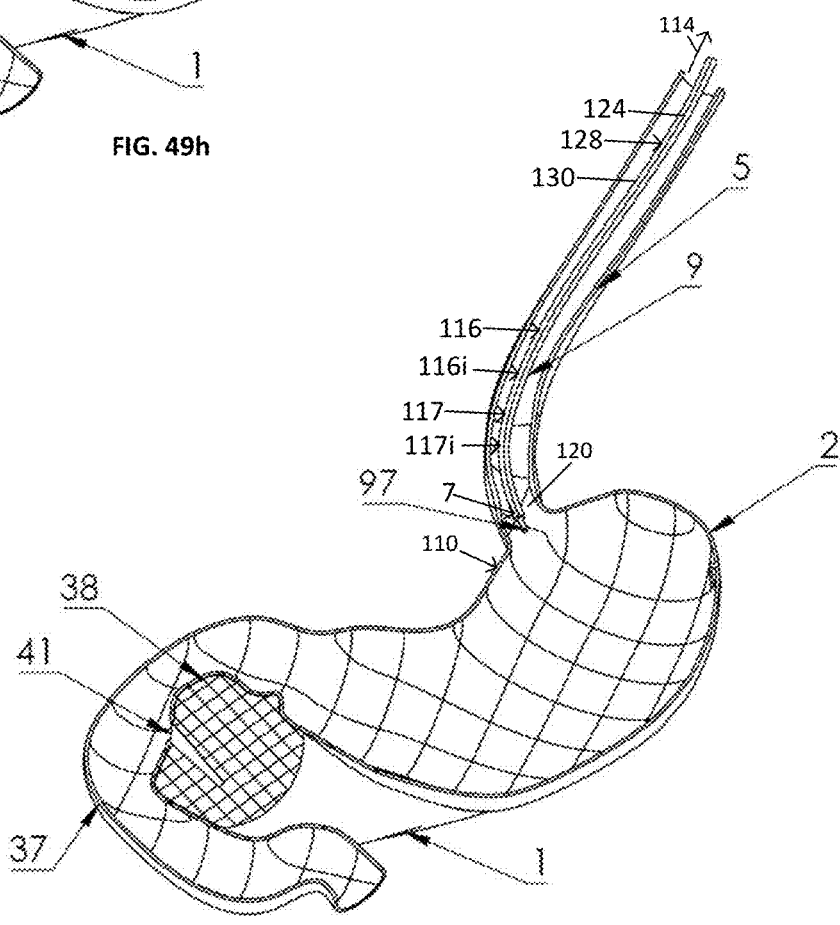

FIGS. 49*e*-49*f* illustrate that the catheter 9 can be removed from the duodenum 37, for example, by withdrawing (e.g., pulling) the catheter 9 out of the stomach 2 as shown by arrow 114.

The catheter 9 can be withdrawn from the duodenum 37 before, during, and/or after the catheter tip 7 is withdrawn from the stomach 2. For example, FIGS. 49*e*-49*i* illustrate that the catheter 9 can be withdrawn from the duodenum 37 before the catheter tip 7 is withdrawn from the stomach 2. The catheter 9 can be withdrawn from the duodenum 37 when the catheter tip 7 is in the stomach 2, in the esophagus 5, in the pylorus 65, in the duodenum 37, and/or outside the body. For example, FIGS. 49*e*-49*i* illustrate that the catheter 9 can be withdrawn from the duodenum 37 when the catheter tip 7 is in the stomach 2. The catheter 9 can be withdrawn from the duodenum 37 before, during, and/or after the proboscis 97 is withdrawn from the stomach 2. For example, FIGS. 49*e*-49*i* illustrate that the catheter 9 can be withdrawn from the duodenum 37 before the proboscis 97 is withdrawn from the stomach 2. The catheter 9 can be withdrawn from the duodenum 37 when the proboscis 97 is in the stomach 2, in the esophagus 5, in the pylorus 65, in the duodenum 37, and/or outside the body. For example, FIGS. 49*e*-49*i* illustrate that the catheter 9 can be withdrawn from the duodenum 37 when the proboscis 97 is in the stomach 2. The catheter 9 can be withdrawn from the duodenum 37 before, during, and/or after the proboscis 97 becomes engaged with the stomach wall 108. For example, FIGS. 49*e*-49*i* illustrate that the catheter 9 can be withdrawn from the duodenum 37 after the proboscis 97 is pushed into engagement with (e.g., into contact with) the stomach wall 108. The catheter 9 can be withdrawn from the duodenum 37 while the catheter tip 7 and/or the proboscis 97 are engaged with the stomach wall 108 (e.g., when the catheter tip 7 and/or the proboscis 97 is in contact with the stomach wall 108) and/or while the catheter tip 7 and/or the proboscis 97 are disengaged from the stomach wall 108 (e.g., when the catheter tip 7 and/or the proboscis 97 is not in contact with the stomach wall 108). For example, FIGS. 49*e*-49*i* illustrate that the catheter 9 can be withdrawn from the duodenum 37 while the proboscis 97 is engaged with (e.g., is in contact with) the stomach wall 108.

The catheter 9 can be withdrawn from the duodenum 37 when at least 10 cm-150 cm or more of the catheter 9 is in the stomach 2, including every 1 cm increment within this range (e.g., at least 10 cm, at least 30 cm, at least 40 cm, at least 70 cm, at least 100 cm). For example, FIGS. 49*e*-49*i* illustrate that the catheter 9 can be withdrawn from the duodenum 37 when at least 30 cm of the catheter 9 is in the stomach 2.

When the catheter 9 is in the duodenum 37, the catheter tip 7 can be in the stomach 2 and/or the duodenum 37. For example, FIG. 49*e* illustrates that when the catheter 9 is in the duodenum 37, the catheter tip 7 can be in the stomach 2.

When the catheter 9 is in the duodenum 37, the proboscis 97 can be in the stomach 2 and/or the duodenum 37. For example, FIG. 49*e* illustrates that when the catheter 9 is in the duodenum 37, the proboscis 97 can be in the stomach 2.

The catheter 9 may or may not be in the stomach 2 and/or the duodenum 37 when the catheter 9 is in a deployed configuration. For example, FIGS. 49*b*-49*d* and 49*f*-49*h* illustrate that the catheter 9 can be in the stomach 2 in a deployed configuration (e.g., the configurations 116*b*-116*d* and 116*f*-116*h*) and FIG. 49*e* illustrates that the catheter 9 can be in the stomach 2 and the duodenum 37 when the catheter is in a deployed configuration (e.g., the configuration 116*e*).

FIGS. 49*b*-49*h* illustrate that the catheter 9 can form a deployed configuration by inserting the catheter 9 into the stomach 2, by inserting the catheter 9 into the duodenum 37, by the catheter 9 migrating out of the stomach 2 through the pylorus 65 and into the duodenum 37 via the natural stomach motility and/or peristalsis, by withdrawing the catheter 9 from the stomach 2, by withdrawing the catheter 9 from the duodenum 37, or any combination thereof.

When the catheter 9 is in a deployed configuration (e.g., a configuration 116), zero, one, or more sections of the catheter 9 can be in the stomach 2 and zero, one, or more sections of the catheter 9 can be in the duodenum 37. For example, FIG. 49e illustrates that when the catheter 9 is in a deployed configuration (e.g., configuration 116e), a first section of the catheter 9 (e.g., section e1-e2) can be in the stomach 2, a second section of the catheter 9 (e.g., section e2-e3) can be in the duodenum 37, and a third section of the catheter 9 (e.g., section e3-e4) can be in the stomach 2. The second section of the catheter 9 can enter the duodenum 37 by forcing the second section of the catheter 9 to enter the duodenum 37 (e.g., by inserting the catheter 9 into the stomach 2), by the natural stomach motility and/or peristalsis urging and/or forcing the second section of the catheter 9 to enter the duodenum 37, or any combination thereof. For example, FIGS. 49d-49e illustrate that the second section of the catheter 9 can enter the duodenum 37 by the natural stomach motility and/or peristalsis urging and/or forcing the second section of the catheter 9 into the duodenum 37 through the pylorus 65. FIG. 49e illustrates that the second section of the catheter 9 can be between the first section and the second section of the catheter 9 along the length of the catheter 9. FIG. 49e illustrates, for example, that when the catheter 9 is in a straight configuration, the first section of the catheter 9 can be distal the second section and the third section of the catheter 9 and that the second section of the catheter 9 can be distal the first section of the catheter 9. FIG. 49e illustrates that when the catheter 9 is in the configuration 116e, the first section of the catheter 9 can be closer to the pancreas 1 than the third section of the catheter 9 and that the third section of the catheter 9 can be closer to the gastroesophageal junction 120 than the first section of the catheter 9 or vice versa.

FIG. 49e illustrates that the loop 118 (e.g., the first loop 118a) can be formed by section e1-e4 of the of the catheter 9. FIG. 49e illustrates, for example, that the first loop 118a can be in the stomach 2 and the duodenum 37. For example, FIG. 49e illustrates that the loop head can be in the duodenum 37 and that the loop base can be in the stomach 2. FIG. 49e illustrates that the cell 122 (e.g., the first cell 122a) can be in the stomach 2 and the duodenum 37. The length of section e1-e4 of the catheter 9 can be, for example, the length 126. FIG. 49e illustrates that the length 126 can be, for example, 50 cm-120 cm (e.g., 80 cm). FIGS. 49d-49e illustrate that the size (e.g., the perimeter) of the first loop 118a can be larger when the catheter 9 is in the fifth configuration 116e than when the catheter 9 is in the fourth configuration 116d. FIG. 49e illustrates that a first gap can be between section e1-e2 and section e3-e4 in the stomach 2, that a second gap can be between a first end of the second section e2-e3 (e.g., the end closer to point e2) and a second end of the second section e2-e3 (e.g., the end closer to point e3) in the duodenum 37, and that the second gap can be less than the first gap. The second gap can be, for example, at least 1 cm-10 cm less than the first gap, including every 1 cm increment within this range (e.g., at least 1 cm, at least 5 cm, at least 10 cm). For example, FIG. 49e illustrates that the second gap can be at least 4 cm less than the first gap. FIGS. 49d-49e illustrate that a middle portion of the catheter 9 between points e1 and e4 can enter the duodenum 37 while the catheter tip 7 and/or the proboscis 97 are in the stomach 2.

In FIG. 49e, reference points e1-e4 are provided to assist in the identification of the first, second, and third sections of the catheter 9. The first, second, and third sections of the catheter 9 (e.g., sections e1-e2, e2-e3, and e3-e4) can be integral with each other and/or attached to each other. For example, FIG. 49e illustrates that section e1-e2 can be integral with section e2-e3, that section e2-e3 can be integral with section e3-e4, and that section e3-e4 can be integral with the portion of the catheter 9 in the esophagus 5. For example, FIG. 49e illustrates that the first, second, and third sections of the catheter 9 can be sections of a single length of the catheter 9 (e.g., sections of the total length 124 of the catheter 9). Reference point e1 can mark, for example, the distal terminal end of the catheter 9, the distal terminal end of the proboscis 97, the distal terminal end of the heat transfer region 128, or any combination thereof. Reference point e2 can mark, for example, a first location that the catheter 9 passes through the pylorus 65. Reference point e3 can mark, for example, a second location that the catheter 9 passes through the pylorus 65. Reference point e4 can mark, for example, the location that catheter 9 enters the target site 147 (e.g., the stomach 2).

The catheter 9 can pass through the pylorus 65, for example, 0-10 or more times, including every 1 increment within this range (e.g., 0 times, 1 time, 2 times, 3 times, 4 times, 10 times). For example, FIGS. 49b-49d and 49f-49h illustrate that when the catheter 9 is in the stomach 2, the catheter 9 can pass through the pylorus 65 zero times. As another example, FIG. 49e illustrates that the when the catheter 9 is in the stomach 2, the catheter 9 can pass through the pylorus 2 times (e.g., at the first and second locations marked by reference points e2 and e3, respectively). For example, FIG. 49e illustrates that two different sections of the catheter 9 can simultaneously pass through the pylorus 65.

When the catheter 9 is in the duodenum 37, the length 126 of the catheter 9 in the stomach 2 can be, for example, at least 20 cm-300 cm, including every 1 cm increment within this range (e.g., at least 30 cm, at least 40 cm, at least 50 cm, at least 60 cm, at least 70 cm, at least 80 cm, at least 90 cm, at least 100 cm). For example, FIG. 49e illustrates that when the catheter 9 is in the duodenum 37, the length 126 of the catheter 9 in the stomach 2 can be at least 50 cm. When the catheter 9 is in the duodenum 37, the length 126 of the catheter 9 in the stomach 2 can be, for example, 20 cm-300 cm or more, including every 1 cm increment within this range (e.g., 20 cm, 50 cm, 100 cm, 150 cm, 300 cm). For example, FIG. 49e illustrates that when the catheter 9 is in the duodenum 37, the length 126 of the catheter 9 in the stomach 2 can be 55 cm. FIG. 49e illustrates that the length 126 of the catheter 9 in the stomach 2 can be, for example, the length of section e1-e2 and section e3-e4.

When the catheter 9 is in the duodenum 37, the length 126 of the catheter 9 in the duodenum 37 can be, for example, at least 1 cm-80 cm, including every 1 cm increment within this range (e.g., at least 1 cm, at least 5 cm, at least 10 cm, at least 20 cm, at least 30 cm, at least 40 cm, at least 60 cm, at least 80 cm). For example, FIG. 49e illustrates that when the catheter 9 is in the duodenum 37, the length 126 of the catheter 9 in the duodenum 37 can be at least 20 cm. When the catheter 9 is in the duodenum 37, the length 126 of the catheter 9 in the duodenum 37 can be, for example, 1 cm-80 cm or more, including every 1 cm increment within this range (e.g., 1 cm, 10 cm, 30 cm, 50 cm, 80 cm). For example, FIG. 49e illustrates that when the catheter 9 is in the duodenum 37, the length 126 of the catheter 9 in the duodenum 37 can be 25 cm. FIG. 49e illustrates that the length 126 of the catheter 9 in the duodenum 37 can be, for example, the length of section e2-e3.

When the catheter 9 is in the duodenum 37, the length 126 of the catheter 9 in the stomach 2 can be, for example, 40 cm-300 cm greater than the length 126 of the catheter 9 in the duodenum 37, including every 1 cm increment within this range (e.g., 40 cm, 50 cm, 60 cm, 100 cm, 200 cm, 300 cm).

FIGS. 49a-49i illustrate that the catheter 9 can extend across the target site 147 multiple times, for example, a first time proximally to distally from the stomach into the duodenum 37 and a second distally to proximally from the duodenum 37 into the stomach 2.

FIG. 49e illustrates that the catheter 9 can have undulations along the length of the catheter 9 when the catheter 9 is in a deployed configuration. FIG. 49e illustrates that the undulations can be, for example, bends in the catheter 9. The undulations can have, for example, a sinusoidal pattern, a serpentine pattern, a zig-zag pattern, or any combination thereof. FIGS. 49e-49f illustrate that the undulations can straighten as the catheter 9 is withdrawn from the body.

FIGS. 49e-49f illustrate that as the total length of the catheter 9 in the duodenum 37 is decreased, the total length of the catheter 9 in the stomach 2 can simultaneously decrease.

FIGS. 49a-49e illustrate, for example, that the target site 147 can be the stomach 2 and that the catheter 9 can enter the duodenum 37. As another example, FIGS. 49a-49e illustrate that the target site 147 can be the stomach 2 and the duodenum 37.

The catheter 9 can transfer heat to and/or from surrounding tissue when the catheter 9 is in the stomach 2, in the duodenum 37, and/or in the intestine caudal the duodenum 37. For example, FIGS. 49b-49d and 49f-49h illustrate that the catheter 9 can transfer heat to and/or from the stomach 2 and FIG. 49e illustrates that the catheter 9 can transfer heat to and/or from the stomach 2 and the duodenum 37.

FIGS. 49a-49i illustrate that the catheter 9 can have the proboscis 97. The proboscis 97 can be attached to the and/or integrated with the catheter tip 7. For example, FIGS. 49a-49i illustrate that the proboscis 97 can be a distal end of the catheter tip 7.

FIGS. 49a-49i illustrate, for example, that the configurations 116 formed by the catheter 9 during withdrawal can be the same as the configurations 116 formed by the catheter 9 during insertion. As another example, the configurations 116 formed by the catheter 9 during withdrawal of the catheter 9 from the body can be different from the configurations 116 formed by the catheter 9 during insertion of the catheter 9 into the body.

FIGS. 50a-50i illustrate that the catheter 9 can be inserted into and/or removed from the stomach 2 and/or the duodenum 37. FIGS. 50a-50i illustrate, for example, that the target site 147 can be the stomach 2 and the duodenum 37. FIGS. 50a-50i illustrate that various lengths of the catheter 9 (e.g., the length 126 shown in FIGS. 50b-50h) can be introduced into and/or removed from the stomach 2 and/or the duodenum 37. FIGS. 50a-50i illustrate various configurations 116 and shapes 117 that the catheter 9 can have. FIGS. 50a-50i illustrate, for example, that when the catheter 9 is in a first through a ninth configuration 116a-116i, the catheter 9 can have the first through the ninth shape 117a-117i, respectively.

Figure 50A:
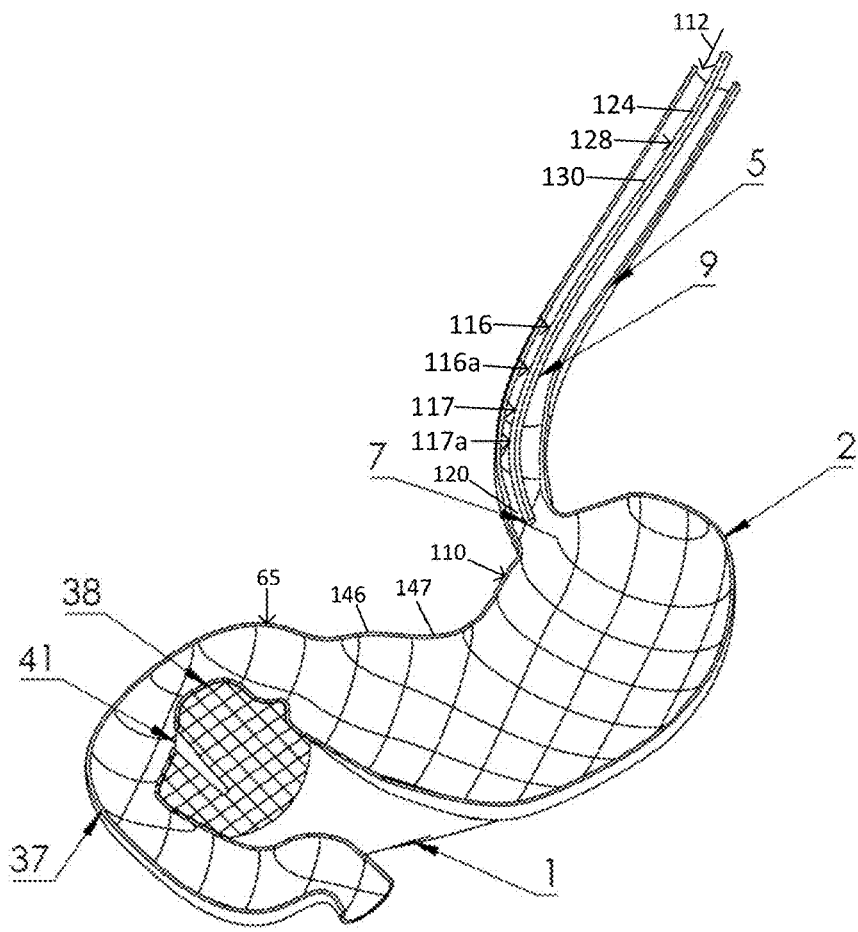
Figure 50B:
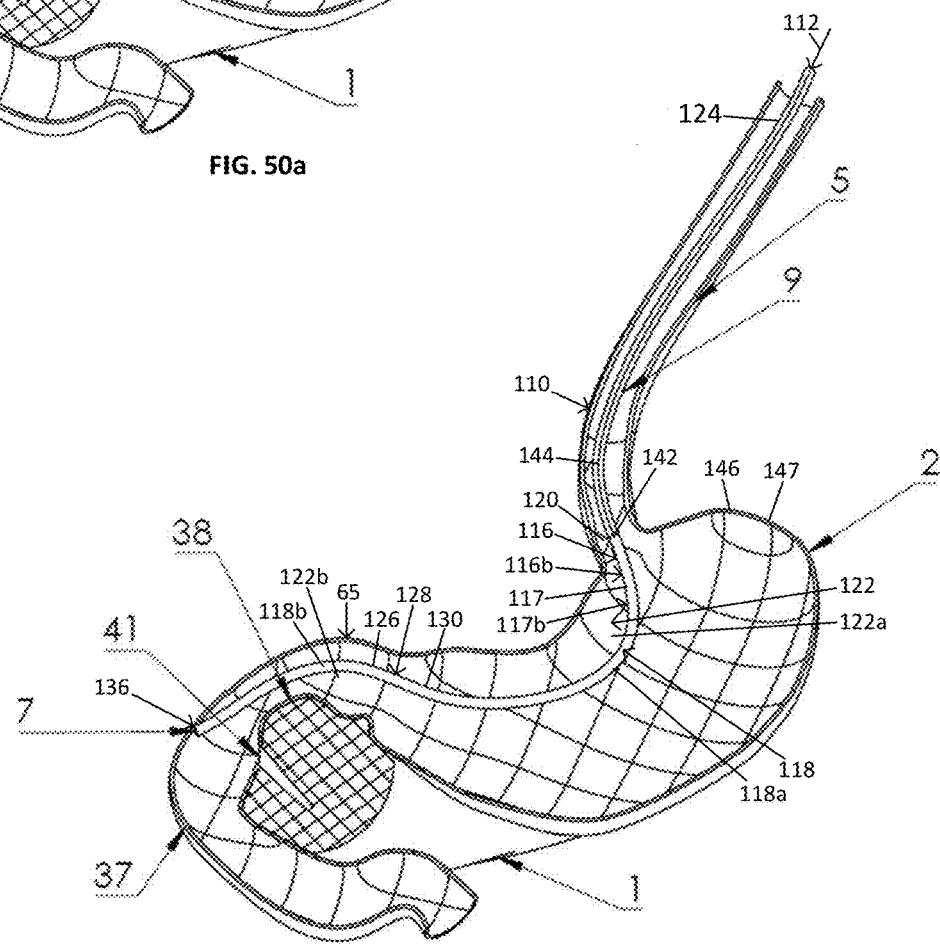
Figure 50C:
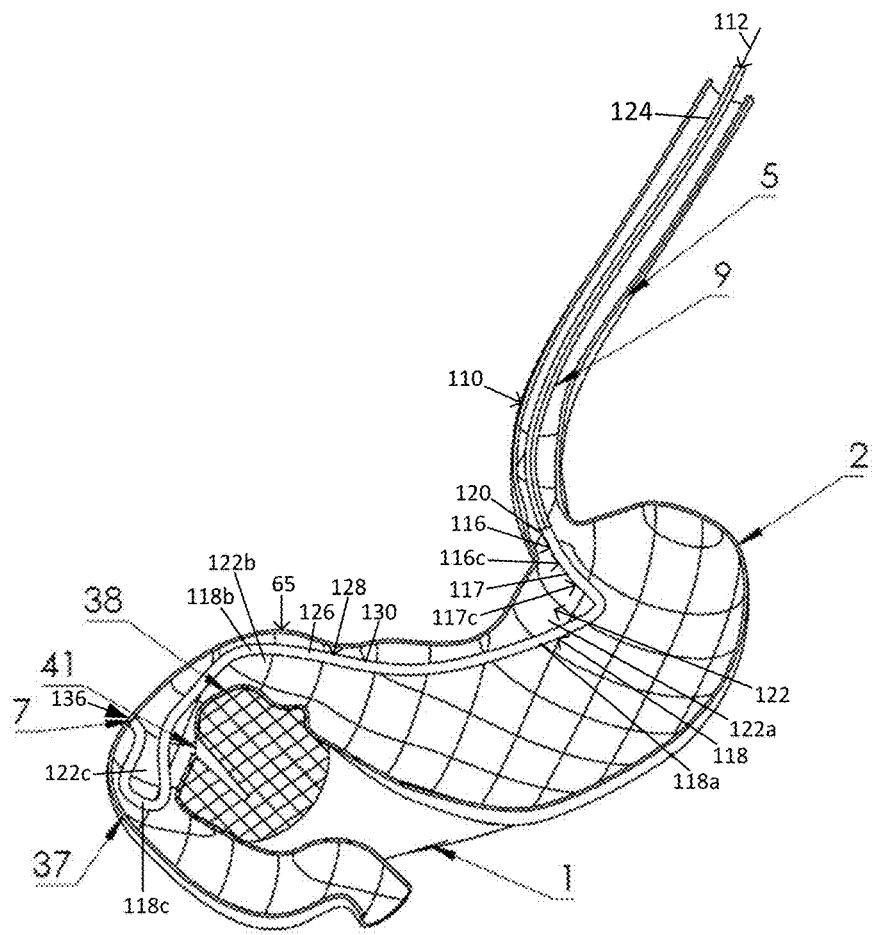
Figure 50D:
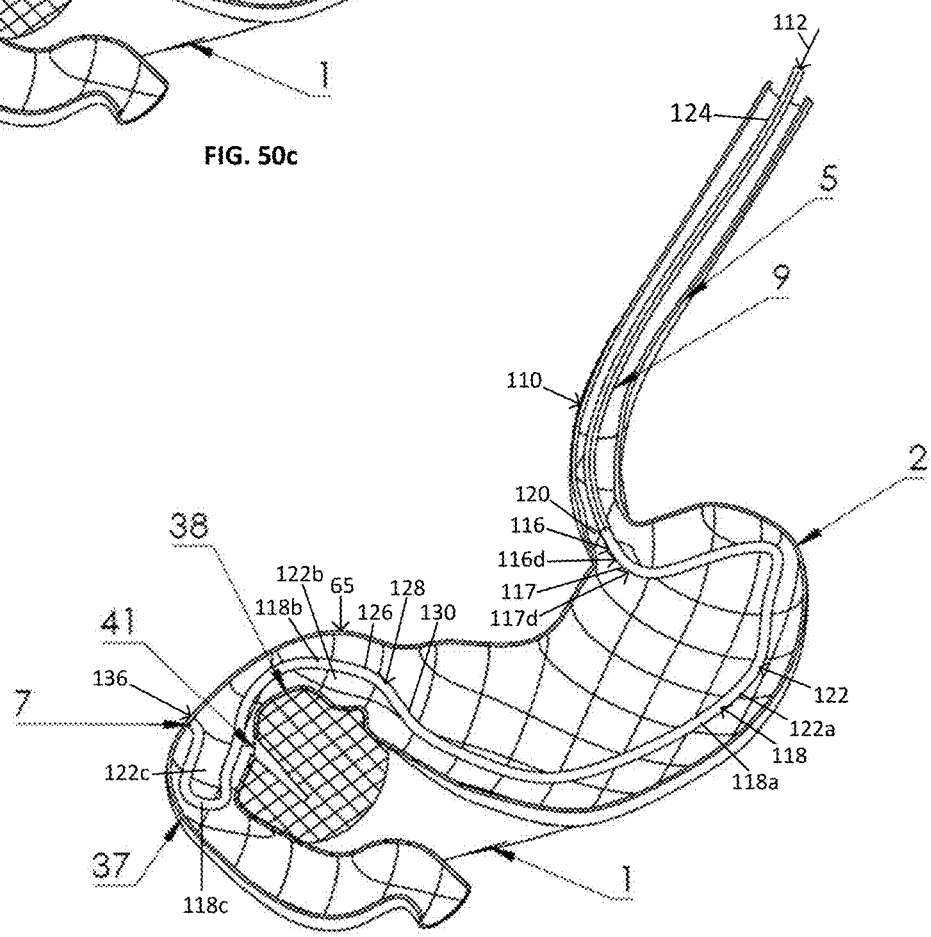
Figure 50E:
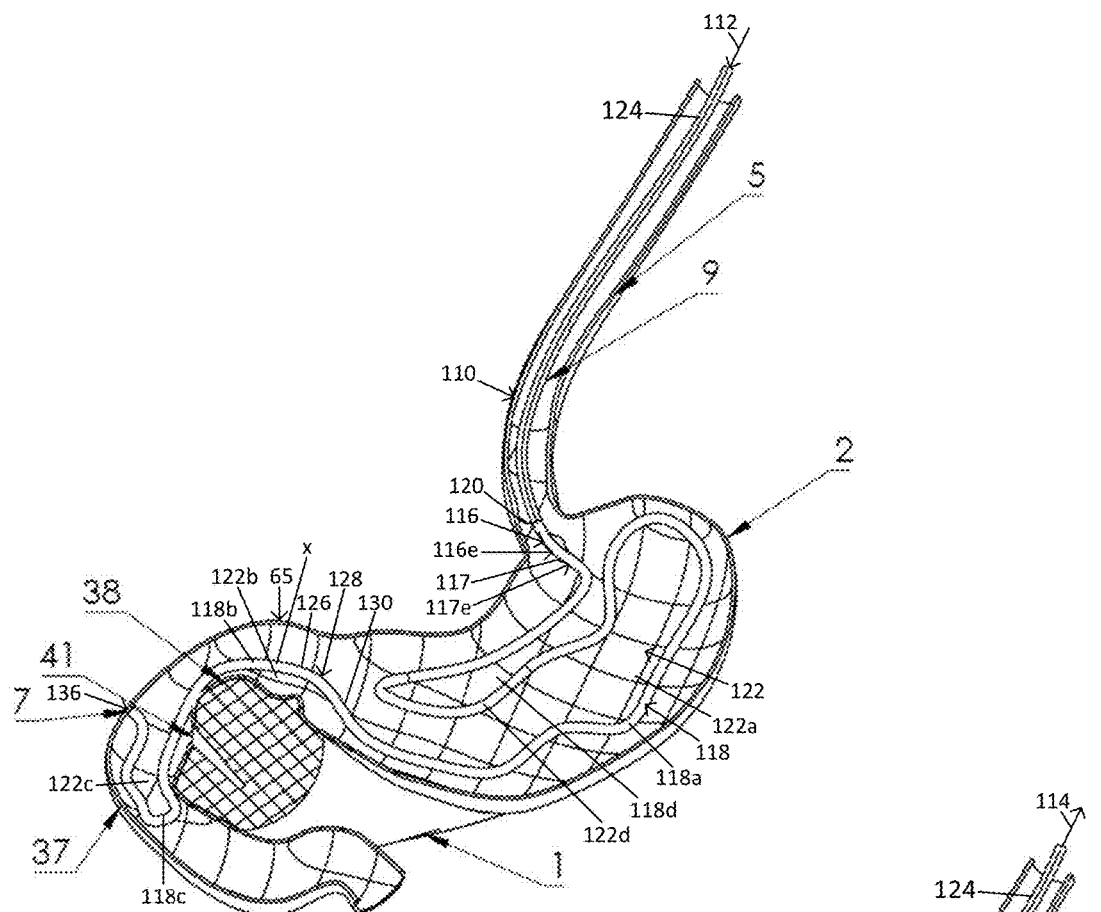
Figure 50F:
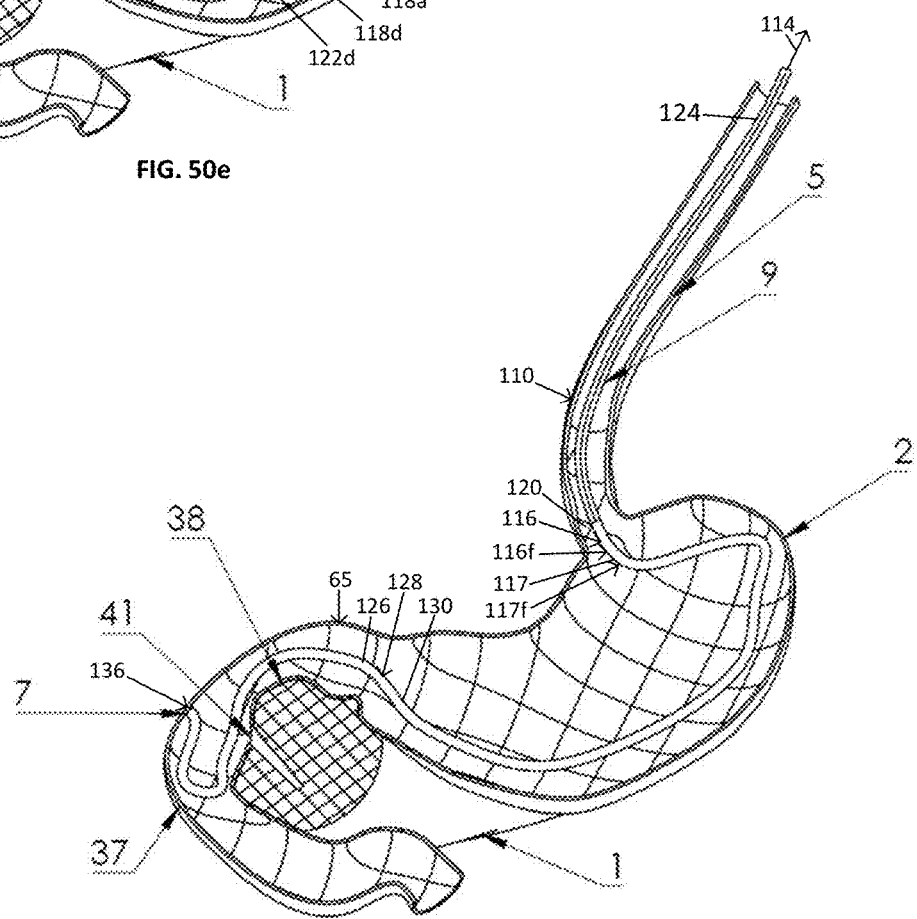
Figure 50G:
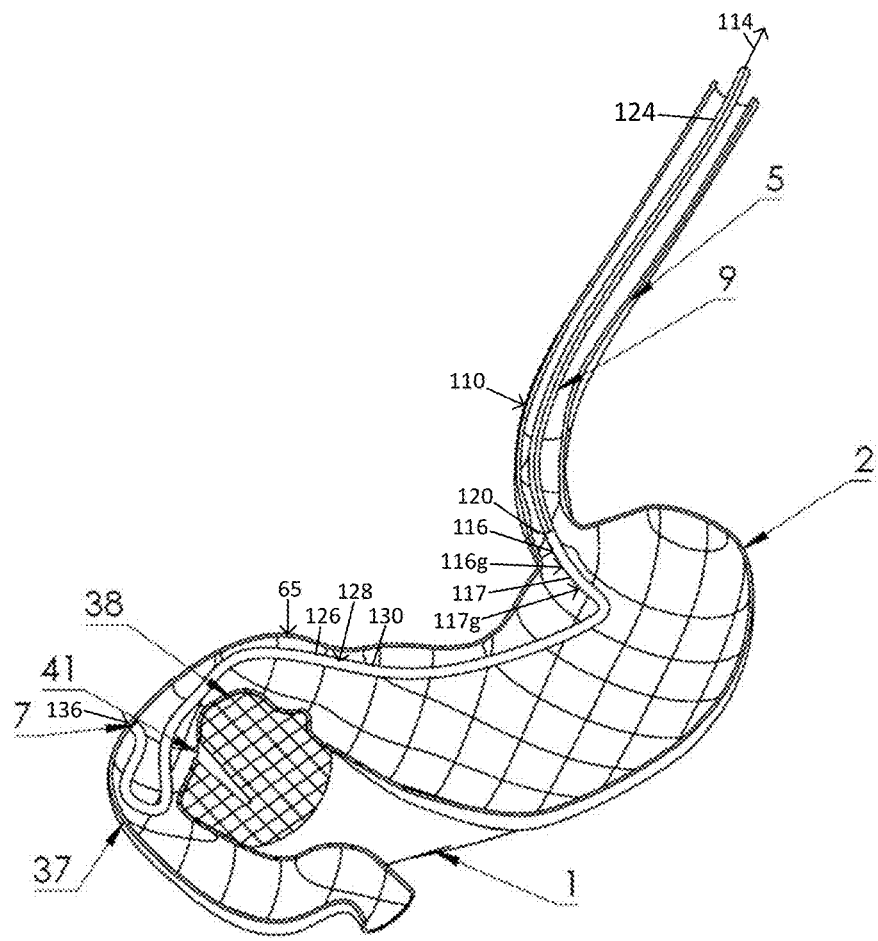
Figure 50H:
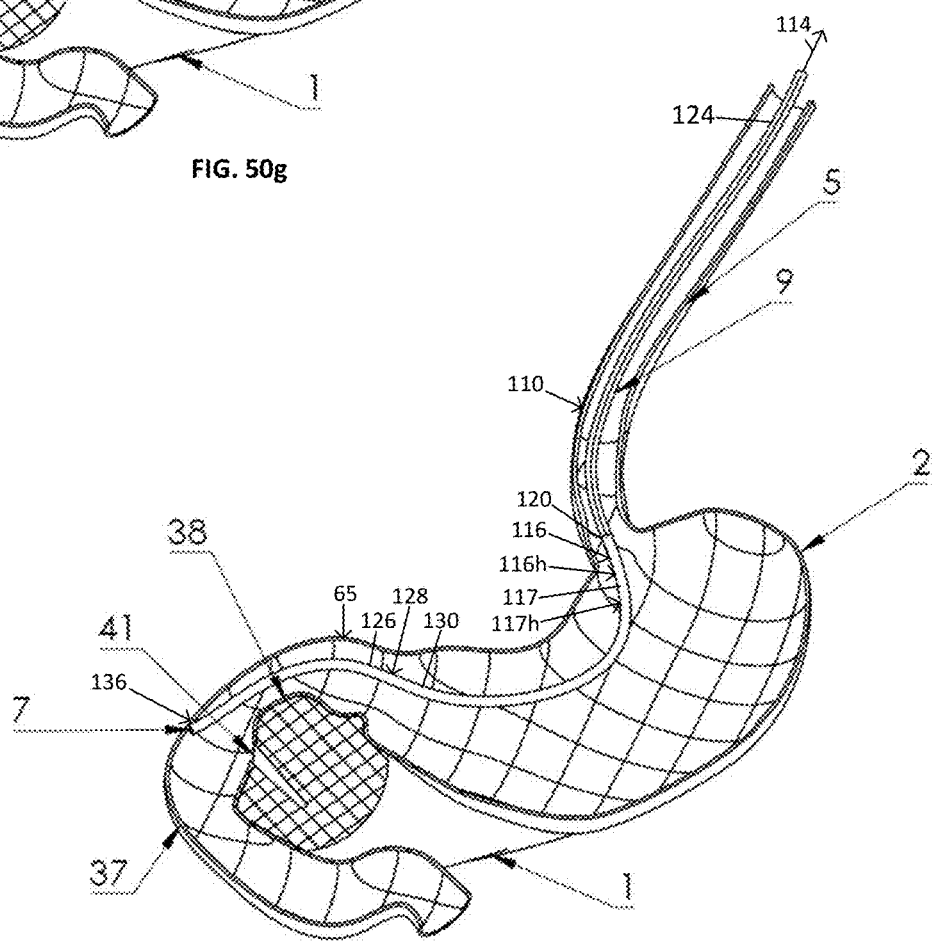

FIGS. 50a-50i illustrate that the catheter tip 7 can be moved into and out of contact with the duodenum 37. For example, FIGS. 50a-50b illustrate that the catheter tip 7 can be moved into contact with the duodenum 37 during insertion and FIGS. 50h-50i illustrate that the catheter tip 7 can be moved out of contact with the duodenum 37 during withdrawal. FIGS. 50a-50b illustrate, for example, that the catheter tip 7 can be moved into contact with the duodenum 37 by advancing the catheter 9 in the stomach 2 as shown by arrow 112 and FIGS. 50h-50i illustrate, for example, that the catheter tip 7 can be moved out of contact with the duodenum 37 by withdrawing the catheter 9 from the stomach 2 as shown by arrow 114. The catheter tip 7 may or may not contact the wall 136 of the duodenum 37 (also referred to as the duodenum wall 136) when the catheter 9 is in a deployed configuration (e.g., a configuration 116). For example, FIGS. 50b-50h illustrate that the proboscis 97 can contact the duodenum wall 136 when the catheter 9 is in a deployed configuration (e.g., the configurations 116b-116h).

The duodenum wall 136 can include a naturally occurring feature in the duodenum 37, including, for example, one or more duodenal folds (also referred to as Kerckring folds). FIGS. 50b-50h illustrate that the catheter tip 7 can be permanently and/or temporarily engageable with the duodenum wall 136, for example, with a duodenal fold. The catheter tip 7 can, for example, releasably anchor and/or releasably engage the distal end of the catheter 9 to the duodenum wall 136 when the catheter 9 is in the duodenum 37. The catheter 9 can, for example, be releasably anchored and/or releasably engaged to the duodenum wall 136 via the catheter tip 7 via friction between the catheter tip 7 and the duodenum wall 136, via the catheter tip 7 being wedged between two duodenal folds (e.g., between two adjacent duodenal folds), or any combination thereof. The catheter 9 can be unanchored and/or disengaged from the duodenum wall 136, for example, by moving (e.g., pulling) the catheter tip 7 away from the duodenum wall 136 by withdrawing the catheter 9 from the duodenum 37 as shown by arrow 114.

FIGS. 50a-50b illustrate that as the catheter 9 is introduced into the duodenum 37, the catheter tip 7 can become engaged with (e.g., can be moved into contact with) the duodenum wall 136. When the catheter tip 7 is engaged with the duodenum wall 136, the catheter tip 7 can remain engaged with (e.g., can remain in contact with) the duodenum wall 136, can disengage from (e.g., can move out of contact with) the duodenum wall 136, can re-engage with the duodenum wall 136, or any combination thereof while the catheter 9 is advanced into the stomach 2, while the catheter 9 is withdrawn from the stomach 2, while the catheter 9 is inserted into the duodenum 37, while the catheter 9 is withdrawn from the duodenum, while the catheter 9 migrates in the stomach 2 and/or in the duodenum 37, or any combination thereof. The catheter tip 7 can move and/or remain in a fixed position relative to the duodenum wall 136 as the catheter 9 moves in the stomach 2 and/or in the duodenum 37, for example, during insertion, withdrawal, and/or migration of the catheter 9. The catheter tip 7 can, for example, move and/or remain in a fixed position relative to the duodenum wall 136 while the catheter 9 is advanced into the stomach 2, while the catheter 9 is forced into and/or migrates into the duodenum 37, while the catheter 9 is withdrawn from the stomach 2, while the catheter 9 is withdrawn from the duodenum 37, or any combination thereof. For example, FIGS. 50b-50h illustrate that the catheter tip 7 can remain in a fixed position relative to the duodenum wall 136 while the catheter 9 is advanced into the stomach 2, while the catheter 9 is inserted into the duodenum 37, while the catheter 9 is withdrawn from the stomach 2, and while the catheter 9 is withdrawn from the duodenum 37.

The catheter tip 7 can move 0.00-5.0 cm or more away from the engaged position (e.g., the engaged position shown in FIG. 50b) in any direction along the duodenum wall 136, in any direction away from the duodenum wall 136 (e.g., perpendicularly away), in any direction toward the duodenum wall 136 (e.g., perpendicularly toward), or any combination thereof while the catheter 9 is advanced into the stomach 2, while the catheter 9 is forced into and/or migrates into the duodenum 37, while the catheter 9 is withdrawn from the stomach 2, while the catheter 9 is withdrawn from the duodenum 37, or any combination thereof, including every 0.1 cm increment within this range (e.g., 0.0 cm, 0.1 cm, 1.0 cm, 2.0 cm, 3.0 cm, 5.0 cm). A 0.0 cm movement of the catheter tip 7 can correspond to the catheter tip 7 remaining stationary relative to the duodenum wall 136. For example, FIGS. 50b-50h illustrate that the catheter tip 7 can remain in the same location (e.g., 0.0 cm movement) relative to the duodenum wall 136 while the catheter 9 is advanced into the stomach 2, while the catheter 9 is forced into and/or migrates into the duodenum 37, while the catheter 9 is withdrawn from the stomach 2, while the catheter 9 is withdrawn from the duodenum 37, or any combination thereof. FIGS. 50h-50i illustrate that the catheter 9 can become disengaged from (e.g., can be moved out of contact with) the duodenum wall 136. FIGS. 50h-50i illustrate, for example, that the catheter tip 7 can be disengaged from the duodenum wall 136 by withdrawing the catheter 9 from the stomach 2. Withdrawing the catheter 9 from the stomach 2 can, for example, include pulling the catheter tip 7 away from the duodenum wall 136 toward the gastroesophageal junction 120.

The proboscis 97 and/or the catheter tip 7 may or may not pivot on the duodenum wall 136 once the proboscis 97 and/or the catheter tip 7 contacts the duodenum wall 136. For example, FIGS. 50b-50c illustrate that the catheter tip 7 can pivot on the duodenum wall 136 when the catheter tip 7 is in contact with the duodenum wall 136 during insertion, and FIGS. 50g-50h illustrate that the catheter tip 7 can pivot on the duodenum wall 136 when the catheter tip 7 is in contact with the duodenum wall 136 during withdrawal.

The catheter tip 7 may or may not be forced into (e.g., pressed into) contact with the duodenum wall 136 during insertion of the catheter 9 into the stomach 2. For example, FIGS. 50a-50b illustrate that the catheter tip 7 can be forced into the duodenum wall 136 during insertion of the catheter 9 into the stomach 2. When the catheter tip 7 is pressed into the duodenum wall 136 during insertion into the stomach 2, the catheter tip 7 can inhibit and/or prevent the catheter tip 7 from tunneling into and/or through the duodenum wall 136, for example, by the catheter 9 bending and/or the catheter tip 7 pivoting on the duodenum wall 136 as shown FIGS. 50b-50c. For example, FIGS. 50b-50c illustrate that the catheter tip 7 can be flexible and/or can be a flexible tip that can deform (e.g., bend) when pushed into the duodenum wall 136.

FIGS. 50a-50e illustrate that the catheter tip 7 and the catheter 9 can be inserted into the duodenum 37. For example, FIGS. 50a-50e illustrate that inserting the catheter tip 7 and the catheter 9 in the stomach 2 as shown by arrow 112 can force the catheter tip 7 and the catheter 9 to enter the duodenum 37.

The catheter 9 can enter the duodenum 37 before, during, and/or after the catheter tip 7 and/or the proboscis 97 enters the duodenum 37. For example, FIGS. 50a-50b illustrate that the catheter tip 7 can enter the duodenum 37 before the body of the catheter 9 (e.g., the body of the catheter 9 can be, for example, the portion of the catheter 9 proximal the catheter tip 7). FIGS. 50a-50e illustrate, for example, that the catheter 9 can enter the duodenum 37 after the catheter tip 7 enters the duodenum 37. FIGS. 50a-50e illustrate, for example, that the catheter 9 can enter the duodenum 37 when the catheter tip 7 is in the duodenum 37. The catheter 9 can enter the duodenum 37 before, during, and/or after the catheter tip 7 and/or the proboscis 97 becomes engaged with the duodenum wall 136. For example, FIGS. 50a-50e illustrate that the catheter 9 can enter the duodenum 37 before the catheter tip 7 is pushed into engagement with (e.g., into contact with) the duodenum wall 136. The catheter 9 can enter the duodenum 37 while the catheter tip 7 and/or the proboscis 97 are engaged with the duodenum wall 136 (e.g., when the catheter tip 7 and/or the proboscis 97 is in contact with the stomach wall 108) and/or while the catheter tip 7 and/or proboscis 97 are disengaged from the stomach wall 108 (e.g., when the catheter tip 7 and/or the proboscis 97 is not in contact with the stomach wall 108). For example, FIGS. 50a-50e illustrate that the catheter 9 can enter the duodenum 37 while the catheter tip 7 is engaged with (e.g., in contact with) the duodenum wall 136. The catheter tip 7 may or may not remain in the duodenum 37 during insertion and/or migration of the catheter 9. For example, FIGS. 50a-50e illustrate that the catheter tip 7 can remain in the duodenum 37 during insertion and/or migration of the catheter 9.

The catheter tip 7 and/or the proboscis 97 can enter the duodenum 37 when any length of the catheter 9 is in the stomach 2. For example, the catheter tip 7 and/or the proboscis 97 can enter the duodenum 37 when at least 10 cm-150 cm or more of the catheter 9 is in the stomach 2, including every 1 cm increment within this range (e.g., at least 10 cm, at least 30 cm, at least 40 cm, at least 70 cm, at least 100 cm).

FIGS. 50e-50i illustrate that the catheter 9 can be removed from the duodenum 37, for example, by withdrawing (e.g., pulling) the catheter 9 out of the stomach 2 as shown by arrow 114.

The catheter 9 can be withdrawn from the duodenum 37 before, during, and/or after the catheter tip 7 and/or the proboscis 97 are withdrawn from the duodenum 2. For example, FIGS. 50e-50i illustrate that the catheter 9 can be withdrawn from the duodenum 37 before the catheter tip 7 is withdrawn from the stomach 2. FIGS. 49e-49i illustrate, for example, that the catheter 9 can be withdrawn from the duodenum 37 when the catheter tip 7 is in the duodenum 37.

The catheter 9 can be withdrawn from the duodenum 37 before, during, and/or after the catheter tip 7 and/or the proboscis 97 becomes engaged with the duodenum wall 136. For example, FIGS. 50e-50i illustrate that the catheter 9 can be withdrawn from the duodenum 37 after the catheter tip 7 is pushed into engagement with (e.g., into contact with) the duodenum wall 136. The catheter 9 can be withdrawn from the duodenum 37 while the catheter tip 7 and/or the proboscis 97 are engaged with the duodenum wall 136 (e.g., when the catheter tip 7 and/or the proboscis 97 is in contact with the duodenum wall 136) and/or while the catheter tip 7 and/or the proboscis 97 are disengaged from the duodenum wall 136 (e.g., when the catheter tip 7 and/or the proboscis 97 is not in contact with the duodenum wall 136). For example, FIGS. 50e-50i illustrate that the catheter 9 can be withdrawn from the duodenum 37 while the catheter tip 7 is engaged with (e.g., is in contact with) the duodenum wall 136.

The catheter tip 7 and/or the catheter 9 can be withdrawn from the duodenum 37 when at least 10 cm-150 cm or more of the catheter 9 is in the stomach 2, including every 1 cm increment within this range (e.g., at least 10 cm, at least 30 cm, at least 40 cm, at least 70 cm, at least 100 cm). For example, FIGS. 50e-50i illustrate that the catheter tip and/or the catheter 9 can be withdrawn from the duodenum 37 when at least 20 cm of the catheter 9 is in the stomach 2.

FIGS. 50b-50h illustrate that when the catheter 9 is in the duodenum 37, the catheter tip 7 can be in the duodenum 37.

FIGS. 50b-50h illustrate that the catheter 9 can be in the stomach 2 and the duodenum 37 when the catheter is in a deployed configuration (e.g., the configurations 116b-116h).

FIGS. 50b-50h illustrate that the catheter 9 can form a deployed configuration by inserting the catheter 9 into the stomach 2, by inserting the catheter 9 into the duodenum 37, by withdrawing the catheter 9 from the stomach 2, by withdrawing the catheter 9 from the duodenum 37, or any combination thereof.

FIGS. 50b-50h illustrate that when the catheter 9 is in the stomach 2, the catheter 9 can pass through the pylorus 65 one time (e.g., at the reference point x in FIG. 50e).

FIGS. 50b-50h illustrate that when the catheter 9 is in a deployed configuration (e.g., configurations 116b-116h), a first section of the catheter 9 can be in the duodenum 37 (e.g., the portion of the catheter 9 distal the pylorus 65) and a second section of the catheter 9 can be in the stomach 2 (e.g., the portion of the catheter proximal the pylorus 65). The portion of the catheter 9 distal the pylorus 65 can be forced into the duodenum 37 and/or can migrate into the duodenum 37. For example, FIGS. 50a-50e illustrate that the portion of the catheter 9 distal the pylorus 65 can be forced into the duodenum 37 by inserting the catheter 9 into the stomach 2.

FIGS. 50a-50i illustrate that the catheter 9 can form the loops 118 and cells 122 shown, for example, as the catheter 9 is inserted into and/or withdrawn from the target site 147. FIGS. 50b-50h illustrate that the loops 118 can be open loops. FIGS. 50a-50i illustrate that the target site 147 can be, for example, the stomach 2 and the duodenum 37.

FIGS. 50a-50b illustrate that the catheter tip 7 can enter the duodenum before the body of the catheter.

FIGS. 50a-50b illustrate that the catheter 9 can form the first loop 118a and the second loop 118b as the catheter 9 is inserted into the stomach 2 and the duodenum 37. FIGS. 50a-50b illustrate that the first loop 118a can be formed in the stomach 2 and that the second loop 118b can be formed in the stomach 2 and the duodenum 37. For example, FIG. 50b illustrates that the first loop first and second ends can be in the stomach 2, that the second loop first end can be in the stomach 2, and that second loop second end can be in the duodenum 37. FIG. 50b illustrates that the lesser curvature of the stomach 2 can be in the first cell 122a and that the pancreas head 38 and the pylorus 65 can be in the second cell 122b.

FIG. 50c illustrates that a loop 118 (e.g., the third loop 118c) can be in the duodenum 37. FIGS. 50b-50c illustrate that the catheter 9 can form the third loop 118c as the catheter 9 is inserted into the stomach 2 and the duodenum 37. FIGS. 50b-50c illustrate that the third loop 118c can be formed in the duodenum 37. FIGS. 50b-50c illustrate that when the catheter tip 7 is in the duodenum 37, the third loop 118c can be formed in the duodenum 37, for example, by advancing the catheter 9 into the duodenum 37 as shown by arrow 112. FIG. 50c illustrates that the third loop first end, third loop second end, and the third loop head can be in the duodenum 37. FIGS. 50b-50c illustrate that when the catheter tip 7 is engaged with the duodenum wall 136 (e.g., to a Kerckring rold) and the catheter 9 continues to be inserted into the stomach 2 as shown by arrow 112, a section of the catheter 9 proximal the catheter tip 7 can be advanced past (e.g., distal, caudal) the catheter tip 7, for example, as the catheter tip 7 pivots against the duodenum wall 136. FIG. 50c illustrates that the section of the catheter 9 advanced past the catheter tip 7 can be the third loop 118c. FIG. 50c illustrates that the third loop 118c can be distal the catheter tip 7 when the catheter 9 is in a deployed configuration (e.g., when the catheter 9 is in the third configuration 116c). FIG. 50b illustrates that before the third loop 118c is formed, the portion of the catheter 9 that defines the third loop 118c in FIG. 50c can be proximal to the catheter tip 7. As another example, when the catheter 9 is in a straight configuration, the portion of the catheter 9 that defines the third loop 118c in FIG. 50c can be proximal to the catheter tip 7. FIG. 50c illustrates that the lesser curvature of the stomach 2 can be in the first cell 122a and that the pancreas head 38, the ampulla of vater 41, and the pylorus 65 can be in the second cell 122b.

The perimeters of the loops 118 can increase, decrease, and/or remain constant as the catheter 9 is inserted into the target site 147. FIGS. 50b-50c illustrate that the size (e.g., the perimeter) of the first loop 118a can be smaller when the catheter 9 is in the third configuration 116c than when the catheter 9 is in the second configuration 116b. FIGS. 50b-50c illustrate that the size (e.g., the perimeter) of the second loop 118b can be larger when the catheter 9 is in the third configuration 116c than when the catheter 9 is in the second configuration 116b. FIGS. 50b-50c illustrate that less of the catheter 9 can be in the stomach 2 when the catheter 9 is in the third configuration 116c than when the catheter 9 is in the second configuration 116b. For example, FIGS. 50b-50c illustrate that as the catheter 9 is inserted into the duodenum 37, 1 cm-10 cm or more of the catheter 9, including every 1 cm increment within this range (e.g., 1 cm, 5 cm, 10 cm) can move out of the stomach 2 through the pylorus 65. FIGS. 50b-50c illustrate that the size (e.g., the area) of the second cell 122b can be larger when the catheter 9 is in the third configuration 116c than when the catheter 9 is in the second configuration 116b.

FIGS. 50c-50d illustrate that the size (e.g., the perimeter) of the first loop 118a and the third loop 118c can be larger when the catheter 9 is in the fourth configuration 116d than when the catheter 9 is in the third configuration 116c. FIGS. 50c-50d illustrate that the gap between the third loop second end (e.g., the catheter tip 7) and the third loop first end (e.g., the portion of the catheter 9 in FIGS. 50c-50d adjacent the ampulla of vater 41) can be larger when the catheter 9 is in the fourth configuration 116d than when the catheter 9 is in the third configuration 116c.

FIGS. 50d-50e illustrate that the catheter 9 can form the fourth loop 118d as the catheter 9 is inserted into the stomach 2 and the duodenum 37. FIGS. 50d-50e illustrate that the fourth loop 118d can be formed in the stomach 2. FIGS. 50d-50e illustrate that when the catheter tip 7 is in the duodenum 37, the fourth loop 118d can be formed in the stomach 2, for example, by advancing the catheter 9 into the stomach 2 as shown by arrow 112. FIG. 50d illustrates that the fourth loop first end, fourth loop second end, and the fourth loop head can be in the stomach 2. FIGS. 50d-50e illustrate that the size (e.g., the perimeter) of the first loop 118a can be smaller when the catheter 9 is in the fifth configuration 116e than when the catheter 9 is in the fourth configuration 116d. FIGS. 50d-50e illustrate that the size (e.g., the perimeter) of the second loop 118b and the third loop 118c can be larger when the catheter 9 is in the fifth configuration 116e than when the catheter 9 is in the fourth configuration 116d.

The third loop 118c can wedge the catheter 9 into the duodenum 37, can inhibit and/or prevent the portion of the catheter 9 in the duodenum 37 from migrating further into the duodenum 37, can inhibit or prevent the portion of the catheter 9 in the stomach 2 from migrating into the duodenum 37, can inhibit or prevent more of the catheter 9 from being inserted into the duodenum 37, or any combination thereof. For example, FIGS. 50c-50e illustrate that the third loop 118c can inhibit (e.g., can start to inhibit) more of the catheter 9 from being inserted into the duodenum 37, which is shown, for example, by more of the catheter 9 being inserted into the stomach 2 than in the duodenum 37 in FIGS. 50c-50e.

FIGS. 50b and 50h illustrate that when the catheter 9 is in the second configuration 116b and the eighth configuration 118h, the portion of the length 126 of the catheter 9 in the stomach 2 can be, for example, 10 cm-30 cm (e.g., 20 cm) and the portion of the length 126 of the catheter 9 in the duodenum 37 can be, for example, 1 cm-20 cm (e.g., 10 cm).

FIGS. 50c and 50g illustrate that when the catheter 9 is in the third configuration 116c and the seventh configuration 118g, the portion of the length 126 of the catheter 9 in the stomach 2 can be, for example, 10 cm-30 cm (e.g., 15 cm) and the portion of the length 126 of the catheter 9 in the duodenum 37 can be, for example, 1 cm-30 cm (e.g., 15 cm).

FIGS. 50d and 50f illustrate that when the catheter 9 is in the fourth configuration 116d and the sixth configuration 118f, the portion of the length 126 of the catheter 9 in the stomach 2 can be, for example, 20 cm-80 cm (e.g., 50 cm) and the portion of the length 126 of the catheter 9 in the duodenum 37 can be, for example, 1 cm-30 cm (e.g., 18 cm).

FIG. 50e illustrates that when the catheter 9 is in the fifth configuration 118e, the portion of the length 126 of the catheter 9 in the stomach 2 can be, for example, 20 cm-300 cm (e.g., 90 cm) and the portion of the length 126 of the catheter 9 in the duodenum 37 can be, for example, 1 cm-30 cm (e.g., 25 cm).

When the catheter 9 is in the duodenum 37, the length 126 of the catheter 9 in the stomach 2 can be, for example, 40 cm-300 cm greater than the length 126 of the catheter 9 in the duodenum 37, including every 1 cm increment within this range (e.g., 40 cm, 50 cm, 60 cm, 100 cm, 200 cm, 300 cm).

FIG. 50e illustrates that the catheter 9 can extend multiple times back and forth in different directions across the target site 147.

FIG. 50e illustrates that the catheter 9 can have undulations along the length of the catheter 9 when the catheter 9 is in a deployed configuration. FIG. 50e illustrates that the undulations can be, for example, bends in the catheter 9. The undulations can have, for example, a sinusoidal pattern, a serpentine pattern, a zig-zag pattern, or any combination thereof. FIGS. 50e-50f illustrate that the undulations can straighten as the catheter 9 is withdrawn from the body.

FIGS. 50e-50f illustrate that as the length of the catheter 9 in the stomach 2 is decreased, the length of the catheter 9 in the duodenum can simultaneously decrease.

The catheter 9 can transfer heat to and/or from surrounding tissue when the catheter 9 is in the stomach 2, in the duodenum 37, and/or in the intestine caudal the duodenum 37. For example, FIGS. 50b-50h illustrate that the catheter 9 can transfer heat to and/or from the stomach 2 and the duodenum 37.

FIGS. 50a-50i illustrate that the catheter 9 may not have the proboscis 97. As another example, the catheter 9 in FIGS. 50a-50i can have the proboscis 97.

FIGS. 50a-50e illustrate that the loops 118 and the cells 122 can be formed by inserting the catheter 9 into the target site 147. The loops 118 can be formed in the target site 147 in any order, for example, sequentially and/or simultaneously. For example, FIGS. 50a-50e illustrate that the first loop 118a, the second loop 118b, the third loop 118c, and the fourth loop 118d can be sequentially formed. For example, FIGS. 50a-50e illustrate that the first loop 118a can be formed in the target site 147, then the second loop 118b can be formed in the target site 147, then the third loop 118c can be formed in the target site 147, and then the fourth loop 118d can be formed in the target site 147. For example, FIGS. 50a-50e illustrate that the second loop 118b can be formed after the first loop 118a is formed, that the third loop 118b can be formed after the first loop 118a and/or the second loop 118b are formed and that the fourth loop 118d can be formed after the first loop 118a, the second loop 118b, and/or the third loop 118c are formed. During the formation of each loop 118, one or more of the other loops 118 can change size and/or shape. FIGS. 50a-50e illustrate, for example, that already formed loops 118 can change size and/or shape while one more other loops 118 are formed. For example, FIGS. 50b-50c illustrate that the first loop 118a and/or the second loop 118b can change size and/or shape while the third loop 118c is formed, and FIGS. 50d-50e illustrate that the first loop 118a and/or the third loop 118c can change size and/or shape while the fourth loop 118d is formed.

FIGS. 50a-50e illustrate, for example, that during a first phase of loop formation, the loop 118a can be formed, that during a second phase of loop formation, the loop 118b can be formed, that during a third phase of loop formation, the loop 118c can be formed, and that during a fourth phase of loop formation, the loop 118d can be formed. The first phase of loop formation can be before the second phase of loop formation. The second phase of loop formation can be after the first phase of loop formation. The third phase of loop formation can be after the second phase of loop formation. The fourth phase of loop formation can be after the second phase of loop formation. While the third loop 118c is being formed (e.g., during the third phase of loop formation), the first loop 118a and/or the second loop 118b can have a constant size and/or shape. As another example, FIGS. 50b-50e illustrate that while the third loop 118c is being formed (e.g., during the third phase of loop formation), the size (e.g., perimeter) of the first loop 118a and/or the second loop 118b can increase and/or decrease, the shape of the first loop 118a and/or the second loop 118b can change, or any combination thereof. While the fourth loop 118d is being formed (e.g., during the fourth phase of loop formation), the first loop 118a, the second loop 118b, and/or the third loop 118c can have a constant size and/or shape. As another example, FIGS. 50d-50e illustrate that while the fourth loop 118d is being formed (e.g., during the fourth phase of loop formation), the size (e.g., perimeter) of the first loop 118a, the second loop 118b, and/or the third loop 118c can increase and/or decrease, the shape of the first loop 118a, the second loop 118b, and/or the third loop 118c can change, or any combination thereof.

FIGS. 50e-50i illustrate that the catheter 9 can be withdrawn from the target site 147. FIGS. 50e-50i illustrate that the loops 118 can be collapsed in and/or removed from the target site 147. FIGS. 50e-50i illustrate that collapsing the loops 118 can include straightening the loop 118, decreasing the curve of a loop, decreasing the perimeter of the loop 118, decreasing the loop length of the loops 118, decreasing the width of the loops 118, decreasing the height of the loops

118, or any combination thereof. FIGS. 50*e*-50*i* illustrate that the loops 118 can be collapsed in the target site 147 by withdrawing the catheter 9 from the target site 147 as shown by arrow 114. FIGS. 50*e*-50*i* illustrate, for example, that the catheter 9 can straighten and/or become less curved in the target site 147 as the catheter 9 is withdrawn (e.g., pulled) from the target site 147 into the esophagus 5 as shown by arrow 114.

The loops 118 can be collapsed in and/or removed from the target site 147 in any order, for example, sequentially and/or simultaneously. For example, FIGS. 50*e*-50*i* illustrate that the first loop 118*a*, the second loop 118*b*, the third loop 118*c*, and the fourth loop 118*d* can be collapsed from the target site 147 in the order shown. FIGS. 50*e*-50*i* illustrate, for example, that the fourth loop 118*d* can be collapsed, then the first loop 118*a* can be collapsed a first time, then the third loop 118*c* can be collapsed, then the second loop 118*b* can be collapsed, and then the first loop 118*a* can be collapsed a second time. FIGS. 50*e*-50*f* illustrate that as the fourth loop 118*d* is collapsing (e.g., decreasing in size) the first loop 118*a* can increase in size and/or the third loop 118*c* can decrease in size. FIGS. 50*f*-50*g* illustrate that as the first loop 118*a* is collapsing (e.g., decreasing in size) the third loop 118*c* can have a constant size and/or shape. FIGS. 50*g*-50*i* illustrate that the third loop 118*c* can be collapsed, then the second loop 118*b* can be collapsed, and then the first loop 118*a* can be collapsed by withdrawing the catheter 9 from the target site 147 as shown by arrow 114.

FIGS. 50*e*-50*i* illustrate, for example, that during a first phase of catheter removal, the section of the catheter 9 defining the fourth loop 118*d* in configuration 116*e* can be removed from the stomach 2, that during a second phase of catheter removal, a portion of the section of the catheter 9 defining the first loop 118*a* in configuration 116*f* can be removed from the stomach 2, that during a third phase of catheter removal, the section of the catheter 9 defining the third loop 118*c* in configurations 116*e*-116*g* can be removed from the duodenum 37, that during a fourth phase of removal, the section of the catheter defining the first and second loops 118*a*, 118*b* can be removed from the stomach 2. The first phase of catheter removal can be before the second phase of catheter removal. The second phase of catheter removal can be after the first phase of catheter removal. The third phase of catheter removal can be after the second phase of catheter removal. The fourth phase of catheter removal can be after the third phase of catheter removal.

FIGS. 50*a*-50*i* illustrate, for example, that the configurations 116 formed by the catheter 9 during withdrawal can be the same as the configurations 116 formed by the catheter 9 during insertion. As another example, the configurations 116 formed by the catheter 9 during withdrawal of the catheter 9 from the body can be different from the configurations 116 formed by the catheter 9 during insertion of the catheter 9 into the body.

Figure 51B:
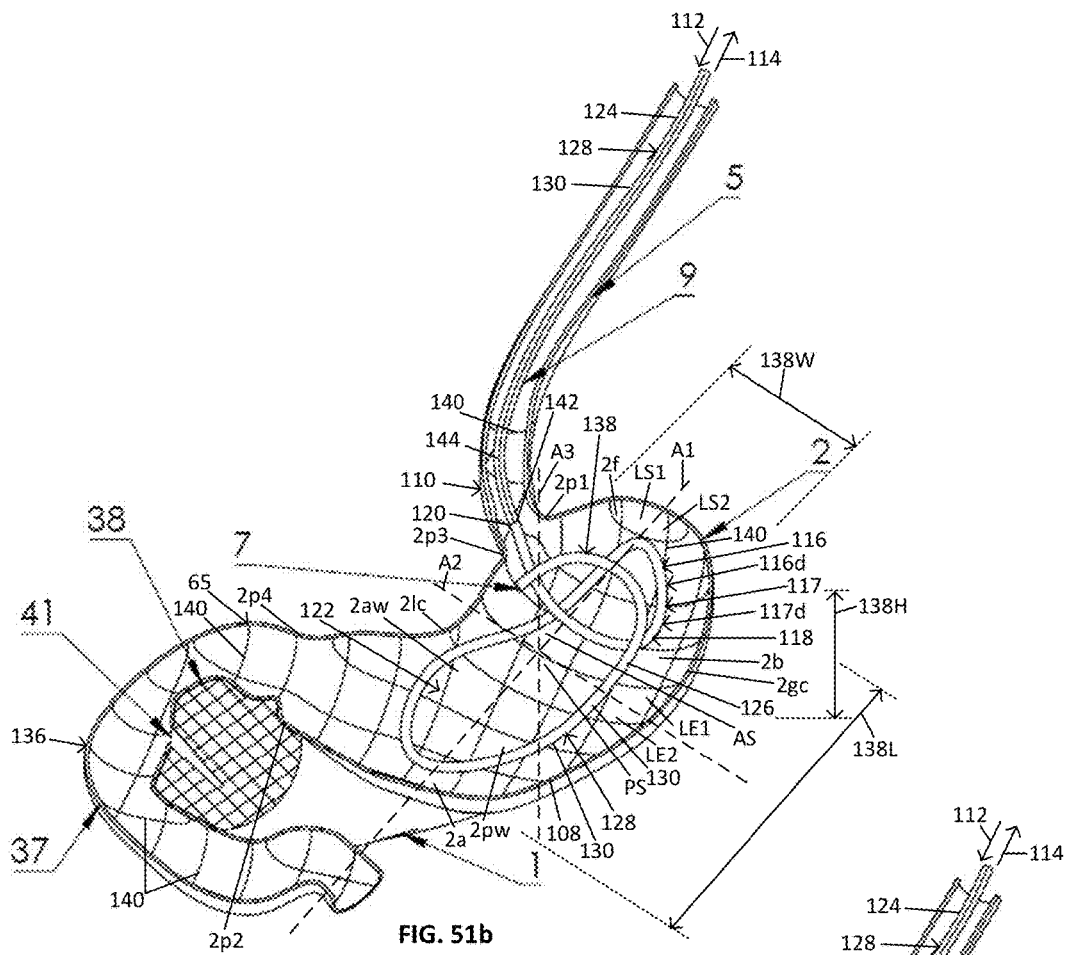

FIGS. 51*a*-51*d* illustrate that the catheter 9 can be inserted into and/or removed from the stomach 2. For example, FIGS. 51*a*-51*d* illustrate that the catheter 9 can be inserted into the stomach 2 as shown by arrow 112 and FIGS. 51*d*-51*a* illustrate that the catheter 9 can be withdrawn from the stomach 2 as shown by arrow 114. FIGS. 51*a*-51*d* illustrate that various lengths of the catheter 9 (e.g., the length 126 shown in FIGS. 51*b*-51*d*) can be introduced into and/or removed from the stomach 2. FIGS. 51*a*-51*d* illustrate various configurations 116 and shapes 117 that the catheter 9 can have. FIGS. 51*a*-51*d* illustrate, for example, that when the catheter 9 is in a first through a fourth configuration 116*a*-116*d*, the catheter 9 can have the first through the fourth shape 117*a*-117*d*, respectively.

FIGS. 51*a*-51*d* illustrate that the catheter 9 can form the coil 138 inside the target site 147 (e.g., the stomach 2), for example, by inserting the catheter 9 into the target site 147 as shown by arrow 112. FIGS. 51*a*-51*d* illustrate, for example, that the coil 138 can have the first shape 117*a* shown in FIG. 51*a*, the second shape 117*b* shown in FIG. 51*b*, the third shape 117*c* shown in FIG. 51*c*, and/or the fourth shape 117*d* shown in FIG. 51*d*. FIGS. 51*a*-51*d* illustrate that the catheter 9 can form the coil 138 in the target site 147 by forming bends, forming loops (e.g., loops 118), folding over itself, crossing over and/or under itself, contacting itself, extending longitudinally across the target site 147, extending transversely across the target site 147, extending vertically across the target site 147, extending anteriorly across the target site 147, extending posteriorly across the target site 147, extending superiorly across the target site 147, extending inferiorly across the target site 147, extending proximally across the target site 147, extending distally across the target site 147, winding back and forth in multiple directions through the target site 147, extending around the target site 147, undulating (e.g., zigzagging) across the target site 147, or any combination thereof as the catheter 9 is inserted into the target site 147. FIGS. 51*a*-51*d* illustrate, for example, that as the catheter 9 is inserted into the target site 147, the catheter 9 can engage with, can be pushed against, and/or can be constrained by a wall of the target site 147 (e.g., the stomach wall 108) which can, for example, cause the catheter 9 to assemble into the coil 138 in the target site 147. FIGS. 51*a*-51*d* illustrate, for example, that the coil 138 can become progressively more complex and/or dense as the catheter 9 is inserted into the stomach 2. FIGS. 51*a*-51*d* illustrate that when the catheter 9 is in a straight configuration, the portion of the catheter 9 that forms the coil 138 can be straight.

FIGS. 51*d*-51*a* illustrate that the catheter 9 can be withdrawn (e.g., pulled) from the coil 138 inside the target site 147, for example, by withdrawing the catheter 9 from the target site 147 as shown by arrow 114. FIGS. 51*d*-51*a* illustrate, for example, that the coil 138 can be uncoiled in the target site 147, for example, by withdrawing the catheter 9 from the target site 147 as shown by arrow 114. The catheter 9 can be withdrawn from an exterior of the coil 138 and/or from an interior of the coil 138. For example, withdrawing a section of catheter on the exterior of the coil 138 and/or on the interior of the coil 138 can uncoil the coil 138. FIGS. 51*d*-51*a* illustrate, for example, that the exterior of the coil 138 can be the portions of the catheter 9 that can contact the target site 147, and that the interior of the coil 138 can be the portions of the catheter 9 that are shielded from contacting the target site 147 by the exterior of the coil. FIGS. 51*d*-51*a* illustrate that the catheter 9 can uncoil from the coil 138 in the target site 147, for example, by straightening and/or becoming less curved which can, for example, cause the coil 138 to unravel, unwind, uncoil, uncurl, unfold, and/or unbend. FIGS. 51*d*-51*a* illustrate, for example, that the coil 138 can become progressively less complex and/or dense as the catheter 9 is withdrawn from the stomach 2.

FIGS. 51*a*-51*d* illustrate a first axis A1, a second axis A2, and a third axis A3 that can intersect each other, for example, in the center of the target site 147. FIGS. 51*a*-51*d* illustrate, for example, that the point at which the first axis A1, the second axis A2, and the third axis A3 intersect can be closer to the lesser curvature 21*c* of the stomach 2 than to the greater curvature 2*gc* of the stomach 2. FIGS. 51*a*-51*d* illustrate that the first axis A1, the second axis A2, and the third axis A3 can be orthogonal to each other. FIGS. 51a-51d illustrate that the first axis A1, the second axis A2, and the third axis A3 can be straight axes. As another example, one or more of the first axis A1, the second axis A2, and the third axis A3 can be a curved axis. FIGS. 51a-51d illustrate, for example, that the first axis A1, the second axis A2, and the third axis A3 can be a longitudinal axis, a transverse axis, and a vertical axis, respectively.

FIGS. 51a-51d illustrate, for example, that the first axis A1 can pass through the fundus 2f, the stomach body 2b, and the antrum 2a. FIGS. 51a-51d illustrate, for example, that the second axis A2 can pass through the greater curvature 2gc of the stomach 2, the stomach body 2b, and the lesser curvature 21c of the stomach 2. FIGS. 51a-51d illustrate that the greater curvature 2gc can be the length along the border of the stomach 2 and/or the pyloric region from point 2p1 to point 2p2. FIGS. 51a-51d illustrate that the lesser curvature 21c can be the length along the border of the stomach 2 and/or the pyloric region from point 2p3 to point 2p4. The greater curvature 2gc can be, for example, 19.0 cm-36.0 cm, including every 0.1 cm increment within this range (e.g., 19.0 cm, 22.2 cm, 25.3 cm, 26.0 cm, 31.0 cm, 34.0 cm, 36.0 cm). The lesser curvature 21c can be, for example, 13.0 cm-19.5 cm, including every 0.1 cm increment within this range (e.g., 13.0 cm, 16.3 cm, 19.3 cm, 19.5 cm). FIGS. 51a-51d illustrate, for example, that the third axis A3 can pass through a posterior wall 2pw of the stomach 2, the stomach body 2b, and an anterior wall 2aw of the stomach 2 (shown transparent).

FIGS. 51a-51d illustrate that the first axis A1 can extend proximally to distally through the stomach 2, for example, from the fundus 2f toward the antrum 2a and vice versa, for example, distally to proximally through the stomach 2, for example, from the antrum 2a toward the fundus 2f. A distal position in the stomach 2 can be, for example, closer to the pylorus 65 and/or the duodenum 37 than a proximal position in the stomach 2. FIGS. 51a-51d illustrate that the first axis A1 can extend superiorly to inferiorly through the stomach 2, for example, from the fundus 2f toward the antrum 2a and vice versa, for example, inferiorly to superiorly through the stomach 2, for example, from the antrum 2a toward the fundus 2f. An inferior position in the stomach 2 can be, for example, closer to the inferior most point of the greater curvature 2gc than a superior position in the stomach 2. The inferior most point of the greater curvature 2gc in FIGS. 51a-51d can be, for example, the location where the lead line extending from point 2pw crosses over the stomach wall 108.

FIGS. 51a-51d illustrate that the second axis A2 can extend laterally through the stomach 2, for example, from the side of the stomach 2 having the greater curvature 2gc toward the side of the stomach 2 having the lesser curvature 21c and vice versa, for example, from the side of the stomach 2 having the lesser curvature 21c to the side of the stomach 2 having the greater curvature 2gc.

FIGS. 51a-51d illustrate that the third axis A3 can extend posteriorly to anteriorly through the stomach 2, for example, from the posterior wall 2pw toward the anterior wall 2aw and vice versa, for example, anteriorly to posteriorly through the stomach 2 from the anterior wall 2aw toward the posterior wall 2pw.

FIGS. 51a-51d illustrate, for example, that the first axis A1 can separate the stomach 2 into a first lateral side LS1 and a second lateral side LS2 opposite the first lateral side LS1.

FIGS. 51a-51d illustrate, for example, that the second axis A2 can separate the stomach 2 into a first longitudinal end LE1 and a second longitudinal end LE2 opposite the first longitudinal end LE1.

FIGS. 51a-51d illustrate, for example, the second axis A2 can separate the stomach 2 into a posterior side PS and an anterior side AS (shown transparent in FIGS. 51a-51d). For example, FIGS. 51a-51d illustrate that a flat plane that extends through the first axis A1 and the second axis A2 can separate the stomach 2 into the posterior side PS and the anterior side AS (shown transparent in FIGS. 51a-51d).

The portion of the catheter 9 that forms the coil 138 can extend back and forth across target site 147 in multiple directions, for example, longitudinally back and forth across the target site 147 along the first axis A1, transversely (e.g., laterally) back and forth across the target site 147 along the second axis A2, vertically back and forth across the target site 147 along the third axis A3, or any combination thereof. For example, FIGS. 51a-51d illustrate that the catheter 9 that defines the coil 138 can extend back and forth across target site 147 in multiple directions, for example, longitudinally back and forth across the target site 147 from the first longitudinal end LE1 to the second longitudinal end LE2 and from the longitudinal end LE2 to the first longitudinal end LE1, transversely (e.g., laterally) back and forth across the target site 147 from the first lateral side LS1 to the second lateral side LS2 and from the second lateral side LS2 to the first lateral side LS1, and vertically back and forth across the target site 147 from the posterior side PS to the anterior side AS and from the anterior side AS to the posterior side PS. FIGS. 51a-51d illustrate, for example, that the catheter 9 can extend superiorly, inferiorly, proximally, distally, laterally, anteriorly, and/or posteriorly across the target site 147, for example, along the first axis A1, the second axis A2, and/or the third axis A3. FIGS. 51a-51d illustrate, for example, that the catheter 9 can wind back and forth in multiple directions through the target site 147, can extend around the target site 147, can undulate (e.g., zigzag) across the target site 147, can extend through an interior of the coil 138, can define an exterior surface of the coil 138, or any combination thereof.

The coil 138 can have a coil first longitudinal end and a coil second longitudinal end. FIGS. 51a-51d illustrate that the coil first longitudinal end can be the portion of the coil 138 in the first longitudinal end LE1 of the stomach 2 and that the coil second longitudinal end can be the portion of the coil 138 in the second longitudinal end LE2 of the stomach 2, in the pylorus 65, and/or in the duodenum 37. The coil first longitudinal end can be opposite the coil second longitudinal end. The coil first longitudinal end can be the coil proximal end and the coil second longitudinal end can be the coil distal end. The coil proximal terminal end can be, for example, the portion of the catheter 9 that is farthest from the second axis A2 in the first longitudinal end LE1 of the stomach 2, and the coil distal terminal end can be, for example, the portion of the catheter 9 that is farthest from the second axis A2 in the second in the second longitudinal end LE2 of the stomach 2, in the pylorus 65, and/or in the duodenum 37.

The coil 138 can have a coil first lateral side and a coil second lateral side. FIGS. 51a-51d illustrate that the coil first lateral side can be the portion of the coil 138 in the first lateral side LS1 of the stomach 2, in the pylorus 65, and/or in the duodenum 37 and that the coil second lateral side can be the portion of the coil 138 in the second lateral side LS2 of the stomach 2 and/or in the duodenum 37. The coil first lateral side can be opposite the coil second lateral side. The coil first lateral side terminal end can be, for example, the portion of the catheter 9 that is farthest from the first axis A1 in the first lateral side LS1 of the stomach 2, in the pylorus 65, and/or in the duodenum 37, and the coil second lateral side terminal end can be, for example, the portion of the catheter 9 that is farthest from the first axis A1 in the second in the second lateral side LS2 of the stomach 2 and/or in the duodenum 37.

The coil 138 can have a coil posterior side and a coil anterior side. FIGS. 51a-51d illustrate that the coil posterior side can be the portion of the coil 138 in the posterior side PS of the stomach 2 and that the coil anterior side can be the portion of the coil 138 in the anterior side AS of the stomach 2 and/or in the duodenum 37. The coil posterior side can be opposite the coil anterior side. A coil posterior side terminal end can be, for example, the portion of the catheter 9 that is farthest from the first axis A1 in the posterior side PS of the stomach 2, in the pylorus 65, and/or in the duodenum 37, and the coil anterior side terminal end can be, for example, the portion of the catheter 9 that is farthest from the first axis A1 in the second in the anterior side AS of the stomach 2 and/or in the duodenum 37.

The coil 138 can have a coil length 138L, a coil width 138W, and a coil height 138H. For example, FIGS. 51a-51d illustrate that the coil length 138L, the coil width 138W, and the coil height 138H can be measured, for example, along the first axis A1, the second axis A2, and the third axis A3, respectively.

FIGS. 51a-51d illustrate that the coil length 138L can be measured, for example, along the first axis A1 between the point on the catheter 9 that is farthest from the second axis A2 in the first longitudinal end LE1 of the stomach 2 and the point on the catheter 9 that is farthest from the second axis A2 in the second longitudinal end LE2 of the stomach 2. For example, FIGS. 51a-51d illustrate that the coil length 138L can be measured along the first axis A1 between the coil proximal terminal end and the coil distal terminal end.

FIGS. 51a-51d illustrate that the coil width 138W can be measured, for example, along the second axis A2 between the point on the catheter 9 that is farthest from the first axis A1 in the first lateral side LS1 of the stomach 2 and the point on the catheter 9 that is farthest from the first axis A1 in the second lateral side LS2 of the stomach 2. For example, FIGS. 51a-51d illustrate that the coil width 138W can be measured along the second axis A2 between the coil first lateral side terminal end and the coil second lateral side terminal end.

FIGS. 51a-51d illustrate that the coil height 138H can be measured, for example, along the third axis A3 between the point on the catheter 9 that is farthest from the first axis A1 and/or the second axis A2 in the posterior side PS of the stomach 2 and the point on the catheter 9 that is farthest from the first axis A1 and/or the second axis A2 in the anterior side AS of the stomach 2. For example, FIGS. 51a-51d illustrate that the coil height 138W can be measured along the third axis A3 between the coil posterior side terminal end and the coil anterior side terminal end.

FIGS. 51a-51d illustrate that the coil length 138L can be, for example, 3 cm-50 cm or more, including every 1 cm increment within this range (e.g., 3 cm, 4 cm, 10 cm, 20 cm, 30 cm, 50 cm). The coil length 138L can be greater than the stomach length 2L, for example, when the coil 138 is in the stomach 2 and in the duodenum 37.

FIGS. 51a-51d illustrate that the coil width 138W can be, for example, 3 cm-20 cm or more, including every 1 cm increment within this range (e.g., 3 cm, 4 cm, 10 cm, 20 cm).

FIGS. 51a-51d illustrate that the coil height 138H can be, for example, 3 cm-20 cm or more, including every 1 cm increment within this range (e.g., 3 cm, 4 cm, 10 cm, 20 cm).

FIG. 51d illustrates, for example, that the coil length 138L, the coil width 138W, and the coil height 138H can be 15 cm, 9 cm, and 8 cm, respectively.

The catheter 9 can have any French size, including, for example, a French size of 5 Fr-30 Fr, including every 1 increment on the French scale within this range (e.g., 5 Fr, 6 Fr, 9 Fr, 12 Fr, 15 Fr, 18 Fr, 24 Fr, 30 Fr). For example, FIGS. 51a-51d illustrate that the catheter 9 can be a 12 Fr catheter.

The outer diameter 19 of the catheter 9 can be, for example, 1.67 mm-10 mm or more, including every 0.01 mm increment within this range (e.g., 1.67 mm, 2.00 mm, 3.00 mm, 4.00 mm, 5.00 mm, 6.00 mm, 7.00 mm, 8.00 mm, 9.00 mm, 10.00 mm). For example, FIGS. 51a-51d illustrate that the catheter 9 can have an outer diameter 19 of 4.00 mm.

The cross-section of the inflow lumen (e.g., the lumen 15) and/or the outflow lumen (e.g., the lumen 16) catheter 9 can be circular or non-circular. FIGS. 2a-2d illustrate, for example, that the inflow lumen and the outflow lumen can have non-circular cross-sections.

The cross-sectional area of the inflow lumen can be, for example, 1.50 mm$^2$-20.00 mm$^2$, including every 0.01 mm$^2$ increment within this range (e.g., 1.50 mm$^2$, 2.00 mm$^2$, 2.54 mm$^2$, 3.00 mm$^2$, 4.00 mm$^2$, 20.00 mm$^2$).

The cross-sectional area of the outflow lumen can be, for example, 1.50 mm$^2$-20.00 mm$^2$, including every 0.01 mm$^2$ increment within this range (e.g., 1.50 mm$^2$, 2.00 mm$^2$, 2.54 mm$^2$, 3.00 mm$^2$, 4.00 mm$^2$, 20.00 mm$^2$).

Figure 2D:
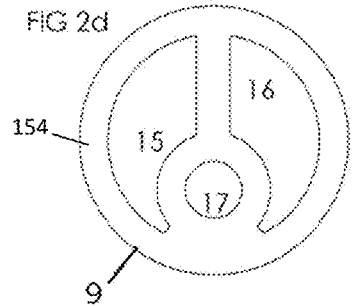

The cross-sectional area of the inflow lumen can be the same as or different than the cross-sectional area of the outflow lumen. For example, FIGS. 2a, 2b, and 2d illustrate that the cross-sectional area of the inflow lumen and the outflow lumen can be the same.

FIGS. 51a-51d illustrate, for example, that the cross-sectional area of the inflow lumen and the outflow lumen in the catheter 9 can each be 2.54 mm$^2$.

The coil length 138L can be, for example, at least 5.0.0-250.0 or times greater than the outer diameter 19 of the catheter 9, including every 0.5 interval increment within this range (e.g., at least 5.0 times, 10.5 times, 20.0 times, 25.0 times, 30.0 times, 40.0 times, 50.0 times). For example, when the outer diameter 19 of the catheter 9 is 4 mm, FIGS. 51a-51d illustrate that the coil length 138L can be at least 30.0-40.0 times (e.g., 37.5 times in FIG. 51d) greater than the outer diameter 19 (e.g., 37.5 times in FIG. 51d=coil length 138L(15 cm)/outer diameter 19(0.4 cm)).

The coil width 138W can be, for example, at least 2.0.0-100.0 or times greater than the outer diameter 19 of the catheter 9, including every 0.5 interval increment within this range (e.g., at least 2.0 times, 10.5 times, 20.0 times, 25.0 times, 30.0 times, 40.0 times, 50.0 times). For example, when the outer diameter 19 of the catheter 9 is 4 mm, FIGS. 51a-51d illustrate that the coil width 138W can be at least 15.0-25.0 times (e.g., 22.5 times in FIG. 51d) greater than the outer diameter 19 (e.g., 22.5 times in FIG. 51d=coil width 138W(9 cm)/outer diameter 19(0.4 cm)).

The coil height 138H can be, for example, at least 2.0.0-100.0 or times greater than the outer diameter 19 of the catheter 9, including every 0.5 interval increment within this range (e.g., at least 2.0 times, 10.5 times, 20.0 times, 25.0 times, 30.0 times, 40.0 times, 50.0 times). For example, when the outer diameter 19 of the catheter 9 is 4 mm, FIGS. 51a-51d illustrate that the coil height 138H can be at least 15.0-25.0 times (e.g., 20.0 times in FIG. 51d) greater than the outer diameter 19 (e.g., 20.0 times in FIG. 51*d*=coil height 138H(8 cm)/outer diameter 19(0.4 cm)).

FIGS. 51*a*-51*d* illustrate that a posterior side of the coil 138 can contact the posterior side PS of the of the stomach 2 and that an anterior side of the coil 138 can contact the anterior side AS of the stomach 2.

FIGS. 51*a*-52*d* illustrate that the coil 138 can assume the coil length 138L, the coil width 138W, and the coil height 138H as the catheter 9 is inserted into the stomach 2 as shown by arrow 112. For example, coil length 138L, the coil width 138W, and the coil height 138H can increase to the dimensions shown in FIGS. 51*a*-51*d* as the catheter 9 is inserted into the stomach 2 as shown by arrow 112.

FIGS. 51*d*-52*a* illustrate that the coil 138 can assume the coil length 138L, the coil width 138W, and the coil height 138H as the catheter 9 is withdrawn from the stomach 2 as shown by arrow 114. For example, coil length 138L, the coil width 138W, and the coil height 138H can decrease to the dimensions shown in FIGS. 51*d*-51*a* as the catheter 9 is withdrawn from the stomach 2 as shown by arrow 114.

Figure 52B:
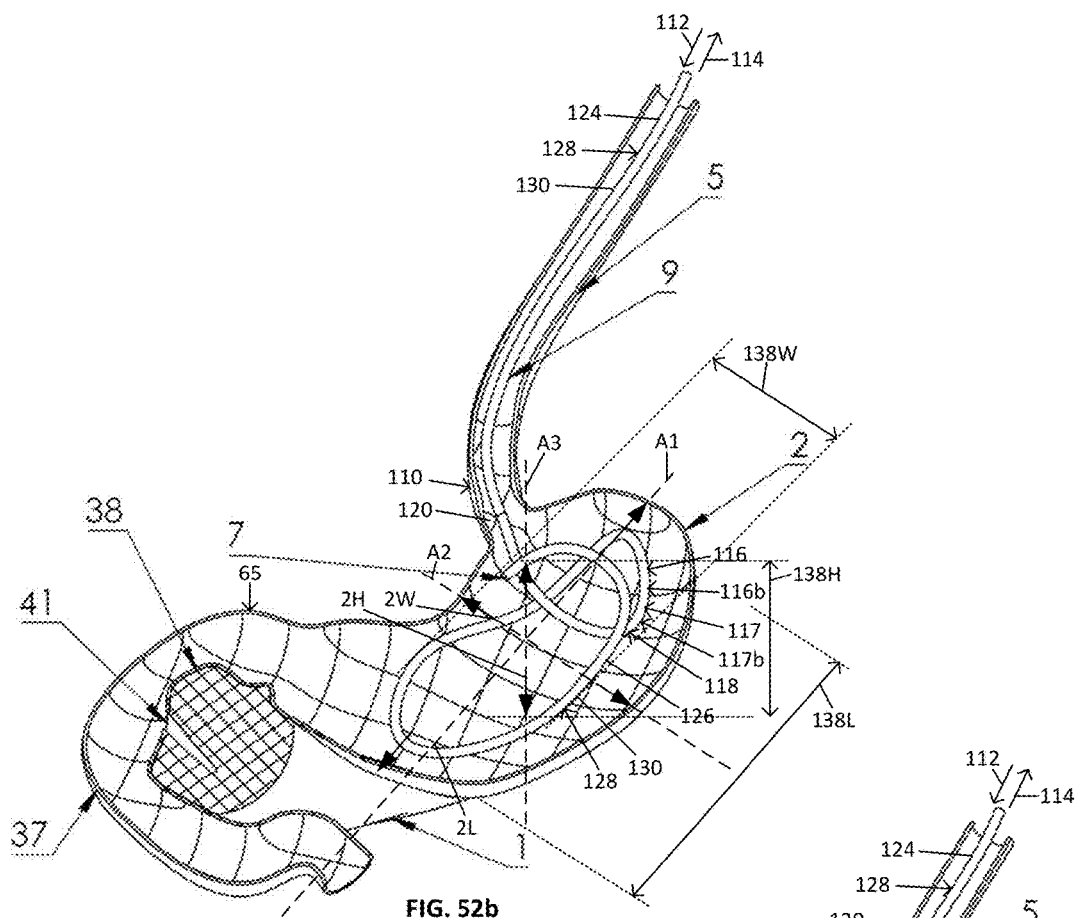
Figure 52C:
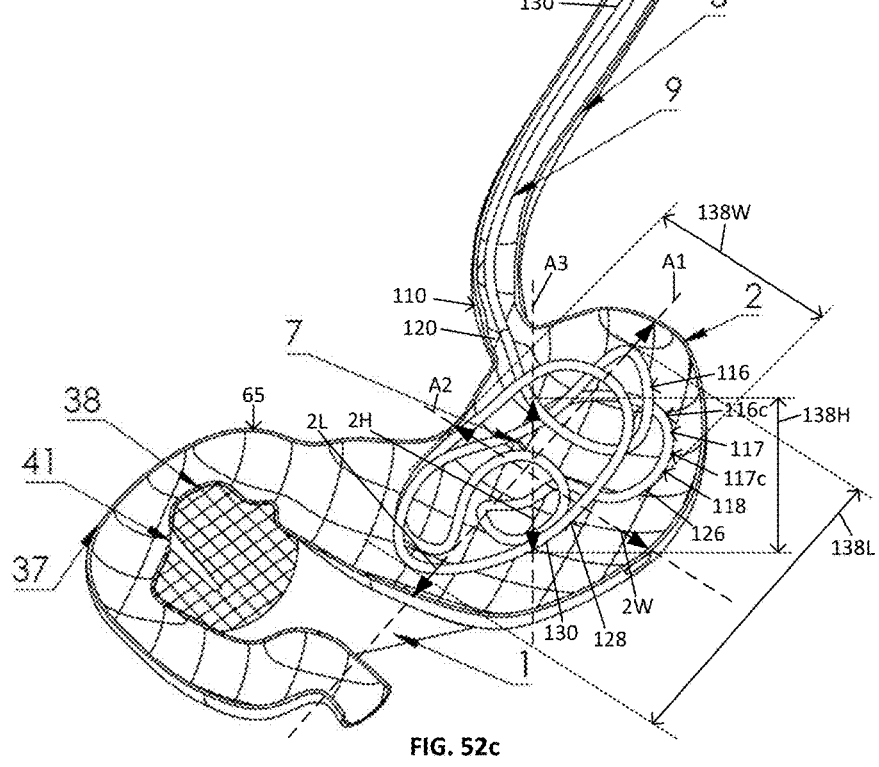

FIGS. 52*b*-52*c* illustrate, for example, that the coil length 138L can be the same when the catheter 9 is in the third configuration 116*c* as when the catheter 9 is in the second configuration 116*b*. FIGS. 52*b*-52*c* illustrate, for example, that the coil width 138W can be greater (e.g., 1 cm-10 cm greater) when the catheter 9 is in the third configuration 116*c* than when the catheter 9 is in the second configuration 116*b*. FIGS. 52*b*-52*c* illustrate, for example, that the coil height 138H can be the same when the catheter 9 is in the third configuration 116*c* as when the catheter 9 is in the second configuration 116*b*.

Figure 52D:
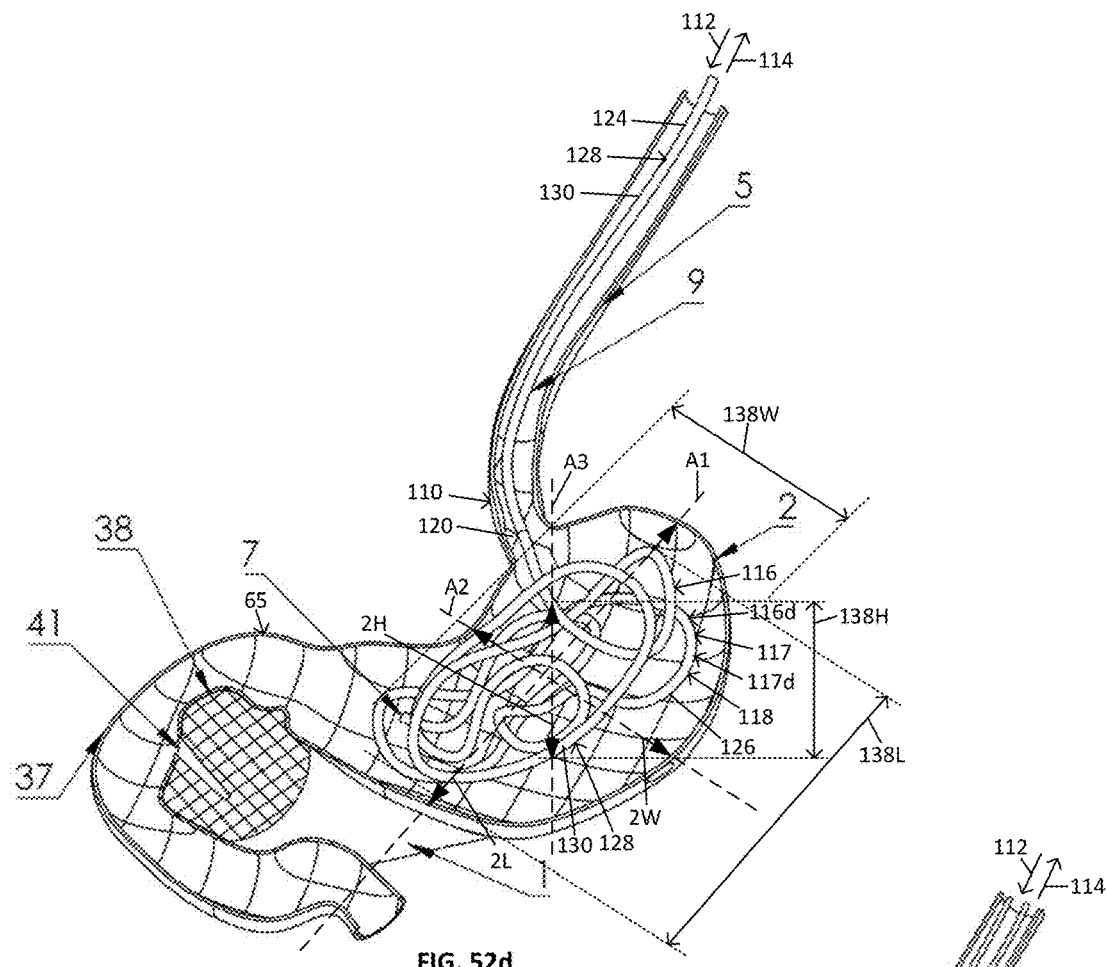

FIGS. 52*c*-52*d* illustrate, for example, that the coil length 138L can be greater (e.g., 1 cm-10 cm greater) when the catheter 9 is in the fourth configuration 116*d* than when the catheter 9 is in the third configuration 116*c*. FIGS. 52*c*-52*d* illustrate, for example, that the coil width 138W can be greater (e.g., 1 cm-10 cm greater) when the catheter 9 is in the fourth configuration 116*d* than when the catheter 9 is in the third configuration 116*c*. FIGS. 52*c*-52*d* illustrate, for example, that the coil height 138H can be the same when the catheter 9 is in the fourth configuration 116*d* as when the catheter 9 is in the third configuration 116*c*.

The stomach 2 can have a stomach length 2L, a stomach width 2W, and a stomach height 2H. For example, FIGS. 51*a*-51*d* illustrates that the stomach length 2L, the stomach width 2W, and the stomach height 2H can be measured, for example, along the first axis A1, the second axis A2, and the third axis A3, respectively.

FIG. 51*a*-51*d* illustrate that the stomach length 2L can be measured, for example, along the first axis A1 between two points on the stomach wall 108 that the first axis A1 crosses (e.g., the two points along the greater curvature 2*gc* shown in FIGS. 51*a*-51*d*).

FIG. 51*a*-51*d* illustrate that the stomach width 2W can be measured, for example, along the second axis A2 between two points on the stomach wall 108 that the second axis A2 crosses (e.g., the first point along the lesser curvature 21*c* and the second point along the greater curvature 2*gc* shown in FIGS. 51*a*-51*d*).

FIG. 51*a*-51*d* illustrate that the stomach height 2H can be measured, for example, along the third axis A3 between two points on the stomach wall 108 that the third axis A3 crosses (e.g., the first point on the posterior wall 2*pw* of the stomach 2 and a second point on the anterior wall 2*aw* of the stomach 2 (the second point is shown transparent).

The stomach 2 can have any size. The stomach 2 can be, for example, an adult's stomach. The stomach 2 can be, for example, a children's stomach.

FIGS. 51*a*-51*d* illustrate that the stomach length 2L can be, for example, 9 cm-30 cm or more, including every 1 cm increment within this range (e.g., 9 cm, 10 cm, 12 cm, 15 cm, 20 cm, 25 cm, 30 cm).

FIGS. 51*a*-51*d* illustrate that the stomach width 2W can be, for example, 6 cm-20 cm or more, including every 1 cm increment with this range (e.g., 6 cm, 8 cm, 10 cm, 15 cm, 20 cm).

FIGS. 51*a*-51*d* illustrate that the stomach height 2H can be, for example, 6 cm-20 cm or more, including every 1 cm increment with this range (e.g., 6 cm, 8 cm, 10 cm, 15 cm, 20 cm).

A smaller length, width, and height can, for example, correspond to the length, width, and height of a child's stomach and a larger length, width, and height can, for example, correspond to the length, width, and height of an adult's stomach.

FIGS. 51*a*-51*d* illustrate, for example, that the stomach length 2L, the stomach width 2W, and the stomach height 2H can be 20 cm, 10 cm, and 10 cm, respectively.

FIGS. 51*a*-51*d* illustrate that the length of the catheter 9 that defines the coil 138 can be the length 126. The length 126 of the catheter 9 can be greater than the lesser curvature 21*c* of the stomach 2, the greater curvature 2*gc* of the stomach 2, the stomach length 2L, the stomach width 2W, the stomach height 2H, or any combination thereof. For example, FIGS. 51*a*-51*d* illustrate that the length 126 of the catheter 9 can be greater than the lesser curvature 21*c* of the stomach 2, the greater curvature 2*gc* of the stomach 2, the stomach length 2L, the stomach width 2W, and the stomach height 2H.

FIGS. 51*a*-51*d* illustrate that the coil 138 can be assembled in the stomach 2, for example, by inserting the catheter 9 into the stomach 2 as shown by arrow 112 and/or FIGS. 51*d*-51*a* illustrate that the coil 138 can be disassembled in the stomach 2, for example, by withdrawing the catheter 9 from the stomach 2 as shown by arrow 114. For example, FIGS. 51*a*-51*d* illustrate that the coil 138 can be formed in the stomach 2 by accumulating the catheter 9 in the stomach 2 by inserting the catheter 9 into the stomach 2 as shown by arrow 112.

FIGS. 51*a*-51*d* illustrate that the catheter 9 can be packed into the target site 147 to form the coil 138 and/or FIGS. 51*d*-51*a* illustrate that the catheter 9 can be unpacked from the target site 147 to uncoil the coil 138. The catheter 9 can be packed into the target site 147, for example, by inserting the catheter 9 into the target site 147. The catheter 9 can be unpacked from the target site 147, for example, by withdrawing the catheter 9 from the target site 147.

FIGS. 51*a*-51*d* illustrate, for example, that the catheter 9 can be stacked into multiple layers in the target site 147 by extending back and forth across the target site 147. The multiple layers of the catheter 9 can define the coil 138.

Figure 51C:
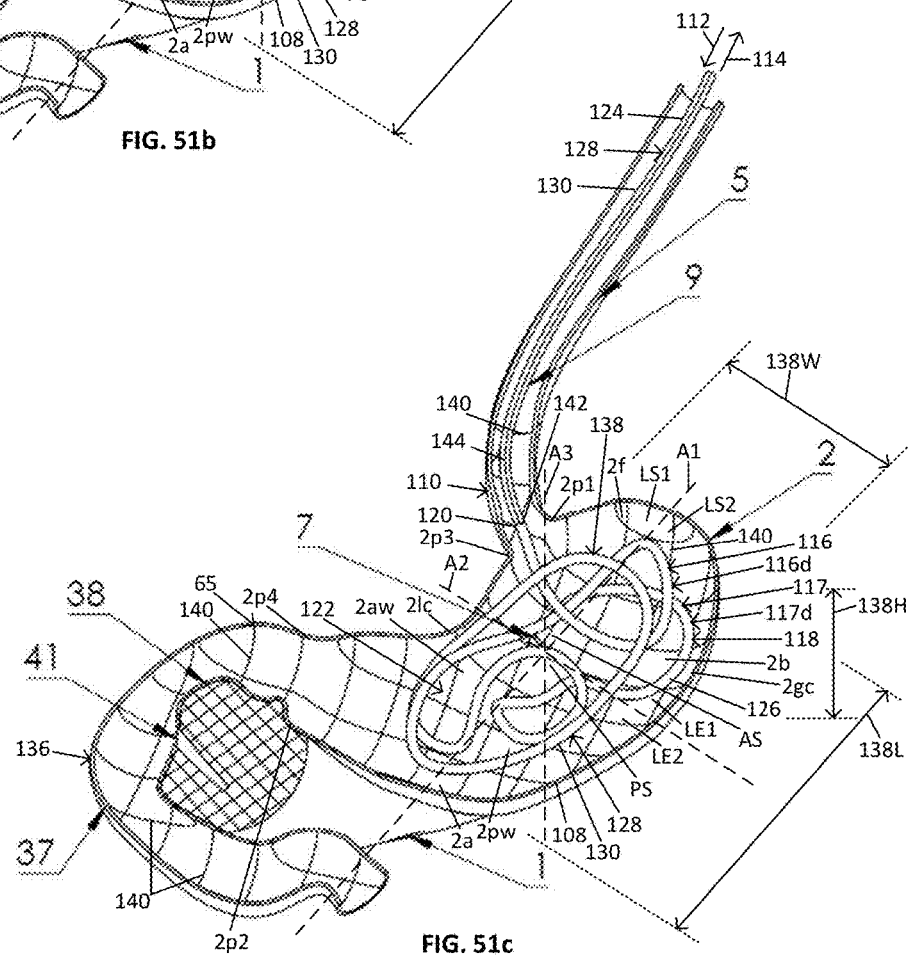

FIGS. 51*b*-51*d* illustrates that the coil 138 can inhibit and/or prevent the catheter 9 from migrating into the pylorus 65 and/or into the duodenum 37. For example, the size of the coil 138 (e.g., the coil length 138L, the coil width 138W, and/or the coil height 138H) can inhibit and/or prevent the catheter 9 and/or the coil 138 from entering the pylorus 65 and/or the duodenum 37. For example, FIGS. 51*b*-52*d* illustrate that the coil 138 can be too large to fit through the pylorus 65. For example, the coil width 138W and/or the coil height 138H can be, for example, 0.5 cm-5.0 cm or greater than the maximum dimension (e.g., height, width, and/or diameter) passable through the pylorus 65, for example, when the pylorus is fully open. As another example, the width and/or height of a portion of the coil distal end can be, for example, 0.5 cm-5.0 cm or greater than the maximum dimension (e.g., height, width, and/or diameter) across the opening of the pylorus 65 when the pylorus is fully open. For example, friction between the coil 138 and the stomach wall 108 can inhibit and/or prevent the catheter 9 and/or the coil 138 from entering the pylorus 65 and/or the duodenum 37. The coil 138 can, for example, wedge the catheter in the stomach 2 and/or in the pylorus 65, for example, via contact between the coil 138 and the stomach wall 108.

The stomach 2 can expand, contact, and/or remain the same size while the catheter 9 is inserted into and/or withdrawn from the stomach 2. Inserting the catheter 9 into the stomach 2 can, for example, expand the stomach 2 and/or withdrawing the catheter 9 from the stomach 2 can, for example, contract the stomach 2. One or more dimensions of the stomach 2 can increase, decrease, and/or remain constant as the catheter 9 is inserted into and/or withdrawn from the stomach 2. For example, the stomach length 2L, the stomach width 2W, and/or the stomach height 2H can increase, decrease, and/or remain constant, as the catheter 9 is inserted into and/or withdrawn from the stomach 2. FIGS. 51*a*-51*d* and 51*d*-51*a* illustrate, for example, that the stomach length 2L, the stomach width 2W, and the stomach height 2H can remain constant as the catheter 9 is inserted into the stomach 2 as shown by arrow 112 and as the catheter 9 is withdrawn from the stomach 2 as shown by arrow 114. FIGS. 52*a*-52*d* illustrate, for example, that the stomach 2 can expand as the catheter 9 is inserted into the stomach 2 as shown by arrow 112 and that the stomach 2 can contract as the catheter 9 is withdrawn from the stomach 2 as shown by arrow 114.

FIGS. 51*a*-51*d* illustrate that density of the catheter 9 in the stomach 2 can increase as the catheter 9 is inserted into the stomach 2 and the density of the catheter 9 in the stomach 2 can decrease as the catheter 9 is withdrawn from the stomach.

The configurations 116 formed by the catheter 9 during withdrawal of the catheter 9 from the body can be the same as or different than the configurations 116 formed by the catheter 9 during insertion of the catheter 9 into the body. FIGS. 51*a*-51*d* and 51*d*-51*a* illustrate, for example, that the configurations 116 formed by the catheter 9 during withdrawal can be the same as the configurations 116 formed by the catheter 9 during insertion. As another example, the configurations 116 formed by the catheter 9 during withdrawal of the catheter 9 from the body can be different from the configurations 116 formed by the catheter 9 during insertion of the catheter 9 into the body.

The catheter 9 can be formed into the coil 138, for example, before, during, and/or after passing (e.g., pumping) a fluid through a lumen in the catheter 9. The catheter 9 can be formed into the coil 138, for example, before, during, and/or after passing (e.g., pumping) a fluid through the first lumen 15 and/or the second lumen 16 in the catheter 9. For example, FIGS. 51*a*-51*d* illustrate that the catheter 9 can be formed into the coil 138 before passing (e.g., pumping) a fluid through a lumen (e.g., the first lumen 15 and/or the second lumen 16) in the catheter 9, and FIGS. 51*d*-51*a* illustrate that the catheter 9 can be uncoiled from the coil 138 after passing (e.g., pumping) a fluid through the lumen in the catheter 9.

Passing a fluid through the catheter 9 may or may not change the shape 117 of the coil 138. For example, FIGS. 51*a*-51*d* illustrate that passing a fluid through the catheter 9 (e.g., through an inflow lumen and/or an outflow lumen in the catheter 9) may not change the shape 117 of the coil 138. The shape 117 of the coil 138 can remain constant before, during, and/or after a fluid is passed (e.g., pumped) through the catheter 9. For example, FIGS. 51-51*d* illustrate that the shapes 117 of the coil 138 (e.g., shapes 117*a*-117*d*) can remain constant before, during, and after a fluid is passed (e.g., pumped) through the catheter 9.

The esophagus 5, the stomach 2, the pylorus 65, and/or the duodenum 37 can have contour lines 140. For example, FIGS. 51*a*-51*d* illustrate that the esophagus 5, the stomach 2, the pylorus 65, and the duodenum 37 can have contour lines 140. Contour lines 140 are also illustrated but not labeled in various other figures.

The catheter 9 can have contour lines 142. FIGS. 51*a*-51*d* illustrate that the catheter 9 can have contour lines 142, for example, to illustrate that the catheter 9 can have a circular cross section. Contour lines 142 are also illustrated but not labeled in various other figures.

The catheter 9 can have a hash line 144. FIGS. 51*a*-51*d* illustrate that the hash line 144 can indicate, for example, the portion of the catheter 9 that is in the esophagus 5 (e.g., the portion of the catheter 9 that is proximal the gastroesophageal junction 120). The hash line 144 is also illustrated but not labeled in various other figures.

The length 126 in FIG. 51*e*1 can be the same as the length 126 in FIG. 51*d*. FIGS. 51*d*-51*e*1 illustrate that the catheter 9 and/or the coil 138 can migrate closer to the pylorus 65, for example, by the natural motility and/or peristalsis of the stomach 2. When the coil 138 migrates in the stomach 2, all or a portion of the coil 138 can migrate distally in the stomach 2, for example, toward the pylorus 65. For example, the coil proximal end and/or the coil distal end can migrate toward the pylorus 65. FIG. 51*e*1 illustrates, for example, that the coil proximal end and the coil distal end can migrate towards the pylorus 65. FIG. 51*e*1 illustrates that the coil 138 can inhibit and/or prevent the catheter 9 and/or the first sensor 21*a* from migrating into the pylorus 65 and/or into the duodenum 37. For example, the size of the coil 138 (e.g., the coil length 138L, the coil width 138W, and/or the coil height 138H) can inhibit and/or prevent the catheter 9, the first sensor 21*a*, and/or the coil 138 from entering the pylorus 65 and/or the duodenum 37. For example, FIG. 51*e*1 illustrates that the coil 138 can be too large to fit through the pylorus 65. For example, FIG. 51*e*1 illustrates that the coil 138 can be too large to fit through the pylorus 65. For example, the coil width 138W and/or the coil height 138H can be, for example, 0.5 cm-5.0 cm or greater than the maximum dimension (e.g., height, width, and/or diameter) passable through the pylorus 65, for example, when the pylorus is fully open. As another example, the width and/or height of a portion of the coil distal end can be, for example, 0.5 cm-5.0 cm or greater than the maximum dimension (e.g., height, width, and/or diameter) across the opening of the pylorus 65 when the pylorus is fully open. For example, friction between the coil 138 and the stomach wall 108 can inhibit and/or prevent the catheter 9, the first sensor 21*a*, and/or the coil 138 from entering the pylorus 65 and/or the duodenum 37. The coil 138 can, for example, wedge the catheter in the stomach 2 and/or in the pylorus 65, for example, via contact between the coil 138 and the stomach wall 108. For example, FIG. 51*e*1 illustrates that a distal portion of the coil 138 can migrate closer to the pylorus 65 but that the coil 138 can inhibit and/or prevent the distal portion of the coil 138 from entering the pylorus 65 and/or the duodenum 37. FIG. 51*e*1 illustrates that the proximal end of the coil 138 and/or the distal end of the coil 138 can be compressed as the coil 138 migrates toward the pylorus 65.

The length 126 in FIG. 51e2 can be the same as the length 126 in FIG. 51d. FIGS. 51d-51e2 illustrate that the catheter 9 and/or the coil 138 can migrate into the pylorus 65 and the duodenum 37, for example, by the natural motility and/or peristalsis of the stomach 2. The portion of the catheter 9 and/or the coil 138 that migrates into the duodenum 37 may or may not include the catheter tip 7. For example, FIG. 51e2 illustrates that the portion of the catheter 9 and/or the coil 138 that migrated into the duodenum 37 can include the catheter tip 7.

The length 126 in FIG. 51e3 can be the same as the length 126 in FIG. 51d. FIGS. 51d-51e3 illustrate that the catheter 9 and/or the coil 138 can migrate into the pylorus 65 and the duodenum 37, for example, by the natural motility and/or peristalsis of the stomach 2. FIG. 51e3 is similar to FIG. 51e2 but FIG. 51e3 illustrates that the portion of the catheter 9 and/or the coil 138 that migrated into the duodenum 37 may not include the catheter tip 7. For example, FIG. 51e3 that the catheter tip 7 can remain in the stomach 2 when the catheter 9 and/or the coil 138 migrates into the duodenum 37.

FIGS. 51e2 and 51e3 illustrate that the that the coil 138 can limit the amount of the catheter 9 and/or the coil 138 that can migrate into the duodenum 37. For example, FIGS. 51e2 and 51e3 illustrate that the portion of the coil 138 in the stomach 2, in the pylorus 65, and/or in the duodenum 37 can inhibit and/or prevent the catheter 9, the first sensor 21a, and/or the coil 138 from moving (e.g., migrating) further into the pylorus 65 and/or the duodenum 37 from the configurations 116 shown in FIGS. 51e2 and 51e3. For example, friction between the coil 138 and the stomach wall 108, the wall of the pylorus 65, and/or the duodenum wall 136 can inhibit and/or prevent the catheter 9, the first sensor 21a, and/or the coil 138 migrating further into the pylorus 65 and/or the duodenum 37. The shape of the coil 138 (e.g., the shape 117 in FIGS. 51e2 and 51e3) can, for example, secure the coil 138 in the positions shown in FIGS. 51e2 and 51e3. For example, the size of the coil 138 (e.g., the coil length 138L, the coil width 138W, and/or the coil height 138H) can inhibit and/or prevent the catheter 9, the first sensor 21a and/or the coil 138 from migrating further into pylorus 65 and/or the duodenum 37. For example, the coil 138 and/or a FIGS. 51e2 and 51e3 illustrate that the coil 138 can, for example, wedge the catheter in the stomach 2, in the pylorus 65, and/or in the duodenum 136, for example, via contact between the coil 138 and the stomach wall 108, the wall of the pylorus 65, and/or the duodenum wall 136, or any combination thereof.

As another example, FIGS. 51e2 and 51e3 illustrate that the that the coil 138 can limit the amount of the catheter 9 and/or the coil 138 that can migrate into the duodenum 37 to a migration threshold. Once the threshold migration threshold is reached, the coil 38 can prevent the catheter 9 from migrating further into the duodenum 37 and/or can prevent more of the catheter 9 and/or the coil 138 from migrating into the duodenum 37. The migration threshold can be, for example, the length of the catheter 9 and/or the coil 38 that can migrate into the duodenum 37 before the coil 138 prevent further migration into the duodenum 37. The migration threshold can be, for example, 30 cm or less, 20 cm or less, and/or 10 cm or less, including every 1 cm increment within these ranges (e.g., 30 cm or less, 20 cm or less, 5 cm or less). For example, FIGS. 51e2 and 51e3 illustrate that the threshold length can be 15 cm or less. FIGS. 51e2 and 51e3 illustrate, for example, that 15 cm of the catheter 9 and/or the coil 138 has migrated into the duodenum 37. Since the migration threshold has been reached, FIGS. 51e2 and 51e3 illustrate that the coil can prevent further migration of the catheter 9 and/or the coil 138 into the duodenum 37 and/or can prevent more of the catheter 9 and/or the coil 138 from migrating into the duodenum 37.

The length 126 in FIG. 51e4 can be the same as the length 126 in FIG. 51d. FIGS. 51d-51e4 illustrate that the catheter 9 and/or the coil 138 can migrate in the stomach 2 without entering the pylorus 65 and/or the duodenum 37. FIGS. 51d-51e4 illustrate that the shape of the coil 138 in the stomach 2 can change, for example, by the natural motility and/or peristalsis of the stomach 2. FIGS. 51d-51e4 illustrate, for example, that the natural motility and/or peristalsis of the stomach can rearrange the catheter 9 in the stomach 2. FIG. 51e4 illustrates, for example, that the arrangement of the catheter 9 that defines the coil 138 in the configuration 116 in FIG. 51e4 can be different than the arrangement of the catheter 9 that defines the coil 138 in the configuration 116 shown in FIG. 51d.

FIGS. 51e5 and 51e6 illustrate that the coil 138 can increase in size as more catheter 9 is inserted into the stomach 2. For example, FIGS. 51d-51e5 illustrate 50 cm more of the catheter 9 inserted into the stomach 2 and FIGS. 51d-51e6 illustrate 100 cm more of the catheter 9 inserted into the stomach 2. FIGS. 51d-51e5 and 51d-51e6 illustrate that the coil 138 can become denser and/or more packed with the catheter 9 as more of the catheter 9 is inserted into the stomach 2. FIG. 51d illustrates, for example, that the length 126 can be 150 cm. FIG. 51e5 illustrates, for example, that the length 126 can be 200 cm. FIG. 51e6 illustrates, for example, that the length 126 can be 250 cm FIGS. 51e1-51e6 illustrate that the catheter 9 can form the coil 138 inside the target site 147 (e.g., the stomach 2), for example, by inserting the catheter 9 into the target site 147 as shown by arrow and/or by the catheter 9 and/or the coil 138 migrating in the stomach 2, in the pylorus 65, and/or in the duodenum 37.

FIGS. 51e1-51e6 illustrate that the catheter 9 can be withdrawn (e.g., pulled) from the coil 138 inside the target site 147, for example, by withdrawing the catheter 9 from the target site 147 as shown by arrow 114.

FIGS. 52a-52d illustrate that inserting the catheter 9 into the target site 147 can expand the target site 147. For example, FIGS. 52a-52d illustrate that inserting the catheter 9 into the stomach 2 as shown by arrow 112 can expand the stomach 2. Inserting the catheter 9 into the stomach 2 can, for example, increase the stomach length 2L, the stomach width 2W, the stomach height 2H, or any combination thereof by the catheter 9 exerting a force against the stomach wall 108 as the catheter 9 is inserted into the stomach 2. FIGS. 52a-52d illustrate, for example, that forming the coil 138 in the target site 147 can expand the stomach 2 as the coil 138 increases in size. For example, the stomach length 2L can increase as the coil length 138L increases, the stomach width 2W can increase as the coil width 138W increases, the stomach height 2H can increase as the coil height 138H increases, or any combination thereof. Inserting the catheter 9 into the stomach 2 can, for example, increase the stomach length 2L by 0.1 cm-10.0 cm, increase the stomach width 2W by 0.1 cm-10.0 cm, increase the stomach height 2H by 0.1 cm-10.0 cm, or any combination thereof, including every 0.1 cm increment within these ranges (e.g., 0.1 cm, 1.0 cm, 3.0 cm, 5.0 cm, 10.0 cm). Inserting the catheter 9 into the stomach 2 can, for example, increase the stomach length 2L by at least 0.1 cm-10.0 cm, increase the stomach width 2W by at least 0.1 cm-10.0 cm, increase the stomach height 2H by at least 0.1 cm-10.0 cm, or any combination thereof, including every 0.1 cm increment within these ranges (e.g., by at least 0.1 cm, 1.0 cm, 3.0 cm, 5.0 cm, 10.0 cm).

FIGS. 52a-52b illustrate, for example, that the stomach width 2W and/or the stomach height 2H can increase as the catheter 9 is inserted into the stomach 2 and/or as the coil 138 is assembled in the stomach 2. FIGS. 52a-52b illustrate, for example, that inserting the catheter 9 into the stomach 2 and/or forming the coil 138 in the stomach 128 can increase the stomach width 2W by at least 2.0 cm and/or can increase the stomach height 2H by at least 1 cm. Zero, one, or more dimensions of the stomach 2 (e.g., the stomach length 2L, the stomach width 2W, and/or the stomach height 2H) can remain constant as the catheter 9 is inserted into the stomach 2. For example, FIGS. 52a-52b illustrate that the stomach length 2L can remain constant while the catheter 9 is inserted into the stomach 2.

FIGS. 52b-52c illustrate, for example, that the stomach width 2W and/or the stomach height 2H can increase as the catheter 9 is inserted into the stomach 2 and/or as the coil 138 is assembled in the stomach 2. FIGS. 52b-52c illustrate, for example, that inserting the catheter 9 into the stomach 2 and/or forming the coil 138 in the stomach 2 can increase the stomach width 2W by at least 1.0 cm and/or can increase the stomach height 2H by at least 0.5 cm. FIGS. 52b-52c illustrate that the stomach length 2L can remain constant while the catheter 9 is inserted into the stomach 2.

FIGS. 52c-52d illustrate that the stomach length 2L, the stomach width 2W, and the stomach height 2H can remain constant while the catheter 9 is inserted into the stomach 2.

FIGS. 52a-52d illustrate that the stomach length 2L can increase more than the stomach height 2H, for example, by 0.1 cm-5.0 cm or more than the stomach height 2H, including every 0.1 cm increment within this range (e.g., 0.1 cm, 1.0 cm, 3.0 cm, 5.0 cm, 5.0 cm).

FIGS. 52a-52d illustrate that the stomach 2 can have a first, second, third, and fourth stomach lengths 2L, respectively, and that the first, second, third, and fourth stomach lengths 2L can be equal to each other.

FIGS. 52a-52c illustrate that the stomach 2 can have a first, second, third stomach, and fourth stomach widths 2W, respectively, that the first stomach width 2W (e.g., the stomach width 2W in FIG. 52a) can be less than the second stomach width 2W (e.g., the stomach width 2W in FIG. 52b), that the stomach second width 2W can be less than the stomach third width 2W (e.g., the stomach width 2W in FIG. 53c), and that the stomach third width can be the same as the stomach fourth width 2W (e.g., the stomach width 2W in FIG. 52d).

FIGS. 52a-52c illustrate that the stomach 2 can have a first, second, third stomach, and fourth stomach heights 2H, respectively, that the first stomach height 2H (e.g., the stomach height 2H in FIG. 52a) can be less than the second stomach height 2H (e.g., the stomach height 2H in FIG. 52b), that the stomach second height 2H can be less than the stomach third height 2H (e.g., the stomach height 2H in FIG. 53c), and that the stomach third height can be the same as the stomach fourth height 2H (e.g., the stomach height 2H in FIG. 52d).

FIGS. 52d-52a illustrate that withdrawing the catheter 9 from the target site 147 can contract the target site 147. For example, FIGS. 52d-52a illustrate that withdrawing the catheter 9 from the stomach 2 as shown by arrow 114 can contract the stomach 2. Withdrawing the catheter 9 from stomach 2 can, for example, decrease the stomach length 2L, the stomach width 2W, the stomach height 2H, or any combination thereof by reducing the force that the catheter 9 exerts against the stomach wall 108 and/or by reducing the size of the coil 138 in the stomach 2 as the catheter 9 is withdrawn from the stomach 2. FIGS. 52d-52a illustrate, for example, that disassembling the coil 138 in the target site 147 can contract the stomach 2 as the coil 138 decreases in size. For example, the stomach length 2L can decrease as the coil length 138L decreases, the stomach width 2W can decrease as the coil width 138W decreases, the stomach height 2H can decrease as the coil height 138H decreases, or any combination thereof. Withdrawing the catheter 9 from the stomach 2 can, for example, decrease the stomach length 2L by 0.1 cm-10.0 cm, decrease the stomach width 2W by 0.1 cm-10.0 cm, decrease the stomach height 2H by 0.1 cm-10.0 cm, or any combination thereof, including every 0.1 cm increment within these ranges (e.g., 0.1 cm, 1.0 cm, 3.0 cm, 5.0 cm, 10.0 cm). Withdrawing the catheter 9 from the stomach 2 can, for example, decrease the stomach length 2L by at least 0.1 cm-10.0 cm, decrease the stomach width 2W by at least 0.1 cm-10.0 cm, decrease the stomach height 2H by at least 0.1 cm-10.0 cm, or any combination thereof, including every 0.1 cm increment within these ranges (e.g., by at least 0.1 cm, 1.0 cm, 3.0 cm, 5.0 cm, 10.0 cm).

FIGS. 52b-52a illustrate, for example, that the stomach width 2W and/or the stomach height 2H can decrease as the catheter 9 is withdrawn from the stomach 2 and/or as the coil 138 is disassembled in the stomach 2. FIGS. 52b-52a illustrate, for example, that withdrawing the catheter 9 from the stomach 2 and/or disassembling the coil 138 in the stomach 128 can decrease the stomach width 2W by at least 2.0 cm and/or can decrease the stomach height 2H by at least 1 cm. Zero, one, or more dimensions of the stomach 2 (e.g., the stomach length 2L, the stomach width 2W, and/or the stomach height 2H) can remain constant as the catheter 9 is withdrawn from the stomach 2. For example, FIGS. 52b-52a illustrate that the stomach length 2L can remain constant while the catheter 9 is withdrawn from the stomach 2.

FIGS. 52c-52b illustrate, for example, that the stomach width 2W and/or the stomach height 2H can decrease as the catheter 9 is withdrawn from the stomach 2 and/or as the coil 138 is disassembled in the stomach 2. FIGS. 52c-52b illustrate, for example, that withdrawing the catheter 9 from the stomach 2 and/or disassembling the coil 138 in the stomach 2 can decrease the stomach width 2W by at least 1.0 cm and/or can decrease the stomach height 2H by at least 0.5 cm. FIGS. 52c-52b illustrate that the stomach length 2L can remain constant while the catheter 9 is withdrawn from the stomach 2.

FIGS. 52a-52b can illustrate the same configurations of the catheter 9 in FIGS. 51a-51d but can illustrate that inserting the catheter 9 and/or forming the coil 138 can expand the stomach 2 (e.g., as shown in FIGS. 52a-52d) and/or that withdrawing the catheter 9 and/or disassembling the coil can contract the stomach 2 (e.g., as shown in FIGS. 52d-52a).

FIGS. 52a-52d illustrate, for example, that expanding the stomach 2 by inserting the catheter 9 into the stomach 2 and/or forming the coil 138 in the stomach can cause folds in the stomach wall 108 to unfold and/or flatten which can increase the heat transfer efficiency through the stomach wall 108 to and/or from surrounding organs (e.g., the pancreas).

FIGS. 52a-52d illustrate, for example, that expanding the stomach 2 by inserting the catheter 9 into the stomach 2 and/or forming the coil 138 in the stomach can, for example, increase the force between the stomach wall 108 and the catheter 9 and/or the coil 138, which can, for example, wedge the catheter 9 in the stomach 2 and/or inhibit and/or prevent the catheter 9 and/or the coil 138 from migrating out of the stomach 2.

Figure 53A:
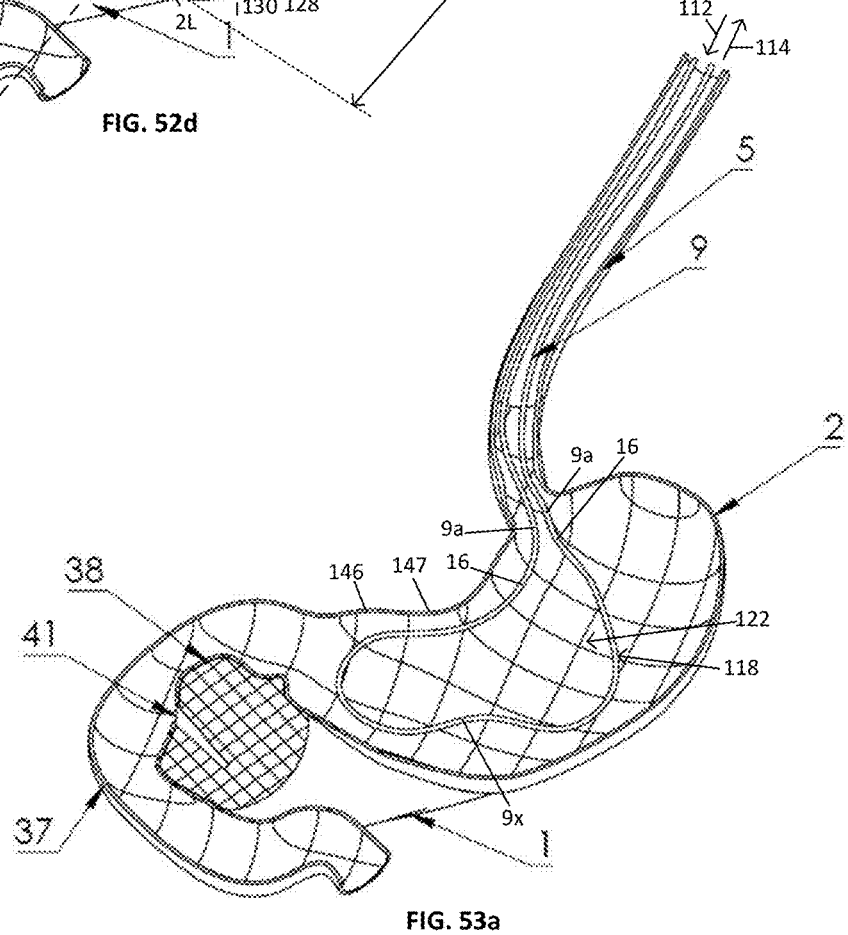

FIGS. 53a-53b illustrate that the catheter 9 can have a first tube 9a connected end to end with a second tube 9b at location 9x. FIGS. 53a-53b illustrate the first tube 9a can have the first lumen 15 and that the second tube 9b can have the second lumen 16. The first tube 9a and the second tube 9b can be inserted and/or withdrawn into the target site 147 as shown by arrows 112 and 114. FIGS. 53a-53b illustrate that the first tube 9a and the second tube 9b can be inserted and/or withdrawn together, for example, simultaneously. The first tube 9a and the second tube 9b can be independently insertable and/or withdrawable. For example, if the first tube 9a enters the duodenum 37, the first tube 9a can be withdrawn independently of the second tube 9b until the first tube 9a is no longer in the duodenum 37. As another example, if the second tube 9b enters the duodenum 37, the second tube 9b can be withdrawn independently of the first tube 9a until the second tube 9b is no longer in the duodenum 37. FIGS. 53a-53b illustrate that the distance between the first lumen 15 and the second lumen 16 can vary, for example, across the target site 147. The first tube 9a can be, for example, the inflow tube and the second tube 9b can be, for example, the outflow tube. 20 cm-200 cm or more of the first tube 9a and 20 cm-200 cm or more of the second tube 9b can be inserted into and/or withdrawn from the target site 147. The length of the first tube 9a in the target site 147 can be the same as or different than the length of the second tube 9b in the target site 147. For example, FIG. 53a-53b illustrates that the length of the first tube 9a and the length of the second tube 9b can be the same. FIGS. 53a-53b illustrate, for example, that the length 126 can be 130 cm (e.g., 65 cm of the inflow tube and 65 cm of the outflow tube). The length 126 can be, for example, the total length of the first tube 9a and the second tube 9b in the target site 147 (e.g., 130 cm). FIGS. 53-a53b illustrate that the first tube 9a and the second tube 9b can form different bends relative to each other. FIGS. 46a-52d illustrate, for example, that the first lumen 15 and the second lumen 16 can form the same bends relative to each other.

FIGS. 54a-54c illustrate that pushing the catheter 9 into a wall of the target site 147 (e.g., the stomach wall 108) can cause the catheter 9 to flex. FIG. 54a illustrates the catheter 9 in a straight configuration spaced apart from the stomach wall 108 being pushed towards the stomach wall 108 as shown by arrow 112. FIG. 54b illustrates the catheter 9 in contact with stomach wall 108 in a straight configuration as the catheter 9 continues to be pushed into the stomach wall 108. FIG. 54c illustrates that continuing to press the catheter 9 into the stomach wall 108 once the catheter 9 is in contact with the stomach wall 108 can cause the catheter 9 to bend, for example, by overcoming the column strength of the catheter 9. The axial load (e.g., represented by arrow 112) can be generated, for example, by a user pushing the catheter 9 into the stomach 2. The axial load that can cause the catheter 9 to bend can be, for example, 2-10 Newtons or more, including every 1 Newton increment within this range (e.g., 2 Newtons, 5 Newtons, 10 Newtons). FIG. 54d illustrates that pulling the catheter 9 away from the stomach wall 108 can cause the catheter 9 to straighten. The catheter 9 can be formed into the various shapes 117 in such a manner as the catheter 9 is inserted into and/or withdrawn from the target site 147. For example, assembling the coil 138 can include bending the catheter 9 by pushing the catheter 9 into the wall of the target site 147 and disassembling the coil 138 can include unbending the catheter 9 by pulling the catheter 9 away from the wall of the target site 147.

Figure 55A:
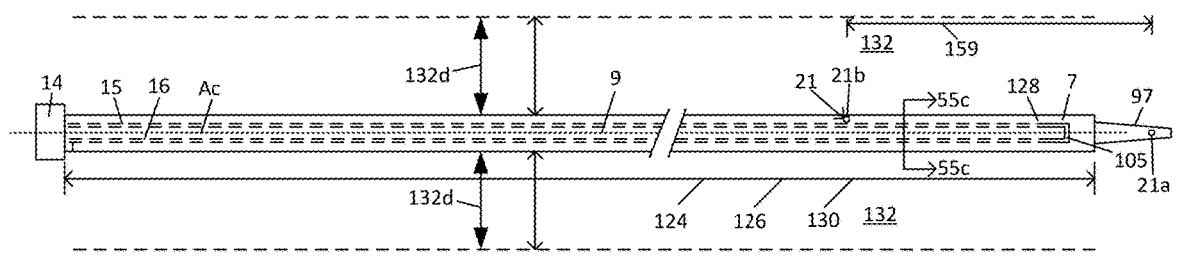
FIG. 55a illustrates a variation of a catheter.
Figure 55B:
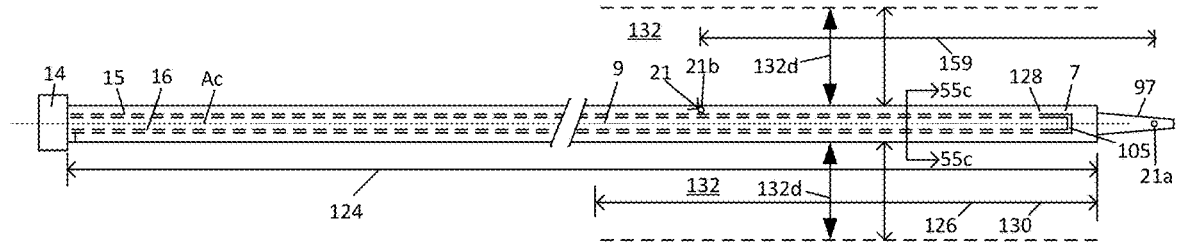
FIG. 55b illustrates a variation of a catheter.

FIGS. 55a-55b illustrate the catheter 9 can have a straight configuration. FIGS. 55a-55b illustrate that the proximal end of the catheter 9 can be connected to the connector 14. FIG. 55a illustrates that the length 126 can be equal to the total length 124. FIG. 55b illustrates that the length 126 can be a portion of the total length 124. FIGS. 55a and 55b illustrate that when the fluid 6 is pumped through the first lumen 15 and the second lumen 16, the heat transfer zone 132 can extend the distance 132d away (e.g., radially away) from the catheter 9. FIGS. 55a-55b illustrate that when the catheter 9 is in a straight configuration, the catheter 9 can define zero cells 122.

FIGS. 55a-55b illustrate that the catheter 9 can have one or multiple sensors 21, for example, a first sensor 21a and a second sensor 21b. The first sensor 21a can be, for example, a first temperature sensor and the second sensor 21b can be, for example, a second temperature sensor. The first sensor 21a and the second sensor 21b can be positioned anywhere along the length of the catheter 9. For example, a first section of the catheter 9 can have the first sensor 21a and a second section of the catheter 9 can have the second sensor 21b. FIGS. 55a-55b illustrate, for example, that the proboscis 97 can have the first sensor 21a and that a portion of the catheter 9 proximal the catheter tip 7 can have the second sensor 21b. FIGS. 55a-55b illustrate that when the catheter 9 is in a straight configuration, the proboscis 97 and the first sensor 21a can be distal the first lumen 15, the second lumen 16, and the second sensor 21b. The first lumen 15 can be the inflow channel and the second lumen 16 can be the outflow channel or vice versa.

The first sensor 21a and/or the proboscis 97 can be positioned closer to the pylorus 65 than the second sensor 21b. For example, inserting the catheter 9 into the target site 147 can position the first sensor 21a and/or the proboscis 97 closer to the pylorus 65 than the second sensor 21b. For example, FIGS. 47e and 48e illustrate that when the catheter 9 is in a deployed configuration (e.g., a configuration 116), the first sensor 21a and the proboscis 97 can be closer to the pylorus 65 than the second sensor 21b. The first sensor 21a and the proboscis 97 can be positioned, for example, 1 cm-20 cm from the pylorus 65. The second sensor 21b can be positioned closer to the lower esophageal junction 120 (also referred to as the lower esophageal sphincter) than the first sensor 21a and/or the proboscis 97. The second sensor 21b can be positioned, for example, 1 cm-20 cm from the lower esophageal junction 120.

FIGS. 55a-55b illustrate that when the catheter is in a straight configuration, the first sensor 21a and the second sensor 21b can be separated by a first distance 159 as measured along the center longitudinal axis Ac of the catheter 9. FIGS. 47e and 48e illustrate that when the catheter is in a deployed configuration, the first sensor 21a and the second sensor 21b can be separated by a second distance 160 as measured along a straight line 161 from the first sensor 21a to the second sensor 21b. FIGS. 55a-55b, 47e, and 48e illustrate that the first distance 159 can be greater than the second distance 161. The first distance 159 can be, for example, 50 cm-300 cm, and the second distance 160 can be, for example, 5 cm-40 cm, including every 1 cm increment within these ranges.

The first sensor 21a and/or the proboscis 97 can be positioned farther from the pylorus 65 than the second sensor 21b. For example, inserting the catheter 9 into the target site 147 can position the first sensor 21a and/or the proboscis 97 farther from the pylorus 65 than the second sensor 21b. For example, FIGS. 46o and 49e illustrate that when the catheter 9 is in a deployed configuration (e.g., a configuration 116), the first sensor 21a and the proboscis 97 can be farther from the pylorus 65 than the second sensor 21b. The first sensor 21a and the proboscis 97 can be positioned, for example, 1 cm-20 cm from the pylorus 65. The second sensor 21b can be positioned farther from the lower esophageal junction 120 (also referred to as the lower esophageal sphincter) than the first sensor 21a and/or the proboscis 97. The second sensor 21b can be positioned, for example, 1 cm-20 cm from the lower esophageal junction 120.

FIGS. 46o and 49e illustrate that when the catheter is in a deployed configuration, the first sensor 21a and the second sensor 21b can be separated by the second distance 160 as measured along the straight line 161 from the first sensor 21a to the second sensor 21b. FIGS. 55a-55b, 46o, and 49e illustrate that the first distance 159 can be greater than the second distance 161. The first distance 159 can be, for example, 50 cm-300 cm, and the second distance 160 can be, for example, 5 cm-40 cm, including every 1 cm increment within these ranges.

The first sensor 21a and/or the second sensor 21b can be positioned in the stomach 2, the pylorus 65, and/or the duodenum 37. For example, when the catheter 9 is in a first operational configuration (e.g., a configuration 116), the first sensor 21a and the second sensor 21b can be in the stomach 2, and when the catheter 9 is in a second operational configuration (e.g., a configuration 116), the first sensor 21a can be in the pylorus 65 or the duodenum 37 and the second sensor 21b can be in the stomach 2. The proboscis 97, the first sensor 21a, and/or the second sensor 21b can be inserted into and/or can migrate into the pylorus 65 and/or the duodenum 37. The catheter 9 and/or the first sensor 21 can, for example, migrate from the first operational configuration to the second operational configuration. FIGS. 51d and 51e1 illustrate two exemplary first operational configurations. FIGS. 51d and 51e1 each illustrate that when the catheter 9 is in a first operational configuration, the first sensor 21a and the second sensor 21b can be in the stomach 2, and FIG. 51e2 illustrates that when the catheter 9 is in a second operational configuration (e.g., any configuration different than the first operational configuration), the first sensor 21a can be in the pylorus 65 or the duodenum 37 and the second sensor 21b can be in the stomach 2. FIGS. 51d-51e2 and 51e1-51e2 illustrate that the catheter 9, the catheter tip 7, the proboscis 97, and the first sensor 21a can migrate into the duodenum 37.

FIGS. 46o, 47e, 48e, 49e, 51d, and 51e illustrate that the temperature of the stomach 2 can be measured with the first sensor 21a and/or the second sensor 21b. FIG. 51e2 illustrates that the temperature of the duodenum 37 can be measured with the first sensor 21a and that the temperature of the stomach 2 can be measured with the second sensor 21b.

FIGS. 55a-55b, 46o, 47e, 48e, 49e, 51d, 51e1, and/or 51e2 illustrate, for example, that the first sensor 21a can be embedded in the proboscis 97.

FIGS. 55a-55b, 46o, 47e, 48e, 49e, 51d, 51e1, and 51e2 illustrate that the catheter 9 can have the proboscis 97.

Measuring the temperature of the target site 147 with multiple sensors 21 (e.g., the first sensor 21a and the second sensor 21b) can create separation between the cooling/warming fluid in the catheter 9 and between the sensors 21. Multiple temperature sensors can be used, for example, to measure the temperature of the same organ in different regions, for example, to determine the temperature gradient in the organ and/or to help determine whether the sensors 21 are in a fluid pocket or a gas pocket in the organ, whereby a temperature differential between two sensors 21 (e.g., the first sensor 21a and the second sensor 21b) can indicate that one of the sensors is in a gas pocket.

Figure 55C:
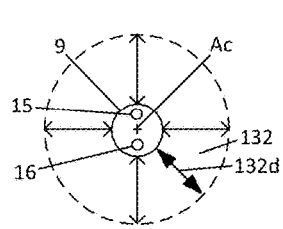
FIG. 55c illustrates a variation of a cross-section view of the catheter of FIG. 55a through the line 55c-55c.
Figure 55D:
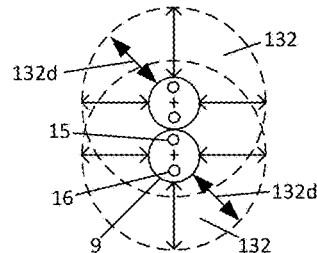
FIG. 55d illustrates a variation of a cross-section view of the catheter of FIG. 46g through the line 55d-55d.

FIGS. 55c-55d illustrates that the heat transfer zone 132 can extend radially to and/or from the catheter 9, for example, as represented by the unlabeled double-headed arrows in FIGS. 55c and 55d. FIG. 55d illustrates that a first heat zone can overlap a second heating zone.

Figure 56:
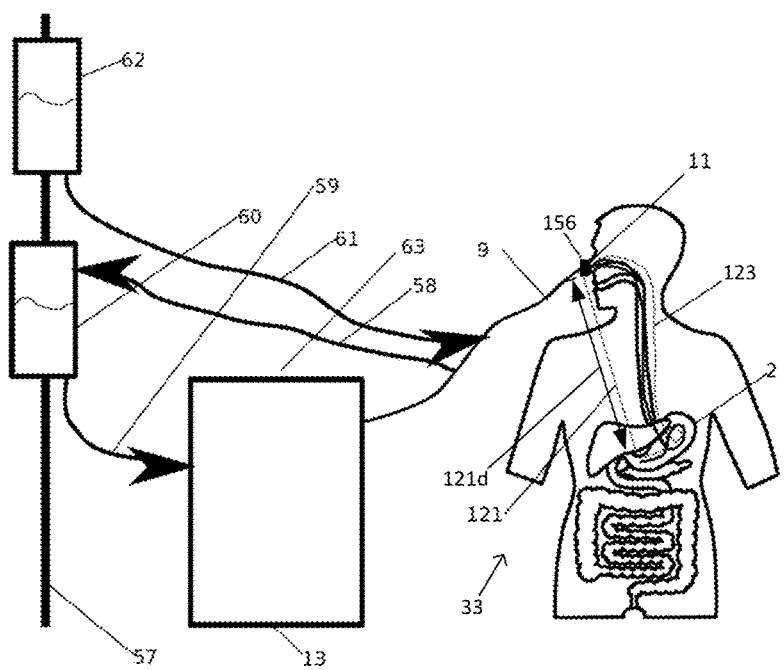
FIG. 56 is a schematic of a system that can provide thermal transfer therapy.

FIG. 56 illustrates that an adherer 156 can attach the catheter 9 to the body, for example, to the face. The adherer 156 can be, for example, an adhesive. The adherer 156 can be, for example, a piece of tape. FIG. 56 illustrates that when the catheter 9 is in a deployed configuration, the adherer can be attached to the catheter 9 and to the body (e.g., to the patient's face). FIG. 56 illustrates that when the catheter 9 is in a deployed configuration, the length of the catheter 9 between the adherer 156 and a distal terminal end of the catheter 9 can be greater than 60-100 cm from the adherer 156 as measured along the center longitudinal axis Ac of the catheter 9 (e.g., as represented by line 123 in FIG. 56), including every 1 cm increment within this range (e.g., greater than 60 cm, greater than 70 cm, greater than 80 cm, greater than 90 cm). For example, FIG. 56 illustrates that the length of the catheter 9 between the adherer 156 and a distal terminal end of the catheter 9 can be greater than 90 cm from the adherer 156 as measured along the center longitudinal axis Ac of the catheter 9. FIG. 56 illustrates that when the catheter 9 is in a deployed configuration, the distance 121d as measured along a straight line 121 from the adherer 156 to the distal terminal end of the catheter 9 can be less than 50-70 cm, including every 1 cm increment with this range (e.g., less than 50 cm, less than 60 cm, less than 70 cm). For example, FIG. 56 illustrates that when the catheter 9 is in a deployed configuration, the distance 121d as measured along the straight line 121 from the adherer 156 to the distal terminal end of the catheter 9 can be less than 60 cm.

Figure 57A:
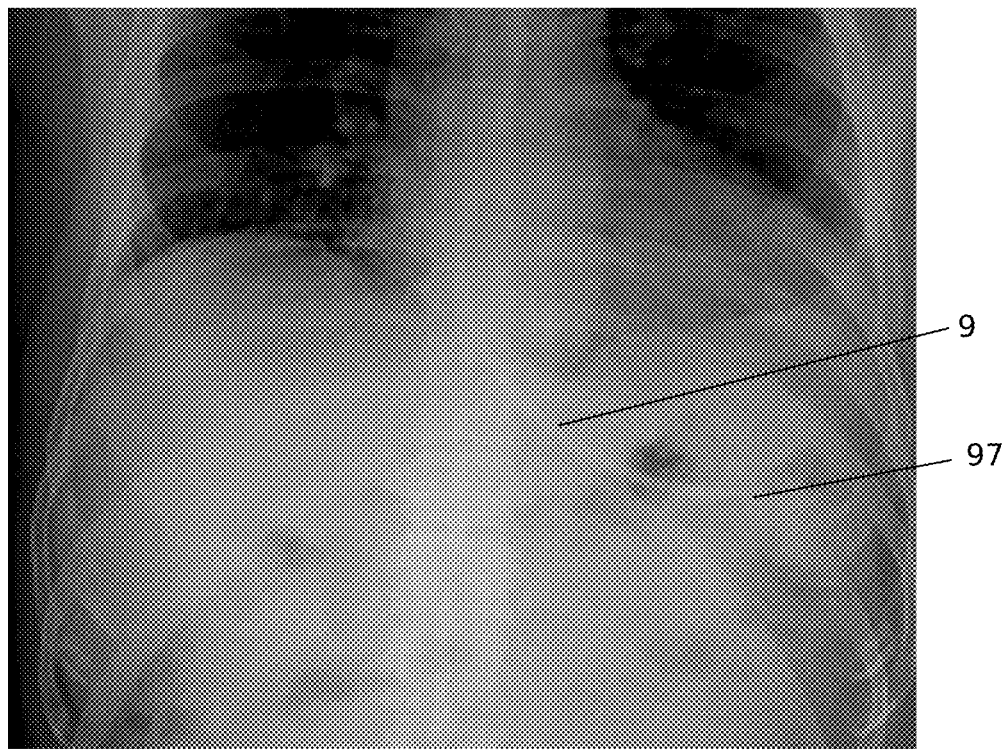
FIGS. 57a-57d are frontal x-rays of the catheter being introduced into the stomach.
Figure 57B:
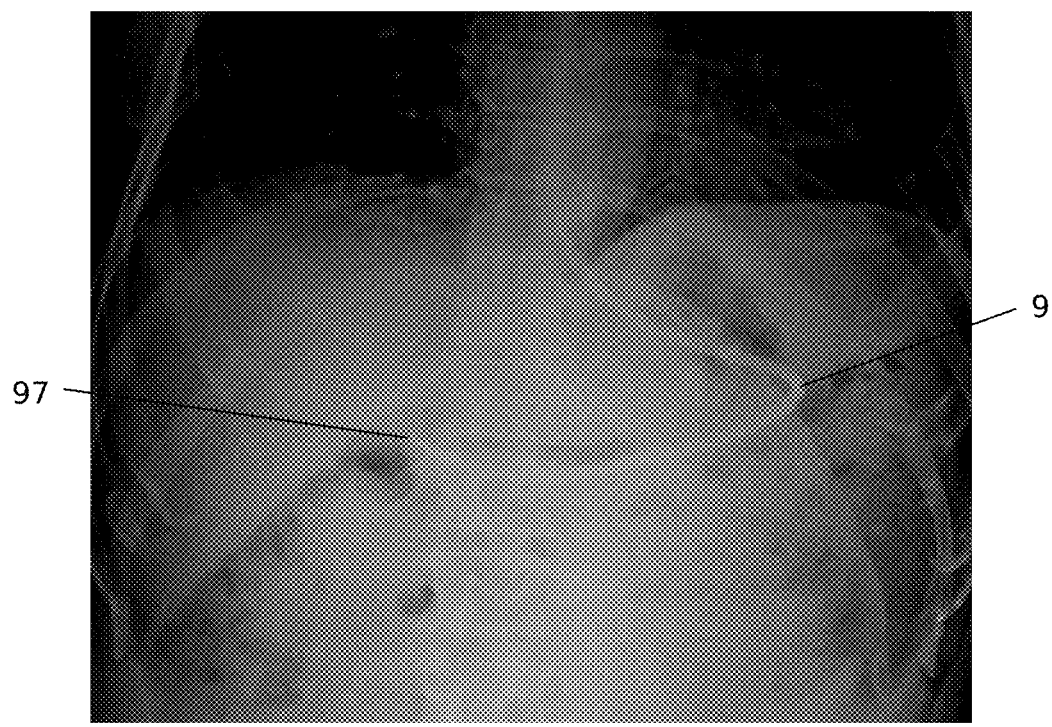
Figure 57C:
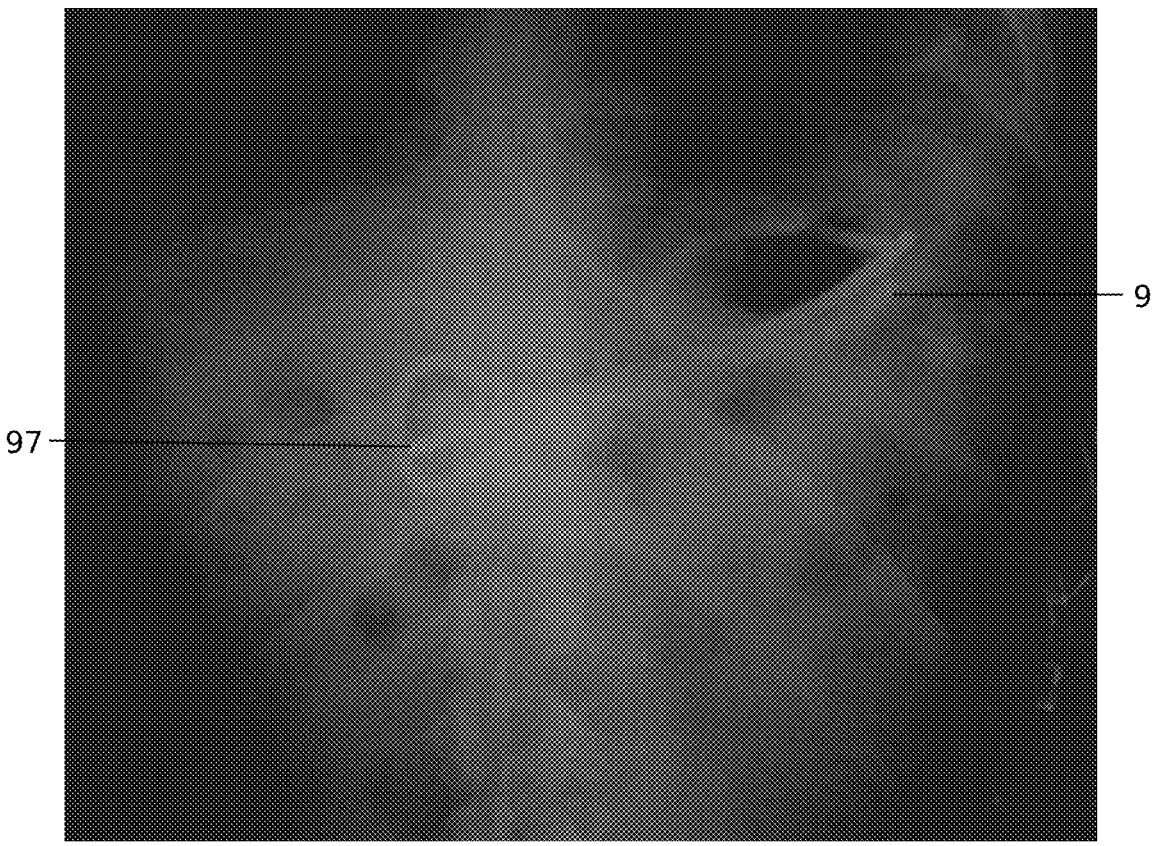
Figure 57D:

FIGS. 57a-57c show that the catheter 9 may form various shapes as it is introduced into the stomach 2. FIG. 57a is an x-ray taken after approximately 55 cm of the catheter 9 was introduced into an adult male. FIG. 57b is an x-ray taken after approximately 100 cm of the catheter 9 was introduced into an adult male. FIG. 57c is an x-ray taken after approximately 150 cm of the catheter 9 was introduced into an adult male. FIG. 57d is an x-ray taken with the same catheter length as FIG. 57c, but taken approximately 24 hours after the x-ray in FIG. 57c. FIG. 57d shows that natural motility and/or peristalsis of the stomach may urge the catheter 9 into the duodenum 37. FIG. 57d shows the remote sensors 93a and 93b in the intestine. FIG. 57c shows that the proboscis may be at and/or near the pylorus. FIG. 57d shows that the proboscis may be at and/or near the duodenum 37 and/or the intestine.

Figure 58A:
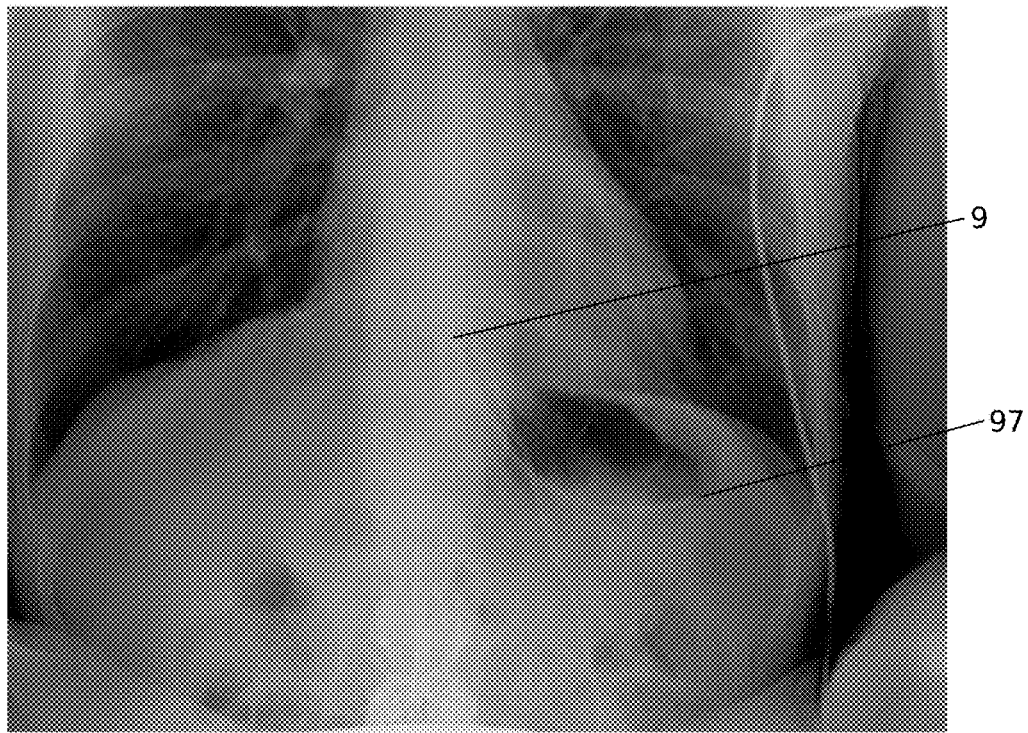
FIGS. 58a-58b are frontal x-rays of the catheter being introduced into the stomach.
Figure 58B:
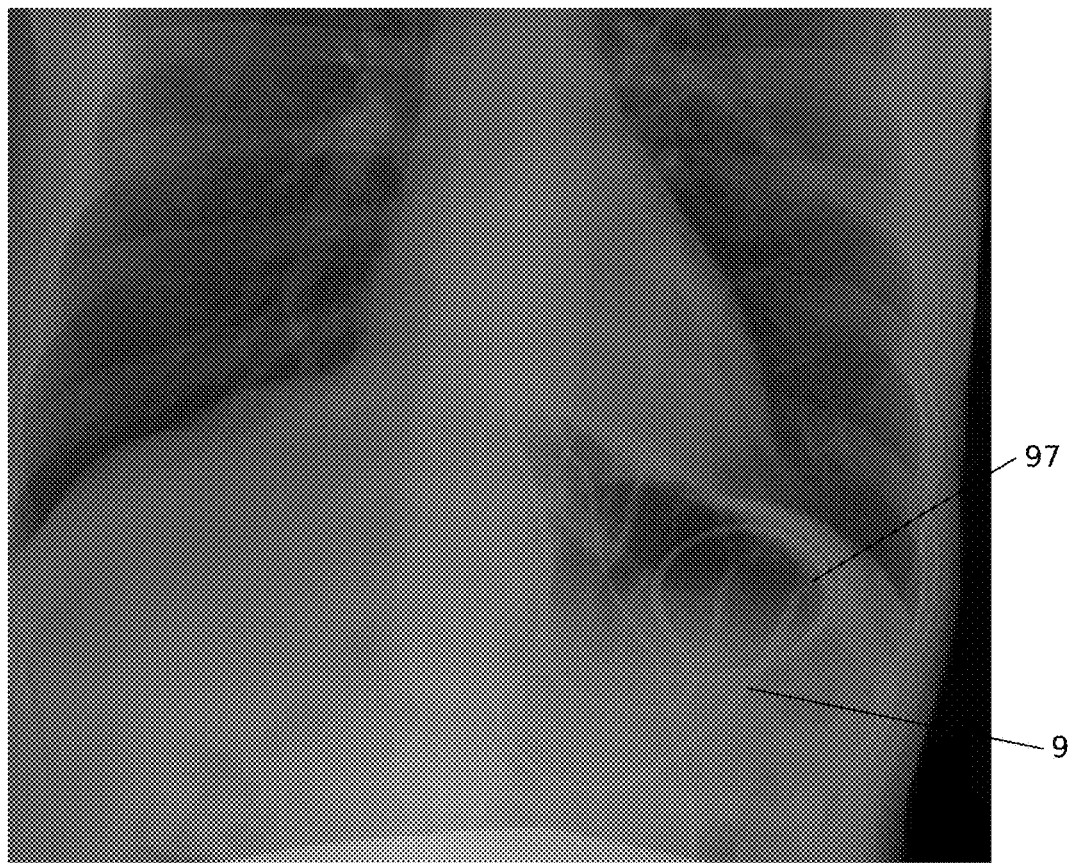

FIGS. 58a-58b show that the catheter 9 may form various shapes as it is introduced into the stomach 2 FIG. 58b shows that the proboscis 97 may be at or near the body and/or the fundus of the stomach 2. FIG. 58a is an x-ray taken after approximately 55 cm of the catheter 9 was introduced into an adult male. FIG. 58b is an x-ray taken after approximately 110 cm of the catheter 9 was introduced into an adult male.

FIGS. 46a-58b illustrate, for example, the widths of the loops 118 can be less than 31 cm, or more narrowly, less than 10 cm.

FIGS. 46a-58b illustrate, for example, that the fluid 6 can be recirculated through the lumen 15 and the lumen 16 when at least one of the loops 118 is closer to the pylorus 65 than the catheter tip 7.

FIGS. 46a-58b illustrate, for example, that the fluid 6 can be recirculated through the lumen 15 and the lumen 16 when at least one of the loops 118 is farther from the pylorus 65 than the catheter tip 7.

FIGS. 46a-58b illustrate, for example, that the fluid 6 can be recirculated through the lumen 15 and the lumen 16 when at least one of the loops 118 and the catheter tip 7 are in the stomach 2.

FIGS. 46a-58b illustrate, for example, that the fluid 6 can be recirculated through the lumen 15 and the lumen 16 when at least one of the loops 118 is in the stomach 2 and the catheter tip 7 is in the duodenum 37.

FIGS. 46a-58b illustrate, for example, that the fluid 6 can be recirculated through the lumen 15 and the lumen 16 when at least one of the loops 118 is in the duodenum 37 and the catheter tip 7 is in the stomach 2.

FIGS. 46a-53b illustrate, for example, that the fluid 6 can be recirculated through the lumen 15 and the lumen 16 when at least one of the loops 118 and the catheter tip 7 are in the duodenum 37.

FIGS. 46a-58b illustrate that a lumen (e.g., an inflow lumen and an outflow lumen) extend through the catheter 9 along the total length 124 and/or the length 126 of the catheter 9 to the catheter tip 7 such that fluid can be circulated and/or recirculated through the catheter 9 in the target site 147. The inflow lumen and the outflow lumen can merge with each other in the catheter tip 7, for example, within 1 mm-50 mm from the distal terminal end of the catheter tip 7, including every 1 mm increment within this range (e.g., 1 mm, 10 mm, 30 mm, 50 mm).

The catheter 9 can be designed and/or configured to not knot. For example, the catheter 9 can have a minimum bending stiffness (e.g., 2N-5N) and/or a lubricious coating. FIG. 46e illustrates that the catheter tip 7 may reside in the pyloric canal, the pyloric antrum and/or the body of the stomach 2.

For a 150 cm long catheter 9 having an outer diameter 19 of 4 mm, an internal volume of the catheter distal to the inflow port and the outflow port can be, for example, 15.0 mL-25.0 mL, including every 1.0 mL increment within this range (e.g., 18.9 mL). The volume of the heat transfer lumens in the catheter 9 can be, for example, 7.0 mL-9.0 mL, including every 1 mL increment within this range (e.g., 7.6 mL, for example, a 3.8 mL volume for the first lumen 15 and a 3.8 mL volume for the second lumen 16. The volume of the aspiration lumen (e.g., the third lumen 16) can be, for example, 1.0 mL-2.0 mL, including every 0.1 mL increment within this range (e.g., 1.5 mL). The volume of the catheter walls can be, for example, 8.0 mL-12.0 mL, including every 0.1 mL increment within this range (e.g., 9.7 mL). The volume of the first lumen 15, can be for example, 0.0150 mL/cm to 0.0500 mL/cm (e.g., 0.0253 mL/cm). The volume of the second lumen 15, can be for example, 0.0150 mL/cm to 0.0500 mL/cm (e.g., 0.0253 mL/cm). The first lumen 15 can have, for example, a cross-sectional area of 0.003944 in$^2$ and a perimeter of 0.251603 in, resulting in a hydraulic diameter of 0.001592629659 in (dh=4*A/p). The second lumen 16 can have, for example, a cross-sectional area of 0.003944 in$^2$ and a perimeter of 0.251603 in, resulting in a hydraulic diameter of 0.001592629659 in (dh=4*A/p).

The catheter 9 can, for example, increase and/or decrease the temperature of the gastrointestinal tract 110 (e.g., the stomach 2, the duodenum 37, and/or the pancreas 1) by 1 degree Celsius to 20 degrees Celsius, by 1 degree Celsius to 15 degrees Celsius, and/or by 1 degree Celsius to 10 degrees Celsius. For example, the stomach 2 can be cooled to 25-30 degrees Celsius, which can provide cooling of the pancreas 1. For example, lowering the temperature of the stomach 2 by 10-15 degrees Celsius (e.g., 10 degrees, 12 degrees, 15 degrees) can provide adequate cooling of the pancreas 1. For core body temperature regulation (e.g., normothermia), the same and/or a smaller change in temperature can be provided. For example, for warming, that temperature change can be lower. For example, for warming, the stomach 2 can be warmed to 37-42 degrees Celsius (e.g., 37 degrees, 38 degrees, 42 degrees). The temperature change of the fluid 6 between the heat exchange system 13 can be 2-10 deg Celsius. The change in the fluid temperature can depend, for example, on the flow rate and input parameters. A higher flow rate can result in a smaller temperature change ($Q=mC_p\Delta T$). The heat exchange system 13 (e.g., a recirculating chiller) can, for example, have a fluid temperature range of 4-42 degrees Celsius for the fluid 6 (e.g., water). By the time the water reaches the body, the temperature of the water when it enters the body can be 9-12 degrees Celsius and the temperature of the water when it exits the body can be 15-20 degrees Celsius. For warming, the temperature of the fluid when it enters the body, can be, for example, 37-38 degrees Celsius, meaning that the temperature change of the fluid 6 for warming can be fairly small when the patient is 30-36 degrees Celsius.

The catheter 9 can, for example, increase and/or decrease a temperature of a wall of the gastrointestinal tract 110 (e.g., the stomach 2, the duodenum 37, and/or the pancreas 1) by 1 degree Celsius to 20 degrees Celsius, by 1 degree Celsius to 15 degrees Celsius, and/or by 1 degree Celsius to 10 degrees Celsius.

The sensor 21 may expand and/or separate from the catheter 9. For example, the sensor 21 can be secured with a dissolvable and/or retractable sheath. The sensor 21 can be a spring member and/or nitinol. For example, the sensor 21 could expand away from the catheter with mechanical manipulation, temperature change, pressure and/or if a sheath is removed from the sensor 21. The sensor 21 can sense if it is submersed in a gas or liquid (e.g., by measuring resistance and/or conductivity across two points). The temperature difference between multiple sensors 21 and/or the remote sensor 93 can be used to determine the location and/or accuracy of the sensors 21.

A temperature sensor 21 can measure the temperature of the fluid in the first lumen 15, the second lumen 16 and/or the third lumen 17. Fluid can periodically be injected and/or withdrawn from the first lumen 15, the second lumen 16 and/or the third lumen 17. The temperature differential between the fluid in the first lumen 15, the second lumen 16 and/or the third lumen 17 can be monitored. The temperature differential over a period of time can be monitored in the first lumen 15, the second lumen 16 and/or the third lumen 17. For example if the fluid 6 enters into the first lumen 15 at 5 degrees Celsius and returns out of the second lumen 16 at 10 degrees Celsius, then one may estimate that the temperature of the stomach 2 is greater than 10 degrees Celsius. The flow rate of the fluid 6 and/or the difference in temperature of the fluid 6 entering the first lumen 15 and exiting the second lumen 16 can be used to estimate the temperature of the stomach 2 and/or the total heat transfer between the catheter 9 and/or the patient.

The catheter 9 may be insulated outside of the patient to minimize heat transfer to the surrounding environment. A fluid bypass may be located external to the patient to reduce the pressure of the fluid entering into the portion of the catheter 9 inside of the patient. The flow rate of the fluid 6 fluid may be different before and/or after the bypass. For example, a high flow rate of the fluid 6 proximal to the fluid bypass may help to reduce and/or increase the temperature of the fluid 6 at the fluid bypass and/or entering the patient through the catheter 9.

An operator can use one or multiple methods and/or techniques to determine if the catheter 9 and/or the catheter tip 7 are in the correct location, including, for example, auscultation of air insufflated through the feeding tube (e.g., 'whoosh' test), testing the acidity/alkalinity of aspirate using blue litmus paper, interpreting the absence of respiratory distress as an indicator of correct positioning, monitoring bubbling at the end of the tube, observing the appearance of NG tube aspirate, measurement of NG aspirate pH using pH indicator paper and/or chest imaging (e.g., X-ray, CT scan, MRI, ultrasound, magnetic sensing, electromagnetic sensing and/or CORTRAK). For example, using such methods and/or techniques, the operator can confirm if the catheter tip 7 is in the duodenum 37, the stomach 2, the pancreas 1, the pylorus 65, the ampulla of vater 41, the pancreatic duct 42, the esophagus 5, the lung and/or a different organ.

The diameter and/or the hydraulic diameter of the first lumen 15, the catheter OD 19, the proboscis tip diameter 95, the second lumen 16, the third lumen 17 and/or the fourth lumen 18 can be greater than approximately 0.25 mm (0.01 in), yet more narrowly greater than approximately 0.5 mm (0.02 in), yet more narrowly greater than approximately 1 mm (0.04 in), yet more narrowly greater than approximately 1.5 mm (0.06 in), yet more narrowly greater than approximately 2 mm (0.08 in), yet more narrowly greater than approximately 2.5 mm (0.10 in) and/or yet more narrowly greater than approximately 3 mm (0.12 in). The diameter and/or the hydraulic diameter of the first lumen 15, the catheter OD 19, the proboscis tip diameter 95, the second lumen 16, the third lumen 17 and/or the fourth lumen 18 can be less than approximately 3 mm (0.12 in), yet more narrowly less than approximately 2.5 mm (0.10 in), yet more narrowly less than approximately 2 mm (0.08 in), yet more narrowly less than approximately 1.5 mm (0.06 in), yet more narrowly less than approximately 1 mm (0.04 in), yet more narrowly less than approximately 0.5 mm (0.02 in) and/or yet more narrowly less than approximately 0.25 mm (0.01 in).

The weight of the duodenal device 40 and/or the catheter tip 7 can be greater than approximately 1 g, yet more narrowly greater than approximately 2 g, yet more narrowly greater than approximately 5 g, yet more narrowly greater than approximately 10 g and/or yet more narrowly greater than approximately 20 g. The weight of the duodenal device 40 and/or the catheter tip 7 can be less than approximately 20 g, yet more narrowly less than approximately 10 g, yet more narrowly less than approximately 5 g, yet more narrowly less than approximately 2 g and/or yet more narrowly less than approximately 1 g.

The length of the catheter 9 and/or the length of the catheter 9 in the stomach 2 can be greater than approximately 10 cm (3.9 in), yet more narrowly greater than approximately 25 cm (9.8 in), yet more narrowly greater than approximately 50 cm (19.7 in), yet more narrowly greater than approximately 75 cm (29.5 in), yet more narrowly greater than approximately 100 cm (39.4 in), yet more narrowly greater than approximately 150 cm (59 in) and/or yet more narrowly greater than approximately 200 cm (78.7 in). The length of the catheter 9 and/or the length of the catheter 9 in the stomach 2 can be less than approximately 200 cm (78.7 in), yet more narrowly less than approximately 150 cm (59 in), yet more narrowly less than approximately 100 cm (39.4 in), yet more narrowly less than approximately 75 cm (29.5 in), yet more narrowly less than approximately 50 cm (19.7 in), yet more narrowly less than approximately 25 cm (9.8 in) and/or yet more narrowly less than approximately 10 cm (3.9 in).

The surface area of the heat transferer 4, the catheter 9, the duodenal device 40 and/or the balloon 3 can be greater than approximately 10 cm2 (1.6 in$^2$), yet more narrowly greater than approximately 50 cm2 (7.8 in$^2$), yet more narrowly greater than approximately 100 cm2 (15.5 in$^2$), yet more narrowly greater than approximately 200 cm2 (31 in$^2$), yet more narrowly greater than approximately 300 cm2 (46.5 in$^2$) and/or yet more narrowly greater than approximately 500 cm2 (77.5 in$^2$). The surface area of the heat transferer 4, the catheter 9, the duodenal device 40 and/or the balloon 3 can be less than approximately 500 cm2 (77.5 in$^2$), yet more narrowly less than approximately 300 cm2 (46.5 in$^2$), yet more narrowly less than approximately 200 cm2 (31 in$^2$), yet more narrowly less than approximately 100 cm2 (15.5 in$^2$), yet more narrowly less than approximately 50 cm2 (7.8 in$^2$) and/or yet more narrowly less than approximately 10 cm2 (1.6 in$^2$).

The balloon 3 and/or the duodenal device 40 can be filled to greater than 10% of its maximum volume, yet more narrowly greater than 25% of its maximum volume, yet more narrowly greater than 50% of its maximum volume, yet more narrowly greater than 75% of its maximum volume and/or yet more narrowly greater than 90% of its maximum volume. The balloon 3 and/or the duodenal device 40 can be filled to less than 95% of its maximum volume, yet more narrowly less than 85% of its maximum volume, yet more narrowly less than 75% of its maximum volume, yet more narrowly less than 55% of its maximum volume, yet more narrowly less than 30% of its maximum volume, yet more narrowly less than 15% of its maximum volume.

The length of the balloon 3 and/or the proboscis length 96 can be greater than approximately 1 cm (0.4 in), yet more narrowly greater than approximately 2 cm (0.8 in), yet more narrowly greater than approximately 4 cm (1.6 in), yet more narrowly greater than approximately 6 cm (2.4 in), yet more narrowly greater than approximately 8 cm (3.1 in), yet more narrowly greater than approximately 10 cm (3.9 in), and/or yet more narrowly greater than approximately 20 cm (7.9 in). The length of the balloon 3 and/or the proboscis length 96 can be less than approximately 20 cm (7.9 in), yet more narrowly less than approximately 10 cm (3.9 in), yet more narrowly less than approximately 8 cm (3.1 in), yet more narrowly less than approximately 6 cm (2.4 in), yet more narrowly less than approximately 4 cm (1.6 in) and/or yet more narrowly less than approximately 2 cm (0.8 in).

The maximum heat transfer rate of the heat transferer 4, the catheter 9, the balloon, and/or the heat exchange system 13 can be fixed and/or controlled by the operator. The maximum heat transfer rate of the heat transferer 4 and/or the heat exchange system 13 can be greater than 10 W, yet more narrowly greater than 30 W, yet more narrowly greater than 50 W, yet more narrowly greater than 100 W, yet more narrowly greater than 150 W, yet more narrowly greater than 250 W, yet more narrowly greater than 500 W and/or yet more narrowly greater than 1000 W. The maximum heat transfer rate of the heat transferer 4 and/or the heat exchange system 13 can be less than 1000 W, yet more narrowly less than 500 W, yet more narrowly less than 250 W, yet more narrowly less than 150 W, yet more narrowly less than 100 W, yet more narrowly less than 50 W and/or yet more narrowly less than 30 W. The heat transferer 4, the catheter 9 and/or the balloon 3 can be used to provide localized cooling and/or heating therapy to specific regions and/or organs. For example, the heat transferer 4, the catheter 9 and/or the balloon 3 can provide heat transfer to the stomach 2 and/or the pancreas 1. The heat transferer 4, the catheter 9 and/or the balloon 3 can be used to provide general cooling. For example, the heat transferer 4, the catheter 9 and/or the balloon 3 can be used to reduce and/or increase the core body temperature. Approximately 50 W of cooling power can be adequate to lower the core body temperature of a human being. Reducing the heating and/or cooling power can localize the temperature therapy.

The balloon 3 can be filled to a volume greater than 50 mL, yet more narrowly greater than 100 mL, yet more narrowly greater than 200 mL, yet more narrowly greater than 300 mL, yet more narrowly greater than 400 mL, yet more narrowly greater than 500 mL, yet more narrowly greater than 600 mL, yet more narrowly greater than 700 mL, yet more narrowly greater than 800 mL, yet more narrowly greater than 900 mL and/or yet more narrowly greater than 1000 mL. The balloon 3 can be filled to a volume less than 1000 mL, yet more narrowly less than 900 mL, yet more narrowly less than 800 mL, yet more narrowly less than 700 mL, yet more narrowly less than 600 mL, yet more narrowly less than 500 mL, yet more narrowly less than 400 mL, yet more narrowly less than 300 mL, yet more narrowly less than 200 mL, yet more narrowly less than 100 mL and/or yet more narrowly less than 50 mL.

The thermal therapy system 33 can use a feedback loop to control heat transfer. For example, a control thermocouple can be placed next to the catheter 9 and/or the heat transferer 4. For example, a thermocouple can be placed on other locations of the body, including but not limited to the rectum, the ear, the mouth, the armpit, the bladder, the pulmonary artery, the skin and/or temporal artery sites. The control thermocouple can monitor the core body temperature of the patient. For example, the user can program the thermal therapy system 33 to heat and/or cool the patient to a preset temperature. The thermal therapy system 33 can adjust the temperature and/or flow rate of the fluid 6. The thermal therapy system 33 can adjust the total surface area of the heat transferer 4 and/or the catheter 9. For example, the catheter 9 can be removed from the stomach 2 to reduce the total surface area of the catheter 9 in the stomach. The user can set the target temperature of the thermal therapy system 33 to a temperature that is higher or lower than the normal body temperature, with the intention of providing additional heating and/or cooling to an organ of the patient. For example, the user can set the target temperature of the thermal therapy system 33 to 1 deg Celsius below normal body temperature, with the expectation that this will not cause general hypothermia, but should cool the stomach 2 and/or the pancreas 1 to a temperature greater than 1 deg Celsius below normal body temperature. The temperature of the control thermocouple can be higher and/or lower than the temperature of the organ targeted for heating and/or cooling. One can expect a thermal gradient between the control thermocouple and the heat transferer 4 and/or the catheter 9.

The volume of the balloon 3 relative to the volume of the stomach 2 can be greater than 10%, yet more narrowly greater than 20%, yet more narrowly greater than 30%, yet more narrowly greater than 40%, yet more narrowly greater than 50%, yet more narrowly greater than 60%, yet more narrowly greater than 70%, yet more narrowly greater than 80% and/or yet more narrowly greater than 90%. The volume of the balloon 3 relative to the volume of the stomach 2 can be less than 100%, yet more narrowly less than 90%, yet more narrowly less than 80%, yet more narrowly less than 70%, yet more narrowly less than 60%, yet more narrowly less than 50%, yet more narrowly less than 40%, yet more narrowly less than 30%, yet more narrowly less than 20% and/or yet more narrowly less than 10%.

The pressure in the balloon 3 when deflated, partially inflated and/or fully inflated can be greater than 0.05 PSI, yet more narrowly greater than 0.1 PSI, yet more narrowly greater than 0.3 PSI, yet more narrowly greater than 0.5 PSI, yet more narrowly greater than 1 PSI, yet more narrowly greater than 2 PSI, yet more narrowly greater than 5 PSI and/or yet more narrowly greater than 10 PSI. The pressure in the balloon 3 when deflated, partially inflated and/or fully inflated can be less than 10 PSI, yet more narrowly less than 5 PSI, yet more narrowly less than 2 PSI, yet more narrowly less than 1 PSI, yet more narrowly less than 0.5 PSI, yet more narrowly less than 0.3 PSI, yet more narrowly less than 0.1 PSI and/or yet more narrowly less than 0.05 PSI.

The maximum diameter of the catheter 9 and/or the uninflated fballoon 3 can be greater than approximately 5 Fr, yet more narrowly greater than 8 Fr, yet more narrowly greater than 11 Fr, yet more narrowly greater than 15 Fr, yet more narrowly greater than 18 Fr, yet more narrowly greater than 22 Fr, yet more narrowly greater than 30 Fr and/or yet more narrowly greater than 50 Fr. The maximum diameter of the catheter 9 and/or the uninflated fballoon 3 can be less than approximately 50 Fr, yet more narrowly less than 30 Fr, yet more narrowly less than 22 Fr, yet more narrowly less than 18 Fr, yet more narrowly less than 15 Fr, yet more narrowly less than 12 Fr, yet more narrowly less than 9 Fr and/or yet more narrowly less than 6 Fr. The French size is three times the diameter in millimeters. Thus, the French size is roughly equivalent to the circumference of a circular catheter; the true circumference being slightly larger.

The pancreas 1, the stomach 2 and/or the gastric pancreas wall 8 can be cooled to reduce the severity of pancreatitis. The pancreas 1, the stomach 2, the fluid 6 and/or the gastric pancreas wall 8 can be cooled from body temperature (e.g., 37° C.) to 20° C.-34° C., more narrowly 25° C.-34° C. For example, the pancreas 1, the stomach 2 and/or the gastric pancreas wall 8 can be cooled to 25° C.-30° C. for severe pancreatitis and 30° C.-34° C. for mild pancreatitis. The pancreas 1, the fluid 6, the stomach 2 and/or the gastric pancreas wall 8 can be 50° C., yet more narrowly less than 45° C., yet more narrowly less than 40° C., yet more narrowly less than 39° C., yet more narrowly less than 36° C., yet more narrowly less than 35° C., yet more narrowly less than 34° C., yet more narrowly less than 33° C., yet more narrowly less than 32° C., yet more narrowly less than 31° C., yet more narrowly less than 30° C., yet more narrowly less than 29° C., yet more narrowly less than 28° C., yet more narrowly less than 27° C., yet more narrowly less than 26° C., yet more narrowly less than 25° C., yet more narrowly less than 24° C., yet more narrowly less than 23° C., yet more narrowly less than 22° C., yet more narrowly less than 21° C., yet more narrowly less than 20° C., yet more narrowly less than 19° C., yet more narrowly less than 18° C., yet more narrowly less than 17° C., yet more narrowly less than 16° C., yet more narrowly less than 15° C., yet more narrowly less than 11° C., yet more narrowly less than 9° C., yet more narrowly less than 7° C., yet more narrowly less than 5° C. and/or yet more narrowly less than 3° C. The pancreas 1, the fluid 6, the stomach 2, the fluid 6 and/or the gastric pancreas wall 8 can be cooled to a temperature greater than 2° C., yet more narrowly greater than 4° C., yet more narrowly greater than 5° C., yet more narrowly greater than 7° C., yet more narrowly greater than 10° C., yet more narrowly greater than 15° C., yet more narrowly greater than 15° C., yet more narrowly greater than 16° C., yet more narrowly greater than 17° C., yet more narrowly greater than 18° C., yet more narrowly greater than 19° C., yet more narrowly greater than 20° C., yet more narrowly greater than 21° C., yet more narrowly greater than 22° C., yet more narrowly greater than 23° C., yet more narrowly greater than 24° C., yet more narrowly greater than 25° C., yet more narrowly greater than 26° C., yet more narrowly greater than 27° C., yet more narrowly greater than 28° C., yet more narrowly greater than 29° C., yet more narrowly greater than 30° C., yet more narrowly greater than 31° C., yet more narrowly greater than 32° C., yet more narrowly greater than 33° C., yet more narrowly greater than 34° C., yet more narrowly greater than 35° C., yet more narrowly greater than 36° C., yet more narrowly greater than 40° C., yet more narrowly greater than 45° C. and/or yet more narrowly greater than 50° C.

The flow rate of the fluid 6 and/or the insulating fluid 25 in the catheter 9 can be greater than 10 mL/min, yet more narrowly greater than 50 mL/min, yet more narrowly greater than 100 mL/min, yet more narrowly greater than 200 mL/min, yet more narrowly greater than 500 mL/min, yet more narrowly greater than 1,000 mL/min and/or yet more narrowly greater than 2,000 mL/min. The flow rate of the fluid 6 in the catheter 9 can be less than 2,000 mL/min, yet more narrowly less than 1,000 mL/min, yet more narrowly less than 500 mL/min, yet more narrowly less than 200 mL/min, yet more narrowly less than 100 mL/min and/or yet more narrowly less than 50 mL/min.

The thermal therapy system 33 can be used continuously for greater than 1 hour, yet more narrowly greater than 6 hours, yet more narrowly greater than 12 hours, yet more narrowly greater than 24 hours, yet more narrowly greater than 48 hours, yet more narrowly greater than 72 hours, yet more narrowly greater than 96 hours and/or yet more narrowly greater than 120 hours. The thermal therapy system 33 can be used continuously for less than 120 hours, yet more narrowly less than 96 hours, yet more narrowly less than 72 hours, yet more narrowly less than 48 hours, yet more narrowly less than 24 hours, yet more narrowly less than 12 hours, yet more narrowly less than 6 hours and/or yet more narrowly less than 2 hours.

Any elements described herein as singular can be pluralized (i.e., anything described as "one" can be more than one). Any species element of a genus element can have the characteristics or elements of any other species element of that genus. The media delivered herein can be any of the fluids (e.g., liquid and/or gas) described herein. The patents and patent applications cited herein are all incorporated by reference herein in their entireties for all purposes. Some elements can be absent from individual FIGS. for reasons of illustrative clarity. The above-described configurations, elements or complete assemblies and methods and their elements for carrying out the disclosure, and variations of aspects of the disclosure can be combined and modified with each other in any combination. All devices, apparatuses, systems, and methods described herein can be used for medical (e.g., diagnostic, therapeutic or rehabilitative) or non-medical purposes.

The thermal therapy system 33 or any or all elements of the tool and/or other tools or apparatuses described herein can be used to adjust the core body temperature of the patient and/or the temperature of specific regions of the patient. The thermal therapy system 33 can be used to increase and/or decrease the temperature of the patient and/or specific regions of the patient. The thermal therapy system 33 can be used to treat various conditions. For example, the thermal therapy system 33 can be used to help with weight loss by reducing the caloric intake and/or absorption of the patient. The thermal therapy system 33 can help to increase and/or reduce the absorption of medications. For example, increasing and/or decreasing the temperature of certain regions of the body can adjust the uptake of drugs, such as chemotherapy medication. The thermal therapy system 33 can be used to cool multiple organs. The thermal therapy system 33 can be used to cool the esophagus (e.g., during cardiac ablation therapy). Medications can be used to increase and/or decrease the motility, peristalsis and/or gastric waves. The catheter 9 and/or the catheter tip 7 can be coated with a medication and/or material that can increase and/or decrease the motility, peristalsis and/or gastric waves.

The thermal therapy system 33 or any or all elements of the tool and/or other tools or apparatuses described herein can be made from or coated with, for example, rubber, thermoplastic elastomer (TPE), polyisoprene rubber, latex-free elastomer, silicone, liquid silicone rubber (LSR), polypropylene, LDPE, HDPE, single or multiple stainless steel alloys, steel, spring steel, nickel titanium alloys (e.g., Nitinol), cobalt-chrome alloys (e.g., ELGILOY® from Elgin Specialty Metals, Elgin, IL; CONICHROME® from Carpenter Metals Corp., Wyomissing, PA), nickel-cobalt alloys (e.g., MP35N® from Magellan Industrial Trading Company, Inc., Westport, CT), molybdenum alloys (e.g., molybdenum TZM alloy), tungsten-rhenium alloys, polymers such as polyethylene teraphathalate (PET), polyester (e.g., DACRON® from E. I. Du Pont de Nemours and Company, Wilmington, DE), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, NJ, or DYNEEMA® from Royal DSM N.V., Heerlen, the Netherlands), polytetrafluoroethylene (PTFE), Parylene poly(p-xylylene) polymers, Parylene N, Parylene C, Parylene D, expanded PTFE (ePTFE), polyether ketone (PEK), polyether ether ketone (PEEK), polycarbonate (PC), Acrylonitrile Butadiene Styrene (ABS), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, MA), polyvinyl chloride (PVC), Nylon, Vinyl, polyurethane, thermoplastic, fluorinated ethylene propylene (FEP), absorbable or resorbable polymers such as polyglycolic acid (PGA), poly-L-glycolic acid (PLGA), polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone), a material with high strength (60 ksi) and biocompatibility, any of the other materials listed herein or any combination thereof. Examples of radiopaque materials are barium sulfate, zinc oxide, titanium, stainless steel, nickel-titanium alloys, tantalum and gold. The device can be made from substantially 100% PEEK, substantially 100% titanium or titanium alloy, or any combination thereof.

Everything in U.S. Pat. No. 8,529,612, in U.S. Pat. No. 9,192,510, in U.S. Pat. No. 9,717,626, in U.S. Pat. No. 10,842,668, and in U.S. patent application Ser. No. 17/084,669 filed Oct. 30, 2020 (now U.S. Publication No. 2021/0069013) is herein incorporated by reference in its entirety for all purposes, including all systems, devices, and methods disclosed therein, and including any combination of features and operations disclosed therein, and can be combined with the present disclosure in any combination. For example, any of the systems, devices, and methods disclosed herein can have any combination of the systems, devices, features, and methods disclosed in U.S. Pat. No. 8,529,612, in U.S. Pat. No. 9,192,510, in U.S. Pat. No. 9,717,626, in U.S. Pat. No. 10,842,668, and in U.S. patent application Ser. No. 17/084,669 filed Oct. 30, 2020 (now U.S. Publication No. 2021/0069013).

Everything in the following journal article is herein incorporated by reference in its entirety for all purposes, including all systems, devices, and methods disclosed therein, and including any combination of features and operations disclosed therein, and can be combined with the present disclosure in any combination: de Oliveira C, Khatua B, Bag A, et al. Multimodal Transgastric Local Pancreatic Hypothermia Reduces Severity of Acute Pancreatitis in Rats and Increases Survival. Gastroenterology. 2019; 156(3):735-747.e10.doi:10.1053/j.gastro.2018.10.034. For example, any of the systems, devices, and methods disclosed herein can have any combination of the systems, devices, features, and methods disclosed in this journal article.

The system 33 and/or the device 4 can have, for example, any combination of features described herein and/or shown in FIGS. 1-58*b*.

The catheter 9 in any of the figures can have any of the features in any of the other figures, including, for example, the balloon 3, the sensors 21, the configurations 116, the shapes 117, the loops 118, the cells 122, the total length 124, the length 126, the heat transfer region 128, the length 130, the heat transfer zones 132, the coil 138, or any combination thereof. For example, the catheter 9 can have any combination of the features in FIGS. 1-58*b*.

Any portion of the catheter 9 can be a first section of the catheter 9 and any portion of the catheter 9 different than the first section can be a second section of the catheter 9. As another example, a portion of the first section of the catheter 9 can be a portion of and/or all of the second section of the catheter 9.

The catheter 9 in the target site 147 can have any combination of the loops 118 and/or cells 122, for example, shown in FIGS. 1-58*b*. The catheter 9 in the target site 147 can have any combination of the loops 118 and/or cells 122, for example, shown in FIGS. 46*a*-58*b*. The catheter 9 in the target site 147 can have any combination of the loops 118 and/or cells 122, for example, shown in FIGS. 1-58*b*.

The systems, methods, and/or devices can have any combination of features, for example, in FIGS. 1-58*b*.

The figures illustrate, for example, a device (e.g., the device 4) for changing a temperature of an organ or a first organ. The device can have a tube (e.g., the catheter 9). The tube can have a lumen, a tube first portion, and a tube second portion. A fluid (e.g., the fluid 6) can be flowable through the lumen. The device can have a tether (e.g., the tether 73). A distance between the tube first portion and the tube second portion can be maintainable via the tether. The tube can have a first configuration and a second configuration. The tether can be under more tension when the tube is in the second configuration than when the tube is in the first configuration. A distance between the tube first portion and the tube second portion can be changeable via the tether. Movement of the tube second portion away from the tube first portion can be limitable via the tether. 50 cm-150 cm of the tube can be positionable in a second organ adjacent the first organ. The tube can be formable into a lattice shape.

FIGS. 1-58*b* illustrate, for example, a method of a method of changing a temperature of a first organ. The method can include positioning a tube (e.g., the catheter 9) having a lumen, a tube first portion, and a tube second portion in a second organ. The method can include positioning a tether (e.g., the tether 73) in the second organ. The method can include maintaining a distance between the tube first portion and the tube second portion via the tether. The method can include changing the tube from a first configuration to a second configuration or allowing the tube to change from the first configuration to the second configuration. The tether can be under more tension when the tube is in the second configuration than when the tube is in the first configuration. The method can include changing a distance between the tube first portion and the tube second portion via the tether. The method can include limiting movement of the tube second portion away from the tube first portion via the tether. The method can include positioning 50 cm-150 cm of the tube in the second organ adjacent the first organ. The method can include forming the tube into a lattice shape in the second organ.

FIGS. 1-56 illustrate, for example, a method of a method of changing a temperature of a first organ. The method can include positioning 50 cm-150 cm of a tube (e.g., the catheter 9) having a lumen, a tube first portion, and a tube second portion in a second organ adjacent the first organ.

The tube can formable into a lattice shape.

When the tether is in a tensioned state, the distance between the tube first portion and the tube second portion can be maintainable via the tether.

When the tether is in a tensioned state, movement of the tube second portion away from the tube first portion can be limitable via the tether.

The tube can have a tube distal terminal end. The tether can have a tether distal terminal end. When the tether is in the tensioned state, the tube distal terminal end can be migratable away from the tether distal terminal end up to a threshold distance. When the tether is in the tensioned state, the tube distal terminal end can migrate away from the tether distal terminal end up to a threshold distance. When the tether is in the tensioned state, the tube distal terminal end can passively migrate away from the tether distal terminal end up to a threshold distance. When the tether is in the tensioned state, the tube distal terminal end can passively move away from the tether distal terminal end up to a threshold distance. When the tether is in the tensioned state, the tube distal terminal end can be movable away from the tether distal terminal end up to a threshold distance.

The tube second portion can have a tube second portion proximal end and a tube second portion distal end. The distance between the tube first portion and the tube second portion can be a distance between the tube first portion and the tube second portion proximal end. When the tether is in the tensioned state, the distance between the tube first portion and the tube second portion proximal end can be maintainable via the tether. When the tether is in the tensioned state, the tube second portion distal end can be migratable away from the tube first portion up to a threshold distance.

The threshold distance can be 1 cm to 50 cm. The threshold distance can be 1 cm to 25 cm. The threshold distance can be 1 cm to 10 cm. The threshold distance can be 1 cm to 5 cm. The threshold distance can be measured along a center longitudinal axis of the tube between the tether distal terminal end and the tube distal terminal end. The threshold distance can be measured along a straight line between the tether distal terminal end and the tube distal terminal end.

When the tube distal terminal end is less than the threshold distance from the tube tether distal terminal end, movement of the tube distal terminal end away from the tether distal terminal end can be permittable. When the tube distal terminal end is the threshold distance from the tether distal terminal end, movement of the tube distal terminal end away from the tether distal terminal end can be preventable by the tether and/or by tension in the tube.

The tube can have a first configuration and a second configuration. The tether distal terminal end can be closer to the tube first portion when the tube is in the second configuration than when the tube is in the first configuration. The tube second portion can be closer to the tube first portion when the tube is in the second configuration than when the tube is in the first configuration. The tube can be movable from the first configuration to the second configuration via the tether. When the tube is in the first configuration, the tube second portion can be a first distance from the tube first portion. When the tube is in the second configuration, the tube second portion can be a second distance from the tube first portion. The second distance can be less than the first distance. The second distance can be the distance between the tube first portion and the tube second portion. The tether can be under more tension when the tube is in the second configuration than when the tube is in the first configuration. When the tube is in the second configuration, the tether can be in the tensioned state. When the tube is in the first configuration, the tether can be in a non-tensioned state.

The tube can have a third configuration. The tube can be movable from the second configuration to the third configuration. When the tube is in the third configuration, the tube distal terminal end can be the threshold distance from the tether distal terminal end.

The tube second portion can have the tube distal terminal end.

When the tube is in the first configuration, the tube second portion can be distal the tube first portion. When the tube is in the second configuration, the tube second portion can be distal the tube first portion.

The tube first portion can have a first port. The tube second portion can have a second port. The second port can be closer to the first port when the tube is in the second configuration than when the tube is in the first configuration. The second port can be farther from the first port when the tube is in the third configuration than when the tube is in the second configuration. The tether can be attached to the tube between the first port and the second port. The tether can be attached to the tube second portion between the first port and the second port. The tether can be movable (e.g., translatable) through the first port. When the tube is in the first configuration, the tether can be in the first port. When the tube is in the second configuration, the tether can be in the first port. When the tube is in the third configuration, the tether can be in the first port. The second port can be at a distal end of the tube or at a distal terminal end of the tube. A tool can be deliverable through the second port. Fluid and/or nutrients can be deliverable through the second port.

When the tube is in the first configuration, the tether can be loose. When the tube is in the second configuration, the tether can be taut. When the tube is in the first configuration, a section of tether can have a bend. When the tube is in the second configuration, the section of tether can be straight or have another bend with a radius of curvature that can be larger than a radius of curvature of the bend. The tether can be under zero tension when the tube is in the first configuration. When the tube is in the first configuration, the tether can have a first tension. When the tube is in the second configuration, the tether can have a second tension. The second tension can be greater than the first tension. The first tension can be zero tension. When the tube is in the first configuration, the tether can be in a non-tensioned state. When the tube is in the second configuration, the tether can be in a tensioned state. When the tether is in the tensioned state, movement of the tube second portion away from the tube first portion can be preventable by the tether. When the tether is in the tensioned state, the tube second portion can be movable toward the tube first portion via the tether. When the tether is in the tensioned state, the tube second portion can be pullable toward the tube first portion via the tether.

The tube can have a port. The tether can have a tether distal terminal end. The tether distal terminal end can be farther from the port when the tube is in the second configuration than when the tube is in the first configuration. The port can be proximal the tether distal terminal end when the tube is in the first configuration and when the tube is in the second configuration. The tether can be in the port when the tube is in the first configuration and when the tube is in the second configuration.

The tether can be movable from a non-actuated position to an actuated position. The tether can be movable from the non-actuated position to the actuated position via a control on a handle of the device. When the tether is in the non-actuated position, the distance between the tube first portion and the tube second portion can be decreasable by tensioning the tether. The non-actuated position can be a non-retracted position of the tether. When the tether is in the actuated position, the distance between the tube first portion and the tube second portion can be increasable by de-tensioning the tether. The actuated position can be a retracted position of the tether. The tether can have a distal terminal end. The tether distal terminal end can be closer to the tube first portion when the tether is in the actuated position than when the tether is in the non-actuated position. The tube second portion can be closer to the tube first portion when the tether is in the actuated position than when the tether is in the non-actuated position. The tether can be under more tension when the tether is in the actuated position than when the tether is in the non-actuated position. When the tether is in the actuated position, the distance between the tube first portion and the tube second portion can be maintainable via the tether.

The tube can have a heat transfer region. A portion of the tube can have a heat transfer region. The heat transfer region can have a heat transfer region length. A ratio of the heat transfer length to a length of the organ, the first organ, or the second organ can be 1.5 to 20.0. The heat transfer region length can be 80%-100% of a length of the tube positionable adjacent the organ or the first organ. The heat transfer region length can be 20 cm-200 cm of the tube. The heat transfer region length can be 20 cm-150 cm. The heat transfer region length can be 75 cm-150 cm. The heat transfer region length can be 50 cm-150 cm.

The heat transfer region length can be 50 cm-100 cm. The heat transfer region can be a length of the tube. The heat transfer region can be continuous length of the tube. The heat transfer region can be the tube first portion and the tube second portion. The heat transfer region can be the tube second portion. The heat transfer region can be distal the tube first portion. The tube can have a tube distal terminal end. The heat transfer region can have the tube distal terminal end.

When the tube is in a deployed configuration, the heat transfer region can cross over itself 0-15 times. When the tube is in a deployed configuration, the heat transfer region can cross over itself 0-10 times. When the tube is in a deployed configuration, the heat transfer region can cross over itself 0-5 times.

When the tube is in a deployed configuration, a first external portion of the heat transfer region can contact a second external portion of the heat transfer region. The first external portion of the heat transfer region can be a first portion of an external surface of the tube. The second external portion of the heat transfer region can be a second portion of an external surface of the tube. The first external portion of the heat transfer region and the second external portion of the heat transfer region can be separated by a distance as measured along a length of the tube.

When the tube is in a deployed configuration, the heat transfer region can have 0-15 bends. When the tube is in a deployed configuration, the heat transfer region can have 0-10 bends. When the tube is in a deployed configuration, the heat transfer region can have 0-5 bends. The heat transfer region can have more bends when the tube is in a deployed configuration than when the tube is in a non-deployed configuration. The tube can be deployable (e.g., changeable, movable) from a deployed first configuration to a deployed second configuration. The tube can have more bends when the tube is in the deployed second configuration than when the tube is in the deployed first configuration. The tube can be deployable (e.g., changeable, movable) from the deployed second configuration to a deployed third configuration. The tube can have more bends when the tube is in the deployed third configuration than when the tube is in the deployed second configuration. When the tube is in the deployed first configuration, the tube can have 1 bend. When the tube is in the deployed second configuration, the tube can have 2 bends. When the tube is in the third deployed configuration, the tube can have 3 bends. When the tube is in the deployed first configuration, the tube can have 1-2 bends. When the tube is in the deployed second configuration, the tube can have 3-4 bends. When the tube is in the third deployed configuration, the tube can have 5-10 bends.

When the tube is in a deployed configuration, the heat transfer region can have 0-15 loops. When the tube is in a deployed configuration, the heat transfer region can have 0-10 loops. When the tube is in a deployed configuration, the heat transfer region can have 0-5 loops. The heat transfer region can have more loops when the tube is in a deployed configuration than when the tube is in a non-deployed configuration. The tube can be deployable (e.g., changeable, movable) from a deployed first configuration to a deployed second configuration such that the tube can have more loops when the tube is in the deployed second configuration than when the tube is in the deployed first configuration. The tube can be deployable (e.g., changeable, movable) from the deployed second configuration to a deployed third configuration such that the tube can have more loops when the tube is in the deployed third configuration than when the tube is in the deployed second configuration. When the tube is in the deployed first configuration, the tube can have 0 loops. When the tube is in the deployed second configuration, the tube can have 1 loop. When the tube is in the third deployed configuration, the tube can have 2 loops. When the tube is in the deployed first configuration, the tube can have 0-2 loops. When the tube is in the deployed second configuration, the tube can have 3-4 loops. When the tube is in the third deployed configuration, the tube can have 5-10 loops.

When the tube is in the deployed configuration, the tube can define a mesh having cells. A mesh having cells can be formable by the tube. When the tube is in the deployed configuration, the tube can define a lattice structure. A lattice structure can be formable by the tube. The lattice structure can have cells.

The deployed configuration can be the second configuration.

When the tube is in a non-deployed configuration, the heat transfer region can be straight or less curved than when the tube is in a deployed configuration.

The tether can be movable along the tube outside of the tube. The tether can be movable into the tube. The tether can be flexible or rigid. The tube can be movable via the tether. The tube first portion and the tube second portion can be a first distance apart when the tether is in a non-actuated state. The tube first portion and the tube second portion can be a second distance part when the tether is in an actuated state. The second distance can be less than the first distance. The tube first portion can be movable closer to the tube second portion via the tether. The tube first portion can be movable into contact with the tube second portion via the tether. The tube can be changeable from a first shape to a second shape via the tether. A bend can be formable in the tube via the tether. The tether can be attached to the tube. The tether can have a non-actuated state and an actuated state. More of a distal end of the tether can be outside the tube when the tether is in the non-actuated state than when the tether is in the actuated state. The tether can have a non-actuated state and an actuated state. More of a distal end of the tether can be inside the tube when the tether is in the actuated state than when the tether is in the non-actuated state. The tether can be retractable through the tube. The tether can have a tether distal end. The tether distal end can be attached to the tube. The tether distal end can be closer to a port in the tube when the tether is in an actuated state than when the tether is in a non-actuated state.

The tether can be configured to prevent knotting of the tube. The tether can be configured to limit or prevent migration of the tube. The tether can be configured to limit or prevent migration of the tube distal the tether distal terminal end. The tether can be configured to limit or prevent migration of a portion of the tube distal the tether distal terminal end away from a portion of the tube proximal tether distal terminal end. When the tube and the tether are in a first body space, the tether can be configured to inhibit or prevent movement of the tube from the first body space to a second body space. When the tube and the tether are in a first body space, the tether can be configured to limit movement of the tube from the first body space to a second body space.

The device can have an engager (e.g., the engager 48). The tube can have the engager. The engager can have the lumen. The engager can include a distal end of the tube. The engager can be a distal coil in the tube having 1 to 5 turns. The distal coil can have a helical profile. The distal coil can have a spiral profile. The engager can be configured to retain a distal end of the catheter in a duodenum. The tube can be insertable into a patient. When the engager is in the patient's duodenum, the tether can be in the patient's stomach. The engager can include the heat transfer region. The engager can include a distal end of the heat transfer region. The engager can have an engager length of 2 cm-10 cm. The engager can have an engager length of 2 cm-20 cm. The engager can have an engager length of 2 cm-40 cm. The lumen can be a first lumen. The tube can have a second lumen. The fluid can be flowable toward a distal end of the tube through the first lumen. The fluid can be flowable toward a proximal end of the tube through the second lumen.

The tube can be a catheter.

The tether can be a wire or a string.

The fluid can be a liquid and/or a gas. The fluid can be flowable through the lumen at a temperature greater than 37 degrees Celsius. The fluid can be flowable through the lumen at a temperature of 37-50 degrees Celsius. The fluid can be flowable through the lumen at a temperature of 37-45 degrees Celsius. The fluid can be flowable through the lumen at a temperature of 37-40 degrees Celsius. The fluid can be flowable through the lumen at a temperature of 37.1-45.0 degrees Celsius. The fluid can be flowable through the lumen at a temperature less than 37 degrees Celsius. The fluid can be flowable through the lumen at a temperature of 2-20 degrees Celsius. The fluid can be flowable through the lumen at a temperature of 4-20 degrees Celsius. The fluid can be flowable through the lumen at a temperature of 5-15 degrees Celsius. The fluid can be flowable through the lumen at a temperature of 5-8 degrees Celsius. The fluid can be flowable through the lumen at a temperature of 10 degrees Celsius. The fluid can be flowable through the first lumen at a temperature of 5-8 degrees Celsius. The fluid can be flowable through the second lumen at a temperature of 11-13 degrees Celsius.

The tube can be configured to maintain flexibility under pressure. The tube can be configured to constrain a maximum volume. The tube can be configured to constrain a maximum volume.

The device can have a balloon. The tube can have the balloon. The balloon can be elastic, inelastic, or both. The balloon can be inflatable with the fluid. The balloon can have bubbles, ridges, ribs, or dots. The balloon can have a first chamber and a second chamber. 50 cm-150 cm of the tube can be insertable in a stomach. The lumen can be expandable. The lumen can be non-expandable.

The device can have a temperature sensor, a pressure sensor, an enzyme sensor, and/or a motion sensor. The tube can have the temperature sensor, the pressure sensor, the enzyme sensor, and/or the motion sensor.

The device can include a visualization aid. The visualization aid can have magnets, a radiopaque marker, and/or an echogenic marker.

The device can have a bypass lumen to allow pre-cooling of the fluid, to allow a cooler to keep running without flow to the tube, and/or to avoid low-flow alarms.

A return height of the fluid can be adjustable for improved pressure control of the device.

The tube can have a first section having a first diameter and a second section having a second diameter. The first diameter can be less than the second diameter for improved comfort when inserted into a nose or moth. The second diameter can be larger than the first diameter for improved flow or surface area in the organ.

The tube can be configured to change the temperature of the organ from a stomach and/or a duodenum. The organ can be a pancreas. The first organ can be a pancreas.

The lumen can be a first lumen. The tube can have a second lumen and a third lumen. The first lumen can be an inflow lumen for the fluid. The second lumen can be an outflow lumen for the fluid. The third lumen can be a working channel. The third lumen can be an aspiration lumen. A tool can be deliverable through the third lumen. A fluid and nutrients are deliverable through the third lumen. The first lumen can have a smaller diameter than the second lumen. The first lumen and the second lumen can have the same diameter. The tube can have bars, a weighted tip, and/or a coiled tip.

1 cm-30 cm of the tube can be positionable in a third organ. The third organ can be adjacent the first organ. The 1 cm-30 cm of the tube positionable in the third organ can be distal the 50 cm-150 cm of the tube positionable in the second organ.

The second organ can be a stomach.

The third organ can be a duodenum.

The first organ can be a pancreas.

The lattice shape can have a strut and a cell. The cell can be a hole in the lattice shape. The tube first portion or the tube second portion can have the strut. A section of the tube can be the strut.

The lattice shape can have a first strut and a second strut. The lattice shape can have a first cell and a second cell. The first cell can be a first hole in the lattice shape. The second cell can be a second hole in the lattice shape. The tube first portion can have the first strut. The tube second portion can have the second strut. The tube first portion can have the first strut and the second strut. The tube second portion can have the first strut and the second strut. A first section of the tube can be the first strut. A second section of the tube can be the second strut.

The lattice shape can have a joint. The joint can be a portion of the lattice shape where the first strut and the second strut intersect each other. The joint can be a portion of the lattice shape where the first strut crosses under or over the second strut. The joint can be a portion of the lattice shape where the first strut contacts the second strut. The joint can be a friction point configured to resist movement of the second strut away from the first strut. The joint can be a friction point configured to resist migration of the tube.

The first strut and the second strut can be continuous with each other. A third strut can be between the first strut and the second strut.

The strut can be a length of the tube between two joints. The first strut can be a length of the tube between two joints. The second strut can be a length of the tube between two joints. The strut can be straight or can have a bend. The first strut can be straight or can have a bend. The second strut can be straight or can have a bend.

The cell can be an open cell or a closed cell. The first cell can be an open cell or a closed cell. The second cell can be an open cell or a closed cell.

The tube can have a non-lattice shape and the lattice shape. The tube can be formable into the lattice shape from the non-lattice shape. The tube can be changeable from the non-lattice shape to the lattice shape. The tube can be changeable from the lattice shape to the non-lattice shape. The tube can have a tube distal terminal end. When the tube has the non-lattice shape, the portion of the tube that defines the first strut when the tube has the lattice shape can be farther from the tube distal terminal than the portion of the tube that defines the second strut when the tube has the lattice shape. When the tube has the lattice shape, the first strut can be farther from the tube distal terminal end than the second strut. When the tube has the lattice shape, the first strut can be closer to the tube distal terminal end than the second strut. When the tube has the lattice shape, a distance between the first strut and the second strut can be increasable or decreasable. When the tube has the lattice shape, the first strut can be movable toward and away from the second strut. The lattice shape can be formable with 20 cm-200 cm of the tube. The lattice shape can be defined by 20 cm-200 cm of the tube. The lattice shape can be formable in the second organ. The lattice shape can be formable in the third organ. The lattice shape can be formed in the second organ and a portion of the tube that defines the lattice shape (e.g., a portion of the tube that defines a distal portion of the lattice shape) can be move (e.g., migrate, advance) into the third organ. Such movement of a portion of the tube that defines the lattice shape into the third organ can be limited, inhibited, and/or prevented by a tether (e.g., the tether 73), an engager (e.g., the engager 48), and/or by tension in the tube. The non-lattice shape can include a straight configuration of the tube or a linear configuration of the tube. The joint can be a portion of the lattice shape where the tube first portion and the tube second portion intersect each other.

The lattice shape can be formable by the tube in the second organ. The lattice shape can be formable by the tube via the tube bending during advancement into the second organ.

When the tube has the lattice shape, the tube can have 1-50 bends. When the tube has the lattice shape, the tube can have 1-30 bends. When the tube has the lattice shape, the tube can have 10-50 bends.

A size of the cell, the first cell, or the second cell can be changeable via the tether.

A shape of the cell, the first cell, or the second cell can be changeable via the tether.

Another fluid can be flowable through the cell, the first cell, or the second cell.

Nutrients can be flowable through the cell, the first cell, or the second cell.

The cell, the first cell, or the second cell can be configured to provide space for nutrients to pass through.

When the tube is in the first configuration, the tube can have the lattice shape.

When the tube is in the second configuration, the tube can have the lattice shape.

When the tube is in the third configuration, the tube can have the lattice shape.

When the tube has the lattice shape, the lattice shape can include 20 cm-200 cm of the tube. When the tube is in a deployed configuration, the tube can have the lattice shape. The lattice shape can be defined by 20 cm-200 cm of the tube.

The lattice shape can have the heat transfer region. The lattice shape can be the heat transfer region.

When the tube has the lattice shape, the fluid can be flowable through the lumen.

When the tube is in a fully deployed configuration, the tube can have the lattice shape.

When the tube is in a fully deployed configuration, the tether can be in the actuated position and the tube can have the lattice shape.

Forming the tube into the lattice shape in the second organ can include advancing the tube into the second organ.

Forming the tube into the lattice shape in the second organ can include progressively advancing the tube into the second organ.

Forming the tube into the lattice shape in the second organ can include bending the tube in the second organ.

The method can include changing the tube from the lattice shape to a non-lattice shape by retracting the tube from the second organ.

The method can include changing the tube from the lattice shape to a non-lattice shape by progressively retracting the tube from the second organ.

The method can include changing the tube from the lattice shape to a non-lattice shape by unbending the tube in the second organ.

The method can include changing the temperature of the first organ by passing the fluid through the lumen in the second organ.

The method can include changing the temperature of the first organ by passing the fluid through the heat transfer region in the second organ.

The method can include changing the temperature of the first organ by passing the fluid through the lumen in the third organ.

The method can include preventing knotting of the tube via the tether.

The method can include preventing kinking of the tube via the tether.

The method can include limiting or preventing migration of the tube from the second organ into the third organ via the tether.

Positioning the tube in the second organ can including positioning 50 cm-150 cm of the tube in the second organ.

The method can include positioning the tube in a third organ.

The first organ can be a pancreas. The second organ can be a stomach. The third organ can be a duodenum.

Positioning the tube in the third organ can include positioning 1 cm-40 cm of the tube in the third organ.

The method can include adding or removing the tube from the second organ to adjust a cooling power of the tube.

50 cm-150 cm of the heat transfer region can be positionable in the second organ.

1 cm-40 cm of the heat transfer region can be positionable in the third organ.

The tube can have a total length of 30 cm-250 cm.

When the tube is in a fully deployed configuration, 50 cm-150 cm of the tube can be in the second organ.

When the tube is in the fully deployed configuration, 0 cm-40 cm of the tube can be in the third organ.

When the tube is in the fully deployed configuration, 50 cm-150 cm of the heat transfer region can be in the second organ.

When the tube is in the fully deployed configuration, 0 cm-40 cm of the heat transfer region can be in the third organ.

The figures illustrate, for example, a method of changing a temperature of a gastrointestinal tract caudal of a gastroesophageal junction of the gastrointestinal tract via a catheter (e.g., the catheter 9). The method can include inserting 50 cm-300 cm of the catheter into a stomach of the gastrointestinal tract. The method can include adding or removing a fluid from the catheter through an inflow port and an outflow port with 10-100 Watts of cooling or warming power. The method can include changing the temperature of the gastrointestinal tract caudal of the gastroesophageal junction of the gastrointestinal tract via the 50 cm-300 cm of the catheter inserted into the stomach. The method can include circulating the fluid through an inflow lumen and an outflow lumen that extend through the 50 cm-300 cm of the catheter inserted into the stomach. The fluid can have a temperature greater than 37 degrees Celsius and/or the fluid can have a temperature less than 37 degrees Celsius. The method can include increasing and/or decreasing the temperature of the gastrointestinal tract caudal of the gastroesophageal junction of the gastrointestinal tract by 1 degree Celsius to 20 degrees Celsius. The method can include increasing and/or decreasing a temperature of a wall of the gastrointestinal tract caudal of the gastroesophageal junction of the gastrointestinal tract by 1 degree Celsius to 20 degrees Celsius. The wall of the gastrointestinal tract caudal of the gastroesophageal junction of the gastrointestinal tract can be adjacent to a pancreas. The length of the inflow lumen can be the same as the length of the outflow lumen. The method can include simultaneously positioning the inflow lumen and the outflow lumen in the gastrointestinal tract. The inflow lumen and the outflow lumen can merge with each other at a merge point. The merge point can be inside the catheter. The merge point can be in a distal end of the catheter. The merge point can be 0.10 cm to 3.00 cm proximal the distal terminal end of the catheter.

The figures illustrate, for example, a method of changing a temperature of a gastrointestinal tract caudal of a gastroesophageal junction of the gastrointestinal tract. The method can include positioning a first section of a catheter in a stomach of the gastrointestinal tract. The method can include transferring heat to or from the gastrointestinal tract comprising recirculating a fluid through an inflow lumen and an outflow lumen in the first section of the catheter. The length of the first section of the catheter can be greater than a length of a greater curvature of the stomach. Transferring the heat to and/or from the gastrointestinal tract can include transferring the heat to and/or from the gastrointestinal tract via the first section of the catheter in the stomach. The length of the first section of the catheter can be greater than the greater curvature of the stomach concurrent with the transferring of the heat to and/or from the gastrointestinal tract. The length of the first section of the catheter can be 10 cm-300 cm greater than the greater curvature of the stomach. The length of the first section of the catheter in the stomach (Lc) can be N times greater than the length of the greater curvature of the stomach (Ls) as represented by equation Lc=NLs. N can be a positive real number comprising 1.00-20.00. A distal end of the catheter can include the first section of the catheter. A proximal end of the catheter can include the first section of the catheter. The fluid can have a temperature greater than 37 degrees Celsius or wherein the fluid has a temperature less than 37 degrees Celsius.

The figures illustrate, for example, a method of changing a temperature of a gastrointestinal tract caudal of a gastroesophageal junction of the gastrointestinal tract. The method can include positioning a length of a lumen in a stomach of the gastrointestinal tract. The method can include passing a fluid through the length of the lumen at a flow rate over a treatment period. The flow rate can be at least 20 mL/min and the treatment period can be at least 2 hours. The length of the lumen in the stomach can be 30 cm-150 cm. A volume of the length of the lumen in the gastrointestinal tract can be 2.0 mL-50.0 mL. The flow rate can be less than 200 mL/min and/or the treatment period can be 2 hours to 31 days. The method can include passing 4 L-9,000 L of the fluid through the length of the lumen. The method can include flowing the fluid through the length of the lumen in the stomach at a flow rate comprising 20 mL/min-200 mL/min. The lumen can be a first lumen. The method can include positioning a length of a second lumen in the stomach. The method can include passing the fluid through the length of the second lumen at the flow rate over the treatment period. The length of the second lumen in the stomach can be 30 cm-150 cm. The first lumen can be an inflow lumen and wherein the second lumen can be an outflow lumen. The first lumen and the second lumen can merge with each other at a merge point. The merge point is inside the catheter.

The figures illustrate, for example, a device (e.g., the heat transferer 4). The device can have a catheter having a heat transfer region. A heating zone can extend radially from the heat transfer region. The heat transfer region can have a length of 50 cm-300 cm. When the catheter is in a deployed configuration, a first heating zone of a first length of the heat transfer region can overlap a second heating zone of a second length of the heat transfer region. The device can have a recirculating pump. The device can have an inflow port and an outflow port at a proximal end of the catheter. When the catheter is in the deployed configuration, the heat transfer region can cross over itself. When the catheter is in the deployed configuration, a first external portion of the heat transfer region can contact a second external portion of the heat transfer region. When the catheter is in a straight configuration, the first length of the heat transfer region and the second length of the heat transfer region can be separated by at least 10 cm. When the catheter is in a straight configuration, the first length of the heat transfer region can be proximal the second length of the heat transfer region. When the catheter is in the deployed configuration, the first length of the heat transfer region is distal the second length of the heat transfer region.

The figures illustrate, for example, a device (e.g., the heat transferer 4). The device can have a recirculating pump. The device can have a catheter having a lumen. A first end of the lumen can have an inflow port and a second end of the lumen can have an outflow port. When the recirculating pump is recirculating fluid, the inflow port and the outflow port can be in fluid communication with the recirculating pump. When the catheter is in a deployed configuration, an adherer can be attached to the catheter. When the catheter is in the deployed configuration, a volume of the lumen distal to the inflow port and the outflow port can be less than 50 mL. When the catheter is in the deployed configuration, a length of the catheter between the adherer and a distal tip of the catheter can be at least 80 cm. When the catheter is in the deployed configuration, the volume of the lumen distal to the inflow port and the outflow port can be less than 20 mL or 10 mL. When the catheter is in the deployed configuration, the length of the catheter between the adherer and the distal tip of the catheter can be less than 175 cm or 300 cm. When the catheter is in the deployed configuration, an internal volume of the device distal to the inflow port and the outflow port can be less than 100 cm, 50 cm, or 20 cm. An internal volume of the device distal to the inflow port and the outflow port can include the volume of the lumen. The adherer can have adhesive. The adherer can be tape.

The figures illustrate, for example, a device (e.g., the heat transferer 4). The device can have a recirculating pump. The device can have a catheter having a having lumen. A first end of the lumen can have an inflow port and a second end of the lumen can have an outflow port. The inflow port and the outflow port can be at a first end of the catheter. When the recirculating pump is recirculating fluid, the inflow port and the outflow port can be in fluid communication with the recirculating pump. When the catheter is in a deployed configuration, an adherer can be attached to the catheter. When the catheter is in the deployed configuration, a length of the catheter between the adherer and a distal terminal end of the catheter can be greater than 90 cm from the adherer. When the catheter is in the deployed configuration, a distance as measured along a straight line from the adherer to the distal terminal end of the catheter can be less than 60 cm. When the catheter is in the deployed configuration, the length of the catheter between the adherer and the distal terminal end of the catheter can be less than 175 cm or 300 cm. The deployed configuration can be a first deployed configuration and the straight line can be a first straight line. When the catheter is in a second deployed configuration, a distance as measured along a second straight line from the adherer to the distal terminal end of the catheter can be greater than 60 cm. The distance as measured along the second straight line from the adherer to the distal terminal end of the catheter can be 1 cm-15 cm greater than the distance as measured along the first straight line from the adherer to the distal terminal end of the catheter. When the catheter is in the deployed configuration, the length of the catheter between the adherer and the distal terminal end of the catheter can cross over itself 1-5 times. The adherer can be adhesive and/or a piece of tape.

The figures illustrate, for example, a method of changing a temperature of a gastrointestinal tract caudal of a gastroesophageal junction of the gastrointestinal tract. The method can include forming a first length of a catheter into a first loop inside a stomach of the gastrointestinal tract. The first loop can have a first loop first end that crosses a first loop second end. A width of the first loop can be greater than 3 cm. The method can include transferring heat to and/or from the gastrointestinal tract which can include recirculating a fluid through an inflow lumen and an outflow lumen in the catheter. The inflow lumen and the outflow lumen can extend through the first length of the catheter. Forming the first length of the catheter into the first loop can include advancing the catheter into the stomach. Forming the first length of the catheter into the first loop can include progressively forming the first length of the catheter into the first loop inside the stomach as the catheter is advanced into the stomach. The first loop first end can contact the first loop second end. The first loop first end and the first loop second end can be movable into and/or out of contact with each other via peristaltic movement of the stomach. Forming the first length of the catheter into the first loop can include crossing the catheter over itself inside the stomach, folding the catheter onto itself inside the stomach, and/or forming a bend in the catheter inside the stomach. The method can include comprising forming a second length of the catheter into a second loop inside the stomach after the first loop is formed inside the stomach.

The figures illustrate, for example, a method of changing a temperature of a gastrointestinal tract caudal of a gastroesophageal junction of the gastrointestinal tract. The method can include forming a first section of a catheter into a first loop defining a first cell in a stomach of the gastrointestinal tract by advancing the catheter into the stomach. The method can include transferring heat to and/or from the gastrointestinal tract which can include recirculating a fluid through an inflow lumen and an outflow lumen in the catheter when the first cell is distal to a distal terminal end of the catheter. Forming the catheter into the first loop in the stomach can include crossing the catheter over itself in the stomach and/or forming a bend in the catheter in the stomach. Forming the catheter into the first loop defining the first cell in the stomach of the gastrointestinal tract by advancing the catheter into the stomach can include pushing the catheter against a wall of the stomach. The inflow lumen and the outflow lumen can be in the first section of the catheter. When the catheter is in a straight configuration, the first section of the catheter can be straight. The method can include forming a second section of the catheter into a second loop defining a second cell in the stomach by advancing the catheter into the stomach. The method can include moving the first loop relative to the second loop and/or moving the second loop relative to the first loop.

The figures illustrate, for example, a method of changing a temperature of a gastrointestinal tract caudal of a gastroesophageal junction of the gastrointestinal tract. The method can include forming a first section of a catheter into a first loop in a stomach of the gastrointestinal tract. The method can include forming a second section of the catheter into a second loop in the stomach which can include forming or moving the second loop distal the first loop. When the catheter is in a straight configuration, the first section of the catheter can be distal the second section of the catheter. The method can include transferring heat to and/or from the gastrointestinal tract via the catheter. The method can include forming the first section of the catheter into the first loop in the stomach by advancing the first section of the catheter into the stomach. Forming the catheter into the first loop in the stomach by advancing the catheter into the stomach can include pushing the catheter against a wall of the stomach. The method can include forming the second section of the catheter into the second loop in the stomach by advancing the second section of the catheter into the stomach. Forming the catheter into the second loop in the stomach by advancing the catheter into the stomach can include pushing the catheter against a wall of the stomach. Forming the second section of the catheter into the second loop can include moving the second section of the catheter against the first section of the catheter and/or moving the second section of the catheter over or under the first section of the catheter.

The figures illustrate, for example, a device (e.g., the heat transferer 4). The device can have a catheter having a first section. The first section can have a first section first configuration and a first section second configuration. When the first section is in first section first configuration, the first section can be straight. When the first section is in the first section second configuration, the first section can include a first loop having a first loop first end that crosses a first loop second end at a first location along the catheter. A width of the first loop can be greater than 3 cm as measured from an axis perpendicular to a center longitudinal axis of the catheter. The device can have a recirculating pump. The catheter can have an inflow lumen and an outflow lumen. When the recirculating pump is recirculating fluid, the inflow lumen and the outflow lumen can be in fluid communication with the recirculating pump. The catheter can have an inflow lumen and an outflow lumen. A fluid can be flowable through the inflow lumen and the outflow lumen. When the fluid is in the inflow lumen and the outflow lumen, heat can be absorbable or emittable by the fluid. The first loop first end can contact the first loop second end at the first location. The first loop first end and the first loop second end can be separated by a first loop gap at the first location. A length of the first loop as measured along a straight line from a base of the first loop to a head of the first loop can be greater than 3 cm. A perimeter of the first loop as measured along a center longitudinal axis of the catheter from the first loop first end to the first loop second end can be greater than 9.5 cm. The catheter can have a second section. The second section can have a second section first configuration and a second section second configuration. When the second section is in second section first configuration, the second section can be straight. When the second section is in the second section second configuration, the second section can have a second loop having a second loop first end and a second loop second end. When the second section is in the second section second configuration, the second loop first end can cross the second loop second end at a second location along the catheter.

The figures illustrate, for example, a device (e.g., the heat transferer 4). The device can have a catheter having a first section and a second section. The catheter can have a first configuration and a second configuration. When the catheter is in the first configuration, the first section and the second section can be less curved than when the catheter is in the second configuration and the first section is distal the second section. When the catheter is in the second configuration, the first section can define a first loop, the second section can define a second loop, and the second section can be distal the first section such that the second loop can be distal the first loop.

When the catheter is in the first configuration, the first section and the second section can be straight. When the catheter is in the second configuration, the first loop can be an open loop or a closed loop and the second loop can be an open loop or a closed loop. The device can have a recirculating pump. The catheter can have an inflow lumen and an outflow lumen. When the recirculating pump is recirculating fluid, the inflow lumen and the outflow lumen can be in fluid communication with the recirculating pump. A perimeter of the first loop as measured along a center longitudinal axis of the catheter can be smaller or larger when the catheter is in the second configuration than when the catheter is in the first configuration. The first loop can define a first cell having a first cell central axis. The second loop can define a second cell having a second cell central axis. The first cell central axis can be offset from the second cell central axis. The first loop can be closer to or farther from the second loop when the catheter is in the second configuration than when the catheter is in a third configuration. A perimeter of the second loop as measured along a center longitudinal axis of the catheter can be smaller or larger when the catheter is in the second configuration than when the catheter is in a third configuration. The first configuration, the second configuration, and the third configuration can be deployed configurations. When the catheter is in the second configuration, the first loop can be an open loop. When the catheter is in a third configuration, the first loop can be a closed loop. When the catheter is in the second configuration, the second loop can be a closed loop. When the catheter is in a third configuration, the first loop can be an open loop, The figures illustrate, for example, a method of changing a temperature of a stomach via a catheter (e.g., the catheter 9). The catheter can have an inflow channel, an outflow channel, a first temperature sensor, a second temperature sensor, and a proboscis. The proboscis can have the first temperature sensor. When the catheter is in a straight configuration, the proboscis and the first temperature sensor can be distal the inflow channel, the outflow channel, and the second temperature sensor. The method can include positioning the catheter in the stomach. Positioning the catheter in the stomach can include positioning the first temperature sensor and the proboscis closer to the pylorus than the second temperature sensor. The method can include transferring heat to and/or from the stomach via the catheter positioned in the stomach. When the catheter is in the straight configuration, the first temperature sensor and the second temperature sensor can be separated by a first distance. When the catheter is in a deployed configuration, the first temperature sensor and the second temperature sensor can be separated by a second distance. The first distance can be greater than the second distance. The first distance can be 50 cm-300 cm. The second distance can be 5 cm-40 cm. Positioning the catheter in the stomach can include positioning the first temperature sensor and the proboscis 1 cm-20 cm from the pylorus. Positioning the catheter in the stomach can include positioning the second temperature sensor closer to the lower esophageal sphincter than the first temperature sensor and the proboscis. Positioning the catheter in the stomach can include positioning the second temperature sensor 1 cm-20 cm from the lower esophageal sphincter. When the catheter is in the straight configuration, the second temperature sensor can be 50 cm-300 cm proximal the first temperature sensor. The method can include measuring a temperature of the stomach with the first temperature sensor and/or measuring a temperature of the stomach with the second temperature sensor. The first temperature sensor can be embedded in the proboscis. Transferring heat to and/or from the stomach via the catheter positioned in the stomach can include flowing a fluid through the inflow channel and the outflow channel. The first temperature sensor can be a first thermocouple. The second temperature sensor can be a second thermocouple. Transferring heat to and/or from the stomach via the catheter positioned in the stomach can include flowing a fluid through the inflow channel and the outflow channel.

The figures illustrate, for example, a method of changing a temperature of a stomach via a catheter (e.g., the catheter 9). The catheter can have an inflow channel, an outflow channel, a first temperature sensor, a second temperature sensor, and a proboscis. The proboscis can have the first temperature sensor. When the catheter is in a straight configuration, the proboscis and the first temperature sensor can be distal the inflow channel, the outflow channel, and the second temperature sensor. The method can include positioning the catheter in the stomach. Positioning the catheter in the stomach can include positioning the first temperature sensor and the proboscis farther from the pylorus than the second temperature sensor. The method can include transferring heat to and/or from the stomach via the catheter positioned in the stomach. When the catheter is in the straight configuration, the first temperature sensor and the second temperature sensor can be separated by a first distance. When the catheter is in a deployed configuration, the first temperature sensor and the second temperature sensor can be separated by a second distance. The first distance can be greater than the second distance. Positioning the catheter in the stomach can include positioning the second temperature sensor 1 cm-20 cm from the pylorus. Positioning the catheter in the stomach can include positioning the second temperature sensor farther from the lower esophageal sphincter than the first temperature sensor and the proboscis. Positioning the catheter in the stomach can include positioning the first temperature sensor and the proboscis 1 cm-20 cm from the lower esophageal sphincter. When the catheter is in the straight configuration, the second temperature sensor can be 50 cm-300 cm proximal the first temperature sensor. The method can include measuring a temperature of the stomach with the first temperature sensor and/or measuring a temperature of the stomach with the second temperature sensor. The first temperature sensor can be embedded in the proboscis. Transferring heat to and/or from the stomach via the catheter positioned in the stomach can include flowing a fluid through the inflow channel and the outflow channel. The first temperature sensor can be a first thermocouple. The second temperature sensor can be a second thermocouple. Transferring heat to and/or from the stomach via the catheter positioned in the stomach can include flowing a fluid through the inflow channel and the outflow channel.

The figures illustrate, for example, a method of changing a temperature of a stomach via a catheter (e.g., the catheter 9). The catheter can have an inflow channel, an outflow channel, a first temperature sensor, a second temperature sensor, and a proboscis. The proboscis can have the first temperature sensor. The method can include positioning the catheter in the stomach in a first operational configuration. When the catheter is in the first operational configuration, the first temperature sensor and the second temperature sensor can be in the stomach. The catheter can move from the first operational configuration to a second operational configuration. When the catheter is in the second operational configuration, the first temperature sensor can be in the pylorus or the duodenum and the second temperature sensor can be in the stomach. The catheter can moving from the first operational configuration to the second operational configuration can include a portion of the catheter migrating out of the stomach, through the pylorus, and into the duodenum. The catheter moving from the first operational configuration to the second operational configuration can include a portion of the catheter passively moving out of the stomach, through the pylorus, and into the duodenum. The method can include transferring heat to and/or from the stomach when the catheter is in the first operational configuration. The method can include transferring heat to and/or from the stomach, the pylorus, and the duodenum when the catheter is in the second operational configuration. Transferring heat to and/or from the stomach when the catheter is in the first operational configuration can include flowing a fluid through an inflow lumen and an outflow lumen in the catheter when the catheter is in the first operational configuration. Transferring heat to and/or from the stomach, the pylorus, and the duodenum when the catheter is in the second operational configuration can include flowing the fluid through the inflow lumen and the outflow lumen in the catheter when the catheter is in the second operational configuration. The method can include transferring heat to and/or from the stomach as the catheter moves from the first operational configuration to the second operational configuration. Transferring heat to and/or from the stomach as the catheter moves from the first operational configuration to the second operational configuration can include flowing the fluid through the inflow lumen and the outflow lumen in the catheter as the catheter moves from the first operational configuration to the second operational configuration.

The figures illustrate, for example, a device (e.g., the heat transferer 4). The device can have a catheter having an inflow channel, an outflow channel, a first temperature sensor, a second temperature sensor, and a proboscis. The proboscis can include the first temperature sensor. When the catheter is in a straight configuration, the proboscis and the first temperature sensor can be distal the inflow channel, the outflow channel, and the second temperature sensor. When the catheter is in the straight configuration, the first temperature sensor and the second temperature sensor can be separated by a first distance. When the catheter is in a first operational configuration, the first temperature sensor and the second temperature sensor can be separated by a second distance. The first distance can be greater than the second distance. The first distance can be 50 cm-300 cm. The second distance can be 5 cm-40 cm. When the catheter is in a second operational configuration, the first temperature sensor and the second temperature sensor can be separated by a third distance. The third distance can be greater than the second distance. The third distance can be 5 cm-30 cm greater than the second distance. When the catheter is in the straight configuration, the second temperature sensor can be 50 cm-300 cm proximal the first temperature sensor. The first temperature sensor can be embedded in the proboscis. The first temperature sensor can be a first thermocouple. The second temperature sensor can be a second thermocouple. A fluid is flowable through the inflow lumen and the outflow lumen. When the fluid flows through the inflow lumen and the outflow lumen, heat is absorbable or emittable by the catheter.

The insertion tube can be positioned at the fundus of the stomach after insertion through the nasal or oral passageway and through the esophagus. Within the insertion tube, a balloon can be folded and contained. The balloon can be configured to be expelled from the insertion tube and can have a two-lumen tether for the inflow and outflow of cooling and/or warming media in the balloon. The balloon can be independently translated from the distal portion of the insertion tube by the tether. For example, the balloon may not be integrated within the shaft of the insertion tube such that the balloon can be independently translated from the distal portion of the insertion tube by the tether. The balloon can be expelled directly from the distal end or from a side port of the insertion tube. Upon filling with cooling and/or warming media, the balloon can drop by gravity and the peristaltic motion in the stomach to the pyloric region. The tether can maintain the attachment of the balloon to the insertion tube. The tether can have a slack portion to allow the balloon to be expelled from the insertion tube at a distance of 5 cm to 20 cm. At the conclusion of the procedure, the balloon can be deflated for removal from the patient. During removal, the tether can be retracted into the insertion tube to bring the deflated balloon back within the insertion tube.

At the proximal end of the insertion tube, the distance of the tether can be adjusted to obtain the proper position in the lower portion of the stomach. Proper positioning can be aided by radiographic, endoscopic, or ultrasonography visualization.

The balloon can be expelled from the insertion tube at the distal end of the insertion tube in which the proboscis of the insertion tube can be retracted by manual actuation of a pull wire. At the proximal end, retraction of the pull wire by the user can collapse the distal end of the insertion tube to open the lumen for the balloon to be expelled.

The manual retraction of the pull wire can be performed automatically by the cooling and/or warming console at the onset of applying cooling and/or warming media into the insertion tube.

The balloon can be expelled from the insertion tube at the distal end of the insertion tube in which the proboscis of the insertion tube can be retracted by rotation of a torque wire that releases the proboscis and distal end of the insertion to release the balloon.

The proboscis of the insertion tube can be the balloon in a heat set configuration. The distal end of the insertion tube can have an open end in which the balloon can be packed and folded. The folding operation can configure the balloon into a proboscis configuration for insertion through the nasal passageway of the patient. Once the insertion tube has passed through the esophagus and at the fundus of the stomach, the balloon can be expelled from the distal end. The packed balloon in a proboscis configuration can be used once for insertion into the patient since once unfolded and inflated with cooling and/or warming media, the user would be unable to fold the balloon into a proboscis. During removal from the patient, the tether can be retracted to pull the deflated balloon back into the open distal end of the insertion tube.

The balloon can be expelled automatically when the cooling and/or warming media is applied to the two-lumen tether. The cooling and/or warming media can be directed through the inflow lumen of the tether and can begin to expand the proboscis portion of the balloon. Upon filling the packed balloon in the distal end portion of the insertion tube, the cooling and/or warming media can distend the balloon out from the distal end of the insertion tube. As the distension process continues, the mechanical action of the fluid can expel the balloon as it expands to allow the balloon to fall to the bottom portion of the stomach. Once expelled from the insertion tube, the balloon can continue to be filled through the inflow tube with return media traveling through the outflow lumen.

The instillation of the cooling and/or warming media can inflate the balloon and the hydraulic energy can evert the balloon from the distal end of the insertion tube as the balloon unfolds.

The balloon can be packed within a side port of the insertion tube in a compact fashion without protrusions to maintain the same profile of the insertion tube for travel through the nasal passageways and esophagus. Once positioned in the stomach, the balloon can be expelled from the insertion tube at an opening on the lateral side of the insertion tube. As described above, the expulsion of the balloon can be performed automatically by the instillation of cooling and/or warming media.

For fitment in the lower portion of the stomach, the balloon can be shaped like a straight or curved cylinder, round ball, donut with an open central hole, or a spiral coil. The balloon shape can prevent the balloon from traveling through the pylorus and into the duodenum.

The balloon can be configured with longitudinal grooves on balloon exterior to allow for fluid passage to the pylorus.

The balloon can have sensors. The sensors can be applied to the balloon. The sensors can measure stomach activity during the course of treatment. Types of sensors include pH, temperature, and pressure sensors to measure the activity of the stomach on the balloon. The sensors can inform the user on the degree of cooling and/or warming and its effect on the activity of the stomach during treatment.

In operation, the inflated balloon within the stomach can pose a risk in the circumstances where inadvertently the system is withdrawn from the stomach before the deflation of the balloon has occurred. This could be caused by the user or by the patient by pulling and removing the insertion tube from the nasal or oral passageway prior to deflation of the balloon. A clip sensor can be applied to the insertion tube once delivery to the stomach is completed and prior to the onset of cooling and/or warming therapy. The clip sensor can be applied to the patient and insertion tube with an electrical connection to the cooling and/or warming console. To remove the insertion tube from the patient, the clip sensor attachment can be broken which can automatically apply aspiration to the inflow and outflow lumens to remove fluid in the balloon and insertion tube. The aspiration force from the cooling and/or warming console can deflate the balloon to facilitate removal from the patient. The clip sensor can include an alarm or alarms to alert the medical staff that an inadvertent removal of the system has occurred.

The clip sensor can be applied to the patient's body temperature sensor. In operation, the cooling and/or warming console can read and direct the amount of cooling and/or warming media and energy in response to the patients' body temperature. In the event the patients' body temperature sensor is inadvertently removed by the user or the patient during use, the clip sensor can inform the cooling and/or warming console to terminate cooling and/or warming energy or apply aspiration force to remove cooling and/or warming media. The clip sensor can include an alarm or alarms to alert the medical staff that an inadvertent removal of the body temperature sensor has occurred.

The catheter or balloon system can include a dynamic actuator at the distal portion of the system that resides in the stomach during cooling and/or warming. Upon the application of cooling and/or warming energy, the distal portion can be configured to rotate or gyrate to provide constant movement of the applicator of cooling and/or warming energy in the stomach. The dynamic movement can ensure that cooling and/or warming energy is applied to varying locations of the stomach during cooling and/or warming treatment without being applied in the same location.

Gyration of the distal portion can occur with an internal torque wire within the catheter system that can be mechanically connected to the cooling and/or warming console. Upon the onset of cooling and/or warming energy, the torque wire can be rotated that applies constant and dynamic movement to the distal portion of the catheter system.

The distal portion of the catheter system can curve and fold up upon retraction of an internal pull wire within the catheter system. The proximal portion of the pull wire can be mechanically attached to the cooling and/or warming console. Upon the onset of cooling and/or warming energy, the pull wire can be retracted and released which can apply constant and dynamic movement to the distal portion of the catheter system.

The distal portion of the catheter system can have a shape memory wire system that reacts to the temperature change to curve and rotate the catheter system.

The balloon system can have cooling and/or warming energy applied with varying pressure to pulsate the balloon in size, shape, and/or location to provide cooling and/or warming energy dynamically to the interior of the stomach.

The distal portion of the catheter system can be configured with drip holes that allow controlled amounts of cooling and/or warming fluid to be dripped into the stomach. This action can apply a controlled volume of fluid to the interior portion of the stomach to facilitate cooling and/or warming action and coupling the cooling and/or warming energy to the stomach. The cooling and/or warming fluid through the drip holes can be controlled by pore size and fluid pressure of the cooling and/or warming media within the catheter. The dripping action can occur automatically as part of the cooling and/or warming treatment. The volume of cooling and/or warming fluid in the stomach can be controlled by the user and cooling and/or warming console by adjusting the cooling and/or warming fluid pressure. A higher inflow pressure can match the rate of absorption of fluid in the stomach to keep the fluid coupling environment optimum for providing cooling and/or warming energy to the stomach.

The distal portion of the first lumen of a catheter system can be configured with drip holes that allow controlled amounts of cooling and/or warming fluid to be dripped into the stomach. This action can apply a controlled volume of fluid to the interior portion of the stomach to facilitate cooling and/or warming action and coupling the cooling and/or warming energy to the stomach. The cooling and/or warming fluid through the drip holes can be controlled by pore size and fluid pressure of the cooling and/or warming media within the first lumen of the catheter. The dripping action can occur automatically as part of the cooling and/or warming treatment. A second lumen of the catheter can have holes for outflow of the fluid to return external to the cooling and/or warming source (temperature regulation device) or discarded. Suction can be applied at the portion of the second lumen external to the body. The volume of cooling and/or warming fluid in the stomach can be by the adjustment of the rate of inflow into the stomach and outflow out of the stomach. A higher inflow pressure can match the outflow rate of fluid in the stomach to keep the fluid coupling optimum for transfer of cooling and/or warming energy to the stomach.

The catheter system can be configured for preferential thermal transfer on the inflow portion of the catheter over the remaining portions of the catheter including exterior portions of the catheter system that are adjacent to the outflow lumen or aspiration lumen. The exterior wall of the inflow lumen can have less insulation or wall thickness than the remaining portions of the catheter.

The preferential thermal transfer region of the inflow lumen can be positioned at the distal portion of the catheter or the region of the body of cooling/warming.

The preferential thermal transfer region can be made by providing a thin-wall membrane on the exterior of the inflow lumen at the distal end portion of the catheter system. Referring to cross-sectional FIGS. 28a and 28b, these figures depict a thin-wall membrane on two locations around the circumference of the catheter. In this configuration, one thin-wall membrane (e.g., only one thin-wall membrane) can be applied on the inflow lumen whereas the outflow lumen can maintain the wall thickness catheter and less preferential thermal transfer to the body.

Preferential thermal transfer can be achieved by impregnating the wall of the inflow lumen with metallic particles for added thermal transfer to the body at that location of the catheter system. These metallic particles can also provide greater radiopacity on the inflow portion of the catheter to facilitate catheter placement by providing an indication of location. Metallic particles can be constructed from titanium, stainless steel, tungsten, cobalt chromium, and other biocompatible metals that have greater thermal conductivity than the polymer used for the catheter system.

A temperature sensor or thermistor can be placed alongside the catheter lumens to measure the temperature fluid in the surrounding organs. The sensor may be a thermistor, thermocouple, RTD and/or another temperature sensor. This measurement can be used to monitor the temperature of the gas, fluids and/or tissue of the surrounding organ during warming or cooling via the catheter. Additionally, the data from the temperature sensor can provide feedback to regulate the rate of cooling or warming applied via the catheter. The temperature sensor may locate so that it does not measure the direct temperature of the catheter or fluid contents and instead measures the temperature of the surrounding environment. The temperature sensor may be embedded and/or secured to the lumen that does not have cooling/and or warming fluids such as an aspiration lumen. Additionally, this sensor may be cantilevered above an aspiration/and or feeding lumen so that the sensor tip is not in direct contact with the catheter. Alternately the sensor maybe located on a tether (73) that connects two sections of the catheter. The proximal end of the sensor cable may connect the temperature sensor to an external console, a DAQ, a data acquisition device, the heat exchange system 13, a computer and/or other systems. The sensor cable 107 may be the remote sensor tether 94. The sensor cable 107 may be wires, cables, fiber optics tubes and/or a conduit that can transmit information. The sensor cable 107 may pass through the outside of the catheter 9 and/or through one of the catheter lumens. The external console, a DAQ, a data acquisition device, the heat exchange system 13, a computer and/or other systems may provide visual or audible feedback to the user regarding the status the target temperatures of the organ/and our surrounding fluids. As an example this maybe an LED, LCD or LED screen, or audible tone.

Changes and modifications can be made to this disclosure, and equivalents employed, or combinations of any of the disclosed elements, characteristics, features, devices, tools, steps, or methods without departing from the spirit and scope of the disclosure. Any of the disclosed elements, characteristics, features, devices, tools, steps, or methods can be present as a singular or as a plurality regardless of whether the elements, characteristics, features, devices, steps, or methods are explicitly disclosed herein as being singular or as a plurality. Elements shown with any variation are exemplary for the specific variation and can be used on other variations within this disclosure. The terms about and approximately can include the exact values following such terms and can include, for example, a tolerance of plus or minus 1% of any such values, a tolerance of plus or minus 5%, or any other tolerance that one of ordinary skill in the art would understand. Any phrase involving an "A and/or B" construction or similar construction can mean (1) A alone, (2) B alone, (3) A and B together. Any range disclosed can include any subrange of the range disclosed, for example, a range of 1-10 units can include 2-10 units, 8-units, or any other subrange. The words "may" and "can" are interchangeable (e.g., "may" can be replaced with "can" and "can" can be replaced with "may"). All systems, devices, and methods described herein can be used for medical (e.g., diagnostic, therapeutic, or rehabilitative) or non-medical purposes. The above-described configurations, elements or complete assemblies and methods and their elements can be combined and modified with each other in any combination.

We claim:

1. A method of changing a temperature of a stomach via a catheter, wherein the catheter comprises an inflow channel, an outflow channel, a first temperature sensor, a second temperature sensor, and a flexible tip, wherein the flexible tip comprises the first temperature sensor, and wherein when the catheter is in a straight configuration, the flexible tip and the first temperature sensor are distal the inflow channel, the outflow channel, and the second temperature sensor, the method comprising:
    positioning the catheter in the stomach, wherein positioning the catheter in the stomach comprises positioning the first temperature sensor and the flexible tip closer to the pylorus than the second temperature sensor; and
    transferring heat to and/or from the stomach via the catheter positioned in the stomach,
    wherein when the catheter is in the straight configuration, the first temperature sensor and the second temperature sensor are separated by a first distance, wherein when the catheter is in a deployed configuration, the first temperature sensor and the second temperature sensor are separated by a second distance, wherein the first distance is greater than the second distance, wherein the first distance is 50 cm-300 cm, and wherein the second distance is 5 cm-40 cm.

2. The method of claim 1, wherein positioning the catheter in the stomach comprises positioning the first temperature sensor and the flexible tip 1 cm-20 cm from the pylorus.

3. The method of claim 1, wherein positioning the catheter in the stomach comprises positioning the second temperature sensor closer to a lower esophageal sphincter than the first temperature sensor and the flexible tip.

4. The method of claim 3, wherein positioning the catheter in the stomach comprises positioning the second temperature sensor 1 cm-20 cm from the lower esophageal sphincter.

5. The method of claim 1, wherein when the catheter is in the straight configuration, the second temperature sensor is 50 cm-300 cm proximal the first temperature sensor.

6. The method of claim 1, further comprising measuring a temperature of the stomach with the first temperature sensor and/or measuring a temperature of the stomach with the second temperature sensor, wherein the first temperature sensor is embedded in the flexible tip, and wherein transferring heat to and/or from the stomach via the catheter positioned in the stomach comprises flowing a fluid through the inflow channel and the outflow channel.

7. A method of changing a temperature of a stomach via a catheter, wherein the catheter comprises an inflow channel, an outflow channel, a first temperature sensor, a second temperature sensor, and a flexible tip, wherein the flexible tip comprises the first temperature sensor, and wherein when the catheter is in a straight configuration, the flexible tip and the first temperature sensor are distal the inflow channel, the outflow channel, and the second temperature sensor, the method comprising:
positioning the catheter in the stomach, wherein positioning the catheter in the stomach comprises positioning the first temperature sensor and the flexible tip farther from the pylorus than the second temperature sensor; and
transferring heat to and/or from the stomach via the catheter positioned in the stomach,
wherein when the catheter is in the straight configuration, the first temperature sensor and the second temperature sensor are separated by a first distance, wherein when the catheter is in a deployed configuration, the first temperature sensor and the second temperature sensor are separated by a second distance, wherein the first distance is greater than the second distance, wherein the first distance is 50 cm-300 cm, and wherein the second distance is 5 cm-40 cm.

8. The method of claim 7, wherein positioning the catheter in the stomach comprises positioning the second temperature sensor 1 cm-20 cm from the pylorus.

9. The method of claim 7, wherein positioning the catheter in the stomach comprises positioning the second temperature sensor farther from a lower esophageal sphincter than the first temperature sensor and the flexible tip.

10. The method of claim 9, wherein positioning the catheter in the stomach comprises positioning the first temperature sensor and the flexible tip 1 cm-20 cm from the lower esophageal sphincter.

11. The method of claim 7, wherein when the catheter is in the straight configuration, the second temperature sensor is 50 cm-300 cm proximal the first temperature sensor.

12. The method of claim 7, further comprising measuring a temperature of the stomach with the first temperature sensor and/or measuring a temperature of the stomach with the second temperature sensor, wherein the first temperature sensor is embedded in the flexible tip, and wherein transferring heat to and/or from the stomach via the catheter positioned in the stomach comprises flowing a fluid through the inflow channel and the outflow channel.

13. A method of changing a temperature of a stomach via a catheter, wherein the catheter comprises an inflow channel, an outflow channel, a first temperature sensor, a second temperature sensor, and a flexible tip, wherein the flexible tip comprises the first temperature sensor, the method comprising:
positioning the catheter in the stomach in a first operational configuration, wherein when the catheter is in the first operational configuration, the first temperature sensor and the second temperature sensor are in the stomach, wherein the catheter moves from the first operational configuration to a second operational configuration, wherein when the catheter is in the second operational configuration, the first temperature sensor is in the pylorus or the duodenum and the second temperature sensor is in the stomach,
wherein when the catheter is in a straight configuration, the first temperature sensor and the second temperature sensor are separated by a first distance, wherein when the catheter is in the first operational configuration or the second operational configuration, the first temperature sensor and the second temperature sensor are separated by a second distance, wherein the first distance is greater than the second distance, wherein the first distance is 50 cm-300 cm, and wherein the second distance is 5 cm-40 cm.

14. The method of claim 13, wherein the catheter moves from the first operational configuration to the second operational configuration comprises a portion of the catheter migrating out of the stomach, through the pylorus, and into the duodenum.

15. The method of claim 13, wherein the catheter moves from the first operational configuration to the second operational configuration comprises a portion of the catheter passively moving out of the stomach, through the pylorus, and into the duodenum.

16. The method of claim 13, further comprising:
transferring heat to and/or from the stomach when the catheter is in the first operational configuration; and
transferring heat to and/or from the stomach, the pylorus, and the duodenum when the catheter is in the second operational configuration,
wherein transferring heat to and/or from the stomach when the catheter is in the first operational configuration comprises flowing a fluid through an inflow lumen and an outflow lumen in the catheter when the catheter is in the first operational configuration, and
wherein transferring heat to and/or from the stomach, the pylorus, and the duodenum when the catheter is in the second operational configuration comprises flowing the fluid through the inflow lumen and the outflow lumen in the catheter when the catheter is in the second operational configuration.

17. The method of claim 16, further comprising transferring heat to and/or from the stomach as the catheter moves from the first operational configuration to the second operational configuration, wherein transferring heat to and/or from the stomach as the catheter moves from the first operational configuration to the second operational configuration comprises flowing the fluid through the inflow lumen and the outflow lumen in the catheter as the catheter moves from the first operational configuration to the second operational configuration.

* * * * *